(12) United States Patent  
Sundermann et al.

(10) Patent No.: US 7,951,815 B2  
(45) Date of Patent: May 31, 2011

(54) SUBSTITUTED 1,4,8-TRIAZASPIRO [4,5]DECAN-2-ONE COMPOUNDS

(75) Inventors: Corinna Sundermann, Aachen (DE); Bernd Sundermann, Aachen (DE); Stefan Ober-Boersch, Aachen (DE); Werner Englberger, Stolberg (DE); Hagen-Heinrich Hennies, Simmerath (DE)

(73) Assignee: Gruenenthal GmbH, Aachen (DE)

( * ) Notice: Subject to any disclaimer, the term of this patent is extended or adjusted under 35 U.S.C. 154(b) by 1060 days.

(21) Appl. No.: 11/525,057

(22) Filed: Sep. 22, 2006

(65) Prior Publication Data

US 2007/0015784 A1 Jan. 18, 2007

Related U.S. Application Data

(63) Continuation of application No. PCT/EP2005/003029, filed on Mar. 22, 2005.

(30) Foreign Application Priority Data

Mar. 22, 2004 (DE) .......................... 10 2004 014 296

(51) Int. Cl.
*A61K 31/438* (2006.01)
*C07D 471/10* (2006.01)
(52) U.S. Cl. .......................................... 514/278; 546/20
(58) Field of Classification Search .................. 514/278; 546/20

See application file for complete search history.

(56) References Cited

U.S. PATENT DOCUMENTS 3,725,389 A 4/1973 McCaully et al.

FOREIGN PATENT DOCUMENTS

| EP | 0 921 125 A1 | 6/1999 |
| EP | 0 963 985 A3 | 1/2001 |
| JP | 01207291 A | 8/1989 |

OTHER PUBLICATIONS

Hendershot, L.C. et al., "Antagonism of the Frequency of Phenylquinone-Induced Writhing in the Mouse by Weak Analgesics and Nonanalgesics", J. Pharmacol. Exp. Ther. 125, Sep. 19, 1958, pp. 237-240, The Biochemical Research Laboratory, The Dow Chemical Company, Midland, Michigan.
Frink, Martin CH. et al., "Influence of Tramadol on Neurotransmitter Systems of the Rat Brain", Arzneim-Forsch./Drug Res. 46 (II), Nr. 11, pp. 1029-1036 (1996).
Cheng, Yung-Chi et al., "Relationship Between the Inhibition Constant ($K_1$) and the Concentration of Inhibitor Which Causes 50 Per Cent Inhibition ($I_{50}$) of an Enzymatic Reaction", Biochemical Pharmacology, vol. 22, pp. 3099-3108, Pergamon Press, 1973, Great Britain.

"Remington's Pharmaceutical Sciences", Editor A.R. Gennaro, 17th Edition, Mack Publishing Company 1985, Chapters 76 to 93, particularly Section 8, provided herewith is the Table of Contents.
Gray, E.G. et al., "The Isolation of Nerve Endings From Brain: An Electron-Microscopic Study of Cell Fragments Derived by Homogenization and Centrifugation", Journal of Anatomy, vol. 96, Part 1, 1962, pp. 79-88.
Pauwels, Petrus et al., "[$^3$H]Batrachotoxinin A 20-α-Benzoate Binding to Sodium Channels in Rat Brain: Characterization and Pharmacological Significance", European Journal of Pharmacology, 124 (1986) pp. 291-298.
Lowry, Oliver H. et al., "Protein Measurement With the Folin Phenol Reagent", J. Biol. Chem., 193, pp. 265-275, 1951, Department of Pharmacology, Washington University School of Medicine, St. Louis, Missouri.
Lidia et al., *Journal of Combinatorial Chemistry* (2003), 5(4).S.356-361, Chemical Abstracts, STN(HCAPLUS), Accession No. (AN):2003-323987; Abstr.
"Acyl . . . ", http://www.roempp.com/prod/roempp.php, Oct. 21, 2004.
Anger et al., Medicinal Chemistry of Neuronal Voltage-Gated Sodium Channel Blockers, *Journal of Medicinal Chemistry*, vol. 44, No. 2, pp. 115-137. Jan. 18, 2001.
Madge, David J., Sodium Channels: Recent Developments and Therapeutic Potential, *Annual Reports in Medicinal Chemistry*, Chapter 6., pp. 51-60. 1998.
Nielsen et al., Sertraline, a serotonin-uptake inhibitor, reduces food intake and body weight in lean rats and genetically obese mice, *The American Journal of Clinical Nutrition*, 1992; 55: 185S-8S.
Pires et al., Acute effects of selective serotonin reuptake inhibitors on neuroleptic-induced catalepsy in mice, *Brazilian Journal of Medical and Biological Research*, 2005; 38: 1867-1872.
Rausch et al., Fluvoxamine treatment of mixed anxiety and depression: evidence for serotonergically mediated anxiolysis, *Journal of Clinical Psychopharmacology*, 2001; 21(2); 139-42. Abstract only.
Sacre et al., Fluxetine and citalopram exhibit potent anti-inflammatory activity in human and murine models of rheumatoid arthritis and inhibit toll-like receptors, *Arthritis & Rheumatism*, published online Jan. 7, 2010.
Sumpton et al., Treatment of neuropathic pain with venlafaxine, *The Annals of Pharmacotherapy*, 2001; vol. 35, No. 5, pp. 557-559. Abstract only.
Sweetnam et al., Receptor binding profile suggests multiple mechanisms of action are responsible for ibogaine's putative anti-addictive activity, *Psychopharmacology*, 1995; 118: 269-376.

*Primary Examiner* — Charanjit S Aulakh
(74) *Attorney, Agent, or Firm* — Crowell & Moring LLP

(57) ABSTRACT

Novel 1,4,8-triazaspiro[4,5]decan-2-one compounds corresponding to formula I

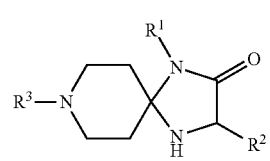

processes for the preparation thereof, related methods of treatment and pharmaceutical formulations containing such compounds.

21 Claims, No Drawings

SUBSTITUTED 1,4,8-TRIAZASPIRO[4,5]DECAN-2-ONE COMPOUNDS

CROSS-REFERENCE TO RELATED APPLICATIONS

This application is a continuation of International patent application Serial No. PCT/EP2005/003029 filed Mar. 22, 2005 which claims benefit to German patent application Serial No. 10 2004 014 296.3 filed Mar. 22, 2004, the entire disclosures of which are hereby incorporated in their entirety.

FIELD OF THE INVENTION

The present invention relates to substituted 1,4,8-triazaspiro[4,5]decan-2-one compounds, to processes for the preparation thereof, to a medicinal drug containing such a compound, and to the use of these compounds for the production of medicinal drugs.

BACKGROUND OF THE INVENTION

Obesity and concomitant disturbances and disorders, such as cardiac diseases represent a serious and ever growing problem for the health of large population groups, particularly in the highly developed industrial countries. In addition to other factors such as lack of exercise and unhealthy nourishment, inhibition of the reuptake of 5-hydroxytryptophane (serotonin) influences the pathogenesis and course of this disorder. There is thus a great need for suitable active pharmacological substances which inhibit reuptake of 5-hydroxytryptophane (serotonin) and are therefore particularly suitable for the therapy of obesity.

SUMMARY OF THE INVENTION

It is thus an object of the present invention to provide compounds which are particularly suitable for use as pharmaceutically active substances in medicinal drugs, preferably in medicinal drugs for the inhibition and/or treatment of obesity.

It has now been found, surprisingly, that the substituted 1,4,8-triazaspiro[4,5]decan-2-one compounds of the general formula I given below are not only suitable for regulation and preferably inhibition of the serotonin (5-hydroxytryptophane) reuptake and/or for regulation and preferably inhibition of the noradrenalin reuptake but show, in addition, a high affinity to opioid receptors, particularly for µ-opioid receptors and also for batrachotoxin (BTX) receptors and are therefore particularly suitable for use as pharmaceutically active substances in medicinal drugs for the inhibition and/or treatment of disorders associated with these receptors or processes. For purposes of this disclosure, inhibit and the forms thereof mean to lessen or limit. The compounds herein may also be useful in the prophylaxis of certain disorders or conditions.

DETAILED DESCRIPTION

The present invention therefore relates to substituted 1,4,8-triazaspiro[4,5]decan-2-one compounds of the general formula I,

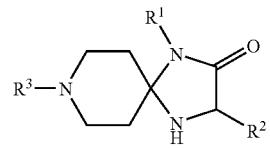

in which $R^1$ stands for a hydrogen radical, or for a linear or branched unsubstituted alkyl group optionally comprising at least one heteroatom as link, or for a linear or branched, unsubstituted or at least monosubstituted alkenyl radical optionally comprising at least one heteroatom as link, or for a linear or branched, unsubstituted or at least monosubstituted alkynyl radical optionally comprising at least one heteroatom as link, or for an unsubstituted or at least monosubstituted aryl radical or heteroaryl radical, which is bonded via a linear or branched alkylene group optionally comprising at least one heteroatom as link, or for a —C(=O)—OR$^5$ radical bonded via a linear or branched alkylene group or for an O—(C=O)—R$^6$ radical bonded via a linear or branched alkylene group, $R^2$ stands for a hydrogen radical, or for a linear or branched, unsubstituted or at least monosubstituted alkyl group optionally comprising at least one heteroatom as link, or for a linear or branched, unsubstituted or at least monosubstituted alkenyl radical optionally comprising at least one heteroatom as link, or for a linear or branched, unsubstituted or at least monosubstituted alkynyl radical optionally comprising at least one heteroatom as link, or for an unsubstituted or at least monosubstituted aryl radical or heteroaryl radical, which can be bonded via a linear or branched alkylene group optionally comprising at least one heteroatom as link, $R^3$ stands for a hydrogen radical, or for a linear or branched unsubstituted or at least monosubstituted alkyl group optionally comprising at least one heteroatom as link, or for a linear or branched unsubstituted or at least monosubstituted alkenyl radical optionally comprising at least one heteroatom as link, or for a linear or branched unsubstituted or at least monosubstituted alkynyl radical optionally comprising at least one heteroatom as link, or for an unsubstituted or at least monosubstituted aryl radical or heteroaryl radical, which is bonded via a linear or branched unsubstituted or at least monosubstituted alkylene group optionally comprising at least one heteroatom as link and optionally condensed with an unsubstituted or at least monosubstituted monocyclic ring system, or for an unsubstituted or at least monosubstituted cycloaliphatic radical optionally comprising at least one heteroatom as ring member and optionally bonded via a linear or branched unsubstituted or at least monosubstituted alkylene group optionally comprising at least one heteroatom as link, which can be bridged by a linear or branched unsubstituted or at least monosubstituted alkylene group optionally comprising at least one heteroatom as link and/or condensed with an unsubstituted or at least monosubstituted monocyclic ring system, or for a —C(=O)—R4 group, $R^4$ stands for a linear or branched unsubstituted or at least monosubstituted alkyl group optionally comprising at least one heteroatom as link, or for a linear or branched unsubstituted or at least monosubstituted alkenyl radical optionally comprising at least one heteroatom as link, or for a linear or branched unsubstituted or at least monosubstituted alkynyl radical optionally comprising at least one heteroatom as link, or for an unsubstituted or at least monosubstituted aryl radical or heteroaryl radical, which radicals can be bonded via a linear or branched unsubstituted or at least monosubstituted alkylene group, alkenylene group, or alkynylene group, which groups optionally comprise at least one heteroatom as link and/or are condensed with an unsubstituted or at least monosubstituted monocyclic ring system, or for an unsubstituted or at least monosubstituted cycloaliphatic radical optionally comprising at least one heteroatom as ring member and optionally bonded via a linear or branched unsubstituted or at least monosubstituted alkylene group optionally comprising at least one heteroatom as link, which can be at least singly bridged by a linear or branched unsubstituted or at least monosubstituted alkylene group and/or condensed with an unsubstituted or at least monosubstituted monocyclic ring system, or for a —C(=O)—OR$^7$ radical bonded via a linear or branched unsubstituted or at least monosubstituted alkylene group, or for an —O—(C=O)—R$^8$ radical bonded via a linear or branched unsubstituted or at least monosubstituted alkylene group or for a —(C=O)—R$^9$ radical bonded via a linear or branched unsubstituted or at least monosubstituted alkylene group, R$^5$ and R$^6$ each independently stand for a linear or branched alkyl group, or for a linear or branched alkenyl radical or for a linear or branched alkynyl radical, R$^7$ and R$^8$ each independently stand for a hydrogen radical, or for a linear or branched alkyl group, or for a linear or branched alkenyl radical, or for a linear or branched alkynyl radical, or for an unsubstituted or at least monosubstituted aryl radical or heteroaryl radical, R$^9$ stands for a linear or branched alkyl group, or for a linear or branched alkenyl radical or for a linear or branched alkynyl radical, in each case optionally in the form of one of the pure stereoisomers thereof particularly enantiomers or diastereoisomers, the racemates thereof or in the form of a mixture of stereoisomers, particularly the enantiomers and/or diastereoisomers, in an arbitrary blending ratio, or in each case in the form of appropriate salts, or in each case in the form of appropriate solvates.

If one of the radicals R$^1$ to R$^9$ stands for an alkyl radical, alkenyl radical or alkynyl radical or exhibits such a radical, this radical can—if not specified otherwise—be unsubstituted or monosubstituted or polysubstituted, preferably substituted by 1, 2, 3, 4, or 5 substituents, the substituents being preferably independently selected from the group consisting of F, Cl, Br, I, C$_{1-6}$ alkoxy, —NO$_2$, —OH, —SH, (C=O)—OH, —(C=O)—OC$_{1-4}$ alkyl, —O—(C=O)—C$_{1-4}$ alkyl, —CH$_2$OCH$_2$ phenyl, CN, —CF$_3$, —CHF$_2$, —CH$_2$F, unsubstituted phenyl, and —NR$^a$R$^b$ in which R$^a$ and R$^b$ can be selected independently from the group consisting of H, methyl, ethyl, n-propyl, isopropyl, n-butyl, sec-butyl, tert-butyl, —(C=O)—OC$_{1-4}$ alkyl, and unsubstituted phenyl. Alkenyl radicals exhibit at least one carbon-carbon double bond and alkynyl radicals at least one carbon-carbon triple bond.

Suitable alkyl, alkenyl, and alkynyl radicals, which may be monosubstituted or polysubstituted, can, for example, be selected from the group consisting of methyl, ethyl, n-propyl, isopropyl, n-butyl, isobutyl, sec-butyl, tert-butyl, n-pentyl, isopentyl, neopentyl, sec-pentyl, 2,2-dimethylpropyl, 1-methylbutyl, 1-ethylpropyl, 1-propylbutyl, 1-ethylpentyl, penta-1,3-dienyl, n-hexyl, 2-hexyl, n-heptyl, n-octyl, n-nonyl, n-decyl, —(CH$_2$)—(CH)—(C$_2$H$_5$)—(CH$_2$)—(CH$_2$)—(CH$_2$)—(CH$_3$), vinyl, ethynyl, propenyl, allyl, propynyl, 1-propynyl, 2-propynyl, butenyl, 1-propenyl, 2-propenyl, 1-butenyl, 2-butenyl, 3-butenyl, 2-methyl-2-butenyl, butynyl, 1-butynyl, 2-butynyl, 3-butynyl, pentenyl, pentynyl, hexenyl, and hexynyl.

The alkyl, alkenyl and alkynyl radicals used in the present invention can—if not specified otherwise—also have one or more heteroatoms, preferably one or more oxygen atoms, and/or one or more sulfur atoms and more preferably 1 or 2 oxygen atoms and/or 1 or 2 sulfur atoms, as link(s). Preferably, these heteroatoms are located in a non-terminal position of the respective radical. Examples of suitable radicals are —CH$_2$CH$_2$SCH$_3$, —CH$_2$OCH$_2$CH$_2$OCH$_3$, and —CH$_2$CH$_2$OCH$_3$.

If one of the radicals R$^3$ or R$^4$ stands for a cycloaliphatic radical or comprises a cycloaliphatic radical, this radical—if not specified otherwise—may be unsubstituted or monosubstituted or polysubstituted, preferably substituted by 1, 2, 3, 4, or 5 substituents, and the substituents can be independently selected preferably from the group consisting of F, Cl, Br, C$_{1-6}$ alkoxy, oxo, C$_{1-6}$ alkyl, hydroxy, —CN, CF$_3$, —CHF$_2$, CH$_2$F, unsubstituted phenyl, —NR$^a$R$^b$ in which R$^a$ and R$^b$ can be selected independently from the group consisting of H, methyl, ethyl, n-propyl, isopropyl, unsubstituted phenyl, thioxo (=S), I, —SF$_5$, —NO$_2$, —OCF$_3$, —SCF$_3$, SH, —SC$_{1-5}$ alkyl, —C(=O)—H, —C(=O)—C$_{1-5}$ alkyl, —C(=O)—OH, C(=O)—OC$_{1-5}$ alkyl, —(CH$_2$)—C(=O)—OH, —(CH$_2$)—C(=O)—OC$_{1-5}$ alkyl, (CH$_2$)-benzo[b]furanyl, —O-phenyl, —O-benzyl, phenyl, benzyl, naphthyl and —(CH$_2$)-naphthyl, and each of the cyclic moieties of the radicals —O-phenyl, —O-benzyl, phenyl, —(CH$_2$)-benzo[b]furanyl, benzyl, naphthyl and —(CH$_2$)-naphthyl can be substituted by 1, 2, 3, 4, or 5 substituents independently selected from the group consisting of F, Cl, Br, —OH, CF$_3$, —SF$_5$, —CN, —NO$_2$, —OC$_{1-5}$ alkyl, —C$_{1-5}$ alkyl, —OCF$_3$, —SCF$_3$, phenyl, and —O-benzyl.

For the purposes of the present invention cycloaliphatic radicals are taken to mean both saturated and unsaturated radicals. The cycloaliphatic radicals can optionally have one or more heteroatoms, preferably 1, 2, 3, 4, or 5 heteroatoms independently selected from the group consisting of nitrogen, oxygen, and sulfur, as ring members.

Suitable cycloaliphatic radicals, which can be monosubstituted or polysubstituted, can, for example, be selected from the group consisting of cyclopropyl, cyclobutyl, cyclopentyl, cyclohexyl, cycloheptyl, cyclooctyl, cyclopentenyl, cyclohexenyl, cycloheptenyl, cyclooctenyl, imidazolidynyl, tetrahydrofuryl, tetrahydrothiophenyl, pyrrolidynyl, piperidynyl, morpholynyl, piperazynyl, thiomorpholynyl, tetrahydropyranyl, azepanyl, diazepanyl, and dithiolanyl.

The cycloaliphatic radicals can further be at least singly bridged by a linear or branched alkylene group and are preferably bridged by one or two linear or branched C$_{1-5}$ alkylene groups. As examples of such cycloaliphatic radicals there may be mentioned the 4,7,7-trimethyl-3-oxo-2-oxabicyclo-[2.2.1]heptyl radical or the adamantyl radical.

If one of the radicals R$^1$ to R$^4$, R$^7$ and R$^8$ stands for an aryl radical or heteroaryl radical or comprises an aryl radical or heteroaryl radical, this aryl radical or heteroaryl radical can—unless otherwise stated—be monosubstituted or polysubstituted, and is preferably substituted by 1, 2, 3, 4, or 5 substituents, and the substituents can be independently selected preferably from the group consisting of F, Cl, Br, I, —CN, —NO$_2$, C$_{1-5}$ alkyl, OH, SH, C$_{1-5}$ alkoxy, C$_{1-5}$ perfluoroalkoxy, —C(=O)—C$_{1-5}$ alkyl, —C(=O)—O—C$_{1-5}$ alkyl, —(CH$_2$)$_{1-3}$—O—(C=O)-phenyl, —S—C$_{1-5}$ alkyl, —S(=O)$_{1-6}$ alkyl, —S(=O)$_2$—NH$_2$, —NH—(C=O)—CH$_3$, —S—CHF$_2$, —S—CH$_2$F, —C(=O)—C$_{1-5}$ perfluoroalkyl, —CF$_3$, CHF$_2$, CH$_2$F, phenyl, phenoxy, and —NR$^a$R$^b$, in which R$^a$ and R$^b$ can be selected independently from the group consisting of H, methyl, ethyl, n-propyl, isopropyl and unsubstituted phenyl, —SF$_5$, —O—C$_{2-5}$ alkenyl, —O—CF$_3$, —O—CHF$_2$, —O—CH$_2$F, C(=O)—OH, —O—C(=O)—C$_{1-5}$ alkyl, O—C(=O) phenyl, —(CH$_2$)—O—C(=O)—C$_{1-5}$ alkyl, —NH—C$_{1-5}$ alkyl, —N(C$_{1-5}$ alkyl)$_2$, —NH—C(=O)—O—C$_{1-5}$ alkyl, C(=O)—H, —C(=O)—C$_{1-5}$ alkyl, —C(=O)—NH$_2$, —C(=O)—NH—C$_{1-5}$ alkyl, C(=O)—N—(C$_{1-5}$ alkyl)$_2$, —S(=O)$_2$—NH—C$_{1-5}$ alkyl, —S(=O)$_2$—NH-phenyl, —(CH$_2$)-benzo[b]furanyl, —O-phenyl, —S-phenyl, —S-benzyl, —O-benzyl, phenyl, and benzyl.

The cyclic moiety of the radicals —S(=O)$_2$—NH-phenyl, —O-phenyl, —S-phenyl, —S-benzyl, —O-benzyl, phenyl, —(CH$_2$)-benzo[b]furanyl, and benzyl can be substituted by 1, 2, 3, 4, or 5 substituents independently selected from the group consisting of F, Cl, Br, —OH, —CF$_3$, —SF$_5$, —CN, —NO$_2$, —O—C$_{1-5}$ alkyl, —C$_{1-5}$ alkyl, —O—CF$_3$, —S—CF$_3$, phenyl, and —O-benzyl.

The phenyl and phenoxy substituents can themselves be monosubstituted or polysubstituted by the same or different substituents selected from the group consisting of F, Cl, Br, —S—CHF$_2$, —CF$_3$, —CHF$_2$, —CH$_2$F, —CN, —NO$_2$, C$_{1-5}$ alkyl, and C$_{1-5}$ alkoxy.

The heteroatoms of the heteroaryl radical can preferably be selected from the group consisting of oxygen, nitrogen, and sulfur. Preferably, the heteroaryl radicals can have 1, 2, 3, 4, or 5 heteroatom(s) independently selected from the group consisting of oxygen, nitrogen, and sulfur as ring member(s). Preferably, the heteroaryl radicals can have 1, 2, 3, 4, or 5 heteroatoms independently selected from the group consisting of oxygen, nitrogen, and sulfur, as ring member(s).

Suitable aryl radicals can preferably be selected from the group consisting of phenyl, 1-naphthyl, and 2-naphthyl.

Suitable heteroaryl radicals can preferably be selected from the group consisting of pyrrolyl, indolyl, furyl (furanyl), benzofuranyl, thienyl (thiophenyl), benzothienyl, pyrazolyl, imidazolyl, thiazolyl, thiadiazolyl, triazolyl, oxazolyl, isoxazolyl, pyridynyl, pyridazynyl, pyrimidynyl, pyrazynyl, pyranyl, indazolyl, purynyl, indolizynyl, quinolynyl, isoquinolynyl, quinazolynyl, carbazolyl, phenazynyl, phenothiazynyl and oxadiazolyl, benzo[1.3]dioxolyl, benzo[1,2,5]oxadiazolyl, and chromanyl, and isoindolyl.

For the purposes of the present invention, a monocyclic ring system is taken to mean a monocyclic hydrocarbon group, which can be saturated, unsaturated, or aromatic and optionally have one or more heteroatoms as ring members. Such a monocyclic ring system can, for example, be condensed, ie anellated, or bonded with an aryl radical or a heteroaryl radical. The heteroatoms of such a monocyclic ring system can in each case be preferably selected from the group consisting of oxygen, nitrogen, and sulfur. Preferably, the ring of the ring system can exhibit 1, 2, 3, 4, or 5 heteroatoms independently selected from the group consisting of oxygen, nitrogen, and sulfur, as ring member(s).

Preferably, the ring of the ring system is five-membered, six-membered, or seven-membered. The ring system can be monosubstituted or polysubstituted and is preferably substituted by 1, 2, 3, 4, or 5 substituents, and the substituents can be preferably selected from the group consisting of F, Cl, Br, I, —CN, —NO$_2$, oxo, C$_{1-5}$ alkyl, C$_{1-5}$ alkoxy, C$_{1-5}$ perfluoroalkoxy, —C(=O)—C$_{1-5}$ alkyl, —C(=O)—O—C$_{1-5}$ alkyl, —S(=O)$_{1-6}$ alkyl, —C(=O)—C$_{1-5}$ perfluoroalkyl, —CF$_3$, CHF$_2$, CH$_2$F, and —NR$^a$R$^b$ in which R$^a$ and R$^b$ can be independently selected from the group consisting of H, methyl, ethyl, n-propyl, isopropyl, and unsubstituted phenyl, thioxo (=S), —SF$_5$, —OH, —O—C$_{2-5}$ alkenyl, —NH$_2$, —NO$_2$, —O—CF$_3$, —O—CHF$_2$, —O—CH$_2$F, —S—CF$_3$, —S—CHF$_2$, —S—CH$_2$F, —SH, —S—C$_{1-5}$ alkyl, —C(=O)—OH, —O—C(=O)—C$_{1-5}$ alkyl, —O—C(=O)-phenyl, —(CH$_2$)—O—C(=O)—C$_{1-5}$ alkyl, —(CH$_2$)—O—C(=O)-phenyl, —NH—C$_{1-5}$ alkyl, —N(C$_{1-5}$ alkyl)$_2$, —NH—C(=O)—O—C$_{1-5}$ alkyl, —NH—C(=O)—C$_{1-5}$ alkyl, —C(=O)—H, —C(=O)—NH$_2$, —C(=O)—NH—C$_{1-5}$ alkyl, C(=O)—N—(C$_{1-5}$ alkyl)$_2$, —S(=O)$_2$—NH$_2$, —S(=O)$_2$—NH—C$_{1-5}$ alkyl, —S(=O)$_2$—NH-phenyl, —(CH$_2$)-benzo[b]furanyl, —O-phenyl, —S-phenyl, —S-benzyl, —O-benzyl, phenyl, and benzyl, and in each case the cyclic moiety of the radicals —O—C(=O)-phenyl, —(CH$_2$)—O—C(=O)-phenyl, —S(=O)$_2$—NH-phenyl, —O-phenyl, —S-phenyl, —S-benzyl, —O-benzyl, phenyl, —(CH$_2$)—benzo[b]furanyl, and benzyl can be substituted by 1, 2, 3, 4, or 5 substituents independently selected from the group consisting of F, Cl, Br, —OH, —CF$_3$, —SF$_5$, —CN, —NO$_2$, —O—C$_{1-5}$ alkyl, —C$_{1-5}$ alkyl, —O—CF$_3$, —S—CF$_3$, phenyl, and —O-benzyl.

If one of the radicals R$^1$ to R$^4$ has a linear or branched alkylene group, alkenylene group, or alkynylene group, these groups can—unless otherwise stated—be unsubstituted or monosubstituted or polysubstituted, and are preferably substituted by 1, 2, 3, 4, or 5 substituents, and the substituents can be independently selected preferably from the group consisting of F, Cl, Br, C$_{1-6}$ alkoxy, hydroxy, CN, CF$_3$, CHF$_2$, CH$_2$F, unsubstituted phenyl and —NR$^a$R$^b$, in which R$^a$ and R$^b$ can be independently selected from the group consisting of H, C$_{1-3}$ alkyl, and unsubstituted phenyl. The alkylene group may alternatively have one or more heteroatoms, preferably at least one oxygen atom and/or at least one sulfur atom, and more preferably 1 or 2 oxygen atom(s) and/or sulfur atom(s), as link(s). An alkenylene group has at least one carbon-carbon double bond, an alkynylene group at least one carbon-carbon triple bond.

The respective alkylene groups, alkenylene groups or alkynylene groups can—unless otherwise stated—alternatively have one or more heteroatoms preferably one or more, for example, 1 or 2, oxygen atoms and/or one or more, for example, 1 or 2, sulfur atoms, as link(s).

Examples which may be mentioned are alkylene groups such as —(CH$_2$)—, —(CH(CH$_3$))—, —(CH$_2$)$_2$—, —(CH$_2$)$_2$—O—, —(CH$_2$)$_3$—, —(CH$_2$)$_4$—, —(CH$_2$)$_5$—, —(CH$_2$)$_6$—, —(CH$_2$)$_7$—, —(CH$_2$)$_8$—, —(CH$_2$)$_9$—, and —(CH$_2$)$_{10}$—, alkenylene groups, such as —CH=CH and alkynylene groups such as —C≡C—.

Preference is given to substituted 1,4,8-triazaspiro[4,5]decan-2-one compounds of the above general formula I, in which R$^1$ stands for a hydrogen radical, or for a linear or branched unsubstituted, C$_{1-10}$ alkyl radical optionally comprising at least one heteroatom as link, or for a linear or branched unsubstituted or at least monosubstituted C$_{2-10}$ alkenyl radical optionally comprising at least one heteroatom as link, or for a linear or branched unsubstituted or at least monosubstituted C$_{2-10}$ alkynyl radical optionally comprising at least one heteroatom as link, or for an unsubstituted or at least monosubstituted five-membered to fourteen-membered aryl radical or heteroaryl radical, which is bonded via a linear or branched C$_{1-5}$ alkylene group optionally comprising at least one heteroatom as link, or for a —C(=O)—OR$^5$ radical bonded via a linear or branched $C_{1-5}$ alkylene group, or for a —O—C(═O)—$R^6$ radical bonded via a linear or branched $C_{1-5}$ alkylene group, preferably for a hydrogen radical, or for a linear or branched, unsubstituted $C_{1-5}$ alkyl radical, or for a linear or branched, unsubstituted $C_{2-5}$ alkenyl radical, or for a linear or branched, unsubstituted $C_{2-5}$ alkynyl radical, or for an unsubstituted or at least monosubstituted phenyl or naphthyl radical bonded via a linear or branched $C_{1-5}$ alkylene group, comprising one or more oxygen atoms as links, or for a —C(═O)—$OR^5$ radical bonded via a linear or branched $C_{1-4}$ alkylene group or for a —O—C(═O)—$R^6$ radical bonded via a linear or branched $C_{1-4}$ alkylene group, more preferably for a hydrogen radical, or for a linear or branched unsubstituted $C_{1-4}$ alkyl radical, or for a linear or branched unsubstituted $C_{2-5}$ alkenyl radical, or for a linear or branched unsubstituted $C_{2-3}$ alkynyl radical, or for a phenyl or naphthyl radical, which is bonded via a —(CH$_2$) bridge, —(CH$_2$)$_2$ bridge, —(CH$_2$)$_3$ bridge or —(CH$_2$)$_2$—O— bridge and is optionally monosubstituted or polysubstituted by the same or different substituents selected from the group consisting of F, Cl, Br, CN, NO$_2$, $C_{1-5}$ alkyl, $C_{1-5}$ alkoxy, —C(═O)—$C_{1-5}$ alkyl, —C(═O)—O—$C_{1-5}$ alkyl, —S(═O)$_{1-6}$ alkyl, —C(═O)—$C_{1-5}$ perfluoroalkyl, —CF$_3$, CHF$_2$, and CH$_2$F, or for a —C(═O)—$OR^5$ radical bonded via a —(CH$_2$) group or for a —O—C(═O)—$R^6$ radical bonded via a —(CH$_2$) group, —(CH$_2$)$_2$ group, —(CH$_2$)$_3$ group or —(CH$_2$)$_4$ group, and in each case the remaining radicals $R^2$-$R^9$ have the meanings stated above, in each case optionally in the form of one of the pure stereoisomers thereof particularly enantiomers or diastereoisomers, the racemates thereof or in the form of a mixture of stereoisomers, particularly the enantiomers and/or diastereoisomers, in an arbitrary blending ratio, or in each case in the form of appropriate salts, or in each case in the form of appropriate solvates.

Also preferred are substituted 1,4,8-triazaspiro[4,5]decan-2-one compounds of the above general formula 1, in which $R^2$ stands for a hydrogen radical, or for a linear or branched unsubstituted or at least monosubstituted $C_{1-10}$ alkyl radical optionally comprising at least one heteroatom as link, or for a linear or branched unsubstituted or at least monosubstituted $C_{2-10}$ alkenyl radical optionally comprising at least one heteroatom as link, or for a linear or branched unsubstituted or at least monosubstituted $C_{2-10}$ alkynyl radical optionally comprising at least one heteroatom as link, or for an unsubstituted or at least monosubstituted, five bis fourteen-membered aryl radical or heteroaryl radical, which can be bonded via a linear or branched $C_{1-5}$ alkylene group optionally comprising at least one heteroatom as link, preferably for a hydrogen radical, or for a linear or branched, unsubstituted $C_{1-5}$ alkyl radical, optionally comprising one or more oxygen atoms and/or one or more sulfur atoms as link(s) or for a phenyl or naphthyl radical which is monosubstituted or polysubstituted by the same or different substituents selected from the group consisting of F, Cl, Br, CN, NO$_2$, $C_{1-5}$ alkyl, $C_{1-5}$ alkoxy, —C(═O)—$C_{1-5}$ alkyl, —C(═O)—O—$C_{1-5}$ alkyl, —S(═O)$_2$—$C_{1-6}$ alkyl, —C(═O)—$C_{1-5}$ perfluoroalkyl, —CF$_3$, CHF$_2$, and CH$_2$F and/or can be bonded via a —(CH$_2$)— bridge, a —(CH$_2$)$_2$— bridge, a —(CH$_2$)$_3$— bridge, or a —(CH$_2$)$_2$—O— bridge, more preferably for a hydrogen radical, or for a linear or branched unsubstituted $C_{1-5}$ alkyl radical optionally comprising one or more sulfur atoms as links or for a phenyl radical, and the phenyl radical is monosubstituted or polysubstituted by the same or different substituents selected from the group consisting of F, Cl, Br, CN, NO$_2$, $C_{1-5}$ alkyl, $C_{1-5}$ alkoxy, —C(═O)—$C_{1-5}$ alkyl, —C(═O)—O—$C_{1-5}$ alkyl, —S(═O)$_{1-6}$ alkyl, —C(═O)—$C_{1-5}$ perfluoroalkyl, —CF$_3$, CHF$_2$, and CH$_2$F and/or can be bonded via a —(CH$_2$)— bridge, and each of the remaining radicals $R^1$ and $R^3$ to $R^9$ has the meanings stated above, in each case optionally in the form of one of the pure stereoisomers thereof particularly enantiomers or diastereoisomers, the racemates thereof or in the form of a mixture of stereoisomers, particularly the enantiomers and/or diastereoisomers, in an arbitrary blending ratio, or in each case in the form of appropriate salts, or in each case in the form of appropriate solvates.

Furthermore, substituted 1,4,8-triazaspiro[4,5]decan-2-one compounds of the above general formula are preferred in which $R^3$ stands for a hydrogen radical, or for a linear or branched unsubstituted or at least monosubstituted $C_{1-10}$ alkyl radical optionally comprising at least one heteroatom as link, or for a linear or branched unsubstituted or at least monosubstituted $C_{2-10}$ alkenyl radical optionally comprising at least one heteroatom as link, or for a linear or branched unsubstituted or at least monosubstituted $C_{2-10}$ alkynyl radical optionally comprising at least one heteroatom as link, or for an unsubstituted or at least monosubstituted five-membered to fourteen-membered aryl radical or heteroaryl radical, which is bonded via a linear or branched unsubstituted or at least monosubstituted $C_{1-5}$ alkylene group optionally comprising at least one heteroatom as link and optionally condensed with an unsubstituted or at least monosubstituted monocyclic ring system, or for an unsubstituted or at least monosubstituted $C_{3-8}$ cycloaliphatic radical, optionally comprising at least one heteroatom as ring member and which can be bonded via a linear or branched unsubstituted or at least monosubstituted $C_{1-5}$ alkylene group optionally comprising at least one heteroatom as link and/or can be condensed with an unsubstituted or at least monosubstituted monocyclic ring system, or for a —C(═O)—$R^4$ group, preferably for a hydrogen radical, or for a biphenyl radical, which is bonded via a —(CH$_2$)— bridge, a —(CH$_2$)$_2$— bridge, or a —(CH$_2$)$_3$— bridge, or for a C(═O)—$R^4$ group, and more preferably for a —C(═O)—$R^4$ group, and each of the remaining $R^1$, $R^2$, and $R^4$ to $R^9$ has the meanings stated above, in each case optionally in the form of one of the pure stereoisomers thereof particularly enantiomers or diastereoisomers thereof, the racemates thereof or in the form of a mixture of stereoisomers, particularly the enantiomers and/or diastereoisomers, in an arbitrary blending ratio, or in each case in the form of appropriate salts, or in each case in the form of appropriate solvates.

Preference is also given to such substituted 1,4,8-triazaspiro[4,5]decan-2-one compounds of the above general formula I in which the radical $R^4$ stands for a linear or branched unsubstituted or at least monosubstituted $C_{1-10}$ alkyl radical optionally comprising at least one heteroatom as link, or for a linear or branched unsubstituted or at least monosubstituted $C_{2-10}$ alkenyl radical optionally comprising at least one heteroatom as link, or for a linear or branched unsubstituted or at least monosubstituted $C_{2-10}$ alkynyl radical optionally comprising at least one heteroatom as link, or for an unsubstituted or at least monosubstituted five-membered to fourteen-membered aryl radical or heteroaryl radical, which can be bonded via a linear or branched unsubstituted or at least monosubstituted $C_{1-5}$-alkylene group, $C_{2-5}$-alkenylene group, or $C_{2-5}$-alkynylene group optionally comprising at least one heteroatom as link and/or condensed with an unsubstituted or at least monosubstituted monocyclic ring system, or for an unsubstituted or at least monosubstituted $C_{3-8}$ cycloaliphatic radical optionally comprising at least one heteroatom as ring member and optionally bonded via a linear or branched unsubstituted or at least monosubstituted $C_{1-6}$ alkylene group optionally comprising at least one heteroatom as link, which can be at least singly bridged by a linear or branched unsubstituted or at least monosubstituted $C_{1-6}$ alkylene group and/or condensed with an unsubstituted or at least monosubstituted monocyclic ring system, or for a —C(=O)—OR$^7$ radical bonded via a linear or branched unsubstituted or at least monosubstituted $C_{1-5}$ alkylene group, or for an —O—(C=O)—R$^8$ radical bonded via a linear or branched unsubstituted or at least monosubstituted $C_{1-5}$ alkylene group or for a —(C=O)—R$^9$ radical bonded via a linear or branched unsubstituted or at least monosubstituted $C_{1-5}$ alkylene group, preferably for a linear or branched $C_{1-10}$-alkyl radical optionally comprising one or more oxygen atoms and/or one or more sulfur atoms as link(s), which can be unsubstituted or at least monosubstituted by the same or different substituents selected from the group consisting of phenyl, di-($C_{1-5}$-alkylamino), carboxy, and —NH—(C=O)—O—$C_{1-5}$ alkyl, or for a linear or branched $C_{2-5}$ alkyl radical, or for a phenyl radical, naphthyl radical, furyl (furanyl) radical, thienyl (thiophenyl) radical or 1,2,3-triazolyl radical, benzo[1.3]dioxolyl radical, benzo[1,2,5]oxadiazoleyl radical, chromanyl radical, pyrimidynyl radical, pyrazolyl radical, pyridynyl radical, isoxazolyl radical, or 1,2,3-thiadiazolyl radical, and in each case the cyclic radical can be bonded via over a —(CH$_2$)—, —(CH$_2$)—O— bridge, a —CH=CH— bridge, a —(CH$_2$)$_2$— bridge, a —(CH$_2$)$_2$—O— bridge or a —(CH$_2$)$_3$— bridge and/or can be monosubstituted or polysubstituted by the same or different substituents selected from the group consisting of F, Cl, Br, I, —CN, —NO$_2$, $C_{1-5}$ alkyl, $C_{1-5}$ alkoxy, $C_{1-5}$ perfluoroalkoxy, —C(=O)—$C_{1-5}$ alkyl, —C(=O)—O—$C_{1-5}$ alkyl, —(CH$_2$)$_{1-3}$—O—C(=O)-phenyl, —N(CH$_3$)$_2$, —S(=O)$_{1-6}$ alkyl, —S(=O)$_2$—NH$_2$, —C(=O)—$C_{1-5}$ perfluoroalkyl, —S—$C_{1-5}$ alkyl, —S—CH$_2$F, —S—CHF$_2$, —SCF$_3$, —CF$_3$, —NH—(C=O)—CH$_3$, —SO$_2$—NH$_2$, —CHF$_2$, —CH$_2$F, phenyl, and phenoxy, and the latter phenyl and phenoxy substituents themselves can be monosubstituted or polysubstituted by the same or different substituents selected from the group consisting of F, Cl, Br, —S—CHF$_2$, —CF$_3$, —CHF$_2$, —CH$_2$F, CN, NO$_2$, $C_{1-5}$ alkyl, and $C_{1-5}$ alkoxy, or for a three-membered, four-membered, five-membered, six-membered, seven-member, or eight-membered cycloaliphatic radical optionally comprising at least one heteroatom as ring member and optionally bonded via a —(CH$_2$)— bridge, a —(CH$_2$)$_2$— bridge, or a —(CH$_2$)$_3$— bridge, which is at least singly bridged at least by one —(C(CH$_3$)$_2$)— or —(CH$_2$) group and/or monosubstituted or polysubstituted by the same or different substituents selected from the group consisting of $C_{1-5}$ alkyl, $C_{1-5}$ alkoxy, —CF$_3$, CHF$_2$, CH$_2$F, and oxo, or for a —C(=O)—OR$^7$ radical bonded via a linear or branched unsubstituted or at least monosubstituted $C_{1-5}$ alkylene group, or for a —O—(C=O)—R$^8$ radical bonded via a linear or branched unsubstituted or at least monosubstituted $C_{1-5}$ alkylene group, or for a —(C=O)—R$^9$ radical bonded via a linear or branched unsubstituted or at least monosubstituted $C_{1-5}$ alkylene group, more preferably for a linear or branched $C_{1-8}$-alkyl radical optionally comprising one or more oxygen atoms and/or one or more sulfur atoms as links, which can be unsubstituted or at least monosubstituted or polysubstituted by the same or different substituents selected from the group consisting of unsubstituted phenyl, dimethylamino, carboxy, and —NH—(C=O)—O—C(CH$_3$)$_3$, or for a linear or branched unsubstituted $C_{2-4}$ alkenyl radical, or for a phenyl radical, naphthyl radical, furyl (furanyl) radical, thienyl (thiophenyl) radical, 1,2,3-triazolyl radical, chromanyl radical, benzo[1.3]dioxolyl radical, benzo[1,2,5]oxadiazoleyl radical, pyrimidynyl radical, pyrazolyl radical, pyridynyl radical, isoxazolyl radical, or 1,2,3-thiadiazolyl radical, and the cyclic radical can in each case be bonded via a —(CH$_2$)— bridge, a —(CH$_2$)—O— bridge, a —CH=CH— bridge, a —(CH$_2$)$_2$— bridge, a —(CH$_2$)$_2$—O— bridge, or a —(CH$_2$)$_3$— bridge and/or monosubstituted or polysubstituted by the same or different substituents selected from the group consisting of F, Cl, Br, I, methyl, ethyl, isopropyl, n-propyl, sec-butyl, tert-butyl, n-butyl, methoxy, ethoxy, —CF$_3$, —OCF$_3$, —CH$_2$—O—C(=O)-phenyl, NO$_2$, —S—CF$_3$, —S—CHF$_2$, —N(CH$_3$)$_2$, —NH—CO—CH$_3$, CN, SO$_2$—NH$_2$, phenyl, and phenoxy and the latter phenyl and phenoxy substituents themselves can be monosubstituted or polysubstituted by the same or different substituents selected from the group consisting of F, Cl, Br, CH$_3$, and OCH$_3$, or for a 4,7,7-trimethyl-3-oxo-2-oxa-bicyclo[2.2.1]heptyl radical or adamantyl radical optionally bonded via a —(CH$_2$)— bridge, a —(CH$_2$)$_2$— bridge, or a —(CH$_2$)$_3$— bridge cyclopropyl, cyclobutyl, cyclopentyl, cyclohexyl, imidazolidine, and which is unsubstituted or monosubstituted or polysubstituted by the same or different substituents selected from the group consisting of $C_{1-5}$ alkyl, $C_{1-5}$ alkoxy, —CF$_3$, CHF$_2$, CH$_2$F, and oxo, or for a —C(=O)—OR$^7$ radical bonded via a —(CH$_2$)— group, a —(CH$_2$)$_2$ group, a —C(H)-phenyl group, or a —C(CH$_3$)$_2$ group, or for a —O—(C=O)—R$^8$ radical bonded via a —(CH$_2$)— group, a —(CH$_2$)$_2$ group, a —C(H)-phenyl group, or a —C(CH$_3$)$_2$ group, or for a —(C=O)—R$^9$ radical bonded via a —(CH$_2$)— group or a —(CH$_2$)$_2$ group, most preferably for a linear or branched $C_{6-8}$ alkyl radical optionally comprising one or more oxygen atoms and/or one or more sulfur atoms as links, which can be unsubstituted or at least monosubstituted or polysubstituted by the same or different substituents selected from the group consisting of unsubstituted phenyl, dimethylamino, carboxy, and —NH—(C=O)—O—C(CH$_3$)$_3$, or for a linear or branched unsubstituted $C_{2-4}$ alkenyl radical, or for a naphthyl radical, furyl (furanyl) radical, thienyl (thiophenyl) radical, [1,2,3]triazolyl radical, chromanyl radical, benzo[1.3]dioxolyl radical, benzo[1,2,5]oxadiazoleyl radical, pyrimidynyl radical, pyrazolyl radical, pyridynyl radical, isoxazolyl radical, or 1,2,3-thiadiazolyl radical, and the cyclic radical can in each case be bonded via a —(CH$_2$)— bridge, a —(CH$_2$)—O— bridge, a —CH=CH— bridge, a —(CH$_2$)$_2$— bridge, a —(CH$_2$)$_2$—O— bridge, or a —(CH$_2$)$_3$ bridge and/or monosubstituted or polysubstituted by the same or different substituents selected from the group consisting of F, Cl, Br, I, methyl, ethyl, isopropyl, n-propyl, sec-butyl, tert-butyl, n-butyl, methoxy, ethoxy, —CF$_3$, —OCF$_3$, —CH$_2$—O—C(=O)-phenyl, —NO$_2$, —S—CF$_3$, —S—CHF$_2$, —N(CH$_3$)$_2$, —NH—CO—CH$_3$, —CN, —SO$_2$—NH$_2$, phenyl, and phenoxy and the latter phenyl and phenoxy substituents themselves can be monosubstituted or polysubstituted by the same or different substituents selected from the group consisting of F, Cl, Br, CH$_3$, and OCH$_3$, or for 2-trifluoromethoxy-phenyl, 3-trifluoromethoxy-phenyl, 4-trifluoromethoxy-phenyl, 2-CF$_3$—S-phenyl, 3-CF$_3$—S-phenyl, 4-CF$_3$—S-phenyl, 2-cyanophenyl, 3-cyanophenyl, 4-cyanophenyl, 2-nitrophenyl, 3-nitrophenyl, 4-nitrophenyl, 2-CHF$_2$—S-phenyl, 3-CHF$_2$—S-phenyl, 4-CHF$_2$—S-phenyl, 2-dimethylamino-phenyl, 3-dimethylamino-phenyl, 4-dimethylamino-phenyl, 2-phenyl-(C=O)—O—CH$_2$-phenyl, 3-phenyl-(C=O)—O—CH$_2$-phenyl, 4-phenyl-(C=O)—O—CH$_2$-phenyl, 2-CH$_3$—(C=O)—NH-phenyl, 3-CH$_3$—(C=O)—NH-phenyl, 4-CH$_3$—(C=O)—NH-phenyl, 2-phenylphenyl, 3-phenylphenyl, 4-phenylphenyl, 2-NH$_2$—SO$_2$-phenyl, 3-NH$_2$—SO$_2$-phenyl, 4-NH$_2$—SO$_2$-phenyl, pentafluorophenyl, 4-methyl-3-nitrophenyl, 2-fluorobenzyl, 3-fluorobenzyl, 4-fluorobenzyl, 2-chlorobenzyl, 3-chlorobenzyl, 4-chlorobenzyl, 2-bromobenzyl, 3-bromobenzyl, 4-bromobenzyl, 2-methylbenzyl, 3-methylbenzyl, 4-methylbenzyl, 2-methoxybenzyl, 3-methoxybenzyl, 4-methoxybenzyl, 3,4-dimethoxybenzyl, 2,5-dimethoxybenzyl, —CH=CH-phenyl, wherein the phenyl radical can be monosubstituted or polysubstituted in the 2, 3, or 4 position by the same or different radicals selected from the group consisting of F, Cl, Br, and CF$_3$, or —CH$_2$—O-phenyl, wherein the phenyl radical can be monosubstituted or polysubstituted in the 2, 3, or 4 position by the same or different radicals selected from the group consisting of F, Cl, Br, and CF$_3$ or for a 4,7,7-trimethyl-3-oxo-2-oxa-bicyclo[2.2.1]heptyl radical or adamantyl radical optionally bonded via a —(CH$_2$)— bridge, a —(CH$_2$)$_2$— bridge, or a —(CH$_2$)$_3$— bridge cyclopropyl, cyclobutyl, cyclopentyl, cyclohexyl, imidazolidine, and which is unsubstituted or monosubstituted or polysubstituted by the same or different substituents selected from the group consisting of C$_{1-5}$ alkyl, C$_{1-5}$ alkoxy, —CF$_3$, CHF$_2$, CH$_2$F, and oxo, or for a —C(=O)—OR$^7$ radical bonded via a —(CH$_2$)— group, a —(CH$_2$)$_2$ group, a —C(H)-phenyl group, or a —C(CH$_3$)$_2$ group, or for a —O—(C=O)—R$^8$ radical bonded via a —(CH$_2$)— group, a —(CH$_2$)$_2$ group, a —C(H)-phenyl group, or a —C(CH$_3$)$_2$ group, or for a —(C=O)—R$^9$ radical bonded via a —(CH$_2$)— group or a —(CH$_2$)$_2$ group, while the remaining radicals R$^1$ to R$^3$ and R$^5$ to R$^9$ have the meanings stated above, in each case optionally in the form of one of the pure stereoisomers thereof particularly enantiomers or diastereoisomers thereof, the racemates thereof or in the form of a mixture of stereoisomers, particularly the enantiomers and/or diastereoisomers, in an arbitrary blending ratio, or in each case in the form of appropriate salts, or in each case in the form of appropriate solvates.

Preference is also given to substituted 1,4,8-triazaspiro[4,5]decan-2-one compounds of the above general formula I, in which the radicals R$^5$ and R$^6$ independently stand for a linear or branched C$_{1-5}$-alkyl radical, a linear or branched C$_{2-5}$ alkenyl radical or a linear or branched C$_{2-5}$ alkynyl radical and preferably for a methyl radical, ethyl radical, n-propyl radical, or isopropyl radical and in each case the remaining radicals R$^1$-R$^4$ and R$^7$-R$^9$ have the meanings stated above, in each case optionally in the form of one of the pure stereoisomers thereof particularly enantiomers or diastereoisomers, the racemates thereof or in the form of a mixture of stereoisomers, particularly the enantiomers and/or diastereoisomers thereof, in an arbitrary blending ratio, or in each case in the form of appropriate salts, or in each case in the form of appropriate solvates.

Preference is also given to substituted 1,4,8-triazaspiro[4,5]decan-2-one compounds of the above general formula I in which the radicals R$^7$ and R$^8$ independently stand for a hydrogen radical, or for a linear or branched C$_{1-5}$-alkyl radical, a linear or branched C$_{2-5}$ alkenyl radical, a linear or branched C$_{2-5}$ alkynyl radical, or for an optionally at least monosubstituted phenyl or naphthyl radical, preferably for a methyl radical, ethyl radical, n-propyl radical, or isopropyl radical, or an unsubstituted phenyl radical, while each of the remaining radicals R$^1$ to R$^6$ and R$^9$ has the meanings stated above, in each case optionally in the form of one of the pure stereoisomers thereof particularly enantiomers or diastereoisomers thereof, the racemates thereof or in the form of a mixture of stereoisomers, particularly the enantiomers and/or diastereoisomers thereof, in an arbitrary blending ratio, or in each case in the form of appropriate salts, or in each case in the form of appropriate solvates.

Preference is further given to substituted 1,4,8-triazaspiro[4,5]decan-2-one compounds of the above general formula I in which the radical R$^9$ stands for a linear or branched C$_{1-5}$-alkyl radical, a linear or branched C$_{2-5}$ alkenyl radical, a linear or branched C$_{2-5}$ alkynyl radical, preferably for a methyl radical, ethyl radical, n-propyl radical, or isopropyl radical, while each of the remaining radicals R$^1$ to R$^8$ has the meanings stated above, in each case optionally in the form of one of the pure stereoisomers thereof particularly enantiomers or diastereoisomers thereof, the racemates thereof or in the form of a mixture of stereoisomers, particularly the enantiomers and/or diastereoisomers thereof, in an arbitrary blending ratio, or in each case in the form of appropriate salts, or in each case in the form of appropriate solvates.

Special preference is given to substituted 1,4,8-triazaspiro[4,5]decan-2-one compounds of the above general formula I

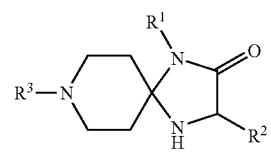

in which

R$^1$ stands for a hydrogen radical, or for a linear or branched unsubstituted C$_{1-4}$-alkyl radical, or for a linear or branched unsubstituted C$_{2-5}$ alkenyl radical, or for a linear or branched unsubstituted $C_{2-3}$ alkynyl radical, or for a phenyl or naphthyl radical, which is unsubstituted or monosubstituted or polysubstituted by the same or different substituents selected from the group consisting of F, Cl, Br, —CN, —NO$_2$, $C_{1-5}$ alkyl, $C_{1-5}$ alkoxy, —C(=O)—$C_{1-5}$ alkyl, —C(=O)—O—$C_{1-5}$ alkyl, —S(=O)$_{1-6}$ alkyl, —C(=O)—$C_{1-5}$ perfluoroalkyl, —CF$_3$, —CHF$_2$, and —CH$_2$F and/or bonded via a —(CH$_2$)— bridge, a —(CH$_2$)$_2$— bridge, a —(CH$_2$)$_3$— bridge or a —(CH$_2$)$_2$—O— bridge, or for a —C(=O)—OR$^5$ radical bonded via a —(CH$_2$) group or stands for a —O—C(=O)—R$^6$ radical bonded via a —(CH$_2$) group, a —(CH$_2$)$_2$ group, a —(CH$_2$)$_3$ group or a —(CH$_2$)$_4$ group, $R^2$ stands for a hydrogen radical, or for a linear or branched unsubstituted $C_{1-5}$-alkyl radical optionally comprising one or more sulfur atoms as link(s) or for a phenyl radical, wherein the phenyl radical can be monosubstituted or polysubstituted by the same or different substituents selected from the group consisting of F, Cl, Br, —CN, —NO$_2$, $C_{1-5}$ alkyl, $C_{1-5}$ alkoxy, —C(=O)—$C_{1-5}$ alkyl, —C(=O)—O—$C_{1-5}$ alkyl, —S(=O)$_{1-6}$ alkyl, —C(=O)—$C_{1-5}$ perfluoroalkyl, —CF$_3$, CHF$_2$, and CH$_2$F, and/or can be bonded via a —(CH$_2$)— bridge, $R^3$ stands for a hydrogen radical, or for a biphenyl radical, which is bonded via a —(CH$_2$)— bridge, a —(CH$_2$)$_2$— bridge, or a —(CH$_2$)$_3$— bridge, or for a C(=O)—R$^4$ group, $R^4$ stands for a radical, which is selected from the group consisting of methyl, ethyl, isopropyl, n-propyl, sec-butyl, isobutyl, tert-butyl, n-butyl, n-pentyl, 1-methylbutyl, 2-dimethylpropyl, 1-ethylpropyl, 1-propylbutyl, 1-ethylpentyl, dimethylaminomethyl, —CH$_2$H$_2$-H=CH$_2$, —CH$_2$—O—CH$_3$, —CH$_2$—O—CH$_2$H$_2$—O—CH$_3$, —CH$_2$H$_2$-phenyl, —CH$_2$—O-phenyl, —CH$_2$—O—CH$_2$-phenyl, —CH$_2$H$_2$H$_2$—O-phenyl, —C(H)-(phenyl)-(C$_2$H$_5$), —C(H)—(CH$_3$)—O-phenyl, —CH$_2$H$_2$—(C=O)—CH$_3$, —CH$_2$—O—(C=O)—CH$_3$, —CH$_2$H$_2$—(C=O)—O—C$_2$H$_5$, —CH$_2$—O—(C=O)-phenyl, —CH$_2$—(C=O)—O—CH$_2$H$_3$, —C(H)-(phenyl)-(C=O)—CH$_3$, —C(H)-(phenyl)-O—(C=O)—CH$_3$, —C(CH$_3$)$_2$—O—(C=O)—CH$_3$, —C(H)—(NH—(C=O)—O—(CH$_3$)$_3$)—(CH$_2$—O—CH$_2$-phenyl), —C(CH$_3$)$_2$H$_2$OH, unsubstituted phenyl, 2-fluorophenyl, 3-fluorophenyl, 4-fluorophenyl, 2-chlorophenyl, 3-chlorophenyl, 4-chlorophenyl, 2-bromophenyl, 3-bromophenyl, 4-bromophenyl, 2-iodophenyl, 3-iodophenyl, 4-iodophenyl, 2-methylphenyl, 3-methylphenyl, 4-methylphenyl, 2-ethylphenyl, 3-ethylphenyl, 4-ethylphenyl, 2-n-propylphenyl, 3-n-propylphenyl, 4-n-propylphenyl, 2-tert-butylphenyl, 3-tert-butylphenyl, 4-tert-butylphenyl, 2-methoxyphenyl, 3-methoxyphenyl, 4-methoxyphenyl, 2-ethoxyphenyl, 3-ethoxyphenyl, 4-ethoxyphenyl, 2-trifluoromethylphenyl, 3 trifluoromethylphenyl, 4-trifluoromethylphenyl, 2-trifluoromethoxyphenyl, 3-trifluoromethoxyphenyl, 4-trifluoromethoxyphenyl, 2-CF$_3$—S-phenyl, 3-CF$_3$—S-phenyl, 4-CF$_3$—S-phenyl, 2-cyanophenyl, 3-cyanophenyl, 4-cyanophenyl, 2-nitrophenyl, 3-nitrophenyl, 4-nitrophenyl, 2-CHF$_2$—S-phenyl, 3-CHF$_2$—S-phenyl, 4-CHF$_2$—S-phenyl, 2-dimethylaminophenyl, 3-dimethylaminophenyl, 4-dimethylaminophenyl, 2-phenyl-(C=O)—O—CH$_2$-phenyl, 3-phenyl-(C=O)—O—CH$_2$-phenyl, 4-phenyl-(C=O)—O—CH$_2$-phenyl, 2-CH$_3$—(C=O)—NH-phenyl, 3-CH$_3$—(C=O)—NH-phenyl, 4-CH$_3$—(C=O)—NH-phenyl, 2-phenylphenyl, 3-phenylphenyl, 4-phenylphenyl, 2-NH$_2$—SO$_2$-phenyl, 3-NH$_2$—SO$_2$-phenyl, 4-NH$_2$—SO$_2$-phenyl, 2,4-dimethoxyphenyl, 2,5-dimethoxyphenyl, 3,5-dimethoxyphenyl, 3,4-dimethoxyphenyl, 2,3-dimethylphenyl, 2,3-dichlorophenyl, 3,4-dichlorophenyl, 2,6-dichlorophenyl, 2,3-difluorophenyl, 3,4-difluorophenyl, 3,5-difluorophenyl, pentafluorophenyl, 2-chloro-6-fluorophenyl, 4-bromo-3-methylphenyl, 3-fluoro-4-methylphenyl, 3-chloro-2-fluorophenyl, 2-chloro-4-nitrophenyl, 5-fluoro-2-trifluoromethylphenyl, 3-fluoro-4-trifluoromethyl, 4-methyl-3-nitrophenyl, 2-chloro-5-trifluoromethyl, 2,5-bis-trifluoromethylphenyl, 3,5-bis-trifluoromethylphenyl, 2-chloro-6-fluoro-3-methylphenyl, 6-chloro-2-fluoro-3-methylphenyl, 2,6-difluoro-4-methylphenyl, 2,6-difluoro-3-methylphenyl, 3,4,5-trimethoxyphenyl, 2,3-difluoro-4-methylphenyl, 2-fluorobenzyl, 3-fluorobenzyl, 4-fluorobenzyl, 2-chlorobenzyl, 3-chlorobenzyl, 4-chlorobenzyl, 2-bromobenzyl, 3-bromobenzyl, 4-bromobenzyl, 2-methylbenzyl, 3-methylbenzyl, 4-methylbenzyl, 2-methoxybenzyl, 3-methoxybenzyl, 4-methoxybenzyl, 3,4-dimethoxybenzyl, 2,5-dimethoxybenzyl, —CH=CH-phenyl, wherein the phenyl radical can be monosubstituted or polysubstituted in the 2, 3, or 4 position by the same or different radicals selected from the group consisting of F, Cl, Br, and CF$_3$, —CH$_2$—O-phenyl, wherein the phenyl radical can be monosubstituted or polysubstituted in 2-, 3 or 4 position by the same or different radical selected from the group consisting of F, Cl, Br, and CF$_3$, 1-naphthyl, 2-naphthyl, 2-thienyl, 3-thienyl, 3-chlorothien-2-yl, 2-furanyl, 3-furanyl, 2,5-dimethylfuran-3-yl, 5-tert-butyl-2-methylfuran-3-yl, pyridin-2-yl, pyridin-3-yl, pyridin-4-yl, 2-chloropyridin-4-yl, 6-chloropyridin-3-yl, 2-chloropyridin-3-yl, 2-ethylsulfanylpyridin-3-yl, 2-phenoxypyridin-3-yl, 2-methylsulfanylpyridin-3-yl, 2-methyl-6-trifluoromethylpyridin-3-yl, isoxazol-5-yl, 5-methylisoxazol-3-yl, 3-(2-chloro-6-fluorophenyl)-5-methylisoxazol-4-yl, 3-(2-chlorophenyl)-5-methylisoxazol-4-yl, 3-(2,6-dichlorophenyl)-5-methylisoxazol-4-yl, 5-tert-butyl-2-methyl-2H-pyrazol-3-yl, 1-phenyl-5-n-propyl-1H-pyrazol-4-yl, 1-(4-chlorophenyl)-5-trifluoromethyl-1H-pyrazol-4-yl, 2-tert-butyl-5-methyl-2H-pyrazol-3-yl, 5-methyl-2-phenyl-2H-[1,2,3]triazol-4-yl, 4-methyl[1,2,3]thiadiazol-5-yl, 2-chloro-6-trifluoromethylpyrimidin-5-yl, 2-chloro-4-trifluoromethylpyrimidin-5-yl, benzo[1,2,5]oxadiazol-5-yl, benzo[1.3]dioxol-5-yl, 6-chloro-2H-chroman-3-yl, imidazolidin-2,4-dion-5-ylmethyl, cyclopropyl, cyclobutyl, cyclopentyl optionally bonded via a —(CH$_2$)— bridge or a —(CH$_2$)$_2$ bridge, cyclohexyl, 4,7,7-trimethyl-3-oxo-2-oxa-bicyclo[2.2.1]heptyl, and adamantyl.

Preferably, those compounds of the above formula I are excluded in which

A)

$R^1$ stands for a hydrogen radical, a $C_{1-6}$-alkyl radical, a $C_{1-6}$ alkoxy radical, a $C_{2-6}$ hydroxyalkyl radical, a $C_{2-6}$ alkenyl radical, a $C_{2-6}$ alkynyl radical, a phenyl radical or for a $C_{1-6}$-alkyl radical that is monosubstituted, disubstituted, or trisubstituted by a phenyl radical, $R^2$ stands for a hydrogen radical, a $C_{1-6}$-alkyl radical, a $C_{1-6}$ alkoxy radical, a $C_{2-6}$ hydroxyalkyl radical, a $C_{2-6}$ alkenyl radical, a $C_{2-6}$ alkynyl radical, a phenyl radical, a $C_{1-6}$-alkyl radical monosubstituted disubstituted, or trisubstituted by a phenyl radical, an O—$C_{1-6}$ alkanoyl radical, an OH radical, an O—$C_{1-6}$ alkyl radical, an O—$C_{1-6}$ alkoxy radical, an O—$C_{2-6}$ hydroxyalkyl radical, a —O—$C_{2-6}$ alkenyl radical, an O—$C_{2-6}$ alkynyl radical, an O-phenyl radical or for an O—$C_{1-6}$ alkyl radical that is monosubstituted, disubstituted, or trisubstituted by a phenyl radical, $R^3$ stands for a hydrogen radical, a $C_{1-6}$-alkyl radical, a $C_{2-6}$ alkenyl radical, a $C_{2-6}$ alkynyl radical, a $C_{3-7}$ cycloalkyl radical, a $C_{1-6}$-alkyl radical that is substituted by 1 to 6 halogen atoms, a hydroxy-$C_{1-6}$ alkyl radical, a $C_{1-6}$ alkoxy radical, a $C_{1-6}$ alkylthio radical, a ($C_{1-6}$ alkoxy)-($C_{1-6}$ alkyl) radical, a carboxy-$C_{1-6}$ alkyl radical, a ($C_{1-6}$ alkoxy)-carbonyl-$C_{1-6}$ alkyl radical, an amino-$C_{1-6}$ alkyl radical, a mono($C_{1-6}$ alkyl)-amino radical, a di($C_{1-6}$ alkyl)-amino radical, a 2-oxo-pyrrolidin-1-ylmethyl radical, an aryl radical, a diarylmethylol radical, a $C_{1-6}$-alkyl radical that is substituted by one or two aryl radicals, a $C_{1-6}$ alkanoyl radical, or an arylcarbonyl radical, wherein aryl in each case stands for an unsubstituted phenyl radical or for a phenyl radical which is substituted by 1-3-substituents selected from the group consisting of halogen, $C_{1-6}$ alkyl, $C_{1-6}$ alkoxy, and $CF_3$, and the physiologically compatible salts, enantiomers and racemates thereof, and/or

B)

$R^1$, $R^2$ and $R^3$ each stand for a hydrogen radical or a hydrocarbon radical and the salts thereof.

Very special preference is given to substituted 1,4,8-triazaspiro[4,5]decan-2-one compounds of the above general formula I selected from the group consisting of (1) 3-(S)-Benzyl-8-(2-ethylbutyryl)-1,4,8-triazaspiro[4,5]decan-2-one,
(2) 8-(2,4-Dimethoxybenzoyl)-3-(S)-(2-methylsulfanylethyl)-1,4,8-triazaspiro[4,5]decan-2-one,
(3) 3-(S,R)-Benzyl-8-(2-ethylbutyryl)-1,4,8-triazaspiro[4,5]decan-2-one,
(4) 8-Acetyl-3-(S)-benzyl-1,4,8-triazaspiro[4,5]decan-2-one,
(5) 3-(S,R)-Benzyl-8-(4-chlorobenzoyl)-1,4,8-triazaspiro[4,5]decan-2-one,
(6) 3-(S)-Benzyl-8-(4-chlorobenzoyl)-1,4,8-triazaspiro[4,5]decan-2-one,
(7) 8-(2-ethylbutyryl)-3-(S)-(2-methylsulfanylethyl)-1,4,8-triazaspiro[4,5]decan-2-one,
(8) 1,3-(S)-Dibenzyl-8-(2-ethylbutyryl)-1,4,8-triazaspiro[4,5]decan-2-one,
(9) 8-Acetyl-1,3-(S)-dibenzyl-1,4,8-triazaspiro[4,5]decan-2-one,
(10) 3-(S,R)-Benzyl-8-(4-chlorobenzoyl)-1-(4-methoxybenzyl)-1,4,8-triazaspiro[4,5]decan-2-one,
(11) 3-(S,R)-Benzyl-8-(4-chlorobenzoyl)-1-(4-fluorobenzyl)-1,4,8-triazaspiro[4,5]decan-2-one,
(12) 1,3-(S,R)-Dibenzyl-8-(4-chlorobenzoyl)-1,4,8-triazaspiro[4,5]decan-2one,
(13) 3-(S,R)-Benzyl-8-(2-ethylbutyryl)-1-(4-methoxybenzyl)-1,4,8-triazaspiro[4,5]decan-2-one,
(14) 3-(S,R)-Benzyl-8-(2-ethylbutyryl)-1-(4-fluorobenzyl)-1,4,8-triazaspiro[4,5]decan-2-one,
(15) 1,3-(S,R)-Dibenzyl-8-(2-ethylbutyryl)-1,4,8-triazaspiro[4,5]decan-2-one,
(16) 1-Benzyl-8-(2-ethylbutyryl)-3-(S)-(2-methylsulfanylethyl)-1,4,8-triazaspiro[4,5]decan-2-one,
(17) 1,3-(S)-Dibenzyl-8-(4-chlorobenzoyl)-1,4,8-triazaspiro[4,5]decan-2-one,
(18) 1,3-(S)-Dibenzyl-8-(2-ethylbutyryl)-1,4,8-triazaspiro[4,5]decan-2-one,
(19) 8-Acetyl-1,3-(S)-dibenzyl-1,4,8-triazaspiro[4,5]decan-2-one,
(20) 3-(S,R)-Benzyl-8-(4-chlorobenzoyl)-1-(4-methoxybenzyl)-1,4,8-triazaspiro[4,5]decan-2-one,
(21) 3-(S,R)-Benzyl-8-(4-chlorobenzoyl)-1-(4-fluorobenzyl)-1,4,8-triazaspiro[4,5]decan-2-one,
(22) 1,3-(S,R)-Dibenzyl-8-(4-chlorobenzoyl)-1,4,8-triazaspiro[4,5]decan-2-one,
(23) 3-(S,R)-Benzyl-8-(2-ethylbutyryl)-1-(4-methoxybenzyl)-1,4,8-triazaspiro[4,5]decan-2-one,
(24) 3-(S,R)-Benzyl-8-(2-ethylbutyryl)-1-(4-fluorobenzyl)-1,4,8-triazaspiro[4,5]decan-2-one,
(25) 1,3-(S,R)-Dibenzyl-8-(2-ethylbutyryl)-1,4,8-triazaspiro[4,5]decan-2-one,
(26) 1-Benzyl-8-(2-ethylbutyryl)-3-(S)-(2-methylsulfanylethyl)-1,4,8-triazaspiro[4,5]decan-2-one,
(27) 1,3-(S)-Dibenzyl-8-(4-chlorobenzoyl)-1,4,8-triazaspiro[4,5]decan-2-one,
(28) 1-Benzyl-8-(2,4-dimethoxybenzoyl)-3-(S)-(2-methylsulfanylethyl)-1,4,8-triazaspiro[4,5]decan-2-one,
(29) 1,3-(S)-Dibenzyl-1,4,8-triazaspiro[4,5]decan-2-one,
(30) 1-Benzyl-3-(S)-(2-methylsulfanylethyl)-1,4,8-triazaspiro[4,5]decan-2-one,
(31) 1,3-(S)-Dibenzyl-8-butyryl-1,4,8-triazaspiro[4,5]decan-2-one,
(32) 1,3-(S)-Dibenzyl-8-(3-fluoro-4-trifluoromethylbenzoyl)-1,4,8-triazaspiro[4,5]decan-2-one,
(33) 1,3-(S)-Dibenzyl-8-(2,3-difluorobenzoyl)-1,4,8-triazaspiro[4,5]decan-2-one,
(34) 1,3-(S)-Dibenzyl-8-[2-(4-chlorophenoxy)-acetyl]-1,4,8-triazaspiro[4,5]decan-2-one,
(35) 1,3-(S)-Dibenzyl-8-diphenylacetyl-1,4,8-triazaspiro[4,5]decan-2-one,
(36) 1,3-(S)-Dibenzyl-8-(2-phenoxyacetyl)-1,4,8-triazaspiro[4,5]decan-2-one,
(37) 1,3-(S)-Dibenzyl-8-(3-phenylpropionyl)-1,4,8-triazaspiro[4,5]decan-2-one,
(38) 1,3-(S)-Dibenzyl-8-(naphthalin-2-carbonyl)-1,4,8-triazaspiro[4,5]decan-2-one,
(39) 1,3-(S)-Dibenzyl-8-(furan-2-carbonyl)-1,4,8-triazaspiro[4,5]decan-2-one,
(40) 1,3-(S)-Dibenzyl-8-(3-methoxybenzoyl)-1,4,8-triazaspiro[4,5]decan-2-one,
(41) 1,3-(S)-Dibenzyl-8-(4-fluorobenzoyl)-1,4,8-triazaspiro[4,5]decan-2-one,
(42) 1-Benzyl-8-(4-fluorobenzoyl)-3-(S)-(2-methylsulfanylethyl)-1,4,8-triazaspiro[4,5]decan-2-one,
(43) 1,3-(S)-Dibenzyl-8-butyryl-1,4,8-triazaspiro[4,5]decan-2-one,
(44) 1,3-(S)-Dibenzyl-8-(3-fluoro-4-trifluoromethylbenzoyl)-1,4,8-triazaspiro[4,5]decan-2-one,
(45) 1,3-(S)-Dibenzyl-8-(2,3-difluorobenzoyl)-1,4,8-triazaspiro[4,5]decan-2-one,
(46) 1,3-(S)-Dibenzyl-8-[2-(4-chlorophenoxy)-acetyl]-1,4,8-triazaspiro[4,5]decan-2-one,
(47) 1,3-(S)-Dibenzyl-8-diphenylacetyl-1,4,8-triazaspiro[4,5]decan-2-one,
(48) 1,3-(S)-Dibenzyl-8-(2-phenoxyacetyl)-1,4,8-triazaspiro[4,5]decan-2-one,
(49) 1,3-(S)-Dibenzyl-8-(3-phenylpropionyl)-1,4,8-triazaspiro[4,5]decan-2-one,
(50) 1,3-(S)-Dibenzyl-8-(naphthalin-2-carbonyl)-1,4,8-triazaspiro[4,5]decan-2-one,
(51) 1,3-(S)-Dibenzyl-8-(furan-2-carbonyl)-1,4,8-triazaspiro[4,5]decan-2-one,
(52) 1,3-(S)-Dibenzyl-8-(3-methoxybenzoyl)-1,4,8-triazaspiro[4,5]decan-2-one,

(53) 1,3-(S)-Dibenzyl-8-(4-fluorobenzoyl)-1,4,8-triazaspiro[4,5]decan-2-one,
(54) 1-Benzyl-8-(4-fluorobenzoyl)-3-(S)-(2-methylsulfanylethyl)-1,4,8-triazaspiro[4,5]decan-2-one,
(55) N-[4-(3-Isobutyl-2-oxo-1-prop-2-ynyl-1,4,8-triazaspiro[4,5]decan-8-carbonyl)-phenyl]-acetamide,
(56) 1-(2-Phenoxyethyl)-8-(thiophene-2-carbonyl)-1,4,8-triazaspiro[4,5]decan-2-one,
(57) 2-(2-Oxo-8-pent-4-enoyl-1,4,8-triazaspiro[4,5]dec-1-ylmethyl)-benzonitrile,
(58) 8-(2,4-Dimethoxybenzoyl)-1-methyl-3-(2-methylsulfanylethyl)-1,4,8-triazaspiro[4,5]decan-2-one,
(59) 2-[8-(2-Ethylbutyryl)-2-oxo-1,4,8-triazaspiro[4,5]dec-1-ylmethyl]-benzonitrile,
(60) 4-(2-Isobutyl-3-oxo-1,4,8-triazaspiro[4,5]decan-8-carbonyl)-benzonitrile,
(61) 8-(6-Chloropyridin-3-carbonyl)-3-isobutyl-1,4,8-triazaspiro[4,5]decan-2-one,
(62) 2-[8-(2-Methylpentanoyl)-2-oxo-1,4,8-triazaspiro[4,5]dec-1-ylmethyl]-benzonitrile,
(63) 1-Benzyl-8-(biphenyl-4-carbonyl)-1,4,8-triazaspiro[4,5]decan-2-one,
(64) 3-Isobutyl-8-(5-methylisoxazole-3-carbonyl)-1,4,8-triazaspiro[4,5]decan-2-one,
(65) Ethyl 3-oxo-3-[2-oxo-1-(2-phenoxyethyl)-1,4,8-triazaspiro[4,5]dec-8-yl]-propionate,
(66) 8-(2-Chlorobenzoyl)-3-isopropyl-1,4,8-triazaspiro[4,5]decan-2-one,
(67) 8-Cyclopentanecarbonyl-3-isopropyl-1,4,8-triazaspiro[4,5]decan-2-one,
(68) 8-(Furan-2-carbonyl)-1-methyl-3-(2-methylsulfanylethyl)-1,4,8-triazaspiro[4,5]decan-2-one,
(69) 3-Benzyl-8-(2-ethylsulfanylpyridin-3-carbonyl)-1-methyl-1,4,8-triazaspiro[4,5]decan-2-one,
(70) 3-Benzyl-8-(4-chlorobenzoyl)-1,4,8-triazaspiro[4,5]decan-2-one,
(71) 8-(2-Benzyloxyacetyl)-3-isobutyl-1,4,8-triazaspiro[4,5]decan-2-one,
(72) 3-Benzyl-8-(2-methoxyacetyl)-1-prop-2-ynyl-1,4,8-triazaspiro[4,5]decan-2-one,
(73) 8-(5-tert-Butyl-2-methyl-2H-pyrazole-3-carbonyl)-3-isobutyl-1,4,8-triazaspiro[4,5]decan-2-one,
(74) 2-{8-[3-(2-chloro-6-fluorophenyl)-5-methylisoxazole-4-carbonyl]-2-oxo-1,4,8-triazaspiro[4,5]dec-1-ylmethyl}-benzonitrile,
(75) 3-Benzyl-8-(2-chlorobenzoyl)-1,4,8-triazaspiro[4,5]decan-2-one,
(76) 3-Benzyl-8-(3-dimethylaminobenzoyl)-1-methyl-1,4,8-triazaspiro[4,5]decan-2-one,
(77) 8-(3-Methylbenzoyl)-1-(2-phenoxyethyl)-1,4,8-triazaspiro[4,5]decan-2-one,
(78) 3-Isopropyl-1-(3-methylbut-2-enyl)-8-(pyridin-4-carbonyl)-1,4,8-triazaspiro[4,5]decan-2-one,
(79) 1-Benzyl-8-(4-methyl[1,2,3]thiadiazole-5-carbonyl)-1,4,8-triazaspiro[4,5]decan-2-one,
(80) 2-{8-[3-(2-chlorophenyl)-acryloyl]-2-oxo-1,4,8-triazaspiro[4,5]dec-1-ylmethyl}-benzonitrile,
(81) 8-(3-Chlorobenzoyl)-3-isobutyl-1,4,8-triazaspiro[4,5]decan-2-one,
(82) Ethyl 2-(2-benzyl-3-oxo-1,4,8-triazaspiro[4,5]dec-8-yl)-2-oxo-1-phenylacetate,
(83) 8-(3,5-Dimethoxybenzoyl)-3-isobutyl-1,4,8-triazaspiro[4,5]decan-2-one,
(84) 3-Benzyl-8-(isoxazole-5-carbonyl)-1,4,8-triazaspiro[4,5]decan-2-one,
(85) 8-(3-Chlorothiophene-2-carbonyl)-3-isobutyl-1,4,8-triazaspiro[4,5]decan-2-one,
(86) 3-Isopropyl-8-pentafluorobenzoyl-1,4,8-triazaspiro[4,5]decan-2-one,
(87) 8-(2,5-Dimethylfuran-3-carbonyl)-3-isobutyl-1,4,8-triazaspiro[4,5]decan-2-one,
(88) 1-Butyl-8-[2-(3,4-dimethoxyphenyl)-acetyl]-3-(2-methylsulfanylethyl)-1,4,8-triazaspiro[4,5]decan-2-one,
(89) 1-Benzyl-3-isopropyl-8-(pyridin-4-carbonyl)-1,4,8-triazaspiro[4,5]decan-2-one,
(90) 1,3-Dibenzyl-8-(3-dimethylaminobenzoyl)-1,4,8-triazaspiro[4,5]decan-2-one,
(91) 5-{2-[1-(4-Fluorobenzyl)-3-(2-methylsulfanylethyl)-2-oxo-1,4,8-triazaspiro[4,5]dec-8-yl]-2-oxoethyl}-imidazolidin-2,4-dione,
(92) 8-(Biphenyl-4-carbonyl)-1-(fluorobenzyl)-3-isobutyl-1,4,8-triazaspiro[4,5]decan-2-one,
(93) 2-[2-Oxo-8-(2-propylpentanoyl)-1,4,8-triazaspiro[4,5]dec-1-ylmethyl]-benzonitrile,
(94) 2-[8-(Furan-2-carbonyl)-3-isopropyl-2-oxo-1,4,8-triazaspiro[4,5]dec-1-ylmethyl]-benzonitrile,
(95) 8-[2-(4-Chlorophenoxy)-acetyl]-3-isobutyl-1-prop-2-ynyl-1,4,8-triazaspiro[4,5]decan-2-one,
(96) 1,3-Dibenzyl-8-(4-bromobenzoyl)-1,4,8-triazaspiro[4,5]decan-2-one,
(97) 8-(3-Difluoromethylsulfanylbenzoyl)-3-isobutyl-1,4,8-triazaspiro[4,5]decan-2-one,
(98) 8-(2,3-Dimethylbenzoyl)-3-isopropyl-1,4,8-triazaspiro[4,5]decan-2-one,
(99) 3-Benzyl-8-(2,3-dimethylbenzoyl)-1,4,8-triazaspiro[4,5]decan-2-one,
(100) 1-(4-Fluorobenzyl)-3-(2-methylsulfanylethyl)-8-(pyridin-2-carbonyl)-1,4,8-triazaspiro[4,5]decan-2-one,
(101) 3-Benzyl-8-(3,3-dimethylbutyryl)-1,4,8-triazaspiro[4,5]decan-2-one,
(102) 2-[8-(3-Dimethylaminobenzoyl)-3-isobutyl-2-oxo-1,4,8-triazaspiro[4,5]dec-1-ylmethyl]-benzonitrile,
(103) 3-[8-(2-Methoxyacetyl)-3-(2-methylsulfanylethyl)-2-oxo-1,4,8-triazaspiro[4,5]dec-1-ylmethyl]-benzonitrile,
(104) Ethyl 2-(3-benzyl-1-methyl-2-oxo-1,4,8-triazaspiro[4,5]dec-8-yl)-2-oxo-1-phenylacetate,
(105) 2-[8-[2-(2-Methoxyethoxy)-acetyl]-3-(2-methylsulfanylethyl)-2-oxo-1,4,8-triazaspiro[4,5]dec-1-ylmethyl]-benzonitrile,
(106) 3-Benzyl-8-[3-(2-chloro-6-fluorophenyl)-5-methylisoxazole-4-carbonyl]-1,4,8-triazaspiro[4,5]decan-2-one,
(107) 8-(2-Chloro-6-fluorobenzoyl)-3-isopropyl-1,4,8-triazaspiro[4,5]decan-2-one,
(108) 1-Methyl-3-(2-methylsulfanylethyl)-8-(2-phenoxyacetyl)-1,4,8-triazaspiro[4,5]decan-2-one,
(109) 8-(2-Chloropyridin-3-carbonyl)-1-(4-fluorobenzyl)-3-isobutyl-1,4,8-triazaspiro[4,5]decan-2-one,
(110) 8-(2-Ethylbutyryl)-1-methyl-3-(2-methylsulfanylethyl)-1,4,8-triazaspiro[4,5]decan-2-one,
(111) 1-Methyl-3-(2-methylsulfanylethyl)-8-(2-phenoxypyridin-3-carbonyl)-1,4,8-triazaspiro[4,5]decan-2-one,
(112) 8-(3-Fluorobenzoyl)-1-methyl-3-(2-methylsulfanylethyl)-1,4,8-triazaspiro[4,5]decan-2-one,
(113) 3-Benzyl-8-(naphthalin-2-carbonyl)-1,4,8-triazaspiro[4,5]decan-2-one,
(114) 8-Cyclohexanecarbonyl-1-(2-phenoxyethyl)-1,4,8-triazaspiro[4,5]decan-2-one,
(115) 8-(2-Phenoxyacetyl)-1-(2-phenoxyethyl)-1,4,8-triazaspiro[4,5]decan-2-one,
(116) 4-[1-Butyl-3-(2-methylsulfanylethyl)-2-oxo-1,4,8-triazaspiro[4,5]decan-8-carbonyl]-benzonitrile,
(117) 3-Benzyl-8-(3,3-dimethylbutyryl)-1-methyl-1,4,8-triazaspiro[4,5]decan-2-one, (118) 3-Benzyl-8-(4-propylbenzoyl)-1,4,8-triazaspiro[4,5]decan-2-one,
(119) 3-Isopropyl-8-(2-phenoxypropionyl)-1,4,8-triazaspiro[4,5]decan-2-one,
(120) 1-Butyl-8-hexanoyl-3-isopropyl-1,4,8-triazaspiro[4,5]decan-2-one,
(121) 8-(4-Bromo-3-methylbenzoyl)-3-isopropyl-1,4,8-triazaspiro[4,5]decan-2-one,
(122) 8-[3-(2-Chloro-6-fluorophenyl)-5-methylisoxazole-4-carbonyl]-3-isopropyl-1-(2-phenoxyethyl)-1,4,8-triazaspiro[4,5]decan-2-one,
(123) 1-(2-Fluorobenzyl)-3-isobutyl-8-(3-methylbenzoyl)-1,4,8-triazaspiro[4,5]decan-2-one,
(124) 8-(2-Ethylhexanoyl)-1-(2-phenoxyethyl)-1,4,8-triazaspiro[4,5]decan-2-one,
(125) 3-Benzyl-8-(3,4-difluorobenzoyl)-1,4,8-triazaspiro[4,5]decan-2-one,
(126) 3-Benzyl-8-(4-ethoxybenzoyl)-1-methyl-1,4,8-triazaspiro[4,5]decan-2-one,
(127) 1-Benzyl-8-(6-chloropyridin-3-carbonyl)-1,4,8-triazaspiro[4,5]decan-2-one,
(128) 8-(3-Dimethylaminobenzoyl)-1-(3,5-dimethylbenzyl)-3-(2-methylsulfanylethyl)-1,4,8-triazaspiro[4,5]decan-2-one,
(129) 3-[8-(Benzo[1,3]dioxol-5-carbonyl)-3-(2-methylsulfanylethyl)-2-oxo-1,4,8-triazaspiro[4,5]dec-1-ylmethyl]-benzonitrile,
(130) 3-Benzyl-1-methyl-8-pent-4-enoyl-1,4,8-triazaspiro[4,5]decan-2-one,
(131) 8-(4-Ethoxybenzoyl)-1-methyl-3-(2-methylsulfanylethyl)-1,4,8-triazaspiro[4,5]decan-2-one,
(132) 3-Benzyl-8-(2-benzyloxyacetyl)-1-methyl-1,4,8-triazaspiro[4,5]decan-2-one,
(133) 8-(3,4-Difluorobenzoyl)-1-(2-phenoxyethyl)-1,4,8-triazaspiro[4,5]decan-2-one,
(134) 3-Benzyl-1-methyl-8-(2-methylsulfanylpyridin-3-carbonyl)-1,4,8-triazaspiro[4,5]decan-2-one,
(135) 1-Butyl-8-(4-methoxybenzoyl)-3-(2-methylsulfanylethyl)-1,4,8-triazaspiro[4,5]decan-2-one,
(136) 1,3-Dibenzyl-8-(2-ethylsulfanylpyridin-3-carbonyl)-1,4,8-triazaspiro[4,5]decan-2-one,
(137) 3-Benzyl-8-(3-difluoromethylsulfanylbenzoyl)-1,4,8-triazaspiro[4,5]decan-2-one,
(138) 1-(4-Fluorobenzyl)-8-(furan-2-carbonyl)-3-(2-methylsulfanylethyl)-1,4,8-triazaspiro[4,5]decan-2-one,
(139) 3-Benzyl-8-(3-fluoro-4-methylbenzoyl)-1-methyl-1,4,8-triazaspiro[4,5]decan-2-one,
(140) 8-[3-(2-Chloro-6-fluorophenyl)-5-methylisoxazole-4-carbonyl]-3-isopropyl-1,4,8-triazaspiro[4,5]decan-2-one,
(141) 1-Butyl-8-(6-Chloro-2H-chroman-3-carbonyl)-3-(2-methylsulfanylethyl)-1,4,8-triazaspiro[4,5]decan-2-one,
(142) 3-[8-(3-Methoxybenzoyl)-3-(2-methylsulfanylethyl)-2-oxo-1,4,8-triazaspiro[4,5]dec-1-ylmethyl]-benzonitrile,
(143) 8-Cyclobutanecarbonyl-3-(2-methylsulfanylethyl)-1-prop-2-ynyl-1,4,8-triazaspiro[4,5]decan-2-one,
(144) 3-Benzyl-1-butyl-8-(furan-2-carbonyl)-1,4,8-triazaspiro[4,5]decan-2-one,
(145) 1-Benzyl-8-(3-chlorothiophene-2-carbonyl)-3-isobutyl-1,4,8-triazaspiro[4,5]decan-2-one,
(146) 3-Benzyl-8-(2,5-bis-trifluoromethylbenzoyl)-1-butyl-1,4,8-triazaspiro[4,5]decan-2-one,
(147) 8-(3-Chloro-2-fluorobenzoyl)-1-(3,5-dimethylbenzyl)-3-(2-methylsulfanylethyl)-1,4,8-triazaspiro[4,5]decan-2-one,
(148) 1-Benzyl-8-(2-chloropyridin-3-carbonyl)-3-isopropyl-1,4,8-triazaspiro[4,5]decan-2-one,
(149) 3-Isobutyl-8-pentafluorobenzoyl-1-prop-2-ynyl-1,4,8-triazaspiro[4,5]decan-2-one,
(150) 8-(2-Benzyloxyacetyl)-1-butyl-3-(2-methylsulfanylethyl)-1,4,8-triazaspiro[4,5]decan-2-one,
(151) 8-(Furan-2-carbonyl)-3-isobutyl-1-prop-2-ynyl-1,4,8-triazaspiro[4,5]decan-2-one,
(152) 1-Butyl-3-(2-methylsulfanylethyl)-8-(4-phenoxybutyryl)-1,4,8-triazaspiro[4,5]decan-2-one,
(153) 3-Benzyl-8-(6-chloropyridin-3-carbonyl)-1-methyl-1,4,8-triazaspiro[4,5]decan-2-one,
(154) 1-(2-Fluorobenzyl)-3-(2-methylsulfanylethyl)-8-(2-phenoxypyridin-3-carbonyl)-1,4,8-triazaspiro[4,5]decan-2-one,
(155) 1-(2-Fluorobenzyl)-3-isobutyl-8-(2-methyl-6-trifluoromethylpyridin-3-carbonyl)-1,4,8-triazaspiro[4,5]decan-2-one,
(156) 8-[2-(3-Chlorophenoxy)-acetyl]-3-isopropyl-1-(2-phenoxyethyl)-1,4,8-triazaspiro[4,5]decan-2-one,
(157) 8-(2,3-Dimethylbenzoyl)-1-methyl-3-(2-methylsulfanylethyl)-1,4,8-triazaspiro[4,5]decan-2-one,
(158) 3-Isopropyl-8-(2-methyl-6-trifluoromethylpyridin-3-carbonyl)-1-(2-phenoxyethyl)-1,4,8-triazaspiro[4,5]decan-2-one,
(159) 3-Benzyl-1-methyl-8-(5-methyl-2-phenyl-2H-[1,2,3]triazole-4-carbonyl)-1,4,8-triazaspiro[4,5]decan-2-one,
(160) 8-[3-(2-Chlorophenyl)-5-methylisoxazole-4-carbonyl]-1-(3,5-dimethylbenzyl)-3-(2-methylsulfanylethyl)-1,4,8-triazaspiro[4,5]decan-2-one,
(161) 1-(2-Fluorobenzyl)-3-(2-methylsulfanylethyl)-8-(pyridin-2-carbonyl)-1,4,8-triazaspiro[4,5]decan-2-one,
(162) 1-Benzyl-3-(2-methylsulfanylethyl)-8-(2-phenoxypyridin-3-carbonyl)-1,4,8-triazaspiro[4,5]decan-2-one,
(163) 1,3-Dibenzyl-8-(3-chlorothiophene-2-carbonyl)-1,4,8-triazaspiro[4,5]decan-2-one,
(164) 3-Benzyl-8-(4-tert-butylbenzoyl)-1-methyl-1,4,8-triazaspiro[4,5]decan-2-one,
(165) 2-[3-Isobutyl-8-(2-methoxyacetyl)-2-oxo-1,4,8-triazaspiro[4,5]dec-1-ylmethyl]-benzonitrile,
(166) 3-Benzyl-1-butyl-8-(5-fluoro-2-trifluoromethylbenzoyl)-1,4,8-triazaspiro[4,5]decan-2-one,
(167) 3-Benzyl-8-[2-(4-methoxyphenyl)-acetyl]-1-methyl-1,4,8-triazaspiro[4,5]decan-2-one,
(168) 1,3-Dibenzyl-8-(4-methyl[1,2,3]thiadiazole-5-carbonyl)-1,4,8-triazaspiro[4,5]decan-2-one,
(169) 1-Benzyl-3-isopropyl-8-(2-methyl-6-trifluoromethylpyridin-3-carbonyl)-1,4,8-triazaspiro[4,5]decan-2-one,
(170) 1-Benzyl-8-(4-ethoxybenzoyl)-3-isobutyl-1,4,8-triazaspiro[4,5]decan-2-one,
(171) 3-Benzyl-1-butyl-8-cyclohexanecarbonyl-1,4,8-triazaspiro[4,5]decan-2-one,
(172) 3-[8-[3-(2-Chloro-6-fluorophenyl)-5-methylisoxazole-4-carbonyl]-3-(2-methylsulfanylethyl)-2-oxo-1,4,8-triazaspiro[4,5]dec-1-ylmethyl]-benzonitrile,
(173) 1-(2-Fluorobenzyl)-3-isobutyl-8-pent-4-enoyl-1,4,8-triazaspiro[4,5]decan-2-one,
(174) 1-Methyl-3-(2-methylsulfanylethyl)-8-(2-propylpentanoyl)-1,4,8-triazaspiro[4,5]decan-2-one,
(175) 3-Benzyl-1-methyl-8-(2-phenoxyacetyl)-1,4,8-triazaspiro[4,5]decan-2-one,
(176) 3-Isobutyl-1-prop-2-ynyl-8-(3-trifluoromethylbenzoyl)-1,4,8-triazaspiro[4,5]decan-2-one,
(177) 3-Benzyl-8-(furan-2-carbonyl)-1-prop-2-ynyl-1,4,8-triazaspiro[4,5]decan-2-one,
(178) 1-Methyl-3-(2-methylsulfanylethyl)-8-(naphthalin-1-carbonyl)-1,4,8-triazaspiro[4,5]decan-2-one,
(179) 3-Benzyl-1-butyl-8-(3-cyclopentylpropionyl)-1,4,8-triazaspiro[4,5]decan-2-one, (180) 1-(3,5-Dimethylbenzyl)-3-(2-methylsulfanylethyl)-8-pentanoyl-1,4,8-triazaspiro[4,5]decan-2-one,
(181) 3-Benzyl-1-butyl-8-(2-methoxyacetyl)-1,4,8-triazaspiro[4,5]decan-2-one,
(182) 3-Benzyl-8-(3-fluoro-4-trifluoromethylbenzoyl)-1-methyl-1,4,8-triazaspiro[4,5]decan-2-one,
(183) 1-Benzyl-8-(3-difluoromethylsulfanylbenzoyl)-3-isopropyl-1,4,8-triazaspiro[4,5]decan-2-one,
(184) 8-(2-Chloro-6-fluoro-3-methylbenzoyl)-1-methyl-3-(2-methylsulfanylethyl)-1,4,8-triazaspiro[4,5]decan-2-one,
(185) Methyl 4-[3-Isopropyl-8-(2-methylsulfanylpyridin-3-carbonyl)-2-oxo-1,4,8-triazaspiro[4,5]dec-1-ylmethyl]benzoate,
(186) 8-[2-(2,5-Dimethoxyphenyl)-acetyl]-1-(2-fluorobenzyl)-3-(2-methylsulfanylethyl)-1,4,8-triazaspiro[4,5]decan-2-one,
(187) 8-(5-tert-Butyl-2-methylfuran-3-carbonyl)-3-isopropyl-1-(2-phenoxyethyl)-1,4,8-triazaspiro[4,5]decan-2-one,
(188) 8-(2-Cyclopentylacetyl)-1-(4-fluorobenzyl)-3-isobutyl-1,4,8-triazaspiro[4,5]decan-2-one,
(189) Methyl 4-[8-(3,3-dimethylbutyryl)-3-isopropyl-2-oxo-1,4,8-triazaspiro[4,5]dec-1-ylmethyl]benzoate,
(190) 3-[8-Cyclopropanecarbonyl-3-(2-methylsulfanylethyl)-2-oxo-1,4,8-triazaspiro[4,5]dec-1-ylmethyl]-benzonitrile,
(191) 3-[3-(2-Methylsulfanylethyl)-2-oxo-8-(3-trifluoromethoxybenzoyl)-1,4,8-triazaspiro[4,5]dec-1-ylmethyl]-benzonitrile,
(192) 1-Butyl-8-(2-cyclopentylacetyl)-3-isopropyl-1,4,8-triazaspiro[4,5]decan-2-one,
(193) 3-Benzyl-1-butyl-8-(pyridin-2-carbonyl)-1,4,8-triazaspiro[4,5]decan-2-one,
(194) 3-Benzyl-8-[3-(2-chlorophenyl)-acryloyl]-1-methyl-1,4,8-triazaspiro[4,5]decan-2-one,
(195) Methyl 4-[8-(3-fluoro-4-trifluoromethylbenzoyl)-3-isopropyl-2-oxo-1,4,8-triazaspiro[4,5]dec-1-ylmethyl]benzoate,
(196) 8-[3-(2,6-Dichlorophenyl)-5-methylisoxazole-4-carbonyl]-1-methyl-3-(2-methylsulfanylethyl)-1,4,8-triazaspiro[4,5]decan-2-one,
(197) 1-Butyl-8-cyclohexanecarbonyl-3-(2-methylsulfanylethyl)-1,4,8-triazaspiro[4,5]decan-2-one,
(198) 3-Benzyl-1-butyl-8-(4-Iodobenzoyl)-1,4,8-triazaspiro[4,5]decan-2-one
(199) 1-Methyl-3-(2-methylsulfanylethyl)-8-[3-(3-trifluoromethylphenyl)-acryloyl]-1,4,8-triazaspiro[4,5]decan-2-one,
(200) 1,3-Dibenzyl-8-(4-phenoxybutyryl)-1,4,8-triazaspiro[4,5]decan-2-one
(201) 3-Benzyl-8-(2-chloro-6-fluorobenzoyl)-1-prop-2-ynyl-1,4,8-triazaspiro[4,5]decan-2-one,
(202) Methyl 4-[8-(2-chloropyridin-3-carbonyl)-3-isopropyl-2-oxo-1,4,8-triazaspiro[4,5]dec-1-ylmethyl]benzoate,
(203) 8-(2,5-Dimethylfuran-3-carbonyl)-3-isopropyl-1-(2-phenoxyethyl)-1,4,8-triazaspiro[4,5]decan-2-one,
(204) 8-(Biphenyl-4-carbonyl)-3-(2-methylsulfanylethyl)-1-prop-2-ynyl-1,4,8-triazaspiro[4,5]decan-2-one,
(205) 8-(3-Chlorothiophene-2-carbonyl)-3-(2-methylsulfanylethyl)-1-prop-2-ynyl-1,4,8-triazaspiro[4,5]decan-2-one,
(206) 1-(4-Fluorobenzyl)-8-[2-(4-methoxyphenyl)-acetyl]-3-(2-methylsulfanylethyl)-1,4,8-triazaspiro[4,5]decan-2-one,
(207) 1-Benzyl-3-isopropyl-8-(4-methyl[1,2,3]thiadiazole-5-carbonyl)-1,4,8-triazaspiro[4,5]decan-2-one,
(208) 2-[3-Isopropyl-8-(2-methylsulfanylpyridin-3-carbonyl)-2-oxo-1,4,8-triazaspiro[4,5]dec-1-ylmethyl]-benzonitrile,
(209) 3-[8-(5-tert-Butyl-2-methyl-2H-pyrazole-3-carbonyl)-3-isobutyl-2-oxo-1,4,8-triazaspiro[4,5]dec-1-ylmethyl]-benzonitrile,
(210) 1-Butyl-8-(2,5-dimethylfuran-3-carbonyl)-3-(2-methylsulfanylethyl)-1,4,8-triazaspiro[4,5]decan-2-one,
(211) 8-(3-Cyclopentylpropionyl)-1-(2-fluorobenzyl)-3-isobutyl-1,4,8-triazaspiro[4,5]decan-2-one,
(212) 1-Benzyl-8-(3-cyclopentylpropionyl)-3-(2-methylsulfanylethyl)-1,4,8-triazaspiro[4,5]decan-2-one,
(213) 3-(2-Methylsulfanylethyl)-8-(4-phenoxybutyryl)-1-prop-2-ynyl-1,4,8-triazaspiro[4,5]decan-2-one,
(214) 1,3-Dibenzyl-8-(3-phenylacryloyl)-1,4,8-triazaspiro[4,5]decan-2-one,
(215) 3-Benzyl-8-(6-chloro-2-fluoro-3-methylbenzoyl)-1-methyl-1,4,8-triazaspiro[4,5]decan-2-one,
(216) 8-[3-(2-Chlorophenyl)-acryloyl]-3-isopropyl-1-(2-phenoxyethyl)-1,4,8-triazaspiro[4,5]decan-2-one,
(217) 2-[3-Isopropyl-2-oxo-8-(3-phenylacryloyl)-1,4,8-triazaspiro[4,5]dec-1-ylmethyl]-benzonitrile,
(218) 3-Benzyl-1-methyl-8-(4-methyl-3-nitrobenzoyl)-1,4,8-triazaspiro[4,5]decan-2-one,
(219) 1-Benzyl-8-(furan-2-carbonyl)-3-isopropyl-1,4,8-triazaspiro[4,5]decan-2-one,
(220) 1-Butyl-8-(3,5-dimethoxybenzoyl)-3-(2-methylsulfanylethyl)-1,4,8-triazaspiro[4,5]decan-2-one,
(221) 1,3-Dibenzyl-8-(3,3-dimethylbutyryl)-1,4,8-triazaspiro[4,5]decan-2-one,
(222) 8-(2,6-Difluoro-3-methylbenzoyl)-1-methyl-3-(2-methylsulfanylethyl)-1,4,8-triazaspiro[4,5]decan-2-one,
(223) 2-[8-(2-Chloro-6-fluorobenzoyl)-3-(2-methylsulfanylethyl)-2-oxo-1,4,8-triazaspiro[4,5]dec-1-ylmethyl]-benzonitrile,
(224) 8-[3-(2-Chloro-6-fluorophenyl)-5-methylisoxazole-4-carbonyl]-3-isopropyl-1-(3-methylbut-2-enyl)-1,4,8-triazaspiro[4,5]decan-2-one,
(225) 3-Isobutyl-1-prop-2-ynyl-8-(4-trifluoromethoxybenzoyl)-1,4,8-triazaspiro[4,5]decan-2-one,
(226) 1-Benzyl-8-(2-chloro-6-fluoro-3-methylbenzoyl)-1,4,8-triazaspiro[4,5]decan-2-one,
(227) Benzyl 2-(1-benzyl-3-isopropyl-2-oxo-1,4,8-triazaspiro[4,5]decan-8-carbonyl)benzoate,
(228) 1,3-Dibenzyl-8-(2-phenylbutyryl)-1,4,8-triazaspiro[4,5]decan-2-one,
(229) 3-Benzyl-1-methyl-8-(4-nitrobenzoyl)-1,4,8-triazaspiro[4,5]decan-2-one,
(230) 3-Benzyl-1-methyl-8-(5-methylisoxazole-3-carbonyl)-1,4,8-triazaspiro[4,5]decan-2-one,
(231) 1-Benzyl-8-(6-chloro-2-fluoro-3-methylbenzoyl)-3-(2-methylsulfanylethyl)-1,4,8-triazaspiro[4,5]decan-2-one,
(232) 1-Benzyl-8-(3-fluoro-4-trifluoromethylbenzoyl)-3-isobutyl-1,4,8-triazaspiro[4,5]decan-2-one,
(233) 3-Benzyl-8-(6-chloro-2H-chroman-3-carbonyl)-1-methyl-1,4,8-triazaspiro[4,5]decan-2-one,
(234) 3-Benzyl-1-butyl-8-(4-methyl[1,2,3]thiadiazole-5-carbonyl)-1,4,8-triazaspiro[4,5]decan-2-one,
(235) 3-Benzyl-8-(4-methyl[1,2,3]thiadiazole-5-carbonyl)-1-prop-2-ynyl-1,4,8-triazaspiro[4,5]decan-2-one,
(236) 2-[8-(6-Chloro-2H-chroman-3-carbonyl)-3-isopropyl-2-oxo-1,4,8-triazaspiro[4,5]dec-1-ylmethyl]-benzonitrile,
(237) 2-[8-(5-Methylisoxazole-3-carbonyl)-3-(2-methylsulfanylethyl)-2-oxo-1,4,8-triazaspiro[4,5]dec-1-ylmethyl]-benzonitrile, (238) 2-[8-(3-Chloro-2-fluorobenzoyl)-3-isopropyl-2-oxo-1,4,8-triazaspiro[4,5]dec-1-ylmethyl]-benzonitrile,
(239) Methyl 4-[8-(5-tert-butyl-2-methyl-2H-pyrazole-3-carbonyl)-3-isopropyl-2-oxo-1,4,8-triazaspiro[4,5]dec-1-ylmethyl]benzoate,
(240) 3-Benzyl-1-butyl-8-(5-tert-butyl-2-methyl-2H-pyrazole-3-carbonyl)-1,4,8-triazaspiro[4,5]decan-2-one,
(241) 3-Benzyl-1-butyl-8-(2-chloro-4-trifluoromethylpyrimidin-5-carbonyl)-1,4,8-triazaspiro[4,5]decan-2-one,
(242) 3-Benzyl-8-(5-methylisoxazole-3-carbonyl)-1-prop-2-ynyl-1,4,8-triazaspiro[4,5]decan-2-one,
(243) Methyl 4-[8-(2-chloropyridin-3-carbonyl)-2-oxo-1,4,8-triazaspiro[4,5]dec-1-ylmethyl]benzoate,
(244) 8-(2-tert-Butyl-5-methyl-2H-pyrazole-3-carbonyl)-1-(2-fluorobenzyl)-1,4,8-triazaspiro[4,5]decan-2-one,
(245) Methyl 4-[8-(2-methylsulfanylpyridin-3-carbonyl)-2-oxo-1,4,8-triazaspiro[4,5]dec-1-ylmethyl]benzoate,
(246) Butyl 4-[8-(4-acetylaminobenzoyl)-3-isobutyl-2-oxo-1,4,8-triazaspiro[4,5]dec-1-yl]acetate,
(247) Ethyl [8-(4-acetylaminobenzoyl)-3-benzyl-2-oxo-1,4,8-triazaspiro[4,5]dec-1-yl]acetate,
(248) Butyl 4-[8-(2-ethylsulfanylpyridin-3-carbonyl)-3-isobutyl-2-oxo-1,4,8-triazaspiro[4,5]dec-1-yl]acetate,
(249) Methyl 4-[8-(4-methyl[1,2,3]thiadiazole-5-carbonyl)-2-oxo-1,4,8-triazaspiro[4,5]dec-1-ylmethyl]benzoate,
(250) 4-[1-Allyl-3-(2-methylsulfanylethyl)-2-oxo-1,4,8-triazaspiro[4,5]decan-8-carbonyl]-benzolsulfonamide,
(251) Methyl 4-(8-cyclobutanecarbonyl-2-oxo-1,4,8-triazaspiro[4,5]dec-1-ylmethyl)benzoate,
(252) Ethyl 2-[1-allyl-3-(2-methylsulfanylethyl)-2-oxo-1,4,8-triazaspiro[4,5]dec-8-yl]-2-oxo-acetate,
(253) 8-(Biphenyl-4-carbonyl)-1-(2-fluorobenzyl)-1,4,8-triazaspiro[4,5]decan-2-one,
(254) Ethyl [3-(2-Methylsulfanylethyl)-2-oxo-8-propionyl-1,4,8-triazaspiro[4,5]dec-1-yl]acetate,
(255) 8-(Benzo[1,3]dioxole-5-carbonyl)-1-(2,6-dichlorobenzyl)-3-isobutyl-1,4,8-triazaspiro[4,5]decan-2-one,
(256) 1-Allyl-8-(biphenyl-4-carbonyl)-3-isopropyl-1,4,8-triazaspiro[4,5]decan-2-one,
(257) Ethyl [3-benzyl-8-(biphenyl-4-carbonyl)-2-oxo-1,4,8-triazaspiro[4,5]dec-1-yl]acetate,
(258) Ethyl [8-(3-dimethylaminobenzoyl)-3-(2-methylsulfanylethyl)-2-oxo-1,4,8-triazaspiro[4,5]dec-1-yl]acetate,
(259) 3-(2-Oxo-8-pentanoyl-1,4,8-triazaspiro[4,5]dec-1-ylmethyl)-benzonitrile,
(260) Methyl 4-(8-cyclopentanecarbonyl-2-oxo-1,4,8-triazaspiro[4,5]dec-1-ylmethyl)benzoate,
(261) Ethyl 4-[1-(2-fluorobenzyl)-2-oxo-1,4,8-triazaspiro[4,5]dec-8-yl]-4-oxo-butanoate,
(262) 1-(2-Fluorobenzyl)-8-(3,4,5-trimethoxybenzoyl)-1,4,8-triazaspiro[4,5]decan-2-one,
(263) Methyl 4-[8-(2-chloropyridin-4-carbonyl)-2-oxo-1,4,8-triazaspiro[4,5]dec-1-ylmethyl]benzoate,
(264) 3-[8-(3,5-Bis-trifluoromethylbenzoyl)-2-oxo-1,4,8-triazaspiro[4,5]dec-1-ylmethyl]-benzonitrile,
(265) 3-Benzyl-1-(2-fluorobenzyl)-8-(2-methoxybenzoyl)-1,4,8-triazaspiro[4,5]decan-2-one,
(266) 8-(Benzo[1,2,5]oxadiazole-5-carbonyl)-1-(2,6-dichlorobenzyl)-3-isobutyl-1,4,8-triazaspiro[4,5]decan-2-one,
(267) Ethyl [3-benzyl-2-oxo-8-(4-sulfamoylbenzoyl)-1,4,8-triazaspiro[4,5]dec-1-yl]acetate,
(268) 3-[2-Oxo-8-(3,4,5-trimethoxybenzoyl)-1,4,8-triazaspiro[4,5]dec-1-ylmethyl]-benzonitrile,
(269) Ethyl 2-[1-(4-acetoxybutyl)-3-isobutyl-2-oxo-1,4,8-triazaspiro[4,5]dec-8-yl]-1,1-dimethyl-2-oxo-acetate,
(270) 8-(6-Chloropyridin-3-carbonyl)-1-(2,6-dichlorobenzyl)-3-isobutyl-1,4,8-triazaspiro[4,5]decan-2-one,
(271) 8-(2-Ethoxybenzoyl)-1-(2-fluorobenzyl)-1,4,8-triazaspiro[4,5]decan-2-one,
(272) 1-Allyl-8-cyclopropanecarbonyl-3-(2-methylsulfanylethyl)-1,4,8-triazaspiro[4,5]decan-2-one,
(273) 3-[3-Isopropyl-8-(2-methoxyacetyl)-2-oxo-1,4,8-triazaspiro[4,5]dec-1-ylmethyl]-benzonitrile,
(274) Methyl 4-(2-oxo-8-phenylacetyl-1,4,8-triazaspiro[4,5]dec-1-ylmethyl)benzoate,
(275) Ethyl 2-[1-(3-cyanobenzyl)-2-oxo-1,4,8-triazaspiro[4,5]dec-8-yl]-2-oxo-1-phenylacetate,
(276) 1-(2-Fluorobenzyl)-8-(4-methoxybenzoyl)-1,4,8-triazaspiro[4,5]decan-2-one,
(277) Methyl 4-(8-cyclohexanecarbonyl-2-oxo-1,4,8-triazaspiro[4,5]dec-1-ylmethyl)benzoate,
(278) 1-(2-Fluorobenzyl)-8-pent-4-enoyl-1,4,8-triazaspiro[4,5]decan-2-one,
(279) Ethyl [3-isobutyl-8-(3-methylbutyryl)-2-oxo-1,4,8-triazaspiro[4,5]dec-1-yl]acetate,
(280) 1-Allyl-8-(3,3-dimethylbutyryl)-3-(2-methylsulfanylethyl)-1,4,8-triazaspiro[4,5]decan-2-one,
(281) 1-Allyl-3-(2-methylsulfanylethyl)-8-(2-methylsulfanylpyridin-3-carbonyl)-1,4,8-triazaspiro[4,5]decan-2-one,
(282) Ethyl [3-isobutyl-8-(2-methylpentanoyl)-2-oxo-1,4,8-triazaspiro[4,5]dec-1-yl]acetate,
(283) Methyl 4-[8-(5-tert-butyl-2-methylfuran-3-carbonyl)-2-oxo-1,4,8-triazaspiro[4,5]dec-1-ylmethyl]benzoate,
(284) Ethyl(3-benzyl-8-cyclopropanecarbonyl-2-oxo-1,4,8-triazaspiro[4,5]dec-1-yl)acetate,
(285) Ethyl [3-benzyl-8-(3-methylbutyryl)-2-oxo-1,4,8-triazaspiro[4,5]dec-1-yl]acetate,
(286) 1-(2,6-Dichlorobenzyl)-8-(2,5-dimethylfuran-3-carbonyl)-3-isobutyl-1,4,8-triazaspiro[4,5]decan-2-one,
(287) 1-Allyl-3-isopropyl-8-[2-(3-methoxyphenyl)-acetyl]-1,4,8-triazaspiro[4,5]decan-2-one,
(288) Ethyl [8-(4-tert-butylbenzoyl)-3-(2-methylsulfanylethyl)-2-oxo-1,4,8-triazaspiro[4,5]dec-1-yl]acetate,
(289) 3-(2-Methylsulfanylethyl)-1-(2-nitrobenzyl)-8-(2-phenoxypyridin-3-carbonyl)-1,4,8-triazaspiro[4,5]decan-2-one,
(290) Ethyl(3-benzyl-2-oxo-8-pentanoyl-1,4,8-triazaspiro[4,5]dec-1-yl)acetate,
(291) 8-(2-Chloropyridin-4-carbonyl)-1-(2-fluorobenzyl)-1,4,8-triazaspiro[4,5]decan-2-one,
(292) Ethyl [8-(3-methylbutyryl)-3-(2-methylsulfanylethyl)-2-oxo-1,4,8-triazaspiro[4,5]dec-1-yl]acetate,
(293) 1-Allyl-3-(2-methylsulfanylethyl)-8-pentafluorobenzoyl-1,4,8-triazaspiro[4,5]decan-2-one,
(294) 1-(2-Fluorobenzyl)-8-(2-trifluoromethylbenzoyl)-1,4,8-triazaspiro[4,5]decan-2-one,
(295) 8-(Benzo[1,2,5]oxadiazole-5-carbonyl)-1-(2-fluorobenzyl)-1,4,8-triazaspiro[4,5]decan-2-one,
(296) Methyl 4-[8-(4-tert-butylbenzoyl)-2-oxo-1,4,8-triazaspiro[4,5]dec-1-ylmethyl]benzoate,
(297) Ethyl [3-benzyl-2-oxo-8-(1-phenyl-5-propyl-1H-pyrazole-4-carbonyl)-1,4,8-triazaspiro[4,5]dec-1-yl]acetate,
(298) 1-Allyl-3-isopropyl-8-pent-4-enoyl-1,4,8-triazaspiro[4,5]decan-2-one,
(299) 3-[2-Oxo-8-(2-trifluoromethylbenzoyl)-1,4,8-triazaspiro[4,5]dec-1-ylmethyl]-benzonitrile,
(300) 8-(2-Dimethylaminoacetyl)-1-(3,5-dimethylbenzyl)-3-isobutyl-1,4,8-triazaspiro[4,5]decan-2-one,
(301) Butyl [8-(2-ethoxybenzoyl)-3-isobutyl-2-oxo-1,4,8-triazaspiro[4,5]dec-1-yl]acetate,
(302) 1-(2-Fluorobenzyl)-8-(3-methoxybenzoyl)-1,4,8-triazaspiro[4,5]decan-2-one, (303) Ethyl [8-(furan-2-carbonyl)-3-isobutyl-2-oxo-1,4,8-triazaspiro[4,5]dec-1-yl]acetate,
(304) 8-(5-tert-Butyl-2-methyl-2H-pyrazole-3-carbonyl)-1-(2-fluorobenzyl)-1,4,8-triazaspiro[4,5]decan-2-one,
(305) 1-(2-Fluorobenzyl)-8-(thiophene-2-carbonyl)-1,4,8-triazaspiro[4,5]decan-2-one,
(306) Ethyl [3-benzyl-8-(2-fluorobenzoyl)-2-oxo-1,4,8-triazaspiro[4,5]dec-1-yl]acetate,
(307) Ethyl [8-(isoxazole-5-carbonyl)-3-(2-methylsulfanylethyl)-2-oxo-1,4,8-triazaspiro[4,5]dec-1-yl]acetate,
(308) 1-(2,6-Dichlorobenzyl)-3-isobutyl-8-(4-propylbenzoyl)-1,4,8-triazaspiro[4,5]decan-2-one,
(309) Ethyl [8-[2-(2,5-dimethoxyphenyl)-acetyl]-3-(2-methylsulfanylethyl)-2-oxo-1,4,8-triazaspiro[4,5]dec-1-yl]acetate,
(310) Ethyl(3-benzyl-8-cyclobutanecarbonyl-2-oxo-1,4,8-triazaspiro[4,5]dec-1-yl)acetate,
(311) 1-(2-Fluorobenzyl)-8-[2-(4-methoxyphenyl)-acetyl]-1,4,8-triazaspiro[4,5]decan-2-one,
(312) 1-Allyl-3-(2-methylsulfanylethyl)-8-(2-methyl-6-trifluoromethylpyridin-3-carbonyl)-1,4,8-triazaspiro[4,5]decan-2-one,
(313) Ethyl [3-(2-methylsulfanylethyl)-2-oxo-8-(4-trifluoromethylbenzoyl)-1,4,8-triazaspiro[4,5]dec-1-yl]acetate,
(314) 1-Allyl-3-(2-methylsulfanylethyl)-8-(1-phenyl-5-propyl-1H-pyrazole-4-carbonyl)-1,4,8-triazaspiro[4,5]decan-2-one,
(315) 1-(2,6-Dichlorobenzyl)-8-(2,3-difluoro-4-methylbenzoyl)-3-isobutyl-1,4,8-triazaspiro[4,5]decan-2-one,
(316) 1-Allyl-3-isopropyl-8-(2-methylbenzoyl)-1,4,8-triazaspiro[4,5]decan-2-one,
(317) 8-(2-Chloro-5-trifluoromethylbenzoyl)-1-(2,6-dichlorobenzyl)-3-isobutyl-1,4,8-triazaspiro[4,5]decan-2-one,
(318) 1-Allyl-8-[2-(3-methoxyphenyl)-acetyl]-3-(2-methylsulfanylethyl)-1,4,8-triazaspiro[4,5]decan-2-one,
(319) 1-Allyl-3-(2-methylsulfanylethyl)-8-(3-phenylpropionyl)-1,4,8-triazaspiro[4,5]decan-2-one,
(320) Ethyl [3-benzyl-8-(2-benzyloxyacetyl)-2-oxo-1,4,8-triazaspiro[4,5]dec-1-yl]acetate,
(321) 1-Allyl-8-(5-tert-butyl-2-methyl-2H-pyrazole-3-carbonyl)-3-(2-methylsulfanylethyl)-1,4,8-triazaspiro[4,5]decan-2-one,
(322) Ethyl 1,1-dimethyl-2-[3-(2-methylsulfanylethyl)-1-(2-nitrobenzyl)-2-oxo-1,4,8-triazaspiro[4,5]dec-8-yl]-2-oxo-acetate,
(323) Benzyl 2-[1-ethoxycarbonylmethyl-3-(2-methylsulfanylethyl)-2-oxo-1,4,8-triazaspiro[4,5]decan-8-carbonyl]benzoate,
(324) 1-Allyl-3-isopropyl-8-(4-methyl[1,2,3]thiadiazole-5-carbonyl)-1,4,8-triazaspiro[4,5]decan-2-one,
(325) 1-Allyl-8-(2,5-dimethylfuran-3-carbonyl)-3-(2-methylsulfanylethyl)-1,4,8-triazaspiro[4,5]decan-2-one,
(326) 1-Allyl-8-(benzo[1,2,5]oxadiazole-5-carbonyl)-3-(2-methylsulfanylethyl)-1,4,8-triazaspiro[4,5]decan-2-one,
(327) 1-(2-Fluorobenzyl)-8-(4-phenoxybutyryl)-1,4,8-triazaspiro[4,5]decan-2-one,
(328) 1-Allyl-8-(2-cyclopentylacetyl)-3-(2-methylsulfanylethyl)-1,4,8-triazaspiro[4,5]decan-2-one,
(329) Ethyl [3-benzyl-8-(naphthalin-2-carbonyl)-2-oxo-1,4,8-triazaspiro[4,5]dec-1-yl]acetate,
(330) 8-[3-(2-Chloro-6-fluorophenyl)-5-methylisoxazole-4-carbonyl]-1-(2-fluorobenzyl)-1,4,8-triazaspiro[4,5]decan-2-one,
(331) 3-[8-(3,5-Dimethoxybenzoyl)-3-isopropyl-2-oxo-1,4,8-triazaspiro[4,5]dec-1-ylmethyl]-benzonitrile,
(332) 3-(2-Methylsulfanylethyl)-1-(2-nitrobenzyl)-8-(1-phenyl-5-propyl-1H-pyrazole-4-carbonyl)-1,4,8-triazaspiro[4,5]decan-2-one,
(333) Ethyl {3-benzyl-8-[3-(2-chloro-6-fluorophenyl)-5-methylisoxazole-4-carbonyl]-2-oxo-1,4,8-triazaspiro[4,5]dec-1-yl}acetate,
(334) 1-(2-Fluorobenzyl)-8-(3-fluoro-4-trifluoromethylbenzoyl)-1,4,8-triazaspiro[4,5]decan-2-one,
(335) Ethyl [8-[1-(4-chlorophenyl)-5-trifluoromethyl-1H-pyrazole-4-carbonyl]-3-(2-methylsulfanylethyl)-2-oxo-1,4,8-triazaspiro[4,5]dec-1-yl]acetate,
(336) 3-[8-(Naphthalin-1-carbonyl)-2-oxo-1,4,8-triazaspiro[4,5]dec-1-ylmethyl]-benzonitrile,
(337) Ethyl [8-(3,3-dimethylbutyryl)-3-(2-methylsulfanylethyl)-2-oxo-1,4,8-triazaspiro[4,5]dec-1-yl]acetate,
(338) 8-Acetyl-3-(2-methylsulfanylethyl)-1-naphthalin-2-ylmethyl-1,4,8-triazaspiro[4,5]decan-2-one,
(339) Ethyl [3-benzyl-8-(3-cyanobenzoyl)-2-oxo-1,4,8-triazaspiro[4,5]dec-1-yl]acetate,
(340) 8-(5-tert-Butyl-2-methyl-2H-pyrazole-3-carbonyl)-1-(2,6-dichlorobenzyl)-3-isobutyl-1,4,8-triazaspiro[4,5]decan-2-one,
(341) 4-[3-Benzyl-1-(2-fluorobenzyl)-2-oxo-1,4,8-triazaspiro[4,5]decan-8-carbonyl]-benzonitrile,
(342) Methyl 4-[3-benzyl-1-(2-fluorobenzyl)-2-oxo-1,4,8-triazaspiro[4,5]dec-8-yl]-4-oxo-butyrate,
(343) 3-(2-Methylsulfanylethyl)-1-naphthalin-2-ylmethyl-8-(3,4,5-trimethoxybenzoyl)-1,4,8-triazaspiro[4,5]decan-2-one,
(344) Ethyl [3-benzyl-8-(isoxazole-5-carbonyl)-2-oxo-1,4,8-triazaspiro[4,5]dec-1-yl]acetate,
(345) 8-(3-Difluoromethylsulfanylbenzoyl)-1-(2-fluorobenzyl)-1,4,8-triazaspiro[4,5]decan-2-one,
(346) Ethyl [3-benzyl-8-(2,3-dimethylbenzoyl)-2-oxo-1,4,8-triazaspiro[4,5]dec-1-yl]acetate,
(347) 1-(2-Fluorobenzyl)-8-(4-propylbenzoyl)-1,4,8-triazaspiro[4,5]decan-2-one,
(348) 3-[8-(4-Iodobenzoyl)-2-oxo-1,4,8-triazaspiro[4,5]dec-1-ylmethyl]-benzonitrile,
(349) 1-(2-Fluorobenzyl)-8-(2-propylpentanoyl)-1,4,8-triazaspiro[4,5]decan-2-one,
(350) 3-[8-(2,6-Difluoro-3-methylbenzoyl)-3-isopropyl-2-oxo-1,4,8-triazaspiro[4,5]dec-1-ylmethyl]-benzonitrile,
(351) 3-(2-Methylsulfanylethyl)-8-(4-methyl[1,2,3]thiadiazole-5-carbonyl)-1-(2-nitrobenzyl)-1,4,8-triazaspiro[4,5]decan-2-one,
(352) Butyl 4-[3-isobutyl-8-(4-methyl[1,2,3]thiadiazole-5-carbonyl)-2-oxo-1,4,8-triazaspiro[4,5]dec-1-yl]acetate,
(353) 8-[2-(4-Chlorophenoxy)-acetyl]-3-(2-methylsulfanylethyl)-1-naphthalin-2-ylmethyl-1,4,8-triazaspiro[4,5]decan-2-one,
(354) Ethyl [3-benzyl-2-oxo-8-(3-trifluoromethylbenzoyl)-1,4,8-triazaspiro[4,5]dec-1-yl]acetate,
(355) 8-(4-Bromobenzoyl)-3-(2-methylsulfanylethyl)-1-naphthalin-2-ylmethyl-1,4,8-triazaspiro[4,5]decan-2-one,
(356) Ethyl [8-(2-chloropyridin-4-carbonyl)-3-(2-methylsulfanylethyl)-2-oxo-1,4,8-triazaspiro[4,5]dec-1-yl]acetate,
(357) 1-Allyl-8-(3,5-dimethoxybenzoyl)-3-(2-methylsulfanylethyl)-1,4,8-triazaspiro[4,5]decan-2-one,
(358) 3-[8-(4-Methyl-3-nitrobenzoyl)-2-oxo-1,4,8-triazaspiro[4,5]dec-1-ylmethyl]-benzonitrile,
(359) 8-(4-tert-Butylbenzoyl)-1-(2-fluorobenzyl)-1,4,8-triazaspiro[4,5]decan-2-one,
(360) 1-Allyl-3-isopropyl-8-(5-methylisoxazole-3-carbonyl)-1,4,8-triazaspiro[4,5]decan-2-one,
(361) 1-Allyl-3-(2-methylsulfanylethyl)-8-(2-trifluoromethylbenzoyl)-1,4,8-triazaspiro[4,5]decan-2-one, (362) Ethyl [3-benzyl-8-(3-cyclopentylpropionyl)-2-oxo-1,4,8-triazaspiro[4,5]dec-1-yl]acetate,
(363) 3-Benzyl-8-(3,5-difluorobenzoyl)-1-(2-fluorobenzyl)-1,4,8-triazaspiro[4,5]decan-2-one,
(364) Ethyl [3-benzyl-8-(5-fluoro-2-trifluoromethylbenzoyl)-2-oxo-1,4,8-triazaspiro[4,5]dec-1-yl]acetate,
(365) Ethyl [3-benzyl-2-oxo-8-(3,4,5-trimethoxybenzoyl)-1,4,8-triazaspiro[4,5]dec-1-yl]acetate,
(366) Benzyl 2-[1-(2-fluorobenzyl)-2-oxo-1,4,8-triazaspiro[4,5]decan-8-carbonyl]benzoate,
(367) 1-(2-Fluorobenzyl)-8-(2-methylbenzoyl)-1,4,8-triazaspiro[4,5]decan-2-one,
(368) 1-(2-Fluorobenzyl)-8-(2-phenylbutyryl)-1,4,8-triazaspiro[4,5]decan-2-one,
(369) 1-Allyl-8-(6-chloropyridin-3-carbonyl)-3-isopropyl-1,4,8-triazaspiro[4,5]decan-2-one,
(370) Ethyl [8-(2,5-dimethylfuran-3-carbonyl)-3-(2-methylsulfanylethyl)-2-oxo-1,4,8-triazaspiro[4,5]dec-1-yl]acetate,
(371) Ethyl [8-(5-tert-butyl-2-methyl-2H-pyrazole-3-carbonyl)-3-(2-methylsulfanylethyl)-2-oxo-1,4,8-triazaspiro[4,5]dec-1-yl]acetate,
(372) Benzyl 2-[1-allyl-3-(2-methylsulfanylethyl)-2-oxo-1,4,8-triazaspiro[4,5]decan-8-carbonyl]benzoate,
(373) Ethyl 2-[1-allyl-3-(2-methylsulfanylethyl)-2-oxo-1,4,8-triazaspiro[4,5]dec-8-yl]-2-oxo-1-phenylacetate,
(374) 3-[8-(2-Chloro-6-fluorobenzoyl)-3-isopropyl-2-oxo-1,4,8-triazaspiro[4,5]dec-1-ylmethyl]-benzonitrile,
(375) 3-(2-Methylsulfanylethyl)-1-(2-nitrobenzyl)-8-(3-phenylpropionyl)-1,4,8-triazaspiro[4,5]decan-2-one,
(376) 3-[8-(2,3-Dimethylbenzoyl)-3-isopropyl-2-oxo-1,4,8-triazaspiro[4,5]dec-1-ylmethyl]-benzonitrile,
(377) Ethyl [8-(5-fluoro-2-trifluoromethylbenzoyl)-3-(2-methylsulfanylethyl)-2-oxo-1,4,8-triazaspiro[4,5]dec-1-yl]acetate,
(378) Ethyl [8-cyclopentanecarbonyl-3-(2-methylsulfanylethyl)-2-oxo-1,4,8-triazaspiro[4,5]dec-1-yl]acetate,
(379) Ethyl [3-(2-methylsulfanylethyl)-2-oxo-8-(thiophene-2-carbonyl)-1,4,8-triazaspiro[4,5]dec-1-yl]acetate,
(380) 1-Allyl-8-[1-(4-chlorophenyl)-5-trifluoromethyl-1H-pyrazole-4-carbonyl]-3-(2-methylsulfanylethyl)-1,4,8-triazaspiro[4,5]decan-2-one,
(381) 1-Allyl-3-(2-methylsulfanylethyl)-8-(naphthalin-1-carbonyl)-1,4,8-triazaspiro[4,5]decan-2-one,
(382) 1-(2-fluorobenzyl)-8-(4-trifluoromethoxybenzoyl)-1,4,8-triazaspiro[4,5]decan-2-one,
(383) 3-Benzyl-8-(2-benzyloxyacetyl)-1-(2-fluorobenzyl)-1,4,8-triazaspiro[4,5]decan-2-one,
(384) 3-[8-(2-chloro-6-fluoro-3-methylbenzoyl)-3-isopropyl-2-oxo-1,4,8-triazaspiro[4,5]dec-1-ylmethyl]-benzonitrile,
(385) 1-Allyl-8-(2-chloro-5-trifluoromethylbenzoyl)-3-isopropyl-1,4,8-triazaspiro[4,5]decan-2-one,
(386) 8-(3-Methylbenzoyl)-3-(2-methylsulfanylethyl)-1-naphthalin-2-ylmethyl-1,4,8-triazaspiro[4,5]decan-2-one,
(387) 1-(3,5-Dimethylbenzyl)-8-(2-ethylbutyryl)-3-isobutyl-1,4,8-triazaspiro[4,5]decan-2-one,
(388) 8-(5-tert-Butyl-2-methyl-2H-pyrazole-3-carbonyl)-3-(2-methylsulfanylethyl)-1-(2-nitrobenzyl)-1,4,8-triazaspiro[4,5]decan-2-one,
(389) Benzyl 2-[1-(3-cyanobenzyl)-3-isopropyl-2-oxo-1,4,8-triazaspiro[4,5]decan-8-carbonyl]benzoate,
(390) 8-(4-Methyl-3-nitrobenzoyl)-3-(2-methylsulfanylethyl)-1-(2-nitrobenzyl)-1,4,8-triazaspiro[4,5]decan-2-one,
(391) 1-(2,6-Dichlorobenzyl)-3-isobutyl-8-(3,4,5-trimethoxybenzoyl)-1,4,8-triazaspiro[4,5]decan-2-one,
(392) 3-{8-[2-(2-Bromophenyl)-acetyl]-3-isopropyl-2-oxo-1,4,8-triazaspiro[4,5]dec-1-ylmethyl}-benzonitrile,
(393) 3-[8-(2,3-Dichlorobenzoyl)-3-isopropyl-2-oxo-1,4,8-triazaspiro[4,5]dec-1-ylmethyl]-benzonitrile,
(394) 1-Allyl-8-(6-chloro-2H-chroman-3-carbonyl)-3-isopropyl-1,4,8-triazaspiro[4,5]decan-2-one,
(395) Ethyl {3-benzyl-8-[2-(4-methoxyphenyl)-acetyl]-2-oxo-1,4,8-triazaspiro[4,5]dec-1-yl}acetate,
(396) 3-[3-Isopropyl-2-oxo-8-(1-phenyl-5-propyl-1H-pyrazole-4-carbonyl)-1,4,8-triazaspiro[4,5]dec-1-ylmethyl]-benzonitrile,
(397) 8-(3-Cyclopentylpropionyl)-1-(2-fluorobenzyl)-1,4,8-triazaspiro[4,5]decan-2-one,
(398) 1-Allyl-8-(3-difluoromethylsulfanylbenzoyl)-3-isopropyl-1,4,8-triazaspiro[4,5]decan-2-one,
(399) 3-[8-(2-chloro-4-nitrobenzoyl)-3-isopropyl-2-oxo-1,4,8-triazaspiro[4,5]dec-1-ylmethyl]-benzonitrile,
(400) Ethyl [8-(2-ethoxybenzoyl)-3-(2-methylsulfanylethyl)-2-oxo-1,4,8-triazaspiro[4,5]dec-1-yl]acetate,
(401) 8-(2,5-Bis-trifluoromethylbenzoyl)-1-(2-fluorobenzyl)-1,4,8-triazaspiro[4,5]decan-2-one,
(402) 8-(2-Chloropyridin-4-carbonyl)-3-(2-methylsulfanylethyl)-1-(2-nitrobenzyl)-1,4,8-triazaspiro[4,5]decan-2-one,
(403) Ethyl {3-benzyl-8-[3-(2,6-dichlorophenyl)-5-methylisoxazol-4-carbonyl]-2-oxo-1,4,8-triazaspiro[4,5]dec-1-yl}acetate,
(404) 1-(3,5-Dimethylbenzyl)-3-isobutyl-8-(2-trifluoromethylbenzoyl)-1,4,8-triazaspiro[4,5]decan-2-one,
(405) 8-(3,5-Dimethoxybenzoyl)-3-(2-methylsulfanylethyl)-1-(2-nitrobenzyl)-1,4,8-triazaspiro[4,5]decan-2-one,
(406) Benzyl 2-[3-benzyl-1-(2-fluorobenzyl)-2-oxo-1,4,8-triazaspiro[4,5]decan-8-carbonyl]benzoate,
(407) 3-[8-(Benzo[1,2,5]oxadiazole-5-carbonyl)-3-isopropyl-2-oxo-1,4,8-triazaspiro[4,5]dec-1-ylmethyl]-benzonitrile,
(408) Ethyl [3-(2-methylsulfanylethyl)-2-oxo-8-(4-trifluoromethoxybenzoyl)-1,4,8-triazaspiro[4,5]dec-1-yl]acetate,
(409) 1-Allyl-3-isopropyl-8-[2-(4-methoxyphenyl)-acetyl]-1,4,8-triazaspiro[4,5]decan-2-one,
(410) 3-(2-Methylsulfanylethyl)-1-(2-nitrobenzyl)-8-(4-propylbenzoyl)-1,4,8-triazaspiro[4,5]decan-2-one,
(411) 3-Benzyl-8-(4-tert-butylbenzoyl)-1-(2-fluorobenzyl)-1,4,8-triazaspiro[4,5]decan-2-one,
(412) 1-Allyl-8-(2,6-difluoro-3-methylbenzoyl)-3-(2-methylsulfanylethyl)-1,4,8-triazaspiro[4,5]decan-2-one,
(413) 8-(3,5-Bis-trifluoromethylbenzoyl)-1-(2-fluorobenzyl)-1,4,8-triazaspiro[4,5]decan-2-one,
(414) 3-[8-(4-Iodobenzoyl)-3-isopropyl-2-oxo-1,4,8-triazaspiro[4,5]dec-1-ylmethyl]-benzonitrile,
(415) 3-(2-Methylsulfanylethyl)-1-naphthalin-2-ylmethyl-8-(thiophene-2-carbonyl)-1,4,8-triazaspiro[4,5]decan-2-one,
(416) Ethyl [3-benzyl-8-(2-chloropyridin-4-carbonyl)-2-oxo-1,4,8-triazaspiro[4,5]dec-1-yl]acetate,
(417) Ethyl [3-(2-methylsulfanylethyl)-8-(4-nitrobenzoyl)-2-oxo-1,4,8-triazaspiro[4,5]dec-1-yl]acetate,
(418) 8-(2-Ethylhexanoyl)-3-(2-methylsulfanylethyl)-1-(2-nitrobenzyl)-1,4,8-triazaspiro[4,5]decan-2-one,
(419) 1-(2,6-Dichlorobenzyl)-3-isobutyl-8-(thiophene-2-carbonyl)-1,4,8-triazaspiro[4,5]decan-2-one,
(420) Ethyl [3-benzyl-8-(2-chloro-4-nitrobenzoyl)-2-oxo-1,4,8-triazaspiro[4,5]dec-1-yl]acetate,
(421) 3-Benzyl-8-(3,5-bis-trifluoromethylbenzoyl)-1-(2-fluorobenzyl)-1,4,8-triazaspiro[4,5]decan-2-one, (422) Ethyl [3-benzyl-8-(4-bromo-3-methylbenzoyl)-2-oxo-1,4,8-triazaspiro[4,5]dec-1-yl]acetate,
(423) 8-Cyclohexanecarbonyl-3-(2-methylsulfanylethyl)-1-(2-nitrobenzyl)-1,4,8-triazaspiro[4,5]decan-2-one,
(424) 8-(2,5-Dimethylfuran-3-carbonyl)-3-(2-methylsulfanylethyl)-1-(2-nitrobenzyl)-1,4,8-triazaspiro[4,5]decan-2-one,
(425) 8-(3-Difluoromethylsulfanylbenzoyl)-3-(2-methylsulfanylethyl)-1-(2-nitrobenzyl)-1,4,8-triazaspiro[4,5]decan-2-one,
(426) 8-(Furan-2-carbonyl)-3-(2-methylsulfanylethyl)-1-(2-nitrobenzyl)-1,4,8-triazaspiro[4,5]decan-2-one,
(427) Ethyl [3-benzyl-8-(2,3-difluorobenzoyl)-2-oxo-1,4,8-triazaspiro[4,5]dec-1-yl]acetate,
(428) 3-[3-Isopropyl-8-(4-methyl[1,2,3]thiadiazole-5-carbonyl)-2-oxo-1,4,8-triazaspiro[4,5]dec-1-ylmethyl]-benzonitrile,
(429) 3-[8-(3-Chloro-2-fluorobenzoyl)-3-isopropyl-2-oxo-1,4,8-triazaspiro[4,5]dec-1-ylmethyl]-benzonitrile,
(430) Ethyl [3-benzyl-8-(naphthalin-1-carbonyl)-2-oxo-1,4,8-triazaspiro[4,5]dec-1-yl]acetate,
(431) 8-(4-tert-Butylbenzoyl)-3-(2-methylsulfanylethyl)-1-(2-nitrobenzyl)-1,4,8-triazaspiro[4,5]decan-2-one,
(432) 3-[3-Benzyl-1-(2-fluorobenzyl)-2-oxo-1,4,8-triazaspiro[4,5]decan-8-carbonyl]-benzonitrile,
(433) 1-(2,6-Dichlorobenzyl)-8-(furan-2-carbonyl)-3-isobutyl-1,4,8-triazaspiro[4,5]decan-2-one,
(434) 8-(2,6-Dichlorobenzoyl)-1-(2-fluorobenzyl)-1,4,8-triazaspiro[4,5]decan-2-one,
(435) 1-(3,5-Dimethylbenzyl)-8-(3-fluoro-4-trifluoromethylbenzoyl)-3-isobutyl-1,4,8-triazaspiro[4,5]decan-2-one,
(436) 1-(2-Fluorobenzyl)-8-(3-fluoro-4-methylbenzoyl)-1,4,8-triazaspiro[4,5]decan-2-one,
(437) 1-Allyl-8-(3-cyclopentylpropionyl)-3-(2-methylsulfanylethyl)-1,4,8-triazaspiro[4,5]decan-2-one,
(438) 8-[2-(3-Chlorophenoxy)-acetyl]-3-(2-methylsulfanylethyl)-1-(2-nitrobenzyl)-1,4,8-triazaspiro[4,5]decan-2-one,
(439) 1-(3,5-Dimethylbenzyl)-3-isobutyl-8-(2-methylsulfanylpyridin-3-carbonyl)-1,4,8-triazaspiro[4,5]decan-2-one,
(440) 3-(2-Methylsulfanylethyl)-1-(2-nitrobenzyl)-8-propionyl-1,4,8-triazaspiro[4,5]decan-2-one,
(441) 3-[8-(3,4-Dimethoxybenzoyl)-3-isopropyl-2-oxo-1,4,8-triazaspiro[4,5]dec-1-ylmethyl]-benzonitrile,
(442) 3-(2-Methylsulfanylethyl)-8-(naphthalin-2-carbonyl)-1-naphthalin-2-ylmethyl-1,4,8-triazaspiro[4,5]decan-2-one,
(443) 8-(6-Chloro-2H-chroman-3-carbonyl)-3-(2-methylsulfanylethyl)-1-(2-nitrobenzyl)-1,4,8-triazaspiro[4,5]decan-2-one,
(444) Ethyl {3-benzyl-2-oxo-8-[3-(3-trifluoromethylphenyl)-acryloyl]-1,4,8-triazaspiro[4,5]dec-1-yl}acetate,
(445) 1-(3,5-Dimethylbenzyl)-3-isobutyl-8-(3-phenylacryloyl)-1,4,8-triazaspiro[4,5]decan-2-one,
(446) 3-[3-Isopropyl-2-oxo-8-(2-phenoxypropionyl)-1,4,8-triazaspiro[4,5]dec-1-ylmethyl]-benzonitrile,
(447) 3-[3-Isopropyl-2-oxo-8-(4-trifluoromethoxybenzoyl)-1,4,8-triazaspiro[4,5]dec-1-ylmethyl]-benzonitrile,
(448) 1-Allyl-3-(2-methylsulfanylethyl)-8-(3-nitrobenzoyl)-1,4,8-triazaspiro[4,5]decan-2-one,
(449) Ethyl [3-benzyl-8-(3,4-dichlorobenzoyl)-2-oxo-1,4,8-triazaspiro[4,5]dec-1-yl]acetate,
(450) 1-(2-Fluorobenzyl)-8-[3-(3-trifluoromethylphenyl)-acryloyl]-1,4,8-triazaspiro[4,5]decan-2-one,
(451) 1-Allyl-8-(3,5-bis-trifluoromethylbenzoyl)-3-(2-methylsulfanylethyl)-1,4,8-triazaspiro[4,5]decan-2-one,
(452) 8-(3-Cyclopentylpropionyl)-3-(2-methylsulfanylethyl)-1-(2-nitrobenzyl)-1,4,8-triazaspiro[4,5]decan-2-one,
(453) 1-(3,5-Dimethylbenzyl)-3-isobutyl-8-(4-nitrobenzoyl)-1,4,8-triazaspiro[4,5]decan-2-one,
(454) 8-(3-Cyclopentylpropionyl)-1-(3,5-dimethylbenzyl)-3-isobutyl-1,4,8-triazaspiro[4,5]decan-2-one,
(455) 3-[3-Isopropyl-8-(isoxazole-5-carbonyl)-2-oxo-1,4,8-triazaspiro[4,5]dec-1-ylmethyl]-benzonitrile und
(456) 3-Benzyl-1-(2-fluorobenzyl)-8-(2-methyl-6-trifluoromethylpyridin-3-carbonyl)-1,4,8-triazaspiro[4,5]decan-2-one, in each case optionally in the form of one of the pure stereoisomers thereof, particularly enantiomers or diastereoisomers thereof, or the racemates thereof or in the form of a mixture of stereoisomers and particularly of the enantiomers and/or diastereoisomers in an arbitrary blending ratio, or in each case in the form of appropriate salts, preferably hydrochlorides, or in each case in the form of appropriate solvates.

Another object of the present invention is the provision of a process for the production of the substituted 1,4,8-triazaspiro[4,5]decan-2-one compounds of the invention, according to which a protected piperidin-4-one of the general formula II,

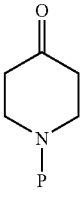

II in which P stands for a protective group, is converted, by reaction with at least one compound of the general formula III,

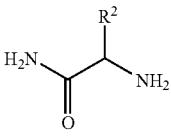

III in which $R^2$ has the aforementioned meaning, to at least one compound of the general formula IV,

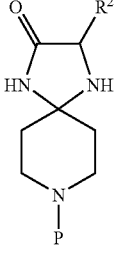

IV in which P and $R^2$ have the aforementioned meanings, which is optionally purified and/or optionally isolated, and optionally converted, by reaction with at least one compound of the general formula $R^1$—$X^1$, in which $R^1$ has the aforementioned meaning and $X^1$ stands for a suitable leaving group, preferably for a halogen radical, optionally in the presence of at least one base, to at least one compound of the general formula V,

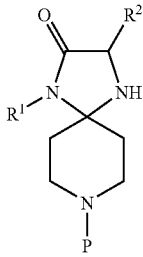

in which $R^1$, $R^2$ and P have the aforementioned meanings, which compound is optionally purified and/or optionally isolated, and optionally converted, by splitting-off the protective group P, to at least one compound of the general formula VI,

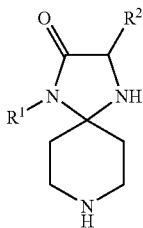

which compound is optionally purified and/or optionally isolated, and optionally at least one compound of the general formula IV, V or VI is converted, by reaction with a carboxylic derivative of the general formula $R^4$—(C=O)—$X^2$, a carboxylic anhydride of the general formula $(R^4$—(C=O)—$)_2$O, or a compound of the general formula $R^3$—$X^3$ in which the radical $R^3$ has the aforementioned meaning with the exception of hydrogen and —(C=O)—$R^4$, each $R^4$ having the aforementioned meaning and $X^2$ and $X^3$ both stand for a suitable leaving group, preferably for a halogen radical, to at least one of the substituted 1,4,8-triazaspiro[4,5]decan-2-one compounds of the invention, and the latter compound is optionally purified and/or optionally isolated, or 4-piperidone of the formula VII, optionally in the form of a corresponding salt,

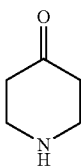

is converted, by reaction with a carboxylic derivative of the general formula $R^4$—(C=O)—$X^2$, a carboxylic anhydride of the general formula $(R^4$—(C=O)—$)_2$O or a compound of the general formula $R^3$—$X^3$ in which $R^3$ has the aforementioned meaning with the exception of hydrogen and (C=O)—$R^4$, each radical $R^4$ having the aforementioned meaning and $X^2$ and $X^3$ each stand for a suitable leaving group, preferably for a halogen radical, to a compound of the general formula VIII,

in which $R^3$ has the aforementioned meaning, this being optionally purified and/or isolated and converted, by reaction with at least one compound of the general formula III

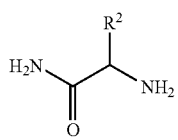

in which $R^2$ has the aforementioned meaning, to at least one compound of the general formula IX,

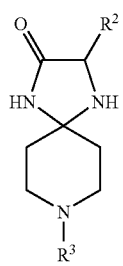

in which $R^2$ and $R^3$ each have the aforementioned meanings, this being optionally purified and/or isolated and converted, by reaction with at least one compound of the general formula $R^1$—$X^1$ in which $R^1$ and $X^1$ have the aforementioned meanings, optionally in the presence of at least one base, to at least one of the substituted 1,4,8-triazaspiro[4,5]decan-2-one compounds of the invention, which is optionally purified and/or isolated.

The N-protected piperidin-4-one compounds of the general formula II are—as are also unprotected piperidin-2-one and appropriate salts such as its hydrochloride—commercially available or can be prepared by conventional methods known to the person skilled in the art. Suitable protective groups are, for example, trifluoroacetamide, methoxycarbonyl, ethoxycarbonyl, tert-butoxycarbonyl, carbobenzoxy, allyloxycarbonyl, or 9-fluorenylmethoxycarbonyl, The amino-acid amides of the general formula III, which can be used in the process of the invention also in the form of the appropriate salt thereof, are likewise commercially available or can be prepared by conventional methods known to the person skilled in the art. The respective amino-acid amides can be used in the process of the invention both in enantiomerically pure form, ie in (S) or (R) configuration, or in the form of a preferably racemic mixture showing an (S,R) configuration.

The reaction of compounds of the general formula II with compounds of the general formula III to produce N-protected, optionally 3-substituted 1,4,8-triazaspiro[4,5]decan-2-one compounds of the general formula IV can be carried out under conventional conditions known to the person skilled in the art. Preferably, the conversion is carried out in a suitable reaction medium, for example, in one or more dry organic solvents. Suitable solvents are, for example, alcohols, such as ethanol, or chlorinated hydrocarbons such as dichloromethane or chloroform. The temperature employed while combining and reacting the reactants can vary over a wide range.

The reaction of an N-protected, optionally 3-substituted 1,4,8-triazaspiro[4,5]decan-2-one compound of the general formula IV with a compound of the general formula $R^1$—$X^1$ to form compounds of the general formula V preferably carried out in a reaction medium in the presence of at least one organic base and/or in the presence of at least one inorganic base under conventional conditions known to the person skilled in the art. The reaction may be advantageously carried out in a microwave oven.

Suitable inorganic bases are, for example, metal alcoholates such as sodium methanolate, sodium ethanolate, potassium tert-butylate, lithium or sodium bases such as lithium diisopropylamide, butyllithium, tert-butyllithium, sodium methoxide or metal hydrides such as potassium hydride, lithium hydride, sodium hydride. Suitable organic bases are, for example, diisopropylethylamine or triethylamine. Suitable reaction media are organic solvents such as tetrahydrofuran.

Elimination of the protective group (P) for the production of non-N-protected, optionally 1-substituted and/or 3-substituted 1,4,8-triazaspiro[4,5]decan-2-one compounds of the general formula VI can likewise be carried out under conventional conditions known to the person skilled in the art, which vary according to the protective group used. Mention may be made, for example, of elimination in the presence of an inorganic base, an inorganic acid, or a Lewis acid, such as potassium carbonate, lithium hydroxide, potassium hydroxide, sulfuric acid, hydrobromic acid, hydrofluoric acid, hydrochloric acid, boron trifluoride etherate, boron trichloride, or in the presence of an organic acid such as trifluoroacetic acid, trifluoromethanesulfonic acid, acetic acid, or in the presence of an organic base, such as morpholine, triethylamine, diethylamine, diisopropylethylamine, pyridine, or by hydrogenation.

The respective compounds of the general formula IV, V, or VI, particularly the respective compound of the general formula VI, can subsequently be converted to the respective substituted 1,4,8-triazaspiro[4,5]decan-2-one compound of the invention including corresponding stereoisomers thereof by reaction with a carboxylic derivative of the general formula $R^4$—(C=O)—$X^2$ or a carboxylic anhydride of the general formula $(R^4$—(C=O)$)_2$O, in which each radical $R^4$ has the aforementioned meaning and $X^2$ stands for a suitable leaving group, preferably for a halogen radical, preferably in the presence of at least one organic base and/or at least one inorganic base such as diisopropylethylamine, triethylamine, pyridine, or diethylamine, optionally in the presence of a suitable catalyst such as DMAP (dimethylaminopyridine), by conventional methods known to the person skilled in the art.

The respective compounds of the general formula IV, V, or VI, particularly the respective compound of the general formula VI, can also then be converted to the respective substituted 1,4,8-triazaspiro[4,5]decan-2-one compound of the invention including corresponding stereoisomers by reaction with a compound of the general formula $R^3$—$X^3$, in which $R^3$ has the aforementioned meaning with the exception of hydrogen and (C=O)—$R^4$ and $X^2$ stands for a suitable leaving group, preferably for a halogen radical such as chlorine, preferably in the presence of at least one organic base and/or at least one inorganic base such as diisopropylethylamine, triethylamine, pyridine, or diethylamine, by conventional methods known to the person skilled in the art.

The conversion of compounds of the general formula IV, V, or VI, particularly compounds of the general formula VI, to a substituted 1,4,8-triazaspiro[4,5]decan-2-one compound of the general formula I of the invention is preferably carried out in a suitable reaction medium, for example, in one or more dry organic solvents. Suitable solvents are, for example, optionally chlorinated and optionally aromatic hydrocarbons such as toluene, dichloromethane, or chloroform. The temperature employed while combining and reacting the reactants can vary over a wide range.

The reaction of 4-piperidone, preferably in the form of the hydrochloride salt, with a carboxylic derivative $R^4$—(C=O)—$X^2$ or a carboxylic acid anhydride $(R^4$—(C=O)$)_2$O is preferably carried out in the presence of at least one organic base and/or in the presence of at least one inorganic base. Examples of suitable bases are diisopropylethylamine, triethylamine, pyridine, or diethylamine.

The reaction of 4-piperidone, preferably in the form of the hydrochloride salt, with a compound $R^3$—$X^3$, in which $R^3$ has the aforementioned meaning with the exception of hydrogen and (C=O)—$R^4$ and $X^3$ stands for a suitable leaving group, preferably for a halogen radical such as chlorine, is preferably carried out in the presence of at least one organic base and/or in the presence of at least one inorganic base. Examples of suitable organic bases are diisopropylethylamine, triethylamine, pyridine, or diethylamine. Dried organic solvents such as dry tetrahydrofuran are preferably used as reaction medium.

The reaction of compounds of the general formula VIII with compounds of the general formula III to produce 3-substituted 1,4,8-triazaspiro[4,5]decan-2-one compounds of the general formula IX can be carried out under conventional conditions known to the person skilled in the art. Preferably, the conversion is carried out in a suitable reaction medium, for example, in one or more dry organic solvents. Suitable solvents are, for example, alcohols, such as ethanol, or chlorinated hydrocarbons such as dichloromethane or chloroform. The temperature employed while combining and reacting the reactants can vary over a wide range.

The reaction of a 3-substituted 1,4,8-triazaspiro[4,5]decan-2-one compound of the general formula IX with a compound of the general formula $R^1$—$X^1$ to produce a 1,4,8-triazaspiro[4,5]decan-2-one compound of the invention is preferably carried out in a reaction medium in the presence of at least one organic base and/or in the presence of at least one inorganic base under conventional conditions known to the person skilled in the art. The reaction may be advantageously carried out in a microwave oven. Suitable inorganic bases are, for example, metal alcoholates such as sodium methanolate, sodium ethanolate, potassium tert-butylate, lithium or sodium bases such as lithium diisopropylamide, butyllithium, tert-butyllithium, sodium methoxide or metal hydrides such as potassium hydride, lithium hydride, sodium hydride. Suitable organic bases are, for example, diisopropylethylamine or triethylamine. Suitable reaction media are organic solvents such as tetrahydrofuran.

The compounds of the general formulas $R^1$—$X^1$, $R^4$—(C=O)—$X^2$ and $(R^4$—(C=O)$)_2$O are commercially available and/or can be prepared by conventional methods known to the person skilled in the art. $X^1$ and $X^2$ are conventional leaving groups known to the person skilled in the art and are preferably halogen radicals and more preferably chlorine radicals.

The intermediates and end products prepared by the aforementioned reactions can in each case be isolated and/or purified by conventional methods known to the person skilled in the art, if desired and/or necessary. Suitable purifying methods are, for example, extraction processes and chromatographic processes such as column chromatography or preparative chromatography.

The substituted 1,4,8-triazaspiro[4,5]decan-2-one compounds of the above general formula I of the invention and also, where applicable, the corresponding stereoisomers can be obtained by conventional methods known to the person skilled in the art in the form of appropriate salts, particularly in the form of corresponding physiologically acceptable salts, and the medicinal drug of the invention can comprise one or more salts of one or more of these compounds.

The respective salts of the substituted 1,4,8-triazaspiro[4,5]decan-2-one compounds of the invention illustrated by the above general formula I can be obtained, for example, by reaction with one or more inorganic acids and/or one or more organic acids. Suitable acids can be selected preferably from the group consisting of perchloric acid, hydrochloric acid, hydrobromic acid, sulfuric acid, methanesulfonic acid, formic acid, acetic acid, oxalic acid, succinic acid, tartaric acid, mandelic acid, fumaric acid, lactic acid, citric acid, glutamic acid, saccharinic acid, cyclohexanesulfamidic acid, aspartame, monomethylsebacic acid, 5-oxoproline, 1-hexane sulfonic acid, nicotinic acid, 2-aminobenzoic acid, 3-aminobenzoic acid, or 4-aminobenzoic acid, 2,4,6-trimethylbenzoic acid, alpha-lipoic acid, acetylglycine, hippuric acid, phosphoric acid, maleic acid, malonic acid, and aspartic acid. The corresponding hydrochloride salts are preferably obtained by reaction with trimethylsilyl chloride in ethyl methyl ketone.

The substituted 1,4,8-triazaspiro[4,5]decan-2-one compounds of the invention illustrated by the above general formula I and also, where applicable, the corresponding stereoisomers and physiologically acceptable salts thereof may also be obtained in the form of the solvates thereof, particularly in the form of the hydrates thereof by conventional methods known to the person skilled in the art.

If the substituted 1,4,8-triazaspiro[4,5]decan-2-one compounds of the invention illustrated by the above general formula I following production thereof are obtained in the form of a mixture of the stereoisomers thereof, preferably in the form of the racemates thereof or other mixtures of the various enantiomers and/or diastereoisomers thereof, they can be separated and optionally isolated by conventional methods known to the person skilled in the art. Mention may be made, for example, of chromatographic separation methods, particularly liquid chromatography methods under standard pressure or at elevated pressure, preferably MPLC and HPLC methods, and also methods involving fractional crystallization. This can particularly involve the separation of individual enantiomers, eg, diastereoisomeric salts formed by means of HPLC in the chiral phase or by means of crystallization with chiral acids, for example (+)-tartaric acid, (−)-tartaric acid, or (+)-10-camphorsulfonic acid.

It has now been found, surprisingly, that the 1,4,8-triazaspiro[4,5]decan-2-one compounds of the above general formula I are not only suitable for regulation and preferably for inhibition of noradrenalin reuptake and/or for regulation, and preferably for inhibition of 5-hydroxy tryptophane reuptake, but also show a high affinity to opioid receptors, particularly for µ-opioid receptors and for batrachotoxin (BTX) receptors and are therefore particularly suitable for use as pharmaceutically active substances in medicinal drugs for the prophylaxis and/or treatment of disorders associated with these receptors or processes.

The 1,4,8-triazaspiro[4,5]decan-2-one compounds of the above general formula I and, if applicable, the corresponding stereoisomers and also the corresponding salts and solvates are toxicologically safe and are therefore suitable for use as pharmaceutically active substances in medicinal drugs.

Another object of the present invention is therefore the provision of a medicinal drug containing at least one 1,4,8-triazaspiro[4,5]decan-2-one compound of the invention of the above general formula I, optionally in the form of a pure stereoisomer thereof particularly enantiomer or diastereoisomer, of the racemate thereof or in the form of a mixture of stereoisomers and particularly of the enantiomers and/or diastereoisomers in an arbitrary blending ratio, or in each case in the form of a corresponding salt, preferably hydrochloride, or in each case in the form of a corresponding solvate, and also, where applicable, containing at least one pharmaceutically compatible adjuvant.

Preference is given to a medicinal drug containing at least one 1,4,8-triazaspiro[4,5]decan-2-one compound of the above general formula I except for the compounds according to A) and/or except for the compound according to B), optionally in the form of one of the pure stereoisomers, particularly enantiomers or diastereoisomers thereof, in the form of the racemate thereof, or in the form of a mixture of stereoisomers, particularly enantiomers and/or diastereoisomers, in an arbitrary blending ratio, or in each case in the form of a corresponding salt, preferably hydrochloride, or in each case in the form of a corresponding solvate, and also optionally containing at least one pharmaceutically compatible adjuvant.

The medicinal drug of the invention is preferably suitable for regulation, particularly for inhibition, of noradrenalin reuptake (noradrenalin uptake), for regulation, particularly for inhibition, of 5-hydroxy tryptophane reuptake (5-HT uptake), for opioid receptor regulation, particularly for µ-opioid receptor regulation and/or for batrachotoxin (BTX) receptor regulation.

The medicinal drug of the invention is likewise preferentially suitable for prophylaxis and/or treatment of disturbances in food intake, preferably selected from the group consisting of bulimia, anorexia, obesity, and cachexia, more preferably for prophylaxis and/or treatment of obesity.

The medicinal drug of the invention is likewise preferentially suitable for prophylaxis and/or treatment of pain, preferably for treatment and/or prophylaxis of acute pain, chronic pain, neuropathic pain and/or cluster headache, or for prophylaxis and/or treatment of depression.

The medicinal drug of the invention is more preferably suitable for combined prophylaxis and/or treatment of depression and pain, preferably for the combined treatment of depression and pain selected from the group consisting of acute pain, chronic pain, neuropathic pain, and cluster headache.

Most preferably, the medicinal drug of the invention is suitable for prophylaxis and/or treatment of abuse of alcohol and/or drugs and/or medicaments, for prophylaxis and/or treatment of addiction to alcohol and/or drugs and/or medicines, for prophylaxis and/or treatment of inflammations, for prophylaxis and/or treatment of lethargy, for prophylaxis and/or treatment of catalepsy, for vigilance enhancement, for libido enhancement, for anxiolysis, for prophylaxis and/or treatment of neurodegenerative disorders, preferably one or more neurodegenerative disorders selected from the group consisting of Morbus Parkinson, Morbus Huntington, Morbus Alzheimer and multiple sclerosis, for prophylaxis and/or treatment of ischemia, and/or for local anesthesia.

Another object of the present invention is the use of at least one substituted 1,4,8-triazaspiro[4,5]decan-2-one compound of the general formula I of the invention, optionally in the form of one of the pure stereoisomers, particularly enantiomers or diastereoisomers thereof, in the form of the racemate thereof, or in the form of a mixture of stereoisomers, particularly enantiomers and/or diastereoisomers, in an arbitrary blending ratio, or in each case in the form of a corresponding salt, preferably hydrochloride, or in each case in the form of a corresponding solvate, for the production of a medicinal drug for regulation of noradrenalin reuptake (noradrenalin uptake), preferably for inhibition of noradrenalin reuptake (noradrenalin uptake), for regulation of 5-hydroxy tryptophane reuptake (5-HT uptake), preferably for inhibition of 5-hydroxy tryptophane reuptake (5-HT uptake), for opioid receptor regulation, preferably for µ-opioid receptor regulation and/or for batrachotoxin (BTX) receptor regulation.

The use of at least one substituted 1,4,8-triazaspiro[4,5]decan-2-one compound of the general formula I of the invention, optionally in the form of one of the pure stereoisomers, particularly enantiomers or diastereoisomers thereof, in the form of the racemate thereof, or in the form of a mixture of stereoisomers, particularly enantiomers and/or diastereoisomers, in an arbitrary blending ratio, or in each case in the form of a corresponding salt, preferably hydrochloride, or in each case in the form of a corresponding solvate is preferred for the production of a medicinal drug for prophylaxis and/or treatment of disturbances in food intake, preferably selected from the group consisting of bulimia, anorexia, obesity, and cachexia, more preferably obesity.

The use of at least one substituted 1,4,8-triazaspiro[4,5]decan-2-one compound of the general formula I of the invention, optionally in the form of one of the pure stereoisomers, particularly enantiomers or diastereoisomers thereof, in the form of the racemate thereof, or in the form of a mixture of stereoisomers, particularly enantiomers and/or diastereoisomers, in an arbitrary blending ratio, or in each case in the form of a corresponding salt, preferably hydrochloride, or in each case in the form of a corresponding solvate is preferred for the production of a medicinal drug for prophylaxis and/or treatment of pain, preferably of acute pain, chronic pain, neuropathic pain, and/or cluster headache.

Also preferred is the use of at least one substituted 1,4,8-triazaspiro[4,5]decan-2-one compound of the general formula I of the invention, optionally in the form of one of the pure stereoisomers, particularly enantiomers or diastereoisomers thereof, in the form of the racemate thereof, or in the form of a mixture of stereoisomers, particularly enantiomers and/or diastereoisomers, in an arbitrary blending ratio, or in each case in the form of a corresponding salt, preferably hydrochloride, or in each case in the form of a corresponding solvate for the production of a medicinal drug for prophylaxis and/or treatment of depression.

It is also preferred to use at least one substituted 1,4,8-triazaspiro[4,5]decan-2-one compound of the general formula I of the invention, optionally in the form of one of the pure stereoisomers, particularly enantiomers or diastereoisomers thereof, in the form of the racemate thereof, or in the form of a mixture of stereoisomers, particularly enantiomers and/or diastereoisomers thereof, in an arbitrary blending ratio, or in each case in the form of a corresponding salt, preferably hydrochloride, or in each case in the form of a corresponding solvate for the production of a medicinal drug for combined prophylaxis and/or treatment of depression and pain, preferably for the combined treatment of depression and pain selected from the group consisting of acute pain, chronic pain, neuropathic pain and cluster headache.

Preferred is also the use of at least one substituted 1,4,8-triazaspiro[4,5]decan-2-one compound of the general formula I of the invention, optionally in the form of one of the pure stereoisomers, particularly enantiomers or diastereoisomers thereof, in the form of the racemate thereof, or in the form of a mixture of stereoisomers thereof, particularly enantiomers and/or diastereoisomers, in an arbitrary blending ratio, or in each case in the form of a corresponding salt, preferably hydrochloride, or in each case in the form of a corresponding solvate, for the production of a medicinal drug for prophylaxis and/or treatment of abuse of alcohol and/or drugs and/or medicaments, for prophylaxis and/or treatment of addiction to alcohol and/or drugs and/or medicines, for prophylaxis and/or treatment of inflammations, for prophylaxis and/or treatment of lethargy, for prophylaxis and/or treatment of catalepsy, for vigilance enhancement, for libido enhancement, for anxiolysis, for prophylaxis and/or treatment of neurodegenerative disorders, preferably one or more neurodegenerative disorders selected from the group consisting of Morbus Parkinson, Morbus Huntington, Morbus Alzheimer and multiple sclerosis, for prophylaxis and/or treatment of ischemia and/or for local anesthesia.

Particularly preferred can be the use in each case of at least one substituted 1,4,8-triazaspiro[4,5]decan-2-one compound of the general formula I of the invention except for the compounds according to A) and/or except for the compound according to B), in each case optionally in the form of one of the pure stereoisomers, particularly enantiomers or diastereoisomers thereof, in the form of the racemate thereof, or in the form of a mixture of stereoisomers, particularly enantiomers and/or diastereoisomers, in an arbitrary blending ratio, or in each case in the form of a corresponding salt, preferably hydrochloride, or in each case in the form of a corresponding solvate, for the production of a medicinal drug for prophylaxis and/or treatment of the aforementioned diseases or disorders.

The medicinal drug of the invention is suitable for administration to adults and children including infants and babies.

The medicinal drug of the invention can exist as liquid, semisolid, or solid pharmaceutical dosage forms, for example in the form of injection fluids, drops, juices, syrups, sprays, suspensions, tablets, patches, capsules, plasters, suppositories, ointments, creams, lotions, gels, emulsions, aerosols or in multiparticular form, for example in the form of pellets or granules, optionally compressed to tablets, filled into capsules or suspended in a liquid, and can be administered as such.

In addition to the said one or more substituted 1,4,8-triazaspiro[4,5]decan-2-one compounds of the above general formula I used in the medicinal drug of the invention optionally in the form of the pure stereoisomers thereof, particularly enantiomers or diastereoisomers thereof or the racemate thereof or in the form of mixtures of the stereoisomers thereof, particularly the enantiomers or diastereoisomers, in an arbitrary blending ratio, or optionally in the form of a corresponding salt or in each case in the form of a corresponding solvate, the medicinal drug of the invention usually contains further physiologically acceptable pharmaceutical adjuvants, which can be selected preferably from the group consisting of support materials, fillers, solvents, diluents, surfactants, dyes, preservatives, blasting agents, lubricants, slip agents, flavors, and binding agents.

The selection of the physiologically acceptable adjuvants and the amounts thereof to be used depends on whether the medicinal drug is to be administered orally, subcutaneously, parenterally, intravenously, intraperitoneally, intradermally, intramuscularly, intranasally, buccally, rectally, or locally, eg, for infections of the skin, the mucous membranes, or the eyes. Preparations preferably suitable for oral administration are in the form of tablets, dragees, capsules, granules, pellets, drops, juices, and syrups, and for parenteral, topical, and inhalative administration, suitable preparations are solutions, suspensions, readily reconstructable dry preparations, and also sprays.

The substituted 1,4,8-triazaspiro[4,5]decan-2-one compounds used in the medicinal drug of the invention in a depot in dissolved form or in a patch, optionally with the addition of skin penetration enhancing agents, are suitable percutane administration forms. Orally or percutaneously administered formulations can afford delayed release of the respective substituted 1,4,8-triazaspiro[4,5]decan-2-one compounds.

The production the medicinal drug of the invention is carried out using conventional well-known means, devices, methods, and processes known in the prior art, as described, for example, in "Remington's Pharmaceutical Sciences", Editor A. R. Gennaro, 17th Edition, Mack Publishing Company, Easton, Pa., 1985, particularly in Section 8, Chapters 76 to 93. The relevant description is included herein by reference and is to be regarded as part of the disclosure.

The amount of the respective substituted 1,4,8-triazaspiro[4,5]decan-2-one compound to be administered to the patient can vary and is dependent, for example, on the weight and age of the patient and also on the method of administration, the indication and the severity of the disorder. Usually from 0.005 to 50 mg/kg, preferably from 0.05 to 50 mg/kg of body weight of the patient of at least one substituted 1,4,8-triazaspiro[4,5]decan-2-one compound of the invention are administered.

Pharmacological Methods:

I. Analgesic Test Using the Writhing Test on Mice

The analysis of analgesic activity is carried out using the phenylquinone-induced writhing assay in mice, modified as described in the article by I. C. Hendershot and J. Forsaith ((1959) in J. Pharmacol. Exp. Ther. 125, 237-240). The relevant description is incorporated herein by reference and is to be regarded as part of the present disclosure.

For the present purpose, male NMRI mice are used having a weight of from 25 to 30 g. Groups of 10 animals per substance dose receive, 10 minutes after an intravenous dose of test substances, an intraperitoneal administration of 0.3 ml/mouse of a 0.02% strength aqueous solution of phenylquinone (phenylbenzoquinone, obtainable from Sigma, Deisenhofen; solution produced with the addition of 5% of ethanol and storage in a water bath at 45° C.). The animals are placed individually in observation cages. Using a pushbutton counter, the number of pain-induced stretching movements (so-called writhing reactions=straightening of the body accompanied by stretching of the rear extremities) was counted over a period of from 5 to 20 minutes following the administration of phenylquinone. The control is provided by animals receiving only physiological saline. All substances are tested using the standard dosage of 10 mg/kg. Percentage inhibition (% inhibition) of the writhing reaction by a substance is calculated using the following formula:

% Inhibition=100−writhing reactions of the treated animals times 100 divided by writhing reactions of the control animals For some substances, the dose-related drop in writhing reactions compared with co-examined phenylquinone control groups is used to calculate, by means of regressional analysis (evaluation program Martens EDV Service, Eckental), the ED50 values showing a 95% confidence interval of the writhing reaction.

II. Method of Determining the Affinity to the Human µ-Opioid Receptor:

The receptor affinity to the human µ-opioid receptor is determined in a homogeneous batch in microtiter plates. For this purpose, dilution series of the substances to be tested are incubated at room temperature for 90 minutes in a total volume of 250 µL with a receptor membrane preparation (15-40 µg of protein/250 µL of incubation batch) of CHO-K1 cells which express the human µ-opioid receptor (RB-HOM receptor membrane preparation supplied by NEN, Zaventem, Belgium) in the presence of 1 nmol/L of the radioactive ligand [$^3$H]-naloxone (NET 719, supplied by NEN, Zaventem, Belgium), and of 1 mg of WGA-SPA beads (wheat germ agglutinin SPA beads supplied by Amersham/Pharmacia, Freiburg, Germany). As incubation buffer, 50 mmol/L of tris HCl supplemented with 0.05% (weight/volume) of sodium azide and with 0.06% (weight/volume) of bovine serum albumin is used. For determination of the nonspecific binding, 25 µmol/L of naloxone are added. On completion of the ninety-minute incubation time, the microtiter plates are centrifuged for 20 minutes at 1000 g and the radioactivity is measured in a β-counter (Microbeta-Trilux, supplied by PerkinElmer Wallac, Freiburg, Germany). The percentage displacement of the radioactive ligand from its binding to the human µ-opioid receptor at a concentration of the test substances of 1 µmol/L is determined and indicated as the percentage inhibition of the specific binding.

Based on the percentage displacement produced by different concentrations of the test substances, $IC_{50}$ inhibitory concentrations are calculated which cause a 50 percent displacement of the radioactive ligand. As a result of recalculation using the Cheng-Prusoff relationship, the $K_i$ values for the test substances can be obtained, as described in the publication of Y. Cheng, W. H. Prusoff, 1973, Biochem. Pharmacol., 22, pages 3099-3108. The relevant description is included herein by reference and is to be regarded as part of the present disclosure.

III. Method of Determining the Inhibition of Noradrenaline Uptake or 5-HT Uptake:

For in vitro studies, synaptosomes of rat brain areas are freshly isolated, as described in the article "The isolation of nerve endings from brain" by E. G. Gray and V. P. Whittaker, J. Anatomy 96, pages 79-88, 1962. The relevant literature reference is enclosed herein by reference and is to be regarded as part of the disclosure.

The tissue (hypothalamus for the determination of the noradrenaline uptake inhibition and marrow and pons for determination of the 5-HT uptake inhibition) is homogenized in ice-cooled 0.32 M sucrose (100 mg of tissue/1 mL) in a glass homogenizer with teflon pestle by carrying out five full up and down strokes at 840 rpm.

The homogenate is centrifuged at 4° C. for 10 minutes at 1000 g. Following subsequent centrifugation at 17,000 g for 55 minutes, the synaptosomes (P2 fraction) are obtained, which are then resuspended in 0.32 M glucose (0.5 mL/100 mg of the original weight).

The respective uptake was measured in a 96 well microtiter plate. The volume was 250 µL and the incubation was carried out at room temperature (ca 20-25° C.) under a blanket of oxygen.

The incubation period was 7.5 minutes for [$^3$H]-NA and 5 minutes for [$^3$H]-5-HT. The 96 samples were then filtered through a Unifilter GF/B® microtiter plate (Packard) and washed with 200 mL of incubated buffer with the aid of a "Brabdel Cell Harvester MPXRI 96T". The Unifilter GF/B plate was dried at 55 C over a period of 1 h. The plate was then sealed with a back Seal® (Packard) and there were then added 35 μL of scintillant fluid per well (Ultima Gold, Packard). Following sealing with a top Seal® (Packard) and following adjustment of the equilibrium (approximately over a period of 5 h), the radioactivity is determined in a 1450 Microbeta® (Wallac).

The amount of protein used in the above determination corresponded to the values known from the literature, such as is described in "Protein measurement with the folin phenol reagent", Lowry et al., J. Biol. Chem., 193, 265-275, 1951.

A detailed description of the method is disclosed in the literature, for example, in M. Ch. Frink, H.-H. Hennis, W. Engelberger, M. Haurand, and B. Wilffert ((1996) Arzneim-.forsch./Drug Res. 46 (III), 11, 1029-1036.

The relevant literature references are incorporated herein by reference and are to be regarded as part of the disclosure.

The following characteristic data are found for the NA transporter and for the 5-HT transporter:

NA uptake:$Km$=0.32±0.11 μM

5-HT uptake:$Km$=0.084±0.011 μM

IV. Method of Determining the Affinity to the Batrachotoxin (BTX) Binding Site of the Sodium Channel:

Binding site 2 of the sodium channel is the so-called batrachotoxin (BTX) binding site. As a ligand, [$^3$H]-batrachotoxinin A20 α-benzoate (10 nM in the batch) is employed. The ion channel particles (synaptosomes) are enriched from rat cerebrocortex, as described in the publication by Gray and Whittaker, 1962, J. Anat. 76, 79-88. The relevant description is included herein by reference and is to be regarded as part of the present disclosure. The nonspecific binding is defined as the radioactivity which is measured in the presence of veratridine ($3\times10^{-4}$ M in the batch).

The assay conditions are carried out according to the publication by Pauwels, Leysen and Laduron, as described in Eur. J. Pharmacol. 124, 291-298. The relevant description is included herein by reference and is to be regarded as part of the present disclosure.

Deviating from this procedure, the total batch is reduced to 250 μL so that the assay can be carried out in 96-well microtiter plates. The incubation time in these microtiter plates is two hours at room temperature (about 20-25° C.).

The following characteristics were determined for the $K_D$ value of the binding site:

$K_D$:24.63±1.56 nM.

The invention is explained below with reference to examples. These explanations are exemplary only and the general scope of the inventive is not restricted thereto.

EXAMPLES

The yields of the compounds prepared are not optimized. All temperatures are uncorrected.

The statement "ether" means diethyl ether, "EA" ethyl acetate, "DCM" dichloromethane, "DMF" dimethylformamide, "DME" dimethoxyethane, "DMSO" dimethyl sulfoxide and "THF" tetrahydrofuran. The statement "equivalent" means amount of substance equivalent, "mp" melting point or melting range, "dec." decomposition, "RT" room temperature, "abs." absolute (anhydrous), "rac." racemic, "conc." concentrated, "min" minutes, "h" hours, "d" days, "vol. %" percent by volume, "m %" mass percent and "M" is a statement of concentration in mol/L.

The chemicals and solvents employed were acquired commercially from the conventional suppliers (for example Acros, Acocado, Aldrich, Bachem, Fluka, Lancaster, Maybridge, Merck, Sigma, Tci etc) or synthesized according to customary methods known to the person skilled in the art.

As a stationary phase for column chromatography, silica gel 60 (0.040-0.063 mm) supplied by E. Merck, Darmstadt, was employed.

The thin-layer chromatographic investigations were carried out using HPTLC ready-to-use plates, silica gel 60 F 254, supplied by E. Merck, Darmstadt.

The blending ratios of eluents for chromatographic investigations are always indicated in volume/volume.

Analysis was carried out by means of HPLC-MS or/and NMR.

The numbering of the following exemplary compounds does not agree with the numbering of the substituted 1,4,8-triazaspiro[4,5]decan-2-one compounds explicitly indicated above.

The preparation of the substituted 1,4,8-triazaspiro[4,5] decan-2-one compounds according to Examples 1-36 was carried out according to the general preparation process I, which is shown schematically below:

General process I:

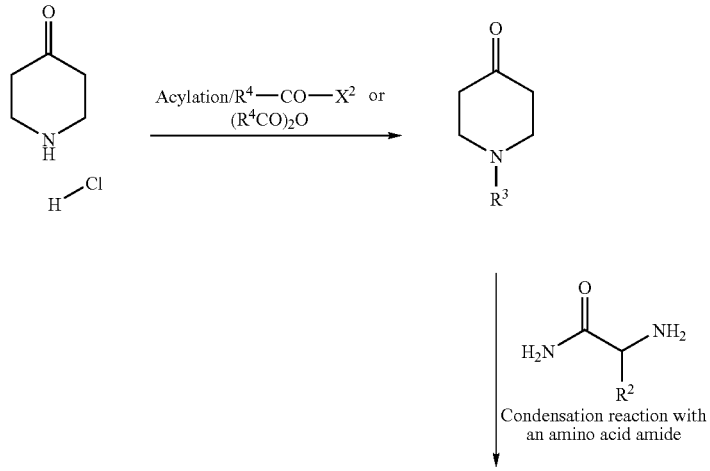

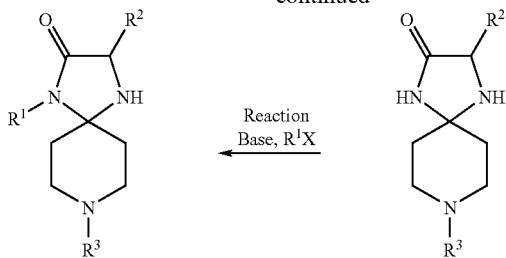

The preparation of individual reactants is exemplified below:

a) Preparation of 1-(2-ethylbutyryl)piperidin-4-one

Triethylamine (5.8 g, 57.3 mmol) and a catalytic amount of DMAP were added to a solution of piperidone hydrochloride (4.0 g, 26 mmol) in $CH_2Cl_2$ (20 ml). After cooling to −10° C., 2-ethylbutyryl chloride (3.9 g, 28.6 mmol) dissolved in $CH_2Cl_2$ (10 ml) was slowly added and the mixture was stirred at RT for 16 h. 5M potassium hydroxide solution (25 ml) was added to the suspension, the organic phase was separated off and the aqueous phase was extracted with $CH_2Cl_2$ (3×10 ml). After drying of the combined organic phases over $Na_2SO_4$, filtration and removal of the solvent, the product 1-(2-ethylbutyryl)piperidin-4-one was obtained in a yield of 4.3 g (84% of theory).

b) Preparation of 1-(4-chlorobenzoyl)piperidin-4-one

Triethylamine (4.4 g, 43.0 mmol) and a catalytic amount of DMAP were added to a solution of piperidone hydrochloride (3.0 g, 19.5 mmol) in $CH_2Cl_2$ (20 ml). After cooling to −10° C., 4-chlorobenzoyl chloride (3.8 g, 21.5 mmol) dissolved in $CH_2Cl_2$ (10 ml) was slowly added and the mixture was stirred at RT for 16 h. 5M potassium hydroxide solution (20 ml) was added to the suspension, the organic phase was separated off and the aqueous phase was extracted with $CH_2Cl_2$ (3×10 ml). After drying of the combined organic phases over $Na_2SO_4$, filtration and removal of the solvent, the product 1-(4-chlorobenzoyl)piperidin-4-one was obtained in a yield of 4.4 g (95%).

c) Preparation of 1-(2,4-dimethoxybenzoyl)piperidin-4-one

Piperidone hydrochloride (3.0 g, 19.5 mmol) dissolved in DMF (25 ml), N,N-diiso-propylcarbodiimide (8.2 g, 65.1 mmol) and 1-hydroxybenzotriazole (8.8 g, 65.1 mmol) were added at 0° C. to a solution of 2,4-dimethoxybenzoic acid (11.8 g, 65.1 mmol) in DMF (25 ml) and the mixture was stirred at 0° C. for 3 h and subsequently at RT for 2 d. Aqueous 1M $Na_2CO_3$ solution (20 ml) was added to the reaction mixture and it was extracted with EA (3×20 ml). After drying of the combined organic phases, the solvent was removed and the residue was purified by means of column chromatography. The product 1-(2,4-dimethoxybenzoyl)piperidin-4-one was obtained in a yield of 2.7 g (39%).

Example 1

3-(S)-Benzyl-8-(2-ethylbutyryl)-1,4,8-triazaspiro[4,5]decan-2-one

A solution of 1-(2-ethylbutyryl)piperidin-4-one (1.8 g, 9.1 mmol) and (S)-phenyl-alaninamide (1.5 g, 9.1 mmol) in EtOH (40 ml) was heated under reflux for 2.5 h and stirred at RT for a further 16 h. After removal of the solvent and drying in vacuo, the product 3-(S)-benzyl-8-(2-ethylbutyryl)-1,4,8-triazaspiro[4,5]decan-2-one was obtained in a yield of 3.1 g (99%).

Example 2

3-(S)-Benzyl-8-(2-ethylbutyryl)-1,4,8-triazaspiro[4,5]decan-2-one hydrochloride 3-(S)-Benzyl-8-(2-ethylbutyryl)-1,4,8-triazaspiro[4,5]decan-2-one (610 mg, 1.8 mmol) was dissolved in ethyl methyl ketone (5 ml), treated with water (18 µL) and TMSCl (247 µL) and stirred overnight. The solid precipitated in this process was filtered off, washed with ether and dried in vacuo. The product 3-(S)-benzyl-8-(2-ethylbutyryl)-1,4,8-triazaspiro[4,5]decan-2-one hydrochloride was obtained in a yield of 590 mg (87%).

Example 3

8-(2,4-Dimethoxybenzoyl)-3-(S)-(2-methylsulfanyl-ethyl)-1,4,8-triazaspiro[4,5]decan-2-one A solution of 1-(2,4-dimethoxybenzoyl)piperidin-4-one (1.4 g, 5.1 mmol), (S)-methioninamide hydrochloride (950 mg, 5.1 mmol) and triethylamine (520 mg, 5.1 mmol) in EtOH (40 ml) was heated under reflux for 2.5 h and stirred at RT for a further 16 h. After removal of the solvent, water (25 ml) and $CH_2Cl_2$ (25 ml) were added to the residue and it was rendered basic using conc. sodium hydroxide solution. The aqueous phase was extracted with $CH_2Cl_2$ (3×20 ml) and the combined organic phases were dried over $Na_2SO_4$. After removal of the solvent and drying in vacuo, the product 8-(2,4-dimethoxybenzoyl)-3-(S)-(2-methylsulfanylethyl)-1,4,8-triazaspiro[4,5]decan-2-one was obtained in a yield of 1.9 g (95%).

Example 4

8-(2,4-Dimethoxybenzoyl)-3-(S)-(2-methylsulfanyl-ethyl)-1,4,8-triazaspiro-[4,5]decan-2-one hydrochloride 8-(2,4-Dimethoxybenzoyl)-3-(S)-(2-methylsulfanyl-ethyl)-1,4,8-triazaspiro[4,5]decan-2-one (300 mg, 0.8 mmol) was dissolved in ethyl methyl ketone (2 ml), treated with water (8 µL) and TMSCl (106 µL) and stirred overnight. The solid was filtered off and dried in vacuo. The product 8-(2,4-dimethoxybenzoyl)-3-(S)-(2-methylsulfanylethyl)-1,4,8-triazaspiro[4,5]decan-2-one hydrochloride was obtained in a yield of 320 mg (97%).

Example 5

3-(S,R)-Benzyl-8-(2-ethylbutyryl)-1,4,8-triazaspiro[4,5]decan-2-one

A solution of 1-(2-ethylbutyryl)piperidin-4-one (1.8 g, 9.0 mmol), (S,R)-phenyl-alaninamide hydrochloride (1.8 g, 9.0 mmol) and triethylamine (910 mg, 9.0 mmol) in EtOH (40 ml) was heated under reflux for 2.5 h and stirred at RT for a further 16 h. After removal of the solvent, water (25 ml) and $CH_2Cl_2$ (25 ml) were added to the residue and it was rendered basic using conc. sodium hydroxide solution. The aqueous phase was extracted with $CH_2Cl_2$ (3×20 ml) and the combined organic phases were dried over $Na_2SO_4$. After removal of the solvent and drying in vacuo, the product 3-(S,R)-benzyl-8-(2-ethylbutyryl)-1,4,8-triazaspiro[4,5]decan-2-one was obtained in a yield of 2.9 g (96%).

Example 6

3-(S,R)-Benzyl-8-(2-ethylbutyryl)-1,4,8-triazaspiro[4,5]decan-2-one hydrochloride 3-(S,R)-Benzyl-8-(2-ethylbutyryl)-1,4,8-triazaspiro[4,5]decan-2-one (300 mg, 0.9 mmol) was dissolved in ethyl methyl ketone (2 ml), treated with water (9 µL) and TMSCl (122 µL) and stirred overnight. The solid was filtered off, washed with ether and dried in vacuo. The product 3-(S,R)-benzyl-8-(2-ethylbutyryl)-1,4,8-triazaspiro[4,5]decan-2-one hydrochloride was obtained in a yield of 300 mg (91%).

Example 7

8-Acetyl-3-(S)-benzyl-1,4,8-triazaspiro[4,5]decan-2-one

A solution of 1-acetylpiperidin-4-one (1.5 g, 10.8 mmol) and (S)-phenylalaninamide (1.8 g, 10.8 mmol) in EtOH (30 ml) was heated under reflux for 2.5 h and stirred at RT for a further 16 h. After removal of the solvent and drying in vacuo, the product 8-acetyl-3-(S)-benzyl-1,4,8-triazaspiro[4,5]decan-2-one was obtained in a yield of 3.0 g (99%).

Example 8

8-Acetyl-3-(S)-benzyl-1,4,8-triazaspiro[4,5]decan-2-one hydrochloride

8-Acetyl-3-(S)-benzyl-1,4,8-triazaspiro[4,5]decan-2-one (300 mg, 1.0 mmol) was dissolved in ethyl methyl ketone (2 ml), treated with water (21 µL) and TMSCl (290 µL) and stirred overnight. The solid precipitated in this process was filtered off, washed with ether and dried in vacuo. The product 8-acetyl-3-(S)-benzyl-1,4,8-triazaspiro[4,5]decan-2-one hydrochloride was obtained in a yield of 330 mg (96%).

Example 9

3-(S,R)-Benzyl-8-(4-chlorobenzoyl)-1,4,8-triazaspiro[4,5]decan-2-one

A solution of 1-(4-chlorobenzoyl)piperidin-4-one (2.1 g, 8.7 mmol), (S,R)-phenyl-alaninamide hydrochloride (1.8 g, 8.7 mmol) and triethylamine (880 mg, 8.7 mmol) in EtOH (40 ml) was heated under reflux for 2.5 h and stirred at RT for a further 16 h. After removal of the solvent, water (25 ml) and $CH_2Cl_2$ (25 ml) were added to the residue and it was rendered basic using conc. sodium hydroxide solution. The aqueous phase was extracted with $CH_2Cl_2$ (3×20 ml) and the combined organic phases were dried over $Na_2SO_4$. After removal of the solvent and drying in vacuo, the product 3-(S,R)-benzyl-8-(4-chlorobenzoyl)-1,4,8-triazaspiro[4,5]decan-2-one was obtained in a yield of 3.3 g (98%).

Example 10

3-(S,R)-Benzyl-8-(4-chlorobenzoyl)-1,4,8-triazaspiro[4,5]decan-2-one hydrochloride 3-(S,R)-Benzyl-8-(4-chlorobenzoyl)-1,4,8-triazaspiro[4,5]decan-2-one (300 mg, 0.8 mmol) was dissolved in ethyl methyl ketone (2 ml), treated with water (8 µL) and TMSCl (109 µL) and stirred overnight. After addition of hexane (10 ml), the aqueous phase was separated off and the residue was dried in vacuo. The product 3-(S,R)-benzyl-8-(4-chlorobenzoyl)-1,4,8-triazaspiro[4,5]decan-2-one hydrochloride was obtained in a yield of 260 mg (77%).

Example 11

3-(S)-Benzyl-8-(4-chlorobenzoyl)-1,4,8-triazaspiro[4,5]decan-2-one

A solution of 1-(4-chlorobenzoyl)piperidin-4-one (2.2 g, 9.1 mmol) and (S)-phenyl-alaninamide (1.5 g, 9.1 mmol) in EtOH (40 ml) was heated under reflux for 2.5 h and stirred at RT for a further 16 h. After removal of the solvent, EA (60 ml) was added and the mixture was stirred at 40° C. for 1 h. After filtration and drying in vacuo, the product 3-(S)-benzyl-8-(4-chlorobenzoyl)-1,4,8-triazaspiro[4,5]decan-2-one was obtained in a yield of 2.6 g (76%).

Example 12

3-(S)-benzyl-8-(4-chlorobenzoyl)-1,4,8-triazaspiro[4,5-]-decan-2-one hydrochloride 3-(S)-benzyl-8-(4-chlorobenzoyl)-1,4,8-triazaspiro[4,5-]-decan-2-one (500 mg, 1.3 mmol) was dissolved in ethyl methyl ketone (4 mL), and water (13 µL) and TMSCl (181 µL) were added and the mixture was stirred overnight. The precipitated solid matter was isolated by filtration, washed with ether, and dried in vacuo. The product 3-(S)-benzyl-8-(4-chlorobenzoyl)-1,4,8-triazaspiro[4,5-]-decan-2-one hydrochloride was obtained in a yield of 390 mg (72%).

Example 13

8-(2-ethylbutyryl)-3-(S)-(2-methylsulfanylethyl)-1,4,8-triazaspiro[4,5-]-decan-2-one A solution of 1-(2-ethylbutyryl)-piperidin-4-one (1.6 g, 8.1 mmol), (S)-methioninamide hydrochloride (1.5 g, 8.1 mmol), and triethylamine (820 mg, 8.1 mmol) in EtOH (66 mL) was heated under reflux over a period of 16 h. Following removal of the solvent, water (50 mL) and $CH_2Cl_2$ (50 mL) were added to the residue and the mixture was basified with concentrated sodium hydroxide solution. The aqueous phase was extracted with $CH_2Cl_2$ (3×20 mL) and the combined organic phases were dried over $Na_2SO_4$. Following removal of the solvent and vacuum drying, there was obtained the product 8-(2-ethylbutyryl)-3-(S)-(2-methylsulfanylethyl)-1,4,8-triazaspiro[4,5-]-decan-2-one in a yield of 1.8 g (69%).

Example 14

8-(2-ethylbutyryl)-3-(S)-(2-methylsulfanylethyl)-1,4,8-triazaspiro[4,5-]-decan-2-one hydrochloride 8-(2-ethylbutyryl)-3-(S)-(2-methylsulfanylethyl)-1,4,8-triazaspiro[4,5-]-decan-2-one (140 mg, 0.4 mmol) was dissolved in ethyl methyl ketone (1 mL), and water (4 µL) and TMSCl (59 µL) were added and the mixture was stirred overnight. The solid matter was isolated by filtration and dried in vacuo. The product 8-(2-ethylbutyryl)-3-(S)-(2-methylsulfanylethyl)-1,4,8-triazaspiro[4,5-]-decan-2-one hydrochloride was obtained in a yield of 117 mg (75%).

Example 15

1,3-(S)-dibenzyl-8-(2-ethylbutyryl)-1,4,8-triazaspiro[4,5]decan-2-one

To a solution of 3-(S)-benzyl-8-(2-ethylbutyryl)-1,4,8-triazaspiro[4,5]decan-2-one (1.0 g, 2.9 mmol) in 40 mL of dry THF there was added sodium hydride (90 mg, 3.8 mmol) at room temperature and under a blanket of nitrogen. Following stirring over a period of 1 h at RT benzyl chloride (1.47 g, 11.6 mmol) was slowly added dropwise and the mixture was then heated over a period of 12 h under reflux. Following the addition of an aqueous saturated $HC_l$ solution (20 mL), the reaction mixture was isolated by filtration and the filtrate was extracted with EE (3×15 mL), and the combined organic phases were dried over $Na_2SO_4$. Following removal, by distillation, of the solvent, there was obtained the crude product as a yellow oil. Further purification was carried out by column chromatography. The product 1,3-(S)-dibenzyl-8-(2-ethylbutyryl)-1,4,8-triazaspiro[4,5]decan-2-one was obtained in a yield of 1.1 g (52%).

Example 25

1,3-(S)-dibenzyl-8-(2-ethylbutyryl)-1,4,8-triazaspiro[4,5]decan-2-one hydrochloride 1,3-(S)-dibenzyl-8-(2-ethylbutyryl)-1,4,8-triazaspiro[4,5]decan-2-one (654 mg, 1.5 mmol) was dissolved in ethyl methyl ketone (5 mL), and water (15 µL) and TMSCl (210 µL) were added and the mixture was stirred overnight. Hexane (10 mL) was then added. The precipitated solid matter was isolated by filtration and dried in vacuo. The product 1,3-(S)-dibenzyl-8-(2-ethylbutyryl)-1,4,8-triazaspiro[4,5]decan-2-one hydrochloride was obtained in a yield of 671 mg (95%).

Example 16

8-acetyl-1,3-(S)-dibenzyl-1,4,8-triazaspiro[4,5]decan-2-one

To a solution of 8-acetyl-3-(S)-benzyl-1,4,8-triazaspiro[4,5]decan-2-one (2.8 g, 9.7 mmol) in 20 mL of dry THF there was added sodium hydride (350 mg, 14.6 mmol) at 0° C. and under a blanket of nitrogen. Following stirring over a period of 1 h at 0° C., benzyl chloride (1.36 g, 10.7 mmol) was slowly added dropwise, and the mixture was allowed to warm up to RT and then heated under reflux over a period of 24 h. Following the addition of an aqueous saturated $HC_l$ solution (25 mL), the reaction mixture was isolated by filtration and the filtrate was extracted with EE (3×20 mL), and the combined organic phases were dried over $Na_2SO_4$. Following removal, by distillation, of the solvent, there was obtained the crude product as a yellow oil. Further purification was carried out by column chromatography. The product 8-acetyl-1,3-(S)-dibenzyl-1,4,8-triazaspiro[4,5]decan-2-one was obtained in a yield of 1.25 g (34%).

Example 26

8-acetyl-1,3-(S)-dibenzyl-1,4,8-triazaspiro[4,5]decan-2-one hydrochloride 8-acetyl-1,3-(S)-dibenzyl-1,4,8-triazaspiro[4,5]decan-2-one (1.25 g, 3.3 mmol) was dissolved in ethyl methyl ketone (10 mL), and water (33 µL) and TMSCl (461 µL) were added and the mixture was stirred overnight. The precipitated solid matter was isolated by filtration, washed with diethyl ether, and dried in vacuo. The product 8-acetyl-1,3-(S)-dibenzyl-1,4,8-triazaspiro[4,5]decan-2-one hydrochloride was obtained in a yield of 939 mg (69%).

Example 17

3-(S,R)-benzyl-8-(4-chloro-benzyl)-1-(4-methoxy-benzyl)-1,4,8-triazaspiro[4,5]decan-2-one To a solution of 3-(S,R)-benzyl-8-(4-chloro-benzoyl)-1,4,8-triazaspiro[4,5]decan-2-one (920 mg, 2.4 mmol) in 20 mL of dry THF there was added sodium hydride (90 mg, 3.6 mmol) at RT and under a blanket of nitrogen. Following stirring over a period of 1 h at RT, 4-methoxybenzyl chloride (410 mg, 2.6 mmol) was slowly added dropwise and the mixture was then heated under reflux over a period of 48 h. Following the addition of an aqueous saturated $NH_4Cl$ solution (15 mL), the reaction mixture was isolated by filtration and the filtrate was extracted with EE (3×10 mL), and the combined organic phases were dried over $Na_2SO_4$. Following removal, by distillation, of the solvent, there was obtained the crude product as a yellow oil. Further purification was carried out by column chromatography. The product 3-(S,R)-benzyl-8-(4-chloro-benzoyl)-1-(4-methoxy-benzyl)-1,4,8-triazaspiro[4,5]decan-2-one was obtained in a yield of 500 mg (41%).

Example 27

3-(S,R)-benzyl-8-(4-chloro-benzoyl)-1-(4-methoxy-benzyl)-1,4,8-triazaspiro[4,5]decan-2-one hydrochloride 3-(S,R)-benzyl-8-(4-chloro-benzoyl)-1-(4-methoxy-benzyl)-1,4,8-triazaspiro[4,5]decan-2-one (500 mg, 1.0 mmol) was dissolved in ethyl methyl ketone (4 mL), and water (10 µL) and TMSCl (138 µL) were added and the mixture was stirred overnight. Hexane (10 mL) was then added, the aqueous phase separated, and the residue dried in vacuo. The product 3-(S,R)-benzyl-8-(4-chloro-benzoyl)-1-(4-methoxy-benzyl)-1,4,8-triazaspiro[4,5]decan-2-one hydrochloride was obtained in a yield of 507 mg (92%).

Example 18

3-(S,R)-benzyl-8-(4-chlorobenzoyl)-1-(4-fluorobenzyl)-1,4,8-triazaspiro[4,5]decan-2-one To a solution of 3-(S,R)-benzyl-8-(4-chloro-benzoyl)-1,4,8-triazaspiro[4,5]decan-2-one (920 mg, 2.4 mmol) in 20 mL of dry THF there was added sodium hydride (90 mg, 3.6 mmol) at RT and under a blanket of nitrogen. Following stirring over a period of 1 h at RT, 4-fluorobenzyl chloride (380 mg, 2.6 mmol) was slowly added dropwise and the mixture was then heated under reflux over a period of 48 h. Following the addition of an aqueous saturated NH$_4$Cl solution (15 mL), the reaction mixture was isolated by filtration and the filtrate was extracted with EE (3×15 mL), and the combined organic phases were dried over Na$_2$SO$_4$. Following removal, by distillation, of the solvent, there was obtained the crude product as a yellow oil. Further purification was carried out by column chromatography. The product 3-(S,R)-benzyl-8-(4-chlorobenzoyl)-1-(4-fluorobenzyl)-1,4,8-triazaspiro[4,5]decan-2-one was obtained in a yield of 566 mg (48%).

Example 28

3-(S,R)-benzyl-8-(4-chlorobenzoyl)-1-(4-fluorobenzyl)-1,4,8-triazaspiro[4,5]decan-2-one hydrochloride 3-(S,R)-benzyl-8-(4-chlorobenzoyl)-1-(4-fluorobenzyl)-1,4,8-triazaspiro[4,5]decan-2-one (560 mg, 1.1 mmol) was dissolved in ethyl methyl ketone (4 mL), and water (11 µL) and TMSCl (158 µL) were added and the mixture was stirred overnight. The precipitated solid matter was isolated by filtration and dried in vacuo. The product 3-(S,R)-benzyl-8-(4-chlorobenzoyl)-1-(4-fluorobenzyl)-1,4,8-triazaspiro[4,5]decan-2-one hydrochloride was obtained in a yield of 450 mg (75%).

Example 19

1,3-(S,R)-dibenzyl-8-(4-chlorobenzoyl)-1,4,8-triazaspiro[4,5]decan-2-one

To a solution of 3-(S,R)-benzyl-8-(4-chloro-benzoyl)-1,4,8-triazaspiro[4,5]decan-2-one (920 mg, 2.4 mmol) in 20 mL of dry THF there was added sodium hydride (90 mg, 3.6 mmol) at RT and under a blanket of nitrogen. Following stirring over a period of 1 h at RT, benzyl chloride (330 mg, 2.6 mmol) was slowly added dropwise and the mixture was then heated under reflux over a period of 48 h. Following the addition of an aqueous saturated NH$_4$Cl solution (15 mL), the reaction mixture was isolated by filtration and the filtrate was extracted with EE (3×10 mL), and the combined organic phases were dried over Na$_2$SO$_4$. Following removal, by distillation, of the solvent, there was obtained the crude product as a yellow oil. Further purification was carried out by column chromatography. The product 1,3-(S,R)-dibenzyl-8-(4-chlorobenzoyl)-1,4,8-triazaspiro[4,5]decan-2-one was obtained in a yield of 375 mg (33%).

Example 29

1,3-(S,R)-dibenzyl-8-(4-chlorobenzoyl)-1,4,8-triazaspiro[4,5]decan-2-one hydrochloride 1,3-(S,R)-dibenzyl-8-(4-chlorobenzoyl)-1,4,8-triazaspiro[4,5]decan-2-one (370 mg, 0.8 mmol) was dissolved in ethyl methyl ketone (3 mL), and water (8 µL) and TMSCl (109 µL) were added and the mixture was stirred overnight. The precipitated solid matter was isolated by filtration and dried in vacuo. The product 1,3-(S,R)-dibenzyl-8-(4-chlorobenzoyl)-1,4,8-triazaspiro[4,5]decan-2-one hydrochloride was obtained in a yield of 355 mg (89%).

Example 20

3-(S,R)-benzyl-8-(2-ethylbutyryl)-1-(4-methoxybenzyl)-1,4,8-triazaspiro[4,5]decan-2-one To a solution of 3-(S,R)-benzyl-8-(2-ethylbutyryl)-1,4,8-triazaspiro[4,5]decan-2-one (850 mg, 2.5 mmol) in 20 mL of dry THF there was added sodium hydride (90 mg, 3.6 mmol) at RT and under a blanket of nitrogen. Following stirring over a period of 1 h at RT, 4-methoxybenzyl chloride (430 mg, 2.7 mmol) was slowly added dropwise and the mixture was then heated under reflux over a period of 48 h. Following the addition of an aqueous saturated NH$_4$Cl solution (15 mL), the reaction mixture was isolated by filtration and the filtrate was extracted with EE (3×10 mL), and the combined organic phases were dried over Na$_2$SO$_4$. Following removal, by distillation, of the solvent, there was obtained the crude product as a yellow oil. Further purification was carried out by column chromatography. The product 3-(S,R)-benzyl-8-(2-ethylbutyryl)-1-(4-methoxybenzyl)-1,4,8-triazaspiro[4,5]decan-2-one was obtained in a yield of 563 mg (51%).

Example 30

3-(S,R)-benzyl-8-(2-ethylbutyryl)-1-(4-methoxybenzyl)-1,4,8-triazaspiro[4,5]decan-2-one hydrochloride 3-(S,R)-benzyl-8-(2-ethylbutyryl)-1-(4-methoxybenzyl)-1,4,8-triazaspiro[4,5]decan-2-one (550 mg, 1.2 mmol) was dissolved in ethyl methyl ketone (4 mL), and water (12 µL) and TMSCl (169 µL) were added and the mixture was stirred overnight.

Hexane (10 mL) was then added, the aqueous phase separated, and the residue dried in vacuo. The product 3-(S,R)-benzyl-8-(2-ethylbutyryl)-1-(4-methoxybenzyl)-1,4,8-triazaspiro[4,5]decan-2-one hydrochloride was obtained in a yield of 530 mg (90%).

Example 21

3-(S,R)-benzyl-8-(2-ethylbutyryl)-1-(4-fluorobenzyl)-1,4,8-triazaspiro[4,5]decan-2-one To a solution of 3-(S,R)-benzyl-8-(2-ethylbutyryl)-1,4,8-triazaspiro[4,5]decan-2-one (850 mg, 2.5 mmol) in 20 mL of dry THF there was added sodium hydride (90 mg, 3.6 mmol) at RT and under a blanket of nitrogen. Following stirring over a period of 1 h at RT, 4-fluorobenzyl chloride (390 mg, 2.7 mmol) was slowly added dropwise and the mixture was then heated under reflux over a period of 48 h. Following the addition of an aqueous saturated NH$_4$Cl solution (15 mL), the reaction mixture was isolated by filtration and the filtrate was extracted with EE (3×10 mL), and the combined organic phases were dried over Na$_2$SO$_4$. Following removal, by distillation, of the solvent, there was obtained the crude product as a yellow oil. Further purification was carried out by column chromatography. The product 3-(S,R)-benzyl-8-(2-ethylbutyryl)-1-(4-fluorobenzyl)-1,4,8-triazaspiro[4,5]decan-2-one was obtained in a yield of 861 mg (75%).

Example 31

3-(S,R)-benzyl-8-(2-ethylbutyryl)-1-(4-fluorobenzyl)-1,4,8-triazaspiro[4,5]decan-2-one hydrochloride 3-(S,R)-benzyl-8-(2-ethylbutyryl)-1-(4-fluorobenzyl)-1,4,8-triazaspiro[4,5]decan-2-one (850 mg, 1.2 mmol) was dissolved in ethyl methyl ketone (7 mL), and water (18 µL) and TMSCl (255 µL) were added and the mixture was stirred overnight.

Hexane (10 mL) was then added, the aqueous phase separated, and the residue dried in vacuo. The product 3-(S,R)-benzyl-8-(2-ethylbutyryl)-1-(4-fluorobenzyl)-1,4,8-triazaspiro[4,5]decan-2-one hydrochloride was obtained in a yield of 853 mg (95%).

Example 22

1,3-(S,R)-dibenzyl-8-(2-ethylbutyryl)-1,4,8-triazaspiro[4,5]decan-2-one

To a solution of 3-(S,R)-benzyl-8-(2-ethylbutyryl)-1,4,8-triazaspiro[4,5]decan-2-one (850 mg, 2.5 mmol) in 20 mL of dry THF there was added sodium hydride (90 mg, 3.6 mmol) at RT and under a blanket of nitrogen. Following stirring over a period of 1 h at RT, benzyl chloride (340 mg, 2.7 mmol) was slowly added dropwise and the mixture was then heated under reflux over a period of 48 h. Benzyl chloride (170 mg, 1.4 mmol) was added and the mixture was heated under reflux for a further 16 h. Following the addition of an aqueous saturated $NH_4Cl$ solution (15 mL), the reaction mixture was isolated by filtration and the filtrate was extracted with EE (3×10 mL), and the combined organic phases were dried over $Na_2SO_4$. Following removal, by distillation, of the solvent, there was obtained the crude product as a yellow oil. Further purification was carried out by column chromatography. The product 1,3-(S,R)-dibenzyl-8-(2-ethylbutyryl)-1,4,8-triazaspiro[4,5]decan-2-one was obtained in a yield of 826 mg (77%).

Example 32

1,3-(S,R)-dibenzyl-8-(2-ethylbutyryl)-1,4,8-triazaspiro[4,5]decan-2-one hydrochloride 1,3-(S,R)-dibenzyl-8-(2-ethylbutyryl)-1,4,8-triazaspiro[4,5]decan-2-one (810 mg, 1.9 mmol) was dissolved in ethyl methyl ketone (6 mL), and water (18 µL) and TMSCl (260 µL) were added and the mixture was stirred overnight. The precipitated solid matter was isolated by filtration and dried in vacuo. The product 1,3-(S,R)-dibenzyl-8-(2-ethylbutyryl)-1,4,8-triazaspiro[4,5]decan-2-one hydrochloride was obtained in a yield of 685 mg (78%).

Example 23

1-benzyl-8-(2-ethylbutyryl)-3-(S)-(2-methylsulfanylethyl)-1,4,8-triazaspiro[4,5]decan-2-one To a solution of 8-(2-ethylbutyryl)-3-(S)-(2-methylsulfanylethyl)-1,4,8-triazaspiro[4,5]decan-2-one (420 mg, 1.3 mmol) in 20 mL of dry THF there was added sodium hydride (50 mg, 1.9 mmol) at 0° C. and under a blanket of nitrogen. Following stirring over a period of 1 h at 0° C., benzyl chloride (140 mg, 1.4 mmol) was slowly added dropwise and the mixture was then heated under reflux over a period of 24 h. Following the addition of an aqueous saturated $NH_4Cl$ solution (15 mL), the reaction mixture was isolated by filtration and the filtrate was extracted with EE (3×10 mL), and the combined organic phases were dried over $Na_2SO_4$. Following removal, by distillation, of the solvent, there was obtained the crude product as a yellow oil. Further purification was carried out by column chromatography. The product 1-benzyl-8-(2-ethylbutyryl)-3-(S)-(2-methylsulfanylethyl)-1,4,8-triazaspiro[4,5]decan-2-one was obtained in a yield of 239 mg (45%).

Example 33

1-benzyl-8-(2-ethylbutyryl)-3-(2-methylsulfanylethyl)-1,4,8-triazaspiro[4,5]decan-2-one hydrochloride 1-benzyl-8-(2-ethylbutyryl)-3-(S)-(2-methylsulfanylethyl)-1,4,8-triazaspiro[4,5]decan-2-one (230 mg, 0.6 mmol) was dissolved in ethyl methyl ketone (2 mL), and water (5 µL) and TMSCl (77 µL) were added and the mixture was stirred overnight.

Hexane (8 mL) was then added, the aqueous phase separated, and the residue dried in vacuo. The product 1-benzyl-8-(2-ethylbutyryl)-3-(S)-(2-methylsulfanylethyl)-1,4,8-triazaspiro[4,5]decan-2-one hydrochloride was obtained in a yield of 246 mg (90%).

Example 24

1,3-(S)-dibenzyl-8-(4-chlorobenzoyl)-1,4,8-triazaspiro[4,5]decan-2-one

To a solution of 3-(S)-benzyl-8-(4-chlorobenzoyl)-1,4,8-triazaspiro[4,5-]-decan-2-one (2.1 g, 5.5 mmol) in 20 mL of dry THF there was added sodium hydride (130 mg, 5.5 mmol) at 0° C. and under a blanket of nitrogen. Following stirring over a period of 1 h at 0° C., benzyl chloride (760 mg, 6.0 mmol) was slowly added dropwise, and the mixture was allowed to warm up to RT and then heated under reflux over a period of 4 d. Following the addition of an aqueous saturated $NH_4Cl$ solution (30 mL), the reaction mixture was isolated by filtration, the filtrate was extracted with EE (3×20 mL), the combined organic phases were dried over $Na_2SO_4$, and the solvent was removed. Further purification was carried out by column chromatography. The product 1,3-(S)-dibenzyl-8-(4-chlorobenzoyl)-1,4,8-triazaspiro[4,5]decan-2-one was obtained as a yellow oil in a yield of 2.62 g (99%).

Example 34

1,3-(S)-dibenzyl-8-(4-chlorobenzoyl)-1,4,8-triazaspiro[4,5]decan-2-one hydrochloride 1,3-(S)-dibenzyl-8-(4-chlorobenzoyl)-1,4,8-triazaspiro[4,5]decan-2-one (2.6 g, 5.5 mmol) was dissolved in ethyl methyl ketone (21 mL), and water (54 µL) and TMSCl (763 µL) were added and the mixture was stirred overnight. Hexane (10 mL) was then added, and the solid matter was isolated by filtration and dried in vacuo. The precipitated solid matter was isolated by filtration and dried in vacuo. The product 1,3-(S)-dibenzyl-8-(4-chlorobenzoyl)-1,4,8-triazaspiro[4,5]decan-2-one hydrochloride was obtained in a yield of 2.53 g (90%). Examples 35 and 36 were prepared with irradiation by microwaves:

Example 35

1-benzyl-8-(2,4-dimethoxybenzoyl)-3-(S)-(2-methylsulfanylethyl)-1,4,8-triazaspiro[4,5]decan-2-one To a solution of 8-(2,4-dimethoxybenzoyl)-3-(S)-(2-methylsulfanylethyl)-1,4,8-triazaspiro[4,5]decan-2-one (400 mg, 1.0 mmol) in 10 mL of DMF there was added sodium hydride (40 mg, 1.5 mmol) at RT and under a blanket of nitrogen. Following stirring over a period of 1 h at RT, 4-fluorobenzyl chloride (160 mg, 1.1 mmol) was slowly added dropwise and the mixture was then heated for 30 min in a microwave oven at 100° C. Following the addition of an aqueous saturated NH$_4$Cl solution (15 mL), the mixture was extracted with ether (3×10 mL), the ethereal phase washed with aqueous saturated NaHCO$_3$ solution (2×10 mL) and the combined organic phases were dried over Na$_2$SO$_4$. Following removal, by distillation, of the solvent, there was obtained the crude product as a yellow oil. Further purification was carried out by column chromatography. The product 1-benzyl-8-(2,4-dimethoxybenzoyl)-3-(S)-(2-methylsulfanylethyl)-1,4,8-triazaspiro[4,5]decan-2-one was obtained in a yield of 296 mg (58%).

Example 36

1-benzyl-8-(2,4-dimethoxybenzoyl)-3-(S)-(2-methylsulfanylethyl)-1,4,8-triazaspiro[4,5]decan-2-one hydrochloride 1-benzyl-8-(2,4-dimethoxybenzoyl)-3-(S)-(2-methylsulfanylethyl)-1,4,8-triazaspiro[4,5]decan-2-one (290 mg, 0.6 mmol) was dissolved in ethyl methyl ketone (2 mL), and water (6 µL) and TMSCl (80 µL) were added and the mixture was stirred overnight. The precipitated solid matter was isolated by filtration and dried in vacuo. The product 1-benzyl-8-(2,4-dimethoxybenzoyl)-3-(S)-(2-methylsulfanylethyl)-1,4,8-triazaspiro[4,5]decan-2-one hydrochloride was obtained in a yield of 105 mg (95%).

The preparation of the substituted 1,4,8-triazaspiro[4,5]decan-2-one compounds described in the following examples was carried out according to the general manufacturing method II, illustrated diagrammatically as follows:

General process II:

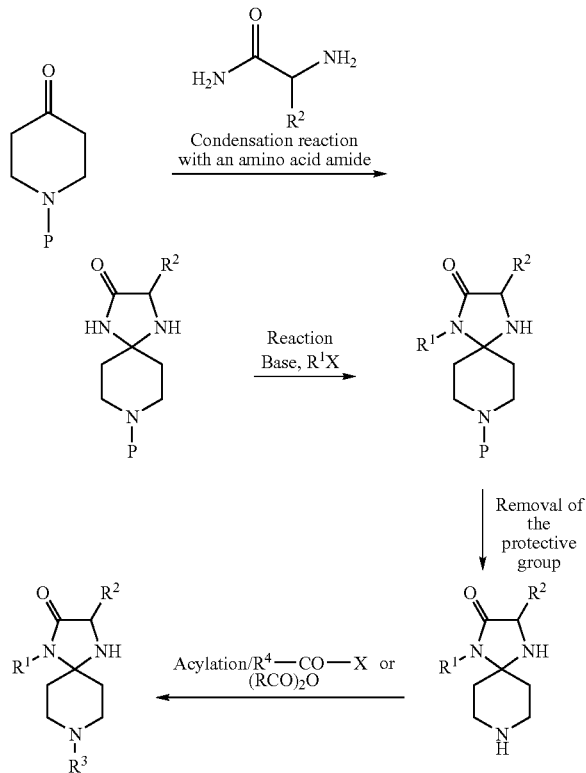

The preparation of some starting materials is given by way of example below:

a) Preparation of tert-butyl 3-(S)-benzyl-2-oxo-1,4,8-triazaspiro[4,5]decane-8-carboxylate N-tert-Butyloxycarbonylpiperidone (6.0 g, 29.8 mmol) was added to a solution of (S)-phenylalaninamide (4.9 g, 29.8 mmol) in dry EtOH (20 ml) and the mixture was heated for 2.5 h under reflux. The solvent was distilled off and the tert-butyl 3-(S)-benzyl-2-oxo-1,4,8-triazaspiro[4,5]decane-8-carboxylate (10.8 g) was used without further workup.

b) Preparation of tert-butyl 3-(S)-(2-methylsulfanylethyl)-2-oxo-1,4,8-triazaspiro[4,5]decane-8-carboxylate N-tert-Butyloxycarbonylpiperidone (5.9 g, 29.8 mmol) and triethylamine (3.02 g, 29.8 mmol) were added to a solution of (S)-methioninamide hydrochloride (5.5 g, 29.8 mmol) in dry EtOH (66 ml) and the mixture was heated for 2.5 h under reflux. After addition of water (50 ml) and CH$_2$Cl$_2$ (200 ml), the organic phase was separated off and the aqueous phase was extracted with CH$_2$Cl$_2$ (3×20 ml). The combined organic phases were dried over Na$_2$SO$_4$. After filtration, the solvent was distilled off. tert-Butyl 3-(S)-(2-methylsulfanylethyl)-2-oxo-1,4,8-triazaspiro[4,5]decane-8-carboxylate was obtained in a yield of 8.0 g (82%).

c) Preparation of tert-butyl 1,3-(S)-dibenzyl-2-oxo-1,4,8-triazaspiro[4,5]decane-8-carboxylate NaH (1.26 g, 52.5 mmol) was added at RT to a solution of tert-butyl 3-(S)-benzyl-2-oxo-1,4,8-triazaspiro[4,5]decane-8-carboxylate (12.1 g, 35 mmol) in THF (250 ml). After stirring for 1 h at 0° C., benzyl chloride (4.9 g, 38.5 mmol) was added dropwise, and the mixture was allowed to warm to RT and heated for 60 h under reflux. Subsequently, benzyl chloride (2.4 g, 19 mmol) was again added and the mixture was heated under reflux for a further 16 h. The reaction mixture was treated with aqueous saturated NH$_4$Cl solution (20 ml) and extracted with EA (3×50 ml). The combined organic phase was dried over Na$_2$SO$_4$, filtered and the solvent was distilled off. Workup was carried out by means of column chromatography and afforded tert-butyl-1,3-(S)-dibenzyl-2-oxo-1,4,8-triazaspiro[4,5]decane-8-carboxylate in a yield of 13.5 g (88%).

d) Preparation of tert-butyl 1-benzyl-3-(S)-(2-methylsulfanylethyl)-2-oxo-1,4,8-triazaspiro[4,5]decane-8-carboxylate A solution of tert-butyl 3-(S)-(2-methylsulfanylethyl)-2-oxo-1,4,8-triazaspiro-[4,5]decane-8-carboxylate (4.4 g, 13.4 mmol) in THF (72 ml) was added dropwise at 0° C. to a suspension of NaH (385 mg, 16.0 mmol) in THF (60 ml). After stirring for 1 h at 0° C., benzyl chloride (2.0 g, 16.0 mmol) was added dropwise, and the mixture was allowed to warm to RT and was heated for 68 h under reflux. The reaction mixture was treated with aqueous saturated NH$_4$Cl solution (20 ml), the organic phase was separated off and the aqueous phase was extracted with EA (3×50 ml). The combined organic phase was dried over Na$_2$SO$_4$, filtered and the solvent was distilled off. The workup was carried out by means of column chromatography and afforded tert-butyl 1-benzyl-3-(S)-(2-methylsulfanylethyl)-2-oxo-1,4,8-triazaspiro[4,5]decane-8-carboxylate in a yield of 1.6 g (30%).

Example 37

1,3-(S)-Dibenzyl-1,4,8-triazaspiro[4,5]decan-2-one

TFA (68.5 g, 601 mmol) was added dropwise at 0° C. to a solution of tert-butyl 1,3-(S)-dibenzyl-2-oxo-1,4,8-triazaspiro[4,5]decane-8-carboxylate (13.5 g, 31.0 mmol) in CH$_2$Cl$_2$ (93 ml) and the mixture was stirred at this temperature for 15 min. After warming to RT, the reaction mixture was stirred for a further 2.5 h. Subsequently, the reaction solution was adjusted with aqueous saturated NaHCO$_3$ solution to pH 7-8, the organic phase was separated off and the aqueous phase was extracted with CH$_2$Cl$_2$ (2×30 ml). The combined organic phase was dried over Na$_2$SO$_4$, filtered and the solvent was distilled off. The workup was carried out by means of column chromatography and afforded 1,3-(S)-dibenzyl-1,4,8-triazaspiro[4,5]decan-2-one in a yield of 7.8 g (75%).

Example 38

1,3-(S)-Dibenzyl-1,4,8-triazaspiro[4,5]decan-2-one hydrochloride 1,3-(S)-Dibenzyl-1,4,8-triazaspiro[4,5]decan-2-one (400 mg, 1.2 mmol) was dissolved in ethyl methyl ketone (3 ml), treated with water (12 µL) and with TMSCl (166 µL) and stirred overnight. The solid was filtered off, washed with ether and dried in vacuo. The product 1,3-(S)-dibenzyl-1,4,8-triazaspiro[4,5]decan-2-one hydrochloride was obtained in a yield of 315 mg (71%).

Example 39

1-Benzyl-3-(S)-(2-methylsulfanylethyl)-1,4,8-triazaspiro[4,5]decan-2-one

TFA (7.8 g, 68.0 mmol) was added dropwise at 0° C. to a solution of tert-butyl 1-benzyl-3-(S)-(2-methylsulfanylethyl)-2-oxo-1,4,8-triazaspiro[4,5]decane-8-carboxylate (1.5 g, 3.5 mmol) in CH$_2$Cl$_2$ (10 ml) and the mixture was stirred at this temperature for 15 min. After warming to RT, the reaction solution was stirred for a further 2.5 h. Subsequently, the reaction solution was adjusted to pH 7-8 using aqueous saturated NaHCO$_3$ solution, the organic phase was separated off and the aqueous phase was extracted with CH$_2$Cl$_2$ (2×10 ml). The combined organic phase was dried over Na$_2$SO$_4$, filtered and the solvent was distilled off. The workup was carried out by means of column chromatography and afforded 1-benzyl-3-(S)-(2-methylsulfanylethyl)-1,4,8-triazaspiro[4,5]decan-2-one in a yield of 655 mg (58%).

The Compounds of Examples 40-51 Below were Obtained According to the Following General Working Procedure:

2 eq. of triethylamine and a catalytic amount of DMAP were added to a solution of 1 eq. of 1,3-(S)-dibenzyl-1,4,8-triazaspiro[4,5]decan-2-one or 1 eq. of 1-benzyl-3-(S)-(2-methylsulfanylethyl)-1,4,8-triazaspiro[4,5]decan-2-one in dry CH$_2$Cl$_2$ (5 mL per mmol of amine), the reaction solution was cooled to 0° C. and 1 eq. of acid chloride dissolved in dry CH$_2$Cl$_2$ (6 ml per mmol of acid chloride) was then added dropwise. The mixture was stirred for 18 h, the reaction solution warming to RT. Aqueous 5M potassium hydroxide solution was added (4 ml per 1.2 mmol of amine), the aqueous phase was extracted with dichloromethane (2×5 ml), the combined organic phases were washed with aqueous saturated NaCl solution (10 ml) and the collected organic phases were dried over Na$_2$SO$_4$. After distilling off the solvent, further purification was carried out by means of column chromatography.

Example 40

1,3-(S)-Dibenzyl-8-butyryl-1,4,8-triazaspiro[4,5]decan-2-one

| | |
|---|---|
| 1,3-(S)-Dibenzyl-1,4,8-triazaspiro[4,5]decan-2-one: | 400 mg (1.19 mmol) |
| Butyric chloride: | 127 mg (1.19 mmol) |
| Triethylamine: | 241 mg (2.39 mmol) |
| Yield following column chromatography: | 263 mg (55%) |

Example 41

1,3-(S)-Dibenzyl-8-(3-fluoro-4-trifluoromethyl-benzoyl)-1,4,8-triazaspiro[4,5]decan-2-one

| | |
|---|---|
| 1,3-(S)-Dibenzyl-1,4,8-triazaspiro[4,5]decan-2-one: | 400 mg (1.19 mmol) |
| 3-Fluoro-4-(trifluoromethylbenzoyl chloride): | 270 mg (1.19 mmol) |
| Triethylamine: | 241 mg (2.39 mmol) |
| Yield following column chromatography: | 409 mg (65%) |

Example 42

1,3-(S)-Dibenzyl-8-(2,3-difluoro-benzoyl)-1,4,8-triazaspiro[4,5]decan-2-one

| | |
|---|---|
| 1,3-(S)-Dibenzyl-1,4,8-triazaspiro[4,5]decan-2-one: | 400 mg (1.19 mmol) |
| 2,3-Difluorobenzoyl chloride: | 211 mg (1.19 mmol) |
| Triethylamine: | 241 mg (2.39 mmol) |
| Yield following column chromatography: | 383 mg (68%) |

Example 43

1,3-(S)-Dibenzyl-8-[2-(4-chlorophenoxy)-acetyl]-1,4,8-triazaspiro[4,5]decan-2-one

| | |
|---|---|
| 1,3-(S)-Dibenzyl-1,4,8-triazaspiro[4,5]decan-2-one: | 400 mg (1.19 mmol) |
| 4-Chlorophenoxyacetyl chloride: | 245 mg (1.19 mmol) |
| Triethylamine: | 241 mg (2.39 mmol) |
| Yield following column chromatography: | 417 mg (69%) |

Example 44

1,3-(S)-Dibenzyl-8-diphenylacetyl-1,4,8-triazaspiro[4,5]decan-2-one

| | |
|---|---|
| 1,3-(S)-Dibenzyl-1,4,8-triazaspiro[4,5]decan-2-one: | 400 mg (1.19 mmol) |
| Diphenylacetyl chloride: | 275 mg (1.19 mmol) |
| Triethylamine: | 241 mg (2.39 mmol) |
| Yield following column chromatography: | 460 mg (73%) |

Example 45

1,3-(S)-Dibenzyl-8-(2-phenoxy-acetyl)-1,4,8-triazaspiro[4,5]decan-2-one

| | |
|---|---|
| 1,3-(S)-Dibenzyl-1,4,8-triazaspiro[4,5]decan-2-one: | 400 mg (1.19 mmol) |
| Phenoxyacetyl chloride: | 203 mg (1.19 mmol) |
| Triethylamine: | 241 mg (2.39 mmol) |
| Yield following column chromatography: | 419 mg (75%) |

Example 46

1,3-(S)-Dibenzyl-8-(3-phenyl-propionyl)-1,4,8-triazaspiro[4,5]decan-2-one

| | |
|---|---|
| 1,3-(S)-Dibenzyl-1,4,8-triazaspiro[4,5]decan-2-one: | 400 mg (1.19 mmol) |
| 3-Phenylpropionyl chloride: | 201 mg (1.19 mmol) |
| Triethylamine: | 241 mg (2.39 mmol) |
| Yield following column chromatography: | 417 mg (75%) |

Example 47

1,3-(S)-Dibenzyl-8-(naphthalin-2-carbonyl)-1,4,8-triazaspiro[4,5]decan-2-one

| | |
|---|---|
| 1,3-(S)-Dibenzyl-1,4,8-triazaspiro[4,5]decan-2-one: | 400 mg (1.19 mmol) |
| 2-Naphthoyl chloride: | 227 mg (1.19 mmol) |
| Triethylamine: | 241 mg (2.39 mmol) |
| Yield following column chromatography: | 411 mg (70%) |

Example 48

1,3-(S)-Dibenzyl-8-(furan-2-carbonyl)-1,4,8-triazaspiro[4,5]decan-2-one

| | |
|---|---|
| 1,3-(S)-Dibenzyl-1,4,8-triazaspiro[4,5]decan-2-one: | 400 mg (1.19 mmol) |
| 2-Furoyl chloride: | 156 mg (1.19 mmol) |
| Triethylamine: | 241 mg (2.39 mmol) |
| Yield following column chromatography: | 365 mg (71%) |

Example 49

1,3-(S)-Dibenzyl-8-(3-methoxy-benzoyl)-1,4,8-triazaspiro[4,5]decan-2-one

| | |
|---|---|
| 1,3-(S)-Dibenzyl-1,4,8-triazaspiro[4,5]decan-2-one: | 400 mg (1.19 mmol) |
| 3-Methoxybenzoyl chloride: | 203 mg (1.19 mmol) |
| Triethylamine: | 241 mg (2.39 mmol) |
| Yield following column chromatography: | 404 mg (72%) |

Example 50

1,3-(S)-Dibenzyl-8-(4-fluoro-benzoyl)-1,4,8-triazaspiro[4,5]decan-2-one

| | |
|---|---|
| 1,3-(S)-Dibenzyl-1,4,8-triazaspiro[4,5]decan-2-one: | 400 mg (1.19 mmol) |
| 3-Methoxybenzoyl chloride: | 189 mg (1.19 mmol) |
| Triethylamine: | 241 mg (2.39 mmol) |
| Yield following column chromatography: | 377 mg (69%) |

Example 51

1-Benzyl-8-(4-fluoro-benzoyl)-3-(S)-(2-methylsulfanyl-ethyl)-1,4,8-triazaspiro[4,5]decan-2-one

| | |
|---|---|
| 1-Benzyl-3-(S)-(2-methylsulfanyl-ethyl)-1,4,8-triazaspiro[4,5]decan-2-one: | 200 mg (1.19 mmol) |
| 3-Methoxybenzoyl chloride: | 99 mg (1.19 mmol) |
| Triethylamine: | 127 mg (2.39 mmol) |
| Yield following column chromatography: | 246 mg (89%) |

Example 52

1,3-(S)-dibenzyl-8-butyryl-1,4,8-triazaspiro[4,5]decan-2-one hydrochloride 1,3-(S)-dibenzyl-8-butyryl-1,4,8-triazaspiro[4,5]decan-2-one (272 mg, 10.7 mmol) was dissolved in ethyl methyl ketone (2.2 mL), and water (7 μL) and TMSCl (93 μL) were added and the mixture was stirred overnight. The solid matter was isolated by filtration, washed with ether, and dried in vacuo. The product 1,3-(S)-dibenzyl-8-butyryl-1,4,8-triazaspiro[4,5]decan-2-one hydrochloride was obtained in a yield of 281 mg (95%).

Example 53

1,3-(S)-dibenzyl-8-(3-fluoro-4-trifluoromethylbenzoyl)-1,4,8-triazaspiro[4,5]decan-2-one hydrochloride 1,3-(S)-dibenzyl-8-(3-fluoro-4-trifluoromethylbenzoyl)-1,4,8-triazaspiro[4,5]decan-2-one (397 mg, 0.8 mmol) was dissolved in ethyl methyl ketone (3.2 mL), water (7 μL), ether (30 mL) and TMSCl (105 μL) were added and the mixture was stirred overnight. The solid matter was isolated by filtration, washed with ether, and dried in vacuo. The product 11,3-(S)-dibenzyl-8-(3-fluoro-4-trifluoromethylbenzoyl)-1,4,8-triazaspiro[4,5]decan-2-one hydrochloride was obtained in a yield of 396 mg (93%).

Example 54

1,3-(S)-dibenzyl-8-(2,3-difluorobenzoyl)-1,4,8-triazaspiro[4,5]decan-2-one hydrochloride 1,3-(S)-dibenzyl-8-(2,3-difluorobenzoyl)-1,4,8-triazaspiro[4,5]decan-2-one (370 mg, 0.8 mmol) was dissolved in ethyl methyl ketone (2.9 mL), water (8 μL), ether (30 mL) and TMSCl (108 μL) were added and the mixture was stirred overnight. The solid matter was isolated by filtration, washed with ether, and dried in vacuo. The product 1,3-(S)-dibenzyl-8-(2,3-difluorobenzoyl)-1,4,8-triazaspiro[4,5]decan-2-one hydrochloride was obtained in a yield of 317 mg (80%).

Example 55

1,3-(S)-dibenzyl-8-[2-(4-chlorophenoxy)acetyl]-1,4,8-triazaspiro[4,5]decan-2-one hydrochloride 1,3-(S)-dibenzyl-8-[2-(4-chlorophenoxy)acetyl]-1,4,8-triazaspiro[4,5]decan-2-one (415 mg, 0.8 mmol) was dissolved in ethyl methyl ketone (3.3 mL), water (8 µL) and TMSCl (115 µL) were added and the mixture was stirred overnight. The solid matter was isolated by filtration, washed with ether, and dried in vacuo. The product 1,3-(S)-dibenzyl-8-[2-(4-chlorophenoxy)acetyl]-1,4,8-triazaspiro[4,5]decan-2-one hydrochloride was obtained in a yield of 385 mg (87%).

Example 56

1,3-(S)-dibenzyl-8-diphenylacetyl-1,4,8-triazaspiro[4,5]decan-2-one hydrochloride 1,3-(S)-dibenzyl-8-diphenylacetyl-1,4,8-triazaspiro[4,5]decan-2-one (450 mg, 0.8 mmol) was dissolved in ethyl methyl ketone (3.6 mL), water (8 µL), TMSCl (118 µL), and ether (10 mL) were added and the mixture was stirred overnight. The solid matter was isolated by filtration, washed with ether, and dried in vacuo. The product 1,3-(S)-dibenzyl-8-diphenylacetyl-1,4,8-triazaspiro[4,5]decan-2-one hydrochloride was obtained in a yield of 402 mg (84%).

Example 57

1,3-(S)-dibenzyl-8-(2-phenoxyacetyl)-1,4,8-triazaspiro[4,5]decan-2-one hydrochloride 1,3-(S)-dibenzyl-8-(2-phenoxyacetyl)-1,4,8-triazaspiro[4,5]decan-2-one (410 mg, 0.9 mmol) was dissolved in ethyl methyl ketone (3.3 mL), water (9 µL), TMSCl (121 µL), and ether (30 mL) were added and the mixture was stirred overnight. The solid matter was isolated by filtration, washed with ether, and dried in vacuo. The product 1,3-(S)-dibenzyl-8-(2-phenoxyacetyl)-1,4,8-triazaspiro[4,5]decan-2-one hydrochloride was obtained in a yield of 347 mg (79%).

Example 58

1,3-(S)-dibenzyl-8-(3-phenylpropionyl)-1,4,8-triazaspiro[4,5]decan-2-one hydrochloride 1,3-(S)-dibenzyl-8-(3-phenylpropionyl)-1,4,8-triazaspiro[4,5]decan-2-one (360 mg, 0.8 mmol) was dissolved in ethyl methyl ketone (2.9 mL), water (8 µL), TMSCl (107 µL), and ether (10 mL) were added and the mixture was stirred overnight. The solid matter was isolated by filtration, washed with ether, and dried in vacuo. The product 1,3-(S)-dibenzyl-8-(3-phenylpropionyl)-1,4,8-triazaspiro[4,5]decan-2-one hydrochloride was obtained in a yield of 323 mg (83%).

Example 59

1,3-(S)-dibenzyl-8-(naphthalin-2-carbonyl)-1,4,8-triazaspiro[4,5]decan-2-one hydrochloride 1,3-(S)-dibenzyl-8-(naphthalin-2-carbonyl)-1,4,8-triazaspiro[4,5]decan-2-one (400 mg, 0.8 mmol) was dissolved in ethyl methyl ketone (3.2 mL), water (8 µL), TMSCl (114 µL), and ether (20 mL) were added and the mixture was stirred overnight. The solid matter was isolated by filtration, washed with ether, and dried in vacuo. The product 1,3-(S)-dibenzyl-8-(naphthalin-2-carbonyl)-1,4,8-triazaspiro[4,5]decan-2-one hydrochloride was obtained in a yield of 407 mg (95%).

Example 60

1,3-(S)-dibenzyl-8-(furan-2-carbonyl)-1,4,8-triazaspiro[4,5]decan-2-one hydrochloride 1,3-(S)-dibenzyl-8-(furan-2-carbonyl)-1,4,8-triazaspiro[4,5]decan-2-one (365 mg, 0.9 mmol) was dissolved in ethyl methyl ketone (2.9 mL), water (8 µL), TMSCl (118 µL), and ether (20 mL) were added and the mixture was stirred overnight. The solid matter was isolated by filtration, washed with ether, and dried in vacuo. The product 1,3-(S)-dibenzyl-8-(furan-2-carbonyl)-1,4,8-triazaspiro[4,5]decan-2-one hydrochloride was obtained in a yield of 338 mg (85%).

Example 61

1,3-(S)-dibenzyl-8-(3-methoxybenzoyl)-1,4,8-triazaspiro[4,5]decan-2-one hydrochloride 1,3-(S)-dibenzyl-8-(3-methoxybenzoyl)-1,4,8-triazaspiro[4,5]decan-2-one (404 mg, 0.9 mmol) was dissolved in ethyl methyl ketone (3.2 mL), and water (9 µL) and TMSCl (120 µL) were added and the mixture was stirred overnight. The solid matter was isolated by filtration, washed with ether, and dried in vacuo. The product 1,3-(S)-dibenzyl-8-(3-methoxybenzoyl)-1,4,8-triazaspiro[4,5]decan-2-one hydrochloride was obtained in a yield of 358 mg (82%).

Example 62

1,3-(S)-dibenzyl-8-(4-fluorobenzoyl)-1,4,8-triazaspiro[4,5]decan-2-one hydrochloride 1,3-(S)-dibenzyl-8-(4-fluorobenzoyl)-1,4,8-triazaspiro[4,5]decan-2-one (254 mg, 0.9 mmol) was dissolved in ethyl methyl ketone (2.0 mL), water (5 µL), TMSCl (77 µL), and ether (20 mL) were added and the mixture was stirred overnight. The solid matter was isolated by filtration, washed with ether, and dried in vacuo. The product 1,3-(S)-dibenzyl-8-(4-fluorobenzoyl)-1,4,8-triazaspiro[4,5]decan-2-one hydrochloride was obtained in a yield of 242 mg (88%).

Example 63

1-benzyl-8-(4-fluorobenzoyl)-3-(S)-(2-methylsulfanylethyl)-1,4,8-triazaspiro[4,5]decan-2-one hydrochloride 1-benzyl-8-(4-fluorobenzoyl)-3-(S)-(2-methylsulfanylethyl)-1,4,8-triazaspiro[4,5]decan-2-one (223 mg, 0.5 mmol) was dissolved in ethyl methyl ketone (1.8 mL), water (5 µL) and TMSCl (70 µL) were added and the mixture was stirred overnight. The solid matter was isolated by filtration, washed with ether, and dried in vacuo. The product 1-benzyl-8-(4-fluorobenzoyl)-3-(S)-(2-methylsulfanylethyl)-1,4,8-triazaspiro[4,5]decan-2-one hydrochloride was obtained in a yield of 227 mg (94%).

The compounds of the following examples were prepared in a manner similar to that described in the above general manufacturing procedure II:

| Ex. | Compound |
|---|---|
| 64 | N-[4-(3-Isobutyl-2-oxo-1-prop-2-ynyl-1,4,8-triazaspiro[4,5]decan-8-carbonyl)phenyl]acetamide |
| 65 | 1-(2-Phenoxyethyl)-8-(thiophene-2-carbonyl)-1,4,8-triazaspiro[4,5]decan-2-one |
| 66 | 2-(2-Oxo-8-pent-4-enoyl-1,4,8-triazaspiro[4,5]dec-1-ylmethyl)benzonitrile |
| 67 | 8-(2,4-Dimethoxybenzoyl)-1-methyl-3-(2-methylsulfanylethyl)-1,4,8-triazaspiro[4,5]decan-2-one |
| 68 | 2-[8-(2-Ethylbutyryl)-2-oxo-1,4,8-triazaspiro[4,5]dec-1-ylmethyl]benzonitrile |
| 69 | 4-(2-Isobutyl-3-oxo-1,4,8-triazaspiro[4,5]decan-8-carbonyl)benzonitrile |
| 70 | 8-(6-Chloropyridin-3-carbonyl)-3-isobutyl-1,4,8-triazaspiro[4,5]decan-2-one |
| 71 | 2-[8-(2-Methylpentanoyl)-2-oxo-1,4,8-triazaspiro[4,5]dec-1-ylmethyl]benzonitrile |
| 72 | 1-Benzyl-8-(biphenyl-4-carbonyl)-1,4,8-triazaspiro[4,5]decan-2-one |
| 73 | 3-Isobutyl-8-(5-methylisoxazole-3-carbonyl)-1,4,8-triazaspiro[4,5]decan-2-one |
| 74 | Ethyl 3-oxo-3-[2-oxo-1-(2-phenoxyethyl)-1,4,8-triazaspiro[4,5]dec-8-yl]propionate |
| 75 | 8-(2-Chlorobenzoyl)-3-isopropyl-1,4,8-triazaspiro[4,5]decan-2-one |
| 76 | 8-Cyclopentanecarbonyl-3-isopropyl-1,4,8-triazaspiro[4,5]decan-2-one |
| 77 | 8-(Furan-2-carbonyl)-1-methyl-3-(2-methylsulfanylethyl)-1,4,8-triazaspiro[4,5]decan-2-one |
| 78 | 3-Benzyl-8-(2-ethylsulfanylpyridin-3-carbonyl)-1-methyl-1,4,8-triazaspiro[4,5]decan-2-one |
| 79 | 3-Benzyl-8-(4-chlorobenzoyl)-1,4,8-triazaspiro[4,5]decan-2-one |
| 80 | 8-(2-Benzyloxyacetyl)-3-isobutyl-1,4,8-triazaspiro[4,5]decan-2-one |
| 81 | 3-Benzyl-8-(2-methoxyacetyl)-1-prop-2-ynyl-1,4,8-triazaspiro[4,5]decan-2-one |
| 82 | 8-(5-tert-Butyl-2-methyl-2H-pyrazole-3-carbonyl)-3-isobutyl-1,4,8-triazaspiro[4,5]decan-2-one |
| 83 | 2-{8-[3-(2-chloro-6-fluorophenyl)-5-methylisoxazole-4-carbonyl]-2-oxo-1,4,8-triazaspiro[4,5]dec-1-ylmethyl}-benzonitrile |
| 84 | 3-Benzyl-8-(2-chlorobenzoyl)-1,4,8-triazaspiro[4,5]decan-2-one |
| 85 | 3-Benzyl-8-(3-dimethylaminobenzoyl)-1-methyl-1,4,8-triazaspiro[4,5]decan-2-one |
| 86 | 8-(3-Methylbenzoyl)-1-(2-phenoxyethyl)-1,4,8-triazaspiro[4,5]decan-2-one |
| 87 | 3-Isopropyl-1-(3-methylbut-2-enyl)-8-(pyridin-4-carbonyl)-1,4,8-triazaspiro[4,5]decan-2-one |
| 88 | 1-Benzyl-8-(4-methyl[1,2,3]thiadiazole-5-carbonyl)-1,4,8-triazaspiro[4,5]decan-2-one |
| 89 | 2-{8-[3-(2-Chlorophenyl)acryloyl]-2-oxo-1,4,8-triazaspiro[4,5]dec-1-ylmethyl}benzonitrile |
| 90 | 8-(3-Chlorobenzoyl)-3-isobutyl-1,4,8-triazaspiro[4,5]decan-2-one |
| 91 | Ethyl 2-(2-benzyl-3-oxo-1,4,8-triazaspiro[4,5]dec-8-yl)-2-oxo-1-phenylacetate |
| 92 | 8-(3,5-Dimethoxybenzoyl)-3-isobutyl-1,4,8-triazaspiro[4,5]decan-2-one |
| 93 | 3-Benzyl-8-(isoxazole-5-carbonyl)-1,4,8-triazaspiro[4,5]decan-2-one |
| 94 | 8-(3-Chlorothiophene-2-carbonyl)-3-isobutyl-1,4,8-triazaspiro[4,5]decan-2-one |
| 95 | 3-Isopropyl-8-pentafluorobenzoyl-1,4,8-triazaspiro[4,5]decan-2-one |
| 96 | 8-(2,5-Dimethylfuran-3-carbonyl)-3-isobutyl-1,4,8-triazaspiro[4,5]decan-2-one |
| 97 | 1-Butyl-8-[2-(3,4-dimethoxyphenyl)acetyl]-3-(2-methylsulfanylethyl)-1,4,8-triazaspiro[4,5]decan-2-one |
| 98 | 1-Benzyl-3-isopropyl-8-(pyridin-4-carbonyl)-1,4,8-triazaspiro[4,5]decan-2-one |
| 99 | 1,3-Dibenzyl-8-(3-dimethylaminobenzoyl)-1,4,8-triazaspiro[4,5]decan-2-one |
| 100 | 5-{2-[1-(4-Fluorobenzyl)-3-(2-methylsulfanylethyl)-2-oxo-1,4,8-triazaspiro[4,5]dec-8-yl]-2-oxoethyl}imidazolidine-2,4-dione |
| 101 | 8-(Biphenyl-4-carbonyl)-1-(4-fluorobenzyl)-3-isobutyl-1,4,8-triazaspiro[4,5]decan-2-one |
| 102 | 2-[2-Oxo-8-(2-propylpentanoyl)-1,4,8-triazaspiro[4,5]dec-1-ylmethyl]benzonitrile |
| 103 | 2-[8-(Furan-2-carbonyl)-3-isopropyl-2-oxo-1,4,8-triazaspiro[4,5]dec-1-ylmethyl]benzonitrile |
| 104 | 8-[2-(4-Chlorophenoxy)acetyl]-3-isobutyl-1-prop-2-ynyl-1,4,8-triazaspiro[4,5]decan-2-one |
| 105 | 1,3-Dibenzyl-8-(4-bromobenzoyl)-1,4,8-triazaspiro[4,5]decan-2-one |
| 106 | 8-(3-Difluoromethylsulfanylbenzoyl)-3-isobutyl-1,4,8-triazaspiro[4,5]decan-2-one |
| 107 | 8-(2,3-Dimethylbenzoyl)-3-isopropyl-1,4,8-triazaspiro[4,5]decan-2-one |
| 108 | 3-Benzyl-8-(2,3-dimethylbenzoyl)-1,4,8-triazaspiro[4,5]decan-2-one |
| 109 | 1-(4-Fluorobenzyl)-3-(2-methylsulfanylethyl)-8-(pyridin-2-carbonyl)-1,4,8-triazaspiro[4,5]decan-2-one |
| 110 | 3-Benzyl-8-(3,3-dimethylbutyryl)-1,4,8-triazaspiro[4,5]decan-2-one |
| 111 | 2-[8-(3-Dimethylaminobenzoyl)-3-isobutyl-2-oxo-1,4,8-triazaspiro[4,5]dec-1-ylmethyl]benzonitrile |
| 112 | 3-[8-(2-Methoxyacetyl)-3-(2-methylsulfanylethyl)-2-oxo-1,4,8-triazaspiro[4,5]dec-1-ylmethyl]benzonitrile |

| Ex. | Compound |
|---|---|
| 113 | Ethyl 2-(3-benzyl-1-methyl-2-oxo-1,4,8-triazaspiro[4,5]dec-8-yl)-2-oxo-1-phenylacetate |
| 114 | 2-[8-[2-(2-Methoxyethoxy)acetyl]-3-(2-methylsulfanylethyl)-2-oxo-1,4,8-triazaspiro[4,5]dec-1-ylmethyl]benzonitrile |
| 115 | 3-Benzyl-8-[3-(2-chloro-6-fluorophenyl)-5-methylisoxazole-4-carbonyl]-1,4,8-triazaspiro[4,5]decan-2-one |
| 116 | 8-(2-Chloro-6-fluorobenzoyl)-3-isopropyl-1,4,8-triazaspiro[4,5]decan-2-one |
| 117 | 1-Methyl-3-(2-methylsulfanylethyl)-8-(2-phenoxyacetyl)-1,4,8-triazaspiro[4,5]decan-2-one |
| 118 | 8-(2-Chloropyridin-3-carbonyl)-1-(4-fluorobenzyl)-3-isobutyl-1,4,8-triazaspiro[4,5]decan-2-one |
| 119 | 8-(2-Ethylbutyryl)-1-methyl-3-(2-methylsulfanylethyl)-1,4,8-triazaspiro[4,5]decan-2-one |
| 120 | 1-Methyl-3-(2-methylsulfanylethyl)-8-(2-phenoxypyridin-3-carbonyl)-1,4,8-triazaspiro[4,5]decan-2-one |
| 121 | 8-(3-Fluorobenzoyl)-1-methyl-3-(2-methylsulfanylethyl)-1,4,8-triazaspiro[4,5]decan-2-one |
| 122 | 3-Benzyl-8-(naphthalin-2-carbonyl)-1,4,8-triazaspiro[4,5]decan-2-one |
| 123 | 8-Cyclohexanecarbonyl-1-(2-phenoxyethyl)-1,4,8-triazaspiro[4,5]decan-2-one |
| 124 | 8-(2-Phenoxyacetyl)-1-(2-phenoxyethyl)-1,4,8-triazaspiro[4,5]decan-2-one |
| 125 | 4-[1-Butyl-3-(2-methylsulfanylethyl)-2-oxo-1,4,8-triazaspiro[4,5]decan-8-carbonyl]benzonitrile |
| 126 | 3-Benzyl-8-(3,3-dimethylbutyryl)-1-methyl-1,4,8-triazaspiro[4,5]decan-2-one |
| 127 | 3-Benzyl-8-(4-propylbenzoyl)-1,4,8-triazaspiro[4,5]decan-2-one |
| 128 | 3-Isopropyl-8-(2-phenoxypropionyl)-1,4,8-triazaspiro[4,5]decan-2-one |
| 129 | 1-Butyl-8-hexanoyl-3-isopropyl-1,4,8-triazaspiro[4,5]decan-2-one |
| 130 | 8-(4-Bromo-3-methylbenzoyl)-3-isopropyl-1,4,8-triazaspiro[4,5]decan-2-one |
| 131 | 8-[3-(2-Chloro-6-fluorophenyl)-5-methylisoxazole-4-carbonyl]-3-isopropyl-1-(2-phenoxyethyl)-1,4,8-triazaspiro[4,5]decan-2-one |
| 132 | 1-(2-Fluorobenzyl)-3-isobutyl-8-(3-methylbenzoyl)-1,4,8-triazaspiro[4,5]decan-2-one |
| 133 | 8-(2-Ethylhexanoyl)-1-(2-phenoxyethyl)-1,4,8-triazaspiro[4,5]decan-2-one |
| 134 | 3-Benzyl-8-(3,4-difluorobenzoyl)-1,4,8-triazaspiro[4,5]decan-2-one |
| 135 | 3-Benzyl-8-(4-ethoxybenzoyl)-1-methyl-1,4,8-triazaspiro[4,5]decan-2-one |
| 136 | 1-Benzyl-8-(6-chloropyridin-3-carbonyl)-1,4,8-triazaspiro[4,5]decan-2-one |
| 137 | 8-(3-Dimethylaminobenzoyl)-1-(3,5-dimethylbenzyl)-3-(2-methylsulfanylethyl)-1,4,8-triazaspiro[4,5]decan-2-one |
| 138 | 3-[8-(Benzo[1,3]dioxol-5-carbonyl)-3-(2-methylsulfanylethyl)-2-oxo-1,4,8-triazaspiro[4,5]dec-1-ylmethyl]benzonitrile |
| 139 | 3-Benzyl-1-methyl-8-pent-4-enoyl-1,4,8-triazaspiro[4,5]decan-2-one |
| 140 | 8-(4-Ethoxybenzoyl)-1-methyl-3-(2-methylsulfanylethyl)-1,4,8-triazaspiro[4,5]decan-2-one |
| 141 | 3-Benzyl-8-(2-benzyloxyacetyl)-1-methyl-1,4,8-triazaspiro[4,5]decan-2-one |
| 142 | 8-(3,4-Difluorobenzoyl)-1-(2-phenoxyethyl)-1,4,8-triazaspiro[4,5]decan-2-one |
| 143 | 3-Benzyl-1-methyl-8-(2-methylsulfanylpyridin-3-carbonyl)-1,4,8-triazaspiro[4,5]decan-2-one |
| 144 | 1-Butyl-8-(4-methoxybenzoyl)-3-(2-methylsulfanylethyl)-1,4,8-triazaspiro[4,5]decan-2-one |
| 145 | 1,3-Dibenzyl-8-(2-ethylsulfanylpyridin-3-carbonyl)-1,4,8-triazaspiro[4,5]decan-2-one |
| 146 | 3-Benzyl-8-(3-difluoromethylsulfanylbenzoyl)-1,4,8-triazaspiro[4,5]decan-2-one |
| 147 | 1-(4-Fluorobenzyl)-8-(furan-2-carbonyl)-3-(2-methylsulfanylethyl)-1,4,8-triazaspiro[4,5]decan-2-one |
| 148 | 3-Benzyl-8-(3-fluoro-4-methylbenzoyl)-1-methyl-1,4,8-triazaspiro[4,5]decan-2-one |
| 149 | 8-[3-(2-Chloro-6-fluorophenyl)-5-methylisoxazole-4-carbonyl]-3-isopropyl-1,4,8-triazaspiro[4,5]decan-2-one |
| 150 | 1-Butyl-8-(6-Chloro-2H-chroman-3-carbonyl)-3-(2-methylsulfanylethyl)-1,4,8-triazaspiro[4,5]decan-2-one |
| 151 | 3-[8-(3-Methoxybenzoyl)-3-(2-methylsulfanylethyl)-2-oxo-1,4,8-triazaspiro[4,5]dec-1-ylmethyl]benzonitrile |
| 152 | 8-Cyclobutanecarbonyl-3-(2-methylsulfanylethyl)-1-prop-2-ynyl-1,4,8-triazaspiro[4,5]decan-2-one |
| 153 | 3-Benzyl-1-butyl-8-(furan-2-carbonyl)-1,4,8-triazaspiro[4,5]decan-2-one |
| 154 | 1-Benzyl-8-(3-chlorothiophene-2-carbonyl)-3-isobutyl-1,4,8-triazaspiro[4,5]decan-2-one |
| 155 | 3-Benzyl-8-(2,5-bis-trifluoromethylbenzoyl)-1-butyl-1,4,8-triazaspiro[4,5]decan-2-one |
| 156 | 8-(3-Chloro-2-fluorobenzoyl)-1-(3,5-dimethylbenzyl)-3-(2-methylsulfanylethyl)-1,4,8-triazaspiro[4,5]decan-2-one |
| 157 | 1-Benzyl-8-(2-chloropyridin-3-carbonyl)-3-isopropyl-1,4,8-triazaspiro[4,5]decan-2-one |
| 158 | 3-Isobutyl-8-pentafluorobenzoyl-1-prop-2-ynyl-1,4,8-triazaspiro[4,5]decan-2-one |
| 159 | 8-(2-Benzyloxyacetyl)-1-butyl-3-(2-methylsulfanylethyl)-1,4,8-triazaspiro[4,5]decan-2-one |

| Ex. | Compound |
|---|---|
| 160 | 8-(Furan-2-carbonyl)-3-isobutyl-1-prop-2-ynyl-1,4,8-triazaspiro[4,5]decan-2-one |
| 161 | 1-Butyl-3-(2-methylsulfanylethyl)-8-(4-phenoxybutyryl)-1,4,8-triazaspiro[4,5]decan-2-one |
| 162 | 3-Benzyl-8-(6-chloropyridin-3-carbonyl)-1-methyl-1,4,8-triazaspiro[4,5]decan-2-one |
| 163 | 1-(2-Fluorobenzyl)-3-(2-methylsulfanylethyl)-8-(2-phenoxypyridin-3-carbonyl)-1,4,8-triazaspiro[4,5]decan-2-one |
| 164 | 1-(2-Fluorobenzyl)-3-isobutyl-8-(2-methyl-6-trifluoromethylpyridin-3-carbonyl)-1,4,8-triazaspiro[4,5]decan-2-one |
| 165 | 8-[2-(3-Chlorophenoxy)acetyl]-3-isopropyl-1-(2-phenoxyethyl)-1,4,8-triazaspiro[4,5]decan-2-one |
| 166 | 8-(2,3-Dimethylbenzoyl)-1-methyl-3-(2-methylsulfanylethyl)-1,4,8-triazaspiro[4,5]decan-2-one |
| 167 | 3-Isopropyl-8-(2-methyl-6-trifluoromethylpyridin-3-carbonyl)-1-(2-phenoxyethyl)-1,4,8-triazaspiro[4,5]decan-2-one |
| 168 | 3-Benzyl-1-methyl-8-(5-methyl-2-phenyl-2H-[1,2,3]triazole-4-carbonyl)-1,4,8-triazaspiro[4,5]decan-2-one |
| 169 | 8-[3-(2-Chlorophenyl)-5-methylisoxazole-4-carbonyl]-1-(3,5-dimethylbenzyl)-3-(2-methylsulfanylethyl)-1,4,8-triazaspiro[4,5]decan-2-one |
| 170 | 1-(2-Fluorobenzyl)-3-(2-methylsulfanylethyl)-8-(pyridin-2-carbonyl)-1,4,8-triazaspiro[4,5]decan-2-one |
| 171 | 1-Benzyl-3-(2-methylsulfanylethyl)-8-(2-phenoxypyridin-3-carbonyl)-1,4,8-triazaspiro[4,5]decan-2-one |
| 172 | 1,3-Dibenzyl-8-(3-chlorothiophene-2-carbonyl)-1,4,8-triazaspiro[4,5]decan-2-one |
| 173 | 3-Benzyl-8-(4-tert-butylbenzoyl)-1-methyl-1,4,8-triazaspiro[4,5]decan-2-one |
| 174 | 2-[3-Isobutyl-8-(2-methoxyacetyl)-2-oxo-1,4,8-triazaspiro[4,5]dec-1-ylmethyl]benzonitrile |
| 175 | 3-Benzyl-1-butyl-8-(5-fluoro-2-trifluoromethylbenzoyl)-1,4,8-triazaspiro[4,5]decan-2-one |
| 176 | 3-Benzyl-8-[2-(4-methoxyphenyl)acetyl]-1-methyl-1,4,8-triazaspiro[4,5]decan-2-one |
| 177 | 1,3-Dibenzyl-8-(4-methyl[1,2,3]thiadiazole-5-carbonyl)-1,4,8-triazaspiro[4,5]decan-2-one |
| 178 | 1-Benzyl-3-isopropyl-8-(2-methyl-6-trifluoromethylpyridin-3-carbonyl)-1,4,8-triazaspiro[4,5]decan-2-one |
| 179 | 1-Benzyl-8-(4-ethoxybenzoyl)-3-isobutyl-1,4,8-triazaspiro[4,5]decan-2-one |
| 180 | 3-Benzyl-1-butyl-8-cyclohexanecarbonyl-1,4,8-triazaspiro[4,5]decan-2-one |
| 181 | 3-[8-[3-(2-Chloro-6-fluorophenyl)-5-methylisoxazole-4-carbonyl]-3-(2-methylsulfanylethyl)-2-oxo-1,4,8-triazaspiro[4,5]dec-1-ylmethyl]benzonitrile |
| 182 | 1-(2-Fluorobenzyl)-3-isobutyl-8-pent-4-enoyl-1,4,8-triazaspiro[4,5]decan-2-one |
| 183 | 1-Methyl-3-(2-methylsulfanylethyl)-8-(2-propylpentanoyl)-1,4,8-triazaspiro[4,5]decan-2-one |
| 184 | 3-Benzyl-1-methyl-8-(2-phenoxyacetyl)-1,4,8-triazaspiro[4,5]decan-2-one |
| 185 | 3-Isobutyl-1-prop-2-ynyl-8-(3-trifluoromethylbenzoyl)-1,4,8-triazaspiro[4,5]decan-2-one |
| 186 | 3-Benzyl-8-(furan-2-carbonyl)-1-prop-2-ynyl-1,4,8-triazaspiro[4,5]decan-2-one |
| 187 | 1-Methyl-3-(2-methylsulfanylethyl)-8-(naphthalin-1-carbonyl)-1,4,8-triazaspiro[4,5]decan-2-one |
| 188 | 3-Benzyl-1-butyl-8-(3-cyclopentylpropionyl)-1,4,8-triazaspiro[4,5]decan-2-one |
| 189 | 1-(3,5-Dimethylbenzyl)-3-(2-methylsulfanylethyl)-8-pentanoyl-1,4,8-triazaspiro[4,5]decan-2-one |
| 190 | 3-Benzyl-1-butyl-8-(2-methoxyacetyl)-1,4,8-triazaspiro[4,5]decan-2-one |
| 191 | 3-Benzyl-8-(3-fluoro-4-trifluoromethylbenzoyl)-1-methyl-1,4,8-triazaspiro[4,5]decan-2-one |
| 192 | 1-Benzyl-8-(3-difluoromethylsulfanylbenzoyl)-3-isopropyl-1,4,8-triazaspiro[4,5]decan-2-one |
| 193 | 8-(2-Chloro-6-fluoro-3-methylbenzoyl)-1-methyl-3-(2-methylsulfanylethyl)-1,4,8-triazaspiro[4,5]decan-2-one |
| 194 | Methyl 4-[3-isopropyl-8-(2-methylsulfanylpyridin-3-carbonyl)-2-oxo-1,4,8-triazaspiro[4,5]dec-1-ylmethyl]benzoate |
| 195 | 8-[2-(2,5-Dimethoxyphenyl)acetyl]-1-(2-fluorobenzyl)-3-(2-methylsulfanylethyl)-1,4,8-triazaspiro[4,5]decan-2-one |
| 196 | 8-(5-tert-Butyl-2-methylfuran-3-carbonyl)-3-isopropyl-1-(2-phenoxyethyl)-1,4,8-triazaspiro[4,5]decan-2-one |
| 197 | 8-(2-Cyclopentylacetyl)-1-(4-fluorobenzyl)-3-isobutyl-1,4,8-triazaspiro[4,5]decan-2-one |
| 198 | Methyl 4-[8-(3,3-dimethylbutyryl)-3-isopropyl-2-oxo-1,4,8-triazaspiro[4,5]dec-1-ylmethyl]benzoate |
| 199 | 3-[8-Cyclopropanecarbonyl-3-(2-methylsulfanylethyl)-2-oxo-1,4,8-triazaspiro[4,5]dec-1-ylmethyl]benzonitrile |
| 200 | 3-[3-(2-Methylsulfanylethyl)-2-oxo-8-(3-trifluoromethoxybenzoyl)-1,4,8-triazaspiro[4,5]dec-1-ylmethyl]benzonitrile |
| 201 | 1-Butyl-8-(2-cyclopentylacetyl)-3-isopropyl-1,4,8-triazaspiro[4,5]decan-2-one |

-continued

| Ex. | Compound |
|---|---|
| 202 | 3-Benzyl-1-butyl-8-(pyridin-2-carbonyl)-1,4,8-triazaspiro[4,5]decan-2-one |
| 203 | 3-Benzyl-8-[3-(2-chlorophenyl)acryloyl]-1-methyl-1,4,8-triazaspiro[4,5]decan-2-one |
| 204 | Methyl 4-[8-(3-fluoro-4-trifluoromethylbenzoyl)-3-isopropyl-2-oxo-1,4,8-triazaspiro[4,5]dec-1-ylmethyl]benzoate |
| 205 | 8-[3-(2,6-Dichlorophenyl)-5-methylisoxazole-4-carbonyl]-1-methyl-3-(2-methylsulfanylethyl)-1,4,8-triazaspiro[4,5]decan-2-one |
| 206 | 1-Butyl-8-cyclohexanecarbonyl-3-(2-methylsulfanylethyl)-1,4,8-triazaspiro[4,5]decan-2-one |
| 207 | 3-Benzyl-1-butyl-8-(4-Iodobenzoyl)-1,4,8-triazaspiro[4,5]decan-2-one |
| 208 | 1-Methyl-3-(2-methylsulfanylethyl)-8-[3-(3-trifluoromethylphenyl)acryloyl]-1,4,8-triazaspiro[4,5]decan-2-one |
| 209 | 1,3-Dibenzyl-8-(4-phenoxybutyryl)-1,4,8-triazaspiro[4,5]decan-2-one |
| 210 | 3-Benzyl-8-(2-chloro-6-fluorobenzoyl)-1-prop-2-ynyl-1,4,8-triazaspiro[4,5]decan-2-one |
| 211 | Methyl 4-[8-(2-chloropyridin-3-carbonyl)-3-isopropyl-2-oxo-1,4,8-triazaspiro[4,5]dec-1-ylmethyl]benzoate |
| 212 | 8-(2,5-Dimethylfuran-3-carbonyl)-3-isopropyl-1-(2-phenoxyethyl)-1,4,8-triazaspiro[4,5]decan-2-one |
| 213 | 8-(Biphenyl-4-carbonyl)-3-(2-methylsulfanylethyl)-1-prop-2-ynyl-1,4,8-triazaspiro[4,5]decan-2-one |
| 214 | 8-(3-Chlorothiophene-2-carbonyl)-3-(2-methylsulfanylethyl)-1-prop-2-ynyl-1,4,8-triazaspiro[4,5]decan-2-one |
| 215 | 1-(4-Fluorobenzyl)-8-[2-(4-methoxyphenyl)acetyl]-3-(2-methylsulfanylethyl)-1,4,8-triazaspiro[4,5]decan-2-one |
| 216 | 1-Benzyl-3-isopropyl-8-(4-methyl[1,2,3]thiadiazole-5-carbonyl)-1,4,8-triazaspiro[4,5]decan-2-one |
| 217 | 2-[3-Isopropyl-8-(2-methylsulfanylpyridin-3-carbonyl)-2-oxo-1,4,8-triazaspiro[4,5]dec-1-ylmethyl]benzonitrile |
| 218 | 3-[8-(5-tert-Butyl-2-methyl-2H-pyrazole-3-carbonyl)-3-isobutyl-2-oxo-1,4,8-triazaspiro[4,5]dec-1-ylmethyl]benzonitrile |
| 219 | 1-Butyl-8-(2,5-dimethylfuran-3-carbonyl)-3-(2-methylsulfanylethyl)-1,4,8-triazaspiro[4,5]decan-2-one |
| 220 | 8-(3-Cyclopentylpropionyl)-1-(2-fluorobenzyl)-3-isobutyl-1,4,8-triazaspiro[4,5]decan-2-one |
| 221 | 1-Benzyl-8-(3-cyclopentylpropionyl)-3-(2-methylsulfanylethyl)-1,4,8-triazaspiro[4,5]decan-2-one |
| 222 | 3-(2-Methylsulfanylethyl)-8-(4-phenoxybutyryl)-1-prop-2-ynyl-1,4,8-triazaspiro[4,5]decan-2-one |
| 223 | 1,3-Dibenzyl-8-(3-phenylacryloyl)-1,4,8-triazaspiro[4,5]decan-2-one |
| 224 | 3-Benzyl-8-(6-chloro-2-fluoro-3-methylbenzoyl)-1-methyl-1,4,8-triazaspiro[4,5]decan-2-one |
| 225 | 8-[3-(2-Chlorophenyl)acryloyl]-3-isopropyl-1-(2-phenoxyethyl)-1,4,8-triazaspiro[4,5]decan-2-one |
| 226 | 2-[3-Isopropyl-2-oxo-8-(3-phenylacryloyl)-1,4,8-triazaspiro[4,5]dec-1-ylmethyl]benzonitrile |
| 227 | 3-Benzyl-1-methyl-8-(4-methyl-3-nitrobenzoyl)-1,4,8-triazaspiro[4,5]decan-2-one |
| 228 | 1-Benzyl-8-(furan-2-carbonyl)-3-isopropyl-1,4,8-triazaspiro[4,5]decan-2-one |
| 229 | 1-Butyl-8-(3,5-dimethoxybenzoyl)-3-(2-methylsulfanylethyl)-1,4,8-triazaspiro[4,5]decan-2-one |
| 230 | 1,3-Dibenzyl-8-(3,3-dimethylbutyryl)-1,4,8-triazaspiro[4,5]decan-2-one |
| 231 | 8-(2,6-Difluoro-3-methylbenzoyl)-1-methyl-3-(2-methylsulfanylethyl)-1,4,8-triazaspiro[4,5]decan-2-one |
| 232 | 2-[8-(2-Chloro-6-fluorobenzoyl)-3-(2-methylsulfanylethyl)-2-oxo-1,4,8-triazaspiro[4,5]dec-1-ylmethyl]benzonitrile |
| 233 | 8-[3-(2-Chloro-6-fluorophenyl)-5-methylisoxazole-4-carbonyl]-3-isopropyl-1-(3-methylbut-2-enyl)-1,4,8-triazaspiro[4,5]decan-2-one |
| 234 | 3-Isobutyl-1-prop-2-ynyl-8-(4-trifluoromethoxybenzoyl)-1,4,8-triazaspiro[4,5]decan-2-one |
| 235 | 1-Benzyl-8-(2-chloro-6-fluoro-3-methylbenzoyl)-1,4,8-triazaspiro[4,5]decan-2-one |
| 236 | Benzyl 2-(1-benzyl-3-isopropyl-2-oxo-1,4,8-triazaspiro[4,5]decan-8-carbonyl)benzoate |
| 237 | 1,3-Dibenzyl-8-(2-phenylbutyryl)-1,4,8-triazaspiro[4,5]decan-2-one |
| 238 | 3-Benzyl-1-methyl-8-(4-nitrobenzoyl)-1,4,8-triazaspiro[4,5]decan-2-one |
| 239 | 3-Benzyl-1-methyl-8-(5-methylisoxazole-3-carbonyl)-1,4,8-triazaspiro[4,5]decan-2-one |
| 240 | 1-Benzyl-8-(6-chloro-2-fluoro-3-methylbenzoyl)-3-(2-methylsulfanylethyl)-1,4,8-triazaspiro[4,5]decan-2-one |
| 241 | 1-Benzyl-8-(3-fluoro-4-trifluoromethylbenzoyl)-3-isobutyl-1,4,8-triazaspiro[4,5]decan-2-one |
| 242 | 3-Benzyl-8-(6-chloro-2H-chroman-3-carbonyl)-1-methyl-1,4,8-triazaspiro[4,5]decan-2-one |
| 243 | 3-Benzyl-1-butyl-8-(4-methyl[1,2,3]thiadiazole-5-carbonyl)-1,4,8-triazaspiro[4,5]decan-2-one |
| 244 | 3-Benzyl-8-(4-methyl[1,2,3]thiadiazole-5-carbonyl)-1-prop-2-ynyl-1,4,8-triazaspiro[4,5]decan-2-one |

| Ex. | Compound |
| --- | --- |
| 245 | 2-[8-(6-Chloro-2H-chroman-3-carbonyl)-3-isopropyl-2-oxo-1,4,8-triazaspiro[4,5]dec-1-ylmethyl]benzonitrile |
| 246 | 2-[8-(5-Methylisoxazole-3-carbonyl)-3-(2-methylsulfanylethyl)-2-oxo-1,4,8-triazaspiro[4,5]dec-1-ylmethyl]benzonitrile |
| 247 | 2-[8-(3-Chloro-2-fluorobenzoyl)-3-isopropyl-2-oxo-1,4,8-triazaspiro[4,5]dec-1-ylmethyl]benzonitrile |
| 248 | Methyl 4-[8-(5-tert-butyl-2-methyl-2H-pyrazole-3-carbonyl)-3-isopropyl-2-oxo-1,4,8-triazaspiro[4,5]dec-1-ylmethyl]benzoate |
| 249 | 3-Benzyl-1-butyl-8-(5-tert-butyl-2-methyl-2H-pyrazole-3-carbonyl)-1,4,8-triazaspiro[4,5]decan-2-one |
| 250 | 3-Benzyl-1-butyl-8-(2-chloro-4-trifluoromethylpyrimidin-5-carbonyl)-1,4,8-triazaspiro[4,5]decan-2-one |
| 251 | 3-Benzyl-8-(5-methylisoxazole-3-carbonyl)-1-prop-2-ynyl-1,4,8-triazaspiro[4,5]decan-2-one |
| 252 | Methyl 4-[8-(2-chloropyridin-3-carbonyl)-2-oxo-1,4,8-triazaspiro[4,5]dec-1-ylmethyl]benzoate |
| 253 | 8-(2-tert-Butyl-5-methyl-2H-pyrazole-3-carbonyl)-1-(2-fluorobenzyl)-1,4,8-triazaspiro[4,5]decan-2-one |
| 254 | Methyl 4-[8-(2-methylsulfanylpyridin-3-carbonyl)-2-oxo-1,4,8-triazaspiro[4,5]dec-1-ylmethyl]benzoate |
| 255 | Butyl 4-[8-(4-acetylaminobenzoyl)-3-isobutyl-2-oxo-1,4,8-triazaspiro[4,5]dec-1-yl]acetate |
| 256 | Ethyl [8-(4-acetylaminobenzoyl)-3-benzyl-2-oxo-1,4,8-triazaspiro[4,5]dec-1-yl]acetate |
| 257 | Butyl 4-[8-(2-ethylsulfanylpyridin-3-carbonyl)-3-isobutyl-2-oxo-1,4,8-triazaspiro[4,5]dec-1-yl]acetate |
| 258 | Methyl 4-[8-(4-methyl[1,2,3]thiadiazole-5-carbonyl)-2-oxo-1,4,8-triazaspiro[4,5]dec-1-ylmethyl]benzoate |
| 259 | 4-[1-Allyl-3-(2-methylsulfanylethyl)-2-oxo-1,4,8-triazaspiro[4,5]decan-8-carbonyl]benzolsulfonamide |
| 260 | Methyl 4-(8-cyclobutanecarbonyl-2-oxo-1,4,8-triazaspiro[4,5]dec-1-ylmethyl)benzoate |
| 261 | Ethyl 2-[1-allyl-3-(2-methylsulfanylethyl)-2-oxo-1,4,8-triazaspiro[4,5]dec-8-yl]-2-oxo-acetate |
| 262 | 8-(Biphenyl-4-carbonyl)-1-(2-fluorobenzyl)-1,4,8-triazaspiro[4,5]decan-2-one |
| 263 | Ethyl [3-(2-methylsulfanylethyl)-2-oxo-8-propionyl-1,4,8-triazaspiro[4,5]dec-1-yl]acetate |
| 264 | 8-(Benzo[1,3]dioxole-5-carbonyl)-1-(2,6-dichlorobenzyl)-3-isobutyl-1,4,8-triazaspiro[4,5]decan-2-one |
| 265 | 1-Allyl-8-(biphenyl-4-carbonyl)-3-isopropyl-1,4,8-triazaspiro[4,5]decan-2-one |
| 266 | Ethyl [3-benzyl-8-(biphenyl-4-carbonyl)-2-oxo-1,4,8-triazaspiro[4,5]dec-1-yl]acetate |
| 267 | Ethyl [8-(3-dimethylaminobenzoyl)-3-(2-methylsulfanylethyl)-2-oxo-1,4,8-triazaspiro[4,5]dec-1-yl]acetate |
| 268 | 3-(2-Oxo-8-pentanoyl-1,4,8-triazaspiro[4,5]dec-1-ylmethyl)benzonitrile |
| 269 | Methyl 4-(8-cyclopentanecarbonyl-2-oxo-1,4,8-triazaspiro[4,5]dec-1-ylmethyl)benzoate |
| 270 | Ethyl 4-[1-(2-fluorobenzyl)-2-oxo-1,4,8-triazaspiro[4,5]dec-8-yl]-4-oxo-butanate |
| 271 | 1-(2-Fluorobenzyl)-8-(3,4,5-trimethoxybenzoyl)-1,4,8-triazaspiro[4,5]decan-2-one |
| 272 | Methyl 4-[8-(2-Chloropyridin-4-earbonyl)-2-oxo-1,4,8-triazaspiro[4,5]dec-1-ylmethyl]benzoate |
| 273 | 3-[8-(3,5-Bis-trifluoromethylbenzoyl)-2-oxo-1,4,8-triazaspiro[4,5]dec-1-ylmethyl]benzonitrile |
| 274 | 3-Benzyl-1-(2-fluorobenzyl)-8-(2-methoxybenzoyl)-1,4,8-triazaspiro[4,5]decan-2-one |
| 275 | 8-(Benzo[1,2,5]oxadiazole-5-carbonyl)-1-(2,6-dichlorobenzyl)-3-isobutyl-1,4,8-triazaspiro[4,5]decan-2-one |
| 276 | Ethyl [3-benzyl-2-oxo-8-(4-sulfamoylbenzoyl)-1,4,8-triazaspiro[4,5]dec-1-yl]acetate |
| 277 | 3-[2-Oxo-8-(3,4,5-trimethoxybenzoyl)-1,4,8-triazaspiro[4,5]dec-1-ylmethyl]benzonitrile |
| 278 | Ethyl 2-[1-(4-acetoxybutyl)-3-isobutyl-2-oxo-1,4,8-triazaspiro[4,5]dec-8-yl]-1,1-dimethyl-2-oxo-acetate |
| 279 | 8-(6-Chloropyridin-3-carbonyl)-1-(2,6-dichlorobenzyl)-3-isobutyl-1,4,8-triazaspiro[4,5]decan-2-one |
| 280 | 8-(2-Ethoxybenzoyl)-1-(2-fluorobenzyl)-1,4,8-triazaspiro[4,5]decan-2-one |
| 281 | 1-Allyl-8-cyclopropanecarbonyl-3-(2-methylsulfanylethyl)-1,4,8-triazaspiro[4,5]decan-2-one |
| 282 | 3-[3-Isopropyl-8-(2-methoxyacetyl)-2-oxo-1,4,8-triazaspiro[4,5]dec-1-ylmethyl]benzonitrile |
| 283 | Methyl 4-(2-oxo-8-phenylacetyl-1,4,8-triazaspiro[4,5]dec-1-ylmethyl)benzoate |
| 284 | Ethyl 2-[1-(3-cyanobenzyl)-2-oxo-1,4,8-triazaspiro[4,5]dec-8-yl]-2-oxo-1-phenylacetate |
| 285 | 1-(2-Fluorobenzyl)-8-(4-methoxybenzoyl)-1,4,8-triazaspiro[4,5]decan-2-one |

| Ex. | Compound |
|---|---|
| 286 | Methyl 4-(8-cyclohexanecarbonyl-2-oxo-1,4,8-triazaspiro[4,5]dec-1-ylmethyl)benzoate |
| 287 | 1-(2-Fluorobenzyl)-8-pent-4-enoyl-1,4,8-triazaspiro[4,5]decan-2-one |
| 288 | Ethyl [3-isobutyl-8-(3-methylbutyryl)-2-oxo-1,4,8-triazaspiro[4,5]dec-1-yl]acetate |
| 289 | 1-Allyl-8-(3,3-dimethylbutyryl)-3-(2-methylsulfanylethyl)-1,4,8-triazaspiro[4,5]decan-2-one |
| 290 | 1-Allyl-3-(2-methylsulfanylethyl)-8-(2-methylsulfanylpyridin-3-carbonyl)-1,4,8-triazaspiro[4,5]decan-2-one |
| 291 | Ethyl [3-isobutyl-8-(2-methylpentanoyl)-2-oxo-1,4,8-triazaspiro[4,5]dec-1-yl]acetate |
| 292 | Methyl 4-[8-(5-tert-butyl-2-methylfuran-3-carbonyl)-2-oxo-1,4,8-triazaspiro[4,5]dec-1-ylmethyl]benzoate |
| 293 | Ethyl (3-benzyl-8-cyclopropanecarbonyl-2-oxo-1,4,8-triazaspiro[4,5]dec-1-yl)acetate |
| 294 | Ethyl [3-benzyl-8-(3-methylbutyryl)-2-oxo-1,4,8-triazaspiro[4,5]dec-1-yl]acetate |
| 295 | 1-(2,6-Dichlorobenzyl)-8-(2,5-dimethylfuran-3-carbonyl)-3-isobutyl-1,4,8-triazaspiro[4,5]decan-2-one |
| 296 | 1-Allyl-3-isopropyl-8-[2-(3-methoxyphenyl)acetyl]-1,4,8-triazaspiro[4,5]decan-2-one |
| 297 | Ethyl [8-(4-tert-butylbenzoyl)-3-(2-methylsulfanylethyl)-2-oxo-1,4,8-triazaspiro[4,5]dec-1-yl]acetate |
| 298 | 3-(2-Methylsulfanylethyl)-1-(2-nitrobenzyl)-8-(2-phenoxypyridin-3-carbonyl)-1,4,8-triazaspiro[4,5]decan-2-one |
| 299 | Ethyl (3-benzyl-2-oxo-8-pentanoyl-1,4,8-triazaspiro[4,5]dec-1-yl)acetate |
| 300 | 8-(2-Chloropyridin-4-carbonyl)-1-(2-fluorobenzyl)-1,4,8-triazaspiro[4,5]decan-2-one |
| 301 | Ethyl [8-(3-methylbutyryl)-3-(2-methylsulfanylethyl)-2-oxo-1,4,8-triazaspiro[4,5]dec-1-yl]acetate |
| 302 | 1-Allyl-3-(2-methylsulfanylethyl)-8-pentafluorobenzoyl-1,4,8-triazaspiro[4,5]decan-2-one |
| 303 | 1-(2-Fluorobenzyl)-8-(2-trifluoromethylbenzoyl)-1,4,8-triazaspiro[4,5]decan-2-one |
| 304 | 8-(Benzo[1,2,5]oxadiazole-5-carbonyl)-1-(2-fluorobenzyl)-1,4,8-triazaspiro[4,5]decan-2-one |
| 305 | Methyl 4-[8-(4-tert-Butylbenzoyl)-2-oxo-1,4,8-triazaspiro[4,5]dec-1-ylmethyl]benzoate |
| 306 | Ethyl [3-benzyl-2-oxo-8-(1-phenyl-5-propyl-1H-pyrazole-4-carbonyl)-1,4,8-triazaspiro[4,5]dec-1-yl]acetate |
| 307 | 1-Allyl-3-isopropyl-8-pent-4-enoyl-1,4,8-triazaspiro[4,5]decan-2-one |
| 308 | 3-[2-Oxo-8-(2-trifluoromethylbenzoyl)-1,4,8-triazaspiro[4,5]dec-1-ylmethyl]benzonitrile |
| 309 | 8-(2-Dimethylaminoacetyl)-1-(3,5-dimethylbenzyl)-3-isobutyl-1,4,8-triazaspiro[4,5]decan-2-one |
| 310 | Butyl 4-[8-(2-ethoxybenzoyl)-3-isobutyl-2-oxo-1,4,8-triazaspiro[4,5]dec-1-yl]acetate |
| 311 | 1-(2-Fluorobenzyl)-8-(3-methoxybenzoyl)-1,4,8-triazaspiro[4,5]decan-2-one |
| 312 | Ethyl [8-(furan-2-carbonyl)-3-isobutyl-2-oxo-1,4,8-triazaspiro[4,5]dec-1-yl]acetate |
| 313 | 8-(5-tert-Butyl-2-methyl-2H-pyrazole-3-carbonyl)-1-(2-fluorobenzyl)-1,4,8-triazaspiro[4,5]decan-2-one |
| 314 | 1-(2-Fluorobenzyl)-8-(thiophene-2-carbonyl)-1,4,8-triazaspiro[4,5]decan-2-one |
| 315 | Ethyl [3-benzyl-8-(2-fluorobenzoyl)-2-oxo-1,4,8-triazaspiro[4,5]dec-1-yl]acetate |
| 316 | Ethyl [8-(isoxazole-5-carbonyl)-3-(2-methylsulfanylethyl)-2-oxo-1,4,8-triazaspiro[4,5]dec-1-yl]acetate |
| 317 | 1-(2,6-Dichlorobenzyl)-3-isobutyl-8-(4-propylbenzoyl)-1,4,8-triazaspiro[4,5]decan-2-one |
| 318 | Ethyl [8-[2-(2,5-dimethoxyphenyl)acetyl]-3-(2-methylsulfanylethyl)-2-oxo-1,4,8-triazaspiro[4,5]dec-1-yl]acetate |
| 319 | Ethyl (3-benzyl-8-cyclobutanecarbonyl-2-oxo-1,4,8-triazaspiro[4,5]dec-1-yl)acetate |
| 320 | 1-(2-Fluorobenzyl)-8-[2-(4-methoxyphenyl)acetyl]-1,4,8-triazaspiro[4,5]decan-2-one |
| 321 | 1-Allyl-3-(2-methylsulfanylethyl)-8-(2-methyl-6-trifluoromethylpyridin-3-carbonyl)-1,4,8-triazaspiro[4,5]decan-2-one |
| 322 | Ethyl [3-(2-methylsulfanylethyl)-2-oxo-8-(4-trifluoromethylbenzoyl)-1,4,8-triazaspiro[4,5]dec-1-yl]acetate |
| 323 | 1-Allyl-3-(2-methylsulfanylethyl)-8-(1-phenyl-5-propyl-1H-pyrazole-4-carbonyl)-1,4,8-triazaspiro[4,5]decan-2-one |
| 324 | 1-(2,6-Dichlorobenzyl)-8-(2,3-difluoro-4-methylbenzoyl)-3-isobutyl-1,4,8-triazaspiro[4,5]decan-2-one |
| 325 | 1-Allyl-3-isopropyl-8-(2-methylbenzoyl)-1,4,8-triazaspiro[4,5]decan-2-one |
| 326 | 8-(2-Chloro-5-trifluoromethylbenzoyl)-1-(2,6-dichlorobenzyl)-3-isobutyl-1,4,8-triazaspiro[4,5]decan-2-one |

| Ex. | Compound |
|---|---|
| 327 | 1-Allyl-8-[2-(3-methoxyphenyl)acetyl]-3-(2-methylsulfanylethyl)-1,4,8-triazaspiro[4,5]decan-2-one |
| 328 | 1-Allyl-3-(2-methylsulfanylethyl)-8-(3-phenylpropionyl)-1,4,8-triazaspiro[4,5]decan-2-one |
| 329 | Ethyl [3-benzyl-8-(2-benzyloxyacetyl)-2-oxo-1,4,8-triazaspiro[4,5]dec-1-yl]acetate |
| 330 | 1-Allyl-8-(5-tert-butyl-2-methyl-2H-pyrazole-3-carbonyl)-3-(2-methylsulfanylethyl)-1,4,8-triazaspiro[4,5]decan-2-one |
| 331 | Ethyl 1,1-dimethyl-2-[3-(2-methylsulfanylethyl)-1-(2-nitrobenzyl)-2-oxo-1,4,8-triazaspiro[4,5]dec-8-yl]-2-oxo-acetate |
| 332 | Benzyl 2-[1-ethoxycarbonylmethyl-3-(2-methylsulfanylethyl)-2-oxo-1,4,8-triazaspiro[4,5]decan-8-carbonyl]benzoate |
| 333 | 1-Allyl-3-isopropyl-8-(4-methyl[1,2,3]thiadiazole-5-carbonyl)-1,4,8-triazaspiro[4,5]decan-2-one |
| 334 | 1-Allyl-8-(2,5-dimethylfuran-3-carbonyl)-3-(2-methylsulfanylethyl)-1,4,8-triazaspiro[4,5]decan-2-one |
| 335 | 1-Allyl-8-(benzo[1,2,5]oxadiazole-5-carbonyl)-3-(2-methylsulfanylethyl)-1,4,8-triazaspiro[4,5]decan-2-one |
| 336 | 1-(2-Fluorobenzyl)-8-(4-phenoxybutyryl)-1,4,8-triazaspiro[4,5]decan-2-one |
| 337 | 1-Allyl-8-(2-cyclopentylacetyl)-3-(2-methylsulfanylethyl)-1,4,8-triazaspiro[4,5]decan-2-one |
| 338 | Ethyl [3-benzyl-8-(naphthalin-2-carbonyl)-2-oxo-1,4,8-triazaspiro[4,5]dec-1-yl]acetate |
| 339 | 8-[3-(2-Chloro-6-fluorophenyl)-5-methylisoxazole-4-carbonyl]-1-(2-fluorobenzyl)-1,4,8-triazaspiro[4,5]decan-2-one |
| 340 | 3-[8-(3,5-Dimethoxybenzoyl)-3-isopropyl-2-oxo-1,4,8-triazaspiro[4,5]dec-1-ylmethyl]benzonitrile |
| 341 | 3-(2-Methylsulfanylethyl)-1-(2-nitrobenzyl)-8-(1-phenyl-5-propyl-1H-pyrazole-4-carbonyl)-1,4,8-triazaspiro[4,5]decan-2-one |
| 342 | Ethyl {3-benzyl-8-[3-(2-chloro-6-fluorophenyl)-5-methylisoxazole-4-carbonyl]-2-oxo-1,4,8-triazaspiro[4,5]dec-1-yl}acetate |
| 343 | 1-(2-Fluorobenzyl)-8-(3-fluoro-4-trifluoromethylbenzoyl)-1,4,8-triazaspiro[4,5]decan-2-one |
| 344 | Ethyl [8-[1-(4-chlorophenyl)-5-trifluoromethyl-1H-pyrazole-4-carbonyl]-3-(2-methylsulfanylethyl)-2-oxo-1,4,8-triazaspiro[4,5]dec-1-yl]acetate |
| 345 | 3-[8-(Naphthalin-1-carbonyl)-2-oxo-1,4,8-triazaspiro[4,5]dec-1-ylmethyl]benzonitrile |
| 346 | Ethyl [8-(3,3-dimethylbutyryl)-3-(2-methylsulfanylethyl)-2-oxo-1,4,8-triazaspiro[4,5]dec-1-yl]acetate |
| 347 | 8-Acetyl-3-(2-methylsulfanylethyl)-1-naphthalin-2-ylmethyl-1,4,8-triazaspiro[4,5]decan-2-one |
| 348 | Ethyl [3-benzyl-8-(3-cyanobenzoyl)-2-oxo-1,4,8-triazaspiro[4,5]dec-1-yl]acetate |
| 20000 | 8-(5-tert-Butyl-2-methyl-2H-pyrazole-3-carbonyl)-1-(2,6-dichlorobenzyl)-3- |
| 349 | isobutyl-1,4,8-triazaspiro[4,5]decan-2-one |
| 350 | 4-[3-Benzyl-1-(2-fluorobenzyl)-2-oxo-1,4,8-triazaspiro[4,5]decan-8-carbonyl]benzonitrile |
| 351 | Methyl 4-[3-benzyl-1-(2-fluorobenzyl)-2-oxo-1,4,8-triazaspiro[4,5]dec-8-yl]-4-oxo-butyrate |
| 352 | 3-(2-Methylsulfanylethyl)-1-naphthalin-2-ylmethyl-8-(3,4,5-trimethoxybenzoyl)-1,4,8-triazaspiro[4,5]decan-2-one |
| 353 | Ethyl [3-benzyl-8-(isoxazole-5-carbonyl)-2-oxo-1,4,8-triazaspiro[4,5]dec-1-yl]acetate |
| 354 | 8-(3-Difluoromethylsulfanylbenzoyl)-1-(2-fluorobenzyl)-1,4,8-triazaspiro[4,5]decan-2-one |
| 355 | Ethyl [3-benzyl-8-(2,3-dimethylbenzoyl)-2-oxo-1,4,8-triazaspiro[4,5]dec-1-yl]acetate |
| 356 | 1-(2-Fluorobenzyl)-8-(4-propylbenzoyl)-1,4,8-triazaspiro[4,5]decan-2-one |
| 357 | 3-[8-(4-Iodobenzoyl)-2-oxo-1,4,8-triazaspiro[4,5]dec-1-ylmethyl]benzonitrile |
| 358 | 1-(2-Fluorobenzyl)-8-(2-propylpentanoyl)-1,4,8-triazaspiro[4,5]decan-2-one |
| 359 | 3-[8-(2,6-Difluoro-3-methylbenzoyl)-3-isopropyl-2-oxo-1,4,8-triazaspiro[4,5]dec-1-ylmethyl]benzonitrile |
| 360 | 3-(2-Methylsulfanylethyl)-8-(4-methyl[1,2,3]thiadiazole-5-carbonyl)-1-(2-nitrobenzyl)-1,4,8-triazaspiro[4,5]decan-2-one |
| 361 | Butyl 4-[3-isobutyl-8-(4-methyl[1,2,3]thiadiazole-5-carbonyl)-2-oxo-1,4,8-triazaspiro[4,5]dec-1-yl]acetate |
| 362 | 8-[2-(4-Chlorophenoxy)acetyl]-3-(2-methylsulfanylethyl)-1-naphthalin-2-ylmethyl-1,4,8-triazaspiro[4,5]decan-2-one |
| 363 | Ethyl [3-benzyl-2-oxo-8-(3-trifluoromethylbenzoyl)-1,4,8-triazaspiro[4,5]dec-1-yl]acetate |
| 364 | 8-(4-Bromobenzoyl)-3-(2-methylsulfanylethyl)-1-naphthalin-2-ylmethyl-1,4,8-triazaspiro[4,5]decan-2-one |
| 365 | Ethyl [8-(2-chloropyridin-4-carbonyl)-3-(2-methylsulfanylethyl)-2-oxo-1,4,8-triazaspiro[4,5]dec-1-yl]acetate |
| 366 | 1-Allyl-8-(3,5-dimethoxybenzoyl)-3-(2-methylsulfanylethyl)-1,4,8-triazaspiro[4,5]decan-2-one |
| 367 | 3-[8-(4-Methyl-3-nitrobenzoyl)-2-oxo-1,4,8-triazaspiro[4,5]dec-1-ylmethyl]benzonitrile |

| Ex. | Compound |
|---|---|
| 368 | 8-(4-tert-Butylbenzoyl)-1-(2-fluorobenzyl)-1,4,8-triazaspiro[4,5]decan-2-one |
| 369 | 1-Allyl-3-isopropyl-8-(5-methylisoxazole-3-carbonyl)-1,4,8-triazaspiro[4,5]decan-2-one |
| 370 | 1-Allyl-3-(2-methylsulfanylethyl)-8-(2-trifluoromethylbenzoyl)-1,4,8-triazaspiro[4,5]decan-2-one |
| 371 | Ethyl [3-benzyl-8-(3-cyclopentylpropionyl)-2-oxo-1,4,8-triazaspiro[4,5]dec-1-yl]acetate |
| 372 | 3-Benzyl-8-(3,5-difluorobenzoyl)-1-(2-fluorobenzyl)-1,4,8-triazaspiro[4,5]decan-2-one |
| 373 | Ethyl [3-benzyl-8-(5-fluoro-2-trifluoromethylbenzoyl)-2-oxo-1,4,8-triazaspiro[4,5]dec-1-yl]acetate |
| 374 | Ethyl [3-benzyl-2-oxo-8-(3,4,5-trimethoxybenzoyl)-1,4,8-triazaspiro[4,5]dec-1-yl]acetate |
| 375 | Benzyl 2-[1-(2-fluorobenzyl)-2-oxo-1,4,8-triazaspiro[4,5]decan-8-carbonyl]benzoate |
| 376 | 1-(2-Fluorobenzyl)-8-(2-methylbenzoyl)-1,4,8-triazaspiro[4,5]decan-2-one |
| 377 | 1-(2-Fluorobenzyl)-8-(2-phenylbutyryl)-1,4,8-triazaspiro[4,5]decan-2-one |
| 378 | 1-Allyl-8-(6-chloropyridin-3-carbonyl)-3-isopropyl-1,4,8-triazaspiro[4,5]decan-2-one |
| 379 | Ethyl [8-(2,5-dimethylfuran-3-carbonyl)-3-(2-methylsulfanylethyl)-2-oxo-1,4,8-triazaspiro[4,5]dec-1-yl]acetate |
| 380 | Ethyl [8-(5-tert-butyl-2-methyl-2H-pyrazole-3-carbonyl)-3-(2-methylsulfanylethyl)-2-oxo-1,4,8-triazaspiro[4,5]dec-1-yl]acetate |
| 381 | Benzyl 2-[1-allyl-3-(2-methylsulfanylethyl)-2-oxo-1,4,8-triazaspiro[4,5]decan-8-carbonyl]benzoate |
| 382 | Ethyl 2-[1-allyl-3-(2-methylsulfanylethyl)-2-oxo-1,4,8-triazaspiro[4,5]dec-8-yl]-2-oxo-1-phenylacetate |
| 383 | 3-[8-(2-Chloro-6-fluorobenzoyl)-3-isopropyl-2-oxo-1,4,8-triazaspiro[4,5]dec-1-ylmethyl]benzonitrile |
| 384 | 3-(2-Methylsulfanylethyl)-1-(2-nitrobenzyl)-8-(3-phenylpropionyl)-1,4,8-triazaspiro[4,5]decan-2-one |
| 385 | 3-[8-(2,3-Dimethylbenzoyl)-3-isopropyl-2-oxo-1,4,8-triazaspiro[4,5]dec-1-ylmethyl]benzonitrile |
| 386 | Ethyl [8-(5-fluoro-2-trifluoromethylbenzoyl)-3-(2-methylsulfanylethyl)-2-oxo-1,4,8-triazaspiro[4,5]dec-1-yl]acetate |
| 387 | Ethyl [8-cyclopentanecarbonyl-3-(2-methylsulfanylethyl)-2-oxo-1,4,8-triazaspiro[4,5]dec-1-yl]acetate |
| 388 | Ethyl [3-(2-methylsulfanylethyl)-2-oxo-8-(thiophene-2-carbonyl)-1,4,8-triazaspiro[4,5]dec-1-yl]acetate |
| 389 | 1-Allyl-8-[1-(4-chlorophenyl)-5-trifluoromethyl-1H-pyrazole-4-carbonyl]-3-(2-methylsulfanylethyl)-1,4,8-triazaspiro[4,5]decan-2-one |
| 390 | 1-Allyl-3-(2-methylsulfanylethyl)-8-(naphthalin-1-carbonyl)-1,4,8-triazaspiro[4,5]decan-2-one |
| 391 | 1-(2-fluorobenzyl)-8-(4-trifluoromethoxybenzoyl)-1,4,8-triazaspiro[4,5]decan-2-one |
| 392 | 3-Benzyl-8-(2-benzyloxyacetyl)-1-(2-fluorobenzyl)-1,4,8-triazaspiro[4,5]decan-2-one |
| 393 | 3-[8-(2-chloro-6-fluoro-3-methylbenzoyl)-3-isopropyl-2-oxo-1,4,8-triazaspiro[4,5]dec-1-ylmethyl]benzonitrile |
| 394 | 1-Allyl-8-(2-chloro-5-trifluoromethylbenzoyl)-3-isopropyl-1,4,8-triazaspiro[4,5]decan-2-one |
| 395 | 8-(3-Methylbenzoyl)-3-(2-methylsulfanylethyl)-1-naphthalin-2-ylmethyl-1,4,8-triazaspiro[4,5]decan-2-one |
| 396 | 1-(3,5-Dimethylbenzyl)-8-(2-ethylbutyryl)-3-isobutyl-1,4,8-triazaspiro[4,5]decan-2-one |
| 397 | 8-(5-tert-Butyl-2-methyl-2H-pyrazole-3-carbonyl)-3-(2-methylsulfanylethyl)-1-(2-nitrobenzyl)-1,4,8-triazaspiro[4,5]decan-2-one |
| 398 | Benzyl 2-[1-(3-cyanobenzyl)-3-isopropyl-2-oxo-1,4,8-triazaspiro[4,5]decan-8-carbonyl]benzoate |
| 399 | 8-(4-Methyl-3-nitrobenzoyl)-3-(2-methylsulfanylethyl)-1-(2-nitrobenzyl)-1,4,8-triazaspiro[4,5]decan-2-one |
| 400 | 1-(2,6-Dichlorobenzyl)-3-isobutyl-8-(3,4,5-trimethoxybenzoyl)-1,4,8-triazaspiro[4,5]decan-2-one |
| 401 | 3-{8-[2-(2-Bromophenyl)acetyl]-3-isopropyl-2-oxo-1,4,8-triazaspiro[4,5]dec-1-ylmethyl}-benzonitrile |
| 402 | 3-[8-(2,3-Dichlorobenzoyl)-3-isopropyl-2-oxo-1,4,8-triazaspiro[4,5]dec-1-ylmethyl]benzonitrile |
| 403 | 1-Allyl-8-(6-chloro-2H-chroman-3-carbonyl)-3-isopropyl-1,4,8-triazaspiro[4,5]decan-2-one |
| 404 | Ethyl {3-benzyl-8-[2-(4-methoxyphenyl)acetyl]-2-oxo-1,4,8-triazaspiro[4,5]dec-1-yl}acetate |
| 405 | 3-[3-Isopropyl-2-oxo-8-(1-phenyl-5-propyl-1H-pyrazole-4-carbonyl)-1,4,8-triazaspiro[4,5]dec-1-ylmethyl]benzonitrile |
| 406 | 8-(3-Cyclopentylpropionyl)-1-(2-fluorobenzyl)-1,4,8-triazaspiro[4,5]decan-2-one |
| 407 | 1-Allyl-8-(3-difluoromethylsulfanylbenzoyl)-3-isopropyl-1,4,8-triazaspiro[4,5]decan-2-one |

-continued

| Ex. | Compound |
|---|---|
| 408 | 3-[8-(2-chloro-4-nitrobenzoyl)-3-isopropyl-2-oxo-1,4,8-triazaspiro[4,5]dec-1-ylmethyl]benzonitrile |
| 409 | Ethyl [8-(2-ethoxybenzoyl)-3-(2-methylsulfanylethyl)-2-oxo-1,4,8-triazaspiro[4,5]dec-1-yl]acetate |
| 410 | 8-(2,5-Bis-trifluoromethylbenzoyl)-1-(2-fluorobenzyl)-1,4,8-triazaspiro[4,5]decan-2-one |
| 411 | 8-(2-Chloropyridin-4-carbonyl)-3-(2-methylsulfanylethyl)-1-(2-nitrobenzyl)-1,4,8-triazaspiro[4,5]decan-2-one |
| 412 | Ethyl {3-benzyl-8-[3-(2,6-dichlorophenyl)-5-methylisoxazole-4-carbonyl]-2-oxo-1,4,8-triazaspiro[4,5]dec-1-yl}acetate |
| 413 | 1-(3,5-Dimethylbenzyl)-3-isobutyl-8-(2-trifluoromethylbenzoyl)-1,4,8-triazaspiro[4,5]decan-2-one |
| 414 | 8-(3,5-Dimethoxybenzoyl)-3-(2-methylsulfanylethyl)-1-(2-nitrobenzyl)-1,4,8-triazaspiro[4,5]decan-2-one |
| 415 | Benzyl 2-[3-benzyl-1-(2-fluorobenzyl)-2-oxo-1,4,8-triazaspiro[4,5]decan-8-carbonyl]benzoate |
| 416 | 3-[8-(Benzo[1,2,5]oxadiazole-5-carbonyl)-3-isopropyl-2-oxo-1,4,8-triazaspiro[4,5]dec-1-ylmethyl]benzonitrile |
| 417 | Ethyl [3-(2-methylsulfanylethyl)-2-oxo-8-(4-trifluoromethoxybenzoyl)-1,4,8-triazaspiro[4,5]dec-1-yl]acetate |
| 418 | 1-Allyl-3-isopropyl-8-[2-(4-methoxyphenyl)acetyl]-1,4,8-triazaspiro[4,5]decan-2-one |
| 419 | 3-(2-Methylsulfanylethyl)-1-(2-nitrobenzyl)-8-(4-propylbenzoyl)-1,4,8-triazaspiro[4,5]decan-2-one |
| 420 | 3-Benzyl-8-(4-tert-butylbenzoyl)-1-(2-fluorobenzyl)-1,4,8-triazaspiro[4,5]decan-2-one |
| 421 | 1-Allyl-8-(2,6-difluoro-3-methylbenzoyl)-3-(2-methylsulfanylethyl)-1,4,8-triazaspiro[4,5]decan-2-one |
| 422 | 8-(3,5-Bis-trifluoromethylbenzoyl)-1-(2-fluorobenzyl)-1,4,8-triazaspiro[4,5]decan-2-one |
| 423 | 3-[8-(4-Iodobenzoyl)-3-isopropyl-2-oxo-1,4,8-triazaspiro[4,5]dec-1-ylmethyl]benzonitrile |
| 424 | 3-(2-Methylsulfanylethyl)-1-naphthalin-2-ylmethyl-8-(thiophene-2-carbonyl)-1,4,8-triazaspiro[4,5]decan-2-one |
| 425 | Ethyl [3-benzyl-8-(2-chloropyridin-4-carbonyl)-2-oxo-1,4,8-triazaspiro[4,5]dec-1-yl]acetate |
| 426 | Ethyl [3-(2-methylsulfanylethyl)-8-(4-nitrobenzoyl)-2-oxo-1,4,8-triazaspiro[4,5]dec-1-yl]acetate |
| 427 | 8-(2-Ethylhexanoyl)-3-(2-methylsulfanylethyl)-1-(2-nitrobenzyl)-1,4,8-triazaspiro[4,5]decan-2-one |
| 428 | 1-(2,6-Dichlorobenzyl)-3-isobutyl-8-(thiophene-2-carbonyl)-1,4,8-triazaspiro[4,5]decan-2-one |
| 429 | Ethyl [3-benzyl-8-(2-chloro-4-nitrobenzoyl)-2-oxo-1,4,8-triazaspiro[4,5]dec-1-yl]acetate |
| 430 | 3-Benzyl-8-(3,5-bis-trifluoromethylbenzoyl)-1-(2-fluorobenzyl)-1,4,8-triazaspiro[4,5]decan-2-one |
| 431 | Ethyl [3-benzyl-8-(4-bromo-3-methylbenzoyl)-2-oxo-1,4,8-triazaspiro[4,5]dec-1-yl]acetate |
| 432 | 8-Cyclohexanecarbonyl-3-(2-methylsulfanylethyl)-1-(2-nitrobenzyl)-1,4,8-triazaspiro[4,5]decan-2-one |
| 433 | 8-(2,5-Dimethylfuran-3-carbonyl)-3-(2-methylsulfanylethyl)-1-(2-nitrobenzyl)-1,4,8-triazaspiro[4,5]decan-2-one |
| 434 | 8-(3-Difluoromethylsulfanylbenzoyl)-3-(2-methylsulfanylethyl)-1-(2-nitrobenzyl)-1,4,8-triazaspiro[4,5]decan-2-one |
| 435 | 8-(Furan-2-carbonyl)-3-(2-methylsulfanylethyl)-1-(2-nitrobenzyl)-1,4,8-triazaspiro[4,5]decan-2-one |
| 436 | Ethyl [3-benzyl-8-(2,3-difluorobenzoyl)-2-oxo-1,4,8-triazaspiro[4,5]dec-1-yl]acetate |
| 438 | 3-[3-Isopropyl-8-(4-methyl[1,2,3]thiadiazole-5-carbonyl)-2-oxo-1,4,8-triazaspiro[4,5]dec-1-ylmethyl]benzonitrile |
| 439 | 3-[8-(3-Chloro-2-fluorobenzoyl)-3-isopropyl-2-oxo-1,4,8-triazaspiro[4,5]dec-1-ylmethyl]benzonitrile |
| 440 | Ethyl [3-benzyl-8-(naphthalin-1-carbonyl)-2-oxo-1,4,8-triazaspiro[4,5]dec-1-yl]acetate |
| 441 | 8-(4-tert-Butylbenzoyl)-3-(2-methylsulfanylethyl)-1-(2-nitrobenzyl)-1,4,8-triazaspiro[4,5]decan-2-one |
| 442 | 3-[3-Benzyl-1-(2-fluorobenzyl)-2-oxo-1,4,8-triazaspiro[4,5]decan-8-carbonyl]benzonitrile |
| 443 | 1-(2,6-Dichlorobenzyl)-8-(furan-2-carbonyl)-3-isobutyl-1,4,8-triazaspiro[4,5]decan-2-one |
| 444 | 8-(2,6-Dichlorobenzoyl)-1-(2-fluorobenzyl)-1,4,8-triazaspiro[4,5]decan-2-one |
| 445 | 1-(3,5-Dimethylbenzyl)-8-(3-fluoro-4-trifluoromethylbenzoyl)-3-isobutyl-1,4,8-triazaspiro[4,5]decan-2-one |
| 446 | 1-(2-Fluorobenzyl)-8-(3-fluoro-4-methylbenzoyl)-1,4,8-triazaspiro[4,5]decan-2-one |
| 447 | 1-Allyl-8-(3-cyclopentylpropionyl)-3-(2-methylsulfanylethyl)-1,4,8-triazaspiro[4,5]decan-2-one |

| Ex. | Compound |
|---|---|
| 448 | 8-[2-(3-Chlorophenoxy)acetyl]-3-(2-methylsulfanylethyl)-1-(2-nitrobenzyl)-1,4,8-triazaspiro[4,5]decan-2-one |
| 449 | 1-(3,5-Dimethylbenzyl)-3-isobutyl-8-(2-methylsulfanylpyridin-3-carbonyl)-1,4,8-triazaspiro[4,5]decan-2-one |
| 450 | 3-(2-Methylsulfanylethyl)-1-(2-nitrobenzyl)-8-propionyl-1,4,8-triazaspiro[4,5]decan-2-one |
| 451 | 3-[8-(3,4-Dimethoxybenzoyl)-3-isopropyl-2-oxo-1,4,8-triazaspiro[4,5]dec-1-ylmethyl]benzonitrile |
| 452 | 3-(2-Methylsulfanylethyl)-8-(naphthalin-2-carbonyl)-1-naphthalin-2-ylmethyl-1,4,8-triazaspiro[4,5]decan-2-one |
| 453 | 8-(6-Chloro-2H-chroman-3-carbonyl)-3-(2-methylsulfanylethyl)-1-(2-nitrobenzyl)-1,4,8-triazaspiro[4,5]decan-2-one |
| 454 | Ethyl {3-benzyl-2-oxo-8-[3-(3-trifluoromethylphenyl)acryloyl]-1,4,8-triazaspiro[4,5]dec-1-yl}acetate |
| 455 | 1-(3,5-Dimethylbenzyl)-3-isobutyl-8-(3-phenylacryloyl)-1,4,8-triazaspiro[4,5]decan-2-one |
| 456 | 3-[3-Isopropyl-2-oxo-8-(2-phenoxypropionyl)-1,4,8-triazaspiro[4,5]dec-1-ylmethyl]benzonitrile |
| 457 | 3-[3-Isopropyl-2-oxo-8-(4-trifluoromethoxybenzoyl)-1,4,8-triazaspiro[4,5]dec-1-ylmethyl]benzonitrile |
| 458 | 1-Allyl-3-(2-methylsulfanylethyl)-8-(3-nitrobenzoyl)-1,4,8-triazaspiro[4,5]decan-2-one |
| 459 | Ethyl [3-benzyl-8-(3,4-dichlorobenzoyl)-2-oxo-1,4,8-triazaspiro[4,5]dec-1-yl]acetate |
| 460 | 1-(2-Fluorobenzyl)-8-[3-(3-trifluoromethylphenyl)acryloyl]-1,4,8-triazaspiro[4,5]decan-2-one |
| 461 | 1-Allyl-8-(3,5-bis-trifluoromethylbenzoyl)-3-(2-methylsulfanylethyl)-1,4,8-triazaspiro[4,5]decan-2-one |
| 462 | 8-(3-Cyclopentylpropionyl)-3-(2-methylsulfanylethyl)-1-(2-nitrobenzyl)-1,4,8-triazaspiro[4,5]decan-2-one |
| 465 | 1-(3,5-Dimethylbenzyl)-3-isobutyl-8-(4-nitrobenzoyl)-1,4,8-triazaspiro[4,5]decan-2-one |
| 466 | 8-(3-Cyclopentylpropionyl)-1-(3,5-dimethylbenzyl)-3-isobutyl-1,4,8-triazaspiro[4,5]decan-2-one |
| 467 | 3-[3-Isopropyl-8-(isoxazole-5-carbonyl)-2-oxo-1,4,8-triazaspiro[4,5]dec-1-ylmethyl]benzonitrile |
| 468 | 3-Benzyl-1-(2-fluorobenzyl)-8-(2-methyl-6-trifluoromethylpyridin-3-carbonyl)-1,4,8-triazaspiro[4,5]decan-2-one |

Pharmacological Data:

The affinity of the substituted 1,4,8-triazaspiro[4,5]decan-2-one compounds of the invention of the general formula I to the human μ-opioid receptor, their affinity to the batrachotoxin (BTX) binding site of the sodium channel and also the inhibition of noradrenalin reuptake or 5-HT reuptake, were determined as described above.

Furthermore, —likewise as described above—the analgesic activity of the substituted 1,4,8-triazaspiro[4,5]decan-2-one compounds of the invention of the general formula I was determined using the writhing test on mice.

The substituted 1,4,8-triazaspiro[4,5]decan-2-one compounds of the invention illustrated by the above general formula I show good to very good inhibition of noradrenalin reuptake and also good to very good inhibition of 5-hydroxy tryptophane reuptake.

In the writhing test on mice the substituted 1,4,8-triazaspiro[4,5]decan-2-one compounds of the invention of the general formula I exhibit marked analgesic activity.

Furthermore, these compounds of the invention also show excellent affinities to opioid receptors, particularly to the μ-opioid receptor and/or to the batrachotoxin (BTX) binding site of the sodium channel.

The following Tables I and II list the respective pharmacological data for substituted 1,4,8-triazaspiro[4,5]decan-2-one compounds according to the examples.

TABLE I

| Example No. | % Inhibition of the writhing reaction (Dosage in mg/kg intravenous) |
|---|---|
| 25 | 42 (10) |
| 31 | 36 (10) |
| 55 | 45 (10) |
| 53 | 30 (10) |
| 2 | 51 (10) |

TABLE II

| Example | BTX inhibition | μ (Naloxone), 1 μM, % inhibition | Uptake 5-HT, rat, 1 μM, % inhibition |
|---|---|---|---|
| 25 | 47 | 66 | 66 |
| 29 | 60 | 38 | 45 |
| 31 | 61 | | 34 |
| 30 | 35 | | 42 |
| 29 | 65 | | 80 |
| 28 | 47 | | |
| 27 | 79 | | 78 |
| 38 | 87 | | 94 |
| 33 | | | 49 |
| 10 | 53 | 94 | |
| 62 | 48 | | 87 |

TABLE II-continued

| Example | BTX inhibition | μ (Naloxone), 1 μM, % inhibition | Uptake 5-HT, rat, 1 μM, % inhibition |
|---|---|---|---|
| 61 | 41 | | |
| 60 | 39 | | 80 |
| 59 | 49 | | 53 |
| 58 | 46 | | 46 |
| 57 | 44 | 60 | 72 |
| 56 | 67 | | |
| 55 | 64 | | |
| 54 | 37 | | 81 |
| 53 | 48 | | |

TABLE III

| Example | BTX inhibition | Uptake 5-HT, rat, 1 μM, % inhibition | Uptake (NA), rat, 10 μM, % inhibition |
|---|---|---|---|
| 67 | | 46 | |
| 68 | | 75 | |
| 71 | | 53 | 52 |
| 72 | 39 | | |
| 74 | | 47 | |
| 78 | | 56 | 33 |
| 80 | | | 30 |
| 81 | | 43 | |
| 84 | | 64 | |
| 86 | | 50 | 38 |
| 87 | | 56 | |
| 88 | | 34 | 32 |
| 89 | | 43 | 41 |
| 90 | | 41 | 35 |
| 92 | | 30 | 30 |
| 94 | | | 38 |
| 95 | | | 31 |
| 97 | | 67 | 30 |
| 98 | | 57 | 36 |
| 99 | 66 | 79 | 42 |
| 100 | | 42 | 32 |
| 101 | 78 | 33 | |
| 103 | | 34 | 30 |
| 104 | 41 | 48 | 36 |
| 105 | 66 | 68 | |
| 108 | | | 37 |
| 109 | | 50 | 32 |
| 110 | | 33 | |
| 111 | 42 | 58 | 38 |
| 112 | | 43 | 42 |
| 113 | | 35 | 46 |
| 114 | | 53 | |
| 115 | | 30 | 34 |
| 116 | | 37 | 34 |
| 118 | 44 | 38 | 30 |
| 120 | | | 32 |
| 121 | | 41 | 37 |
| 122 | | 34 | 38 |
| 123 | | | 36 |
| 125 | | 44 | 36 |
| 126 | 34 | | 44 |
| 129 | 30 | 47 | |
| 130 | | 32 | |
| 131 | 37 | | |
| 132 | 54 | | |
| 133 | 35 | | |
| 135 | 31 | | |
| 137 | 59 | | |
| 138 | | | 30 |
| 139 | | | 31 |
| 141 | 45 | | 36 |
| 142 | 32 | | |
| 143 | | 42 | |
| 144 | | 51 | |
| 145 | 64 | 89 | |
| 147 | | 45 | |

TABLE III-continued

| Example | BTX inhibition | Uptake 5-HT, rat, 1 μM, % inhibition | Uptake (NA), rat, 10 μM, % inhibition |
|---|---|---|---|
| 148 | | 43 | 32 |
| 149 | 33 | 33 | |
| 150 | 56 | 72 | |
| 152 | | 56 | |
| 153 | | 63 | |
| 155 | | 74 | |
| 156 | 60 | | |
| 157 | | 64 | |
| 159 | | 40 | |
| 161 | | 39 | |
| 163 | | 71 | |
| 165 | 63 | | |
| 166 | 47 | | |
| 167 | 38 | 52 | |
| 168 | 44 | 46 | |
| 169 | 51 | | |
| 170 | | 46 | |
| 171 | | 62 | |
| 172 | 49 | 76 | |
| 175 | 38 | 69 | |
| 176 | 30 | 37 | |
| 177 | 30 | 79 | |
| 178 | | 49 | |
| 179 | 46 | | |
| 180 | 42 | 63 | |
| 181 | 43 | | |
| 184 | 62 | | |
| 186 | | 32 | |
| 187 | | 47 | |
| 188 | 69 | 70 | |
| 189 | 40 | | |
| 190 | | 43 | |
| 191 | | 30 | |
| 192 | | 53 | |
| 194 | | 32 | |
| 195 | 34 | 50 | |
| 196 | 52 | | |
| 197 | 41 | | |
| 198 | 30 | | |
| 200 | 44 | 45 | |
| 201 | 42 | | |
| 202 | | 56 | |
| 203 | 48 | 34 | |
| 204 | 44 | 42 | |
| 206 | | 55 | |
| 207 | 57 | 76 | |
| 208 | 33 | | |
| 209 | 67 | 69 | |
| 210 | | 51 | 31 |
| 213 | 43 | | |
| 215 | 32 | | |
| 216 | | 55 | |
| 218 | 39 | 57 | |
| 219 | | 30 | |
| 220 | 62 | | |
| 221 | 36 | 79 | |
| 222 | | 60 | |
| 223 | 62 | 49 | |
| 224 | | 30 | |
| 225 | 55 | 32 | |
| 228 | | 32 | |
| 229 | | 36 | |
| 230 | 30 | 72 | |
| 231 | | 31 | |
| 233 | | 30 | |
| 234 | | 45 | |
| 236 | 50 | 48 | |
| 237 | 42 | 63 | |
| 238 | | | 31 |
| 239 | | 36 | |
| 240 | 30 | 54 | |
| 241 | 58 | | |
| 242 | 42 | | |
| 243 | | 46 | |
| 244 | | 51 | |
| 245 | 60 | | |

TABLE III-continued

| Example | BTX inhibition | Uptake 5-HT, rat, 1 μM, % inhibition | Uptake (NA), rat, 10 μM, % inhibition |
|---|---|---|---|
| 247 | 32 | | |
| 248 | | | |
| 249 | 34 | 55 | |
| 251 | | 50 | |
| 252 | | 73 | |
| 253 | | 82 | |
| 254 | | 34 | |
| 255 | | 44 | |
| 256 | 48 | 94 | 57 |
| 257 | 35 | 59 | |
| 258 | 32 | | |
| 259 | | 50 | |
| 261 | | 39 | |
| 262 | 70 | 60 | |
| 263 | | 50 | |
| 264 | 63 | | 36 |
| 265 | 34 | | 32 |
| 266 | 57 | 94 | 38 |
| 268 | 31 | | |
| 269 | | 40 | |
| 270 | 33 | 31 | 37 |
| 271 | | 44 | 31 |
| 272 | | | 31 |
| 273 | | 51 | 38 |
| 274 | 85 | 97 | 64 |
| 275 | 61 | 33 | |
| 276 | | 95 | 46 |
| 277 | | 43 | |
| 278 | | 39 | 56 |
| 279 | 60 | 48 | |
| 280 | 30 | 60 | 35 |
| 281 | | 56 | 30 |
| 282 | | 49 | |
| 283 | | 51 | |
| 284 | | 51 | |
| 285 | 32 | 65 | |
| 286 | | 47 | |
| 287 | 32 | 41 | 41 |
| 288 | 32 | 45 | |
| 290 | 30 | | 31 |
| 291 | 33 | 38 | |
| 292 | 40 | 40 | |
| 293 | 31 | 55 | |
| 294 | 33 | 53 | |
| 295 | 63 | | 36 |
| 296 | 36 | 30 | |
| 297 | 36 | | 32 |
| 298 | 48 | 34 | 30 |
| 299 | 36 | 66 | |
| 300 | 33 | | |
| 302 | 39 | | |
| 303 | 30 | | |
| 304 | 33 | 34 | 37 |
| 305 | 51 | 37 | |
| 306 | 68 | 85 | |
| 307 | 31 | | |
| 308 | | 59 | |
| 309 | 82 | 43 | |
| 310 | | 48 | |
| 311 | | 49 | |
| 313 | | 60 | |
| 315 | | 61 | |
| 317 | 62 | 33 | |
| 319 | | 70 | |
| 320 | | 38 | |
| 322 | 36 | | |
| 323 | 43 | 33 | |
| 324 | 62 | 31 | |
| 325 | | 32 | |
| 326 | 68 | | |
| 328 | | 32 | 33 |
| 329 | 43 | 55 | |
| 330 | 31 | 45 | |
| 331 | 46 | 58 | 38 |
| 332 | | | 36 |

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A 1,4,8-triazaspiro[4,5]decan-2-one compound corresponding to formula I,

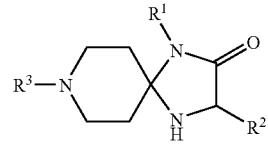

wherein
$R^1$ represents hydrogen; a linear or branched unsubstituted alkyl group which may comprise at least one heteroatom as a link; a linear or branched, unsubstituted or at least monosubstituted alkenyl group which may comprise at least one heteroatom as a link; a linear or branched, unsubstituted or at least monosubstituted alkynyl group which may comprise at least one heteroatom as a link; an unsubstituted or at least monosubstituted aryl group or heteroaryl group, which is bonded via a linear or branched alkylene group which may comprise at least one heteroatom as a link; a —C(=O)—OR$^5$ group bonded via a linear or branched alkylene group; or an —O—(C=O)—R$^6$ group bonded via a linear or branched alkylene group;

$R^2$ represents hydrogen; a linear or branched, unsubstituted or at least monosubstituted alkyl group which may comprise at least one heteroatom as a link; a linear or branched, unsubstituted or at least monosubstituted alkenyl group which may comprise at least one heteroatom as a link; a linear or branched, unsubstituted or at least monosubstituted alkynyl group which may comprise at least one heteroatom as link; or an unsubstituted or at least monosubstituted aryl group or heteroaryl group, which may be bonded via a linear or branched alkylene group which may comprise at least one heteroatom as a link;

$R^3$ represents hydrogen; a linear or branched unsubstituted or at least monosubstituted alkyl group which may comprise at least one heteroatom as a link; or a linear or branched unsubstituted or at least monosubstituted alkenyl group which may comprise at least one heteroatom as a link; a linear or branched unsubstituted or at least monosubstituted alkynyl group which may comprise at least one heteroatom as a link; an unsubstituted or at least monosubstituted aryl group or heteroaryl group, which is bonded via a linear or branched unsubstituted or at least monosubstituted alkylene group which may comprise at least one heteroatom as a link and may be condensed with an unsubstituted or at least monosubstituted monocyclic ring system; an unsubstituted or at least monosubstituted cycloaliphatic group which may comprise at least one heteroatom as ring member and may be bonded via a linear or branched unsubstituted or at least monosubstituted alkylene group which may comprise at least one heteroatom as link, which may be bridged by a linear or branched unsubstituted or at least monosubstituted alkylene group which may comprise at least one heteroatom as link and may be condensed with an unsubstituted or at least monosubstituted monocyclic ring system; or a —C(=O)—$R^4$ group;

$R^4$ represents
- a linear or branched unsubstituted or at least monosubstituted alkyl group which may comprise at least one heteroatom as a link; a linear or branched unsubstituted or at least monosubstituted alkenyl group which may comprise at least one heteroatom as a link; a linear or branched unsubstituted or at least monosubstituted alkynyl group which may comprise at least one heteroatom as a link;
- an unsubstituted or at least monosubstituted aryl group or heteroaryl group, which groups may be bonded via a linear or branched unsubstituted or at least monosubstituted alkylene group, alkenylene group, or alkynylene group, which groups may comprise at least one heteroatom as a link and may be condensed with an unsubstituted or at least monosubstituted monocyclic ring system;
- an unsubstituted or at least monosubstituted cycloaliphatic group which may comprise at least one heteroatom as ring member and may be bonded via a linear or branched unsubstituted or at least monosubstituted alkylene group which may comprise at least one heteroatom as a link, which may be at least singly bridged by a linear or branched unsubstituted or at least monosubstituted alkylene group and may be condensed with an unsubstituted or at least monosubstituted monocyclic ring system;
- a —C(=O)—$OR^7$ group bonded via a linear or branched unsubstituted or at least monosubstituted alkylene group; an —O—(C=O)—$R^8$ group bonded via a linear or branched unsubstituted or at least monosubstituted alkylene group; or a —(C=O)—$R^9$ group bonded via a linear or branched unsubstituted or at least monosubstituted alkylene group;

$R^5$ and $R^6$ each independently are a linear or branched alkyl group; a linear or branched alkenyl group; or a linear or branched alkynyl group;

$R^7$ and $R^8$ each independently are hydrogen; a linear or branched alkyl group; a linear or branched alkenyl group; a linear or branched alkynyl group; or an unsubstituted or at least monosubstituted aryl group or heteroaryl group;

$R^9$ is a linear or branched alkyl group; or a linear or branched alkenyl group or a linear or branched alkynyl group, or a physiologically acceptable salt thereof, excluding those compounds corresponding to formula I wherein

A)

$R^1$ represents hydrogen, a $C_{1-6}$-alkyl group, a $C_{1-6}$ alkoxy group, a $C_{2-6}$ hydroxyalkyl group, a $C_{2-6}$ alkenyl group, a $C_{2-6}$ alkynyl group, a phenyl group or a $C_{1-6}$-alkyl group that is monosubstituted, disubstituted, or trisubstituted by a phenyl group, $R^2$ represents hydrogen, a $C_{1-6}$-alkyl group, a $C_{1-6}$ alkoxy group, a $C_{2-6}$ hydroxyalkyl group, a $C_{2-6}$ alkenyl group, a $C_{2-6}$ alkynyl group, a phenyl group, a $C_{1-6}$-alkyl group that is monosubstituted, disubstituted, or trisubstituted by a phenyl group, an —O—$C_{1-6}$ alkanoyl group, an OH group, an —O—$C_{1-6}$ alkyl group, an —O—$C_{1-6}$ alkoxy group, an —O—$C_{2-6}$ hydroxyalkyl group, a —O—$C_{2-6}$ alkenyl group, an —O—$C_{2-6}$ alkynyl group, an —O-phenyl group or an —O—$C_{1-6}$ alkyl group that is monosubstituted, disubstituted, or trisubstituted by a phenyl group, and $R^3$ represents hydrogen, a $C_{1-6}$-alkyl group, a $C_{2-6}$ alkenyl group, a $C_{2-6}$ alkynyl group, a $C_{3-7}$ cycloalkyl group, a $C_{1-6}$-alkyl group that is substituted by 1 to 6 halogen atoms, a hydroxy-$C_{1-6}$ alkyl group, a $C_{1-6}$ alkoxy group, a $C_{1-6}$ alkylthio group, a ($C_{1-6}$ alkoxy)-($C_{1-6}$ alkyl) group, a carboxy-$C_{1-6}$ alkyl group, a ($C_{1-6}$ alkoxy)-carbonyl-$C_{1-6}$ alkyl group, an amino-$C_{1-6}$ alkyl group, a mono($C_{1-6}$ alkyl)-amino group, a di($C_{1-6}$ alkyl)-amino group, a 2-oxo-pyrrolidin-1-ylmethyl group, an aryl group, a diarylmethylol group, a $C_{1-6}$-alkyl group that is substituted by one or two aryl groups, a $C_{1-6}$ alkanoyl group, or an arylcarbonyl group, wherein aryl in each case stands for an unsubstituted phenyl group or for a phenyl group which is substituted by 1 to 3 substituents selected from the group consisting of halogen, $C_{1-6}$ alkyl, $C_{1-6}$ alkoxy, and $CF_3$, and the salts thereof, or

B)

$R^1$, $R^2$, and $R^3$ each represent hydrogen or a hydrocarbon group;

wherein heteroaryl groups are five-membered, six-membered or seven-membered aromatic ring structures containing from 1 to 5 heteroatoms selected from the group consisting of oxygen, nitrogen and sulfur as ring members and optionally may be annellated with a further ring structure;

wherein monosubstituted or polysubstituted alkyl, alkenyl or alkinyl groups may be substituted with one or more substituents independently selected from the group consisting of F, Cl, Br, I, $C_{1-6}$ alkoxy, —$NO_2$, —OH, —SH, (C=O)—OH, —(C=O)—$OC_{1-4}$ alkyl, —O—(C=O)—$C_{1-4}$ alkyl, —$CH_2$ $OCH_2$ phenyl, CN, —$CF_3$, —$CHF_2$, —$CH_2F$, unsubstituted phenyl, and —$NR^aR^b$ in which $R^a$ and $R^b$ can be selected independently from the group consisting of H, methyl, ethyl, n-propyl, isopropyl, n-butyl, sec-butyl, tert-butyl, —(C=O)—$OC_{1-4}$ alkyl, and unsubstituted phenyl;

wherein a monosubstituted or polysubstituted cycloaliphatic group may be substituted by one or more substituents independently selected from the group consisting of F; Cl; Br; $C_{1-6}$ alkoxy; oxo; $C_{1-6}$ alkyl; hydroxyl; —CN; —$CF_3$; —$CHF_2$; $CH_2F$; unsubstituted phenyl; —$NR^aR^b$ in which $R^a$ and $R^b$ can be selected independently from the group consisting of H, methyl, ethyl, n-propyl, isopropyl and unsubstituted phenyl; thioxo; I; —$SF_5$; —$NO_2$; —$OCF_3$; —$SCF_3$; SH; —$SC_{1-5}$ alkyl; —C(=O)—H; —C(=O)—$C_{1-5}$ alkyl; —C(=O)—OH; C(=O)—$OC_{1-5}$ alkyl; —($CH_2$)—C(=O)—OH; —($CH_2$)—C(=O)—$OC_{1-5}$ alkyl; ($CH_2$)-benzo[b]furanyl; —O-phenyl; —O-benzyl; phenyl; benzyl, naphthyl and —($CH_2$)-naphthyl, and each of the cyclic moieties of the —O-phenyl, —O-benzyl, phenyl, —($CH_2$)-benzo[b]furanyl, benzyl, naphthyl and —($CH_2$)—naphthyl groups optionally may be substituted by from 1 to 5 substituents independently selected from the group consisting of F, Cl, Br, —OH, —$CF_3$, —$SF_5$, —CN, —$NO_2$, —$OC_{1-5}$ alkyl, —$C_{1-5}$ alkyl, —$OCF_3$, —$SCF_3$, phenyl, and —O-benzyl;

wherein monosubstituted and polysubstituted aryl or heteroaryl groups may be substituted by from 1 to 5 substituents independently selected from the group consisting of F, Cl, Br, I, —CN, —NO$_2$, C$_{1-5}$ alkyl, OH, SH, C$_{1-5}$ alkoxy, C$_{1-5}$ perfluoroalkoxy, —C(=O)—C$_{1-5}$ alkyl, —C(=O)—O—C$_{1-5}$ alkyl, —(CH$_2$)$_{1-3}$—O—(C=O)-phenyl, —S—C$_{1-5}$ alkyl, —S(=O)$_{1-6}$ alkyl, —S(=O)$_2$—NH$_2$, —NH—(C=O)—CH$_3$, —S—CHF$_2$, —S—CH$_2$F, —C(=O)—C$_{1-5}$ perfluoroalkyl, —CF$_3$, CHF$_2$, CH$_2$F, phenyl, phenoxy, and —NR$^a$R$^b$, in which R$^a$ and R$^b$ can be selected independently from the group consisting of H, methyl, ethyl, n-propyl, isopropyl and unsubstituted phenyl, —SF$_5$, —O—C$_{2-5}$ alkenyl, —O—CF$_3$, —O—CHF$_2$, —O—CH$_2$F, C(=O)—OH, —O—C(=O)—C$_{1-5}$ alkyl, O—C(=O) phenyl, —(CH$_2$)—O—C(=O)—C$_{1-5}$ alkyl, —NH—C$_{1-5}$ alkyl, —N(C$_{1-5}$ alkyl)$_2$, —NH—C(=O)—O—C$_{1-5}$ alkyl, C(=O)—H, —C(=O)—C$_{1-5}$ alkyl, —C(=O)—NH$_2$, —C(=O)—NH—C$_{1-5}$ alkyl, C(=O)—N—(C$_{1-5}$ alkyl)$_2$, —S(=O)$_2$—NH—C$_{1-5}$ alkyl, —S(=O)$_2$—NH-phenyl, —(CH$_2$)—benzo[b]furanyl, —O-phenyl, —S-phenyl, —S-benzyl, —O-benzyl, phenyl, and benzyl;

wherein a monosubstituted or polysubstituted monocyclic ring system may be substituted by from 1 to 5 substituents independently selected from the group consisting of F, Cl, Br, I, —CN, —NO$_2$, oxo, C$_{1-5}$ alkyl, C$_{1-5}$ alkoxy, C$_{1-5}$ perfluoroalkoxy, —C(=O)—C$_{1-5}$ alkyl, —C(=O)—O—C$_{1-5}$ alkyl, —S(=O)$_{1-6}$ alkyl, —C(=O)—C$_{1-5}$ perfluoroalkyl, —CF$_3$, —CHF$_2$, —CH$_2$F, and —NR$^a$R$^b$ wherein R$^a$ and R$^b$ are independently selected from the group consisting of H, methyl, ethyl, n-propyl, isopropyl, and unsubstituted phenyl, thioxo, —SF$_5$, —OH, —O—C$_{2-5}$ alkenyl, —NH$_2$, —NO$_2$, —O—CF$_3$, —O—CHF$_2$, —O—CH$_2$F, —S—CF$_3$, —S—CHF$_2$, —S—CH$_2$F, —SH, —S—C$_{1-5}$ alkyl, —C(=O)—OH, —O—C(=O)—C$_{1-5}$ alkyl, —O—C(=O)-phenyl, —(CH$_2$)—O—C(=O)—C$_{1-5}$ alkyl, —(CH$_2$)—O—C(=O)-phenyl, —NH—C$_{1-5}$ alkyl, —N(C$_{1-5}$ alkyl)$_2$, —NH—C(=O)—O—C$_{1-5}$ alkyl, —NH—C(=O)—C$_{1-5}$ alkyl, —C(=O)—H, —C(=O)—NH$_2$, —C(=O)—NH—C$_{1-5}$ alkyl, C(=O)—N—(C$_{1-5}$ alkyl)$_2$, —S(=O)$_2$—NH$_2$, —S(=O)$_2$—NH—C$_{1-5}$ alkyl, —S(=O)$_2$—NH-phenyl, —(CH$_2$)—benzo[b]furanyl, —O-phenyl, —S-phenyl, —S-benzyl, —O-benzyl, phenyl, and benzyl, and in each case the cyclic moiety of the —O—C(=O)-phenyl, —(CH$_2$)—O—C(=O)-phenyl, —S(=O)$_2$—NH-phenyl, —O-phenyl, —S-phenyl, —S-benzyl, —O-benzyl, phenyl, —(CH$_2$)—benzo[b]furanyl, and benzyl groups optionally may be substituted by from 1 to 5 substituents independently selected from the group consisting of F, Cl, Br, —OH, —CF$_3$, —SF$_5$, —CN, —NO$_2$, —O—C$_{1-5}$ alkyl, —C$_{1-5}$ alkyl, —O—CF$_3$, —S—CF$_3$, phenyl, and —O-benzyl; and wherein monosubstituted and polysubstituted alkylene, alkenylene and alkinylene groups may be substituted by one or more substituents independently selected from the group consisting of F, Cl, Br, C$_{1-6}$ alkoxy, hydroxy, CN, CF$_3$, CHF$_2$, CH$_2$F, unsubstituted phenyl and —NR$^a$R$^b$, in which R$^a$ and R$^b$ can be independently selected from the group consisting of H, C$_{1-3}$ alkyl, and unsubstituted phenyl, and wherein an alkylene, alkenylene or alkinylene group optionally may contain one or more oxygen or sulfur atoms as chain links;

and the salts thereof.

2. The compound of claim 1, wherein said compound is present in the form of a pure enantiomer or pure diastereoisomer.

3. The compound of claim 1, wherein said compound is present in the form of a mixture of stereoisomers.

4. The compound of claim 1, wherein said compound is present in the form of a racemic mixture.

5. The compound of claim 1, wherein R$^1$ represents hydrogen; a linear or branched unsubstituted, C$_{1-10}$ alkyl group which may comprise at least one heteroatom as a link; a linear or branched unsubstituted or at least monosubstituted C$_{2-10}$ alkenyl group which may comprise at least one heteroatom as a link; a linear or branched unsubstituted or at least monosubstituted C$_{2-10}$ alkynyl group which may comprise at least one heteroatom as a link; an unsubstituted or at least monosubstituted five-membered to fourteen-membered aryl group or heteroaryl group, which is bonded via a linear or branched C$_{1-5}$ alkylene group which may comprise at least one heteroatom as a link, a —C(=O)—OR$^5$ group bonded via a linear or branched C$_{1-5}$ alkylene group; or a —O—C(=O)—R$^6$ group bonded via a linear or branched C$_{1-5}$ alkylene group, R$^2$ represents hydrogen; a linear or branched unsubstituted or at least monosubstituted C$_{1-10}$ alkyl group which may comprise at least one heteroatom as a link; a linear or branched unsubstituted or at least monosubstituted C$_{2-10}$ alkenyl group which may comprise at least one heteroatom as a link; a linear or branched unsubstituted or at least monosubstituted C$_{2-10}$ alkynyl group which may comprise at least one heteroatom as a link; an unsubstituted or at least monosubstituted, five to fourteen-membered aryl group or heteroaryl group, which may be bonded via a linear or branched C$_{1-5}$ alkylene group which may comprise at least one heteroatom as a link;

R$^3$ represents hydrogen; a linear or branched unsubstituted or at least monosubstituted C$_{1-10}$ alkyl group which may comprise at least one heteroatom as a link; a linear or branched unsubstituted or at least monosubstituted C$_{2-10}$ alkenyl group which may comprise at least one heteroatom as a link; a linear or branched unsubstituted or at least monosubstituted C$_{2-10}$ alkynyl group which may comprise at least one heteroatom as a link; an unsubstituted or at least monosubstituted five-membered to fourteen-membered aryl group or heteroaryl group, which is bonded via a linear or branched unsubstituted or at least monosubstituted C$_{1-5}$ alkylene group which may comprise at least one heteroatom as a link and may be condensed with an unsubstituted or at least monosubstituted monocyclic ring system; an unsubstituted or at least monosubstituted C$_{3-8}$ cycloaliphatic group, which may comprise at least one heteroatom as a ring member and which may be bonded via a linear or branched unsubstituted or at least monosubstituted C$_{1-5}$ alkylene group which may comprise at least one heteroatom as a link and may be condensed with an unsubstituted or at least monosubstituted monocyclic ring system; or a —C(=O)—R$^4$ group;

R$^4$ represents
  a linear or branched unsubstituted or at least monosubstituted C$_{1-10}$ alkyl group which may comprise at least one heteroatom as a link; a linear or branched unsubstituted or at least monosubstituted C$_{2-10}$ alkenyl group which may comprising at least one heteroatom as a link; a linear or branched unsubstituted or at least monosubstituted C$_{2-10}$ alkynyl group which may comprise at least one heteroatom as a link;
  an unsubstituted or at least monosubstituted five-membered to fourteen-membered aryl group or heteroaryl group, which may be bonded via a linear or branched unsubstituted or at least monosubstituted $C_{1-5}$-alkylene group, $C_{2-5}$-alkenylene group, or $C_{2-5}$-alkynylene group which may comprise at least one heteroatom as a link and may be condensed with an unsubstituted or at least monosubstituted monocyclic ring system;

an unsubstituted or at least monosubstituted $C_{3-8}$ cycloaliphatic group which may comprising at least one heteroatom as a ring member and may be bonded via a linear or branched unsubstituted or at least monosubstituted $C_{1-6}$ alkylene group which may comprise at least one heteroatom as a link, which may be at least singly bridged by a linear or branched unsubstituted or at least monosubstituted $C_{1-6}$ alkylene group and may be condensed with an unsubstituted or at least monosubstituted monocyclic ring system; or a —C(=O)—OR$^7$ group bonded via a linear or branched unsubstituted or at least monosubstituted $C_{1-5}$ alkylene group; an —O—(C=O)—R$^8$ group bonded via a linear or branched unsubstituted or at least monosubstituted $C_{1-5}$ alkylene group; or a —(C=O)—R$^9$ group bonded via a linear or branched unsubstituted or at least monosubstituted $C_{1-5}$ alkylene group;

R$^5$ and R$^6$ independently represent a linear or branched $C_{1-5}$-alkyl group, a linear or branched $C_{2-5}$ alkenyl group or a linear or branched $C_{2-5}$ alkynyl group;

R$^7$ and R$^8$ independently represent hydrogen; a linear or branched $C_{1-5}$-alkyl group; a linear or branched $C_{2-5}$ alkenyl group; a linear or branched $C_{2-5}$ alkynyl group; or a phenyl or naphthyl group which phenyl or napthyl group may be at least monosubstituted; and R$^9$ represents a linear or branched $C_{1-5}$-alkyl group; a linear or branched $C_{2-5}$ alkenyl group; or a linear or branched $C_{2-5}$ alkynyl group.

6. The compound of claim 1, wherein

R$^1$ represents hydrogen; a linear or branched, unsubstituted $C_{1-5}$ alkyl group; a linear or branched, unsubstituted $C_{2-5}$ alkenyl group; a linear or branched, unsubstituted $C_{2-5}$ alkynyl group; an unsubstituted or at least monosubstituted phenyl or naphthyl group bonded via a linear or branched $C_{1-5}$ alkylene group, comprising one or more oxygen atoms; a —C(=O)—OR$^5$ group bonded via a linear or branched $C_{1-4}$ alkylene group; or a —O—C(=O)—R$^6$ group bonded via a linear or branched $C_{1-4}$ alkylene group;

R$^2$ represents hydrogen; a linear or branched, unsubstituted $C_{1-5}$ alkyl group which may comprise one or more oxygen atoms and may comprise one or more sulfur atoms; or a phenyl or naphthyl group which is monosubstituted or polysubstituted by the same or different substituents selected from the group consisting of F, Cl, Br, CN, NO$_2$, $C_{1-5}$ alkyl, $C_{1-5}$ alkoxy, —C(=O)—$C_{1-5}$ alkyl, —C(=O)—O—$C_{1-5}$ alkyl, —S(=O)$_2$—$C_{1-6}$ alkyl, —C(=O)—$C_{1-5}$ perfluoroalkyl, —CF$_3$, CHF$_2$, and CH$_2$F and which may be bonded via a —(CH$_2$)— ridge, a —(CH$_2$)$_2$— bridge, a —(CH$_2$)$_3$— bridge, or a —(CH$_2$)$_2$—O— bridge;

R$^3$ represents hydrogen; a biphenyl group, which is bonded via a —(CH$_2$)— bridge, a —(CH$_2$)$_2$— bridge, or a —(CH$_2$)$_3$— bridge; or a C(=O)—R$^4$ group;

R$^4$ represents a linear or branched $C_{1-10}$ alkyl group which may comprise one or more oxygen atoms and may comprise one or more sulfur atoms, and which may be unsubstituted or at least monosubstituted by the same or different substituents selected from the group consisting of phenyl, di-($C_{1-5}$ alkylamino), carboxy, and —NH—(C=O)—O—$C_{1-5}$ alkyl; a linear or branched $C_{2-5}$ alkyl group; a cyclic group selected from phenyl, naphthyl, furyl (furanyl), thienyl (thiophenyl), 1,2,3-triazolyl, benzo[1,3]dioxolyl, benzo[1,2,5]oxadiazoleyl, chromanyl, pyrimidynyl, pyrazolyl, pyridynyl, isoxazolyl, and 1,2,3-thiadiazolyl, wherein, in each case the cyclic group may be bonded via a —(CH$_2$)—, —(CH$_2$)—O— bridge, a —CH=CH— bridge, a —(CH$_2$)$_2$— bridge, a —(CH$_2$)$_2$—O— bridge or a —(CH$_2$)$_3$-bridge and the cyclic group may be monosubstituted or polysubstituted by the same or different substituents selected from the group consisting of F, Cl, Br, I, —CN, —NO$_2$, $C_{1-5}$ alkyl, $C_{1-5}$ alkoxy, $C_{1-5}$ perfluoroalkoxy, —C(=O)—$C_{1-5}$ alkyl, —C(=O)—O—$C_{1-5}$ alkyl, —(CH$_2$)$_{1-3}$—O—C(=O)-phenyl, —N(CH$_3$)$_2$, —S(=O)$_{2-1-6}$ alkyl, —S(=O)$_2$—NH$_2$, —C(=O)—$C_{1-5}$ perfluoroalkyl, —S—$C_{1-5}$ alkyl, —S—CH$_2$F, —S—CHF$_2$, —SCF$_3$, —CF$_3$, —NH—(C=O)—CH$_3$, —SO$_2$—NH$_2$, —CHF$_2$, —CH$_2$F, phenyl, and phenoxy, and the latter phenyl and phenoxy substituents themselves may be monosubstituted or polysubstituted by the same or different substituents selected from the group consisting of F, Cl, Br, —S—CHF$_2$, —CF$_3$, —CH$_2$F, CN, NO$_2$, $C_{1-5}$ alkyl, and $C_{1-5}$ alkoxy;

a three-membered, four-membered, five-membered, six-membered, seven-member, or eight-membered cycloaliphatic group which may comprise at least one heteroatom as a ring member and may be bonded via a —(CH$_2$)— bridge, a —(CH$_2$)$_2$— bridge, or a —(CH$_2$)$_3$— bridge, which is at least singly bridged at least by one —(C(CH$_3$)$_2$)— or —(CH$_2$) group and may be monosubstituted or polysubstituted by the same or different substituents selected from the group consisting of $C_{1-5}$ alkyl, $C_{1-5}$ alkoxy, —CF$_3$, CHF$_2$, CH$_2$F, and oxo;

a —C(=O)—OR$^7$ group bonded via a linear or branched unsubstituted or at least monosubstituted $C_{1-5}$ alkylene group; a —O—(C=O)—R$^8$ group bonded via a linear or branched unsubstituted or at least monosubstituted $C_{1-5}$ alkylene group; or a —(C=O)—R$^9$ group bonded via a linear or branched unsubstituted or at least monosubstituted $C_{1-5}$ alkylene group;

R$^5$ and R$^6$ each independently represent a methyl group, ethyl group, n-propyl group, or isopropyl group;

R$^7$ and R$^8$ each independently represent methyl; ethyl; n-propyl; isopropyl; or unsubstituted phenyl; and R$^9$ represents methyl; ethyl; n-propyl; or isopropyl.

7. The compound of claim 1, wherein

R$^1$ represents hydrogen; a linear or branched unsubstituted $C_{1-4}$ alkyl group; a linear or branched unsubstituted $C_{2-5}$ alkenyl group; a linear or branched unsubstituted $C_{2-3}$ alkynyl group; or a phenyl or naphthyl group which is bonded via a —(CH$_2$) bridge, —(CH$_2$)$_2$ bridge, —(CH$_2$)$_3$ bridge or —(CH$_2$)$_2$—O— bridge and may be monosubstituted or polysubstituted by the same or different substituents selected from the group consisting of F, Cl, Br, CN, NO$_2$, $C_{1-5}$ alkyl, $C_{1-5}$ alkoxy, —C(=O)—$C_{1-5}$ alkyl, —C(=O)—O—$C_{1-5}$ alkyl, —S(=O)$_{2-1-6}$ alkyl, —C(=O—$C_{1-5}$ perfluoroalkyl, —CF$_3$, CHF$_2$, and CH$_2$F; a —C(=O)—OR$^5$ group bonded via a —($CH_2$) group; or a —O—C(=O)—$R^6$ group bonded via a —($CH_2$) group, —($CH_2$)$_2$ group, —($CH_2$)$_3$ group or —($CH_2$)$_4$ group;

$R^2$ represents hydrogen; a linear or branched unsubstituted $C_{1-5}$ alkyl group which may comprise one or more sulfur atoms as links; a phenyl group, wherein the phenyl group is monosubstituted or polysubstituted by the same or different substituents selected from the group consisting of F, Cl, Br, CN, $NO_2$, $C_{1-5}$ alkyl, $C_{1-5}$ alkoxy, —C(=O)—$C_{1-5}$ alkyl, —C(=O)—O—$C_{1-5}$ alkyl, —S(=O)$_{2-1-6}$ alkyl, —C(=O)—$C_{1-5}$ perfluoroalkyl, —$CF_3$, $CHF_2$, and $CH_2F$ and which may be bonded via a —($CH_2$)— bridge; and $R^4$ represents a linear or branched $C_{1-8}$-alkyl group which may comprise one or more oxygen atoms and may comprise one or more sulfur atoms, and which may be unsubstituted or at least monosubstituted or polysubstituted by the same or different substituents selected from the group consisting of unsubstituted phenyl, dimethylamino, carboxy, and —NH—(C=O)—O—C($CH_3$)$_3$; a linear or branched unsubstituted $C_{2-4}$ alkenyl group; a cyclic group selected from phenyl, naphthyl, furyl (furanyl), thienyl (thiophenyl), 1,2,3-triazolyl, chromanyl, benzo[1,3]dioxolyl, benzo[1,2,5]oxadiazoleyl, pyrimidynyl, pyrazolyl, pyridynyl, isoxazolyl, or 1,2,3-thiadiazolyl, wherein the cyclic group may be bonded via a —($CH_2$)— bridge, a —($CH_2$)—O— bridge, a —CH=CH— bridge, a —($CH_2$)$_2$— bridge, a —($CH_2$)$_2$—O— bridge, or a —($CH_2$)$_3$-bridge and the cyclic group may be monosubstituted or polysubstituted by the same or different substituents selected from the group consisting of F, Cl, Br, I, methyl, ethyl, isopropyl, n-propyl, sec-butyl, tert-butyl, n-butyl, methoxy, ethoxy, —$CF_3$, —$OCF_3$, —$CH_2$—O—C(=O)-phenyl, $NO_2$, —S—$CF_3$, —S—$CHF_2$, —N($CH_3$)$_2$, —NH—CO—$CH_3$, CN, $SO_2$—$NH_2$, phenyl, and phenoxy wherein the latter phenyl and phenoxy substituents may be monosubstituted or polysubstituted by the same or different substituents selected from the group consisting of F, Cl, Br, $CH_3$, and $OCH_3$;

a cyclopropyl group; cyclobutyl group; cyclopentyl group; cyclohexyl group; a imidazolidine; 4,7,7-trimethyl-3-oxo-2-oxa-bicyclo[2,2,1]heptyl group or adamantyl group which may be bonded via a —($CH_2$)— bridge, a —($CH_2$)$_2$— bridge, or a —($CH_2$)$_3$— bridge; and which may be unsubstituted or monosubstituted or polysubstituted by the same or different substituents selected from the group consisting of $C_{1-5}$ alkyl, $C_{1-5}$ alkoxy, —$CF_3$, $CHF_2$, $CH_2F$, and oxo; or a —C(=O)—$OR^7$ group bonded via a —($CH_2$)— group, a —($CH_2$)$_2$ group, a —C(H)-phenyl group, or a —C($CH_3$)$_2$ group; an —O—(C=O)—$R^8$ group bonded via a —($CH_2$)— group, a —($CH_2$)$_2$ group, a —C(H)-phenyl group, or a —C($CH_3$)$_2$ group; or a —(C=O)—$R^9$ group bonded via a —($CH_2$)— group or a —($CH_2$)$_2$ group.

8. The compound of claim 1, wherein $R^4$ represents a linear or branched $C_{6-8}$ alkyl group which may comprise one or more oxygen atoms and may comprise one or more sulfur atoms, and which may be unsubstituted or at least monosubstituted or polysubstituted by the same or different substituents selected from the group consisting of unsubstituted phenyl, dimethylamino, carboxy, and —NH—(C=O)—O—C($CH_3$)$_3$; a linear or branched unsubstituted $C_{2-4}$ alkenyl group;

a cyclic group selected from naphthyl, furyl (furanyl), thienyl (thiophenyl), [1,2,3]triazolyl, chromanyl, benzo[1,3]dioxolyl, benzo[1,2,5]oxadiazoleyl, pyrimidynyl, pyrazolyl, pyridynyl, isoxazolyl, and 1,2,3-thiadiazolyl, wherein the cyclic group may, in each case, be bonded via a —($CH_2$)— bridge, a —($CH_2$)—O— bridge, a —CH=CH— bridge, a —($CH_2$)$_2$—bridge, a —($CH_2$)$_2$—O— bridge, or a —($CH_2$)$_3$ bridge and which cyclic group may be monosubstituted or polysubstituted by the same or different substituents selected from the group consisting of F, Cl, Br, I, methyl, ethyl, isopropyl, n-propyl, sec-butyl, tert-butyl, n-butyl, methoxy, ethoxy, —$CF_3$, —$OCF_3$, —$CH_2$—O—C(=O)-phenyl, —$NO_2$, —S—$CF_3$, —S—$CHF_2$, —N($CH_3$)$_2$, —NH—CO—$CH_3$, —CN, —$SO_2$—$NH_2$, phenyl, and phenoxy and the latter phenyl and phenoxy substituents themselves may be monosubstituted or polysubstituted by the same or different substituents selected from the group consisting of F, Cl, Br, $CH_3$, and $OCH_3$;

a group selected from cyclopropyl, cyclobutyl, cyclopentyl, cyclohexyl, imidazolidine group, 4,7,7-trimethyl-3-oxo-2-oxa-bicyclo[2,2,1]heptyl, or adamantyl, which groups are may be bonded via a —($CH_2$)— bridge, a —($CH_2$)$_2$— bridge, or a —($CH_2$)$_3$— bridge, and which groups may be unsubstituted or monosubstituted or polysubstituted by the same or different substituents selected from the group consisting of $C_{1-5}$ alkyl, $C_{1-5}$ alkoxy, —$CF_3$, $CHF_2$, $CH_2F$, and oxo; or a —C(=O)—$OR^7$ group bonded via a —($CH_2$)— group, a —($CH_2$)$_2$ group, a —C(H)-phenyl group, or a —C($CH_3$)$_2$ group; an —O—(C=O)—$R^8$ group bonded via a —($CH_2$)— group, a —($CH_2$)$_2$ group, a —C(H)-phenyl group, or a —C($CH_3$)$_2$ group; or a —(C=O)—$R^9$ group bonded via a —($CH_2$)— group or a —($CH_2$)$_2$ group.

9. The compound of claim 1, wherein $R^4$ represents a linear or branched $C_{6-8}$-alkyl group which may comprise one or more oxygen atoms and may comprise one or more sulfur atoms, and which may be unsubstituted or at least monosubstituted or polysubstituted by the same or different substituents selected from the group consisting of unsubstituted phenyl, dimethylamino, carboxy, and —NH—(C=O)—O—C($CH_3$)$_3$;

a linear or branched unsubstituted $C_{2-4}$ alkenyl group; or a cyclic group selected from naphthyl, furyl (furanyl), thienyl (thiophenyl), [1,2,3]-triazolyl, chromanyl, benzo[1,3]dioxolyl, benzo[1,2,5]oxadiazoleyl, pyrimidynyl, pyrazolyl, pyridynyl, isoxazolyl, 1,2,3-thiadiazolyl, wherein the cyclic group may, in each case, be bonded via a —($CH_2$)— bridge, a —($CH_2$)—O— bridge, a —CH=CH— bridge, a —($CH_2$)$_2$— bridge, a —($CH_2$)$_2$—O— bridge, or a —($CH_2$)$_3$ bridge and the cyclic group may be monosubstituted or polysubstituted by the same or different substituents selected from the group consisting of F, Cl, Br, I, methyl, ethyl, isopropyl, n-propyl, sec-butyl, tert-butyl, n-butyl, methoxy, ethoxy, —$CF_3$, —$OCF_3$, —$CH_2$—O—C(=O)-phenyl, —$NO_2$, —S—$CF_3$, —S—$CHF_2$, —N($CH_3$)$_2$, —NH—CO—$CH_3$, —CN, —$SO_2$—$NH_2$, phenyl, and phenoxy and the latter phenyl and phenoxy substituents themselves may be monosubstituted or polysubstituted by the same or different substituents selected from the group consisting of F, Cl, Br, —$CH_3$, and —$OCH_3$; or a group selected from 2-trifluoromethoxyphenyl, 3 trifluoromethoxyphenyl, 4-trifluoromethoxyphenyl, 2-$CF_3$—S-phenyl, 3-CF$_3$—S-phenyl, 4-CF$_3$—S-phenyl, 2-cyanophenyl, 3-cyanophenyl, 4-cyanophenyl, 2-nitrophenyl, 3-nitrophenyl, 4-nitrophenyl, 2-CHF$_2$—S-phenyl, 3-CHF$_2$—S-phenyl, 4-CHF$_2$—S-phenyl, 2-dimethylaminophenyl, 3-dimethylaminophenyl, 4-dimethylaminophenyl, 2-phenyl-(C=O)—O—CH$_2$-phenyl, 3-phenyl-(C=O)—O—CH$_2$-phenyl, 4-phenyl-(C=O)—O—CH$_2$-phenyl, 2-CH$_3$—(C=O)—NH-phenyl, 3-CH$_3$—(C=O)—NH-phenyl, 4-CH$_3$—(C=O)—NH-phenyl, 2-phenylphenyl, 3-phenylphenyl, 4-phenylphenyl, 2-NH$_2$—SO$_2$-phenyl, 3-NH$_2$—SO$_2$-phenyl, 4-NH$_2$—SO$_2$-phenyl, pentafluorophenyl, 4-methyl-3-nitrophenyl, 2-fluorobenzyl, 3-fluorobenzyl, 4-fluorobenzyl, 2-chlorobenzyl, 3-chlorobenzyl, 4-chlorobenzyl, 2-bromobenzyl, 3-bromobenzyl, 4-bromobenzyl, 2-methylbenzyl, 3-methylbenzyl, 4-methylbenzyl, 2-methoxybenzyl, 3-methoxybenzyl, 4-methoxybenzyl, 3,4-dimethoxybenzyl, 2,5-dimethoxybenzyl, —CH=CH-phenyl, wherein the phenyl group may be monosubstituted or polysubstituted in the 2, 3 or 4 position by the same or different group selected from F, Cl, Br, and CF$_3$, —CH$_2$—O-phenyl, and the latter phenyl group may be monosubstituted or polysubstituted in 2, 3 or 4 position by the same or different group selected from F, Cl, Br, and CF$_3$; a cyclo group selected from cyclopropyl, cyclobutyl, cyclopentyl, cyclohexyl, imidazolidine, 4,7,7-trimethyl-3-oxo-2-oxa-bicyclo[2,2,1]heptyl, and adamantyl, which cyclo groups are may be bonded via a —(CH$_2$)— bridge, a —(CH$_2$)$_2$— bridge, or a —(CH$_2$)$_3$— bridge, wherein the cyclic groups may, in each case, be unsubstituted or monosubstituted or polysubstituted by the same or different substituents selected from the group consisting of C$_{1-5}$ alkyl, C$_{1-5}$ alkoxy, —CF$_3$, CHF$_2$, CH$_2$F, and oxo; —C(=O)—OR$^7$ bonded via a —(CH$_2$) group, —(CH$_2$)$_2$ group, —C(H)(phenyl) group, or —C(CH$_3$)$_2$ group; —O—(C=O)—R$^8$ bonded via a —(CH$_2$) group, —(CH$_2$)$_2$ group, —C(H)(phenyl) group, or —C(CH$_3$)$_2$ group; —(C=O)—R$^9$ group bonded via a —(CH$_2$) group or a —(CH$_2$)$_2$ group.

10. The compound of claim 1, wherein

R$^1$ represents hydrogen;

a linear or branched unsubstituted C$_{1-4}$-alkyl group;

a linear or branched unsubstituted C$_{2-5}$ alkenyl group;

a linear or branched unsubstituted C$_{2-3}$ alkynyl group;

a phenyl or naphthyl group, which is unsubstituted or monosubstituted or polysubstituted by the same or different substituents selected from the group consisting of F, Cl, Br, —CN, —NO$_2$, C$_{1-5}$ alkyl, C$_{1-5}$ alkoxy, —C(=O)—C$_{1-5}$ alkyl, —C(=O)—O—C$_{1-5}$ alkyl, —S(=O)$_{2-1-6}$ alkyl, —C(=O)—C$_{1-5}$ perfluoroalkyl, —CF$_3$, —CHF$_2$, and —CH$_2$F and which may be bonded via a —(CH$_2$)— bridge, a —(CH$_2$)$_2$— bridge, a —(CH$_2$)$_3$— bridge or a —(CH$_2$)$_2$—O— bridge, a —C(=O)—OR$^5$ group bonded via a —(CH$_2$) group; or a —O—C(=O)—R$^6$ group bonded via a —(CH$_2$) group, a —(CH$_2$)$_2$ group, a —(CH$_2$)$_3$ group, or —(CH$_2$)$_4$ group;

R$^2$ represents hydrogen; a linear or branched unsubstituted C$_{1-5}$-alkyl group which may comprise one or more sulfur atoms; or a phenyl group, wherein the phenyl group may be monosubstituted or polysubstituted by the same or different substituents selected from the group consisting of F, Cl, Br, —CN, —NO$_2$, C$_{1-5}$ alkyl, C$_{1-5}$ alkoxy, —C(=O)—C$_{1-5}$ alkyl, —C(=O)—O—C$_{1-5}$ alkyl, —S(=O)$_{2-1-6}$ alkyl, —C(=O)—C$_{1-5}$ perfluoroalkyl, —CF$_3$, CHF$_2$, and —CH$_2$F, and which may be bonded via a —(CH$_2$)— bridge;

R$^3$ represents hydrogen; a biphenyl group, which is bonded via a —(CH$_2$)— bridge, a —(CH$_2$)$_2$— bridge, or a —(CH$_2$)$_3$— bridge; or a C(=O)—R$^4$ group; and R$^4$ represents a group selected from methyl, ethyl, isopropyl, n-propyl, sec-butyl, isobutyl, tert-butyl, n-butyl, n-pentyl, 1-methylbutyl, 2-dimethylpropyl, 1-ethylpropyl, 1-propylbutyl, 1-ethylpentyl, dimethylaminomethyl, —CH$_2$—H$_2$—H=CH$_2$, —CH$_2$—O—CH$_3$, —CH$_2$—O—CH$_2$—H$_2$—O—CH$_3$, —CH$_2$—H$_2$-phenyl, —CH$_2$—O-phenyl, —CH$_2$—O—CH$_2$-phenyl, —CH$_2$—H$_2$—H$_2$—O-phenyl, —C(H)(phenyl)-(C$_2$H$_5$), —C(H)(CH$_3$)—O-phenyl, —CH$_2$—H$_2$—(C=O)—CH$_3$, —CH$_2$—O—(C=O)—CH$_3$, —CH$_2$—H$_2$—(C=O)—O—C$_2$H$_5$, —CH$_2$—O—(C=O)-phenyl, —CH$_2$—(C=O)—O—CH$_2$—H$_3$, —C(H)(phenyl)-(C=O)—CH$_3$, —C(H)(phenyl)-O—(C=O)—CH$_3$, —C(CH$_3$)$_2$—O—(C=O)—CH$_3$, —C(H)(NH—(C=O)—O—(CH$_3$)$_3$)—(CH$_2$—O—CH$_2$-phenyl), —C(CH$_3$)$_2$—H$_2$—OH, unsubstituted phenyl, 2-fluorophenyl, 3-fluorophenyl, 4-fluorophenyl, 2-chlorophenyl, 3-chlorophenyl, 4-chlorophenyl, 2-bromophenyl, 3-bromophenyl, 4-bromophenyl, 2-iodophenyl, 3-iodophenyl, 4-iodophenyl, 2-methylphenyl, 3-methylphenyl, 4-methylphenyl, 2-ethylphenyl, 3-ethylphenyl, 4-ethylphenyl, 2-n-propylphenyl, 3-n-propylphenyl, 4-n-propylphenyl, 2-tert-butylphenyl, 3-tert-butylphenyl, 4-tert-butylphenyl, 2-methoxyphenyl, 3-methoxyphenyl, 4-methoxyphenyl, 2-ethoxyphenyl, 3-ethoxyphenyl, 4-ethoxyphenyl, 2-trifluoromethylphenyl, 3-trifluoromethylphenyl, 4-trifluoromethylphenyl, 2-trifluoromethoxyphenyl, 3-trifluoromethoxyphenyl, 4-trifluoromethoxyphenyl, 2-F$_3$—S-phenyl, 3-CF$_3$—S-phenyl, 4-CF$_3$—S-phenyl, 2-cyanophenyl, 3-cyanophenyl, 4-cyanophenyl, 2-nitrophenyl, 3-nitrophenyl, 4-nitrophenyl, 2-CHF$_2$—S-phenyl, 3-CHF$_2$—S-phenyl, 4-CHF$_2$—S-phenyl, 2-dimethylaminophenyl, 3-dimethylaminophenyl, 4-dimethylaminophenyl, 2-phenyl-(C=O)—O—CH$_2$-phenyl, 3-phenyl-(C=O)—O—CH$_2$-phenyl, 4-phenyl-(C=O)—O—CH$_2$-phenyl, 2-CH$_3$—(C=O)—NH-phenyl, 3-CH$_3$—(C=O)—NH-phenyl, 4-CH$_3$—(C=O)—NH-phenyl, 2-phenylphenyl, 3-phenylphenyl, 4-phenylphenyl, 2-NH$_2$—SO$_2$-phenyl, 3-NH$_2$—SO$_2$-phenyl, 4-NH$_2$—SO$_2$-phenyl, 2,4-dimethoxyphenyl, 2,5-dimethoxyphenyl, 3,5-dimethoxyphenyl, 3,4-dimethoxyphenyl, 2,3-dimethylphenyl, 2,3-dichlorophenyl, 3,4-dichlorophenyl, 2,6-dichlorophenyl, 2,3-difluorophenyl, 3,4-difluorophenyl, 3,5-difluorophenyl, pentafluorophenyl, 2-chloro-6-fluorophenyl, 4-bromo-3-methylphenyl, 3-fluoro-4-methylphenyl, 3-chloro-2-fluorophenyl, 2-chloro-4-nitrophenyl, 5-fluoro-2-trifluoromethylphenyl, 3-fluoro-4-trifluoromethyl, 4-methyl-3-nitrophenyl, 2-chloro-5-trifluoromethyl, 2,5-bis-trifluoromethylphenyl, 3,5-bis-trifluoromethylphenyl, 2-chloro-6-fluoro-3-methylphenyl, 6-chloro-2-fluoro-3-methylphenyl, 2,6-difluoro-4-methylphenyl, 2,6-difluoro-3-methylphenyl, 3,4,5-trimethoxyphenyl, 2,3-difluoro-4-methylphenyl, 2-fluorobenzyl, 3-fluorobenzyl, 4-fluorobenzyl, 2-chlorobenzyl, 3-chlorobenzyl, 4-chlorobenzyl, 2-bromobenzyl, 3-bromobenzyl, 4-bromobenzyl, 2-methylbenzyl, 3-methylbenzyl, 4-methylbenzyl, 2-methoxybenzyl,

95

3-methoxybenzyl, 4-methoxybenzyl, 3,4-dimethoxybenzyl, 2,5-dimethoxybenzyl, —CH=CH-phenyl,
wherein the phenyl group may be monosubstituted or polysubstituted in the 2, 3, or 4 position by the same or different members selected from the group consisting of F, Cl, Br, and $CF_3$, —$CH_2$—O-phenyl, and the latter phenyl group may be monosubstituted or polysubstituted in the 2, 3 or 4 position by the same or different members selected from the group consisting of F, Cl, Br, and $CF_3$;
1-naphthyl, 2-naphthyl, 2-thienyl, 3-thienyl, 3-chlorothien-2-yl, 2-furanyl, 3-furanyl, 2,5-dimethylfuran-3-yl, 5-tert-butyl-2-methylfuran-3-yl, pyridin-2-yl, pyridin-3-yl, pyridin-4-yl, 2-chloropyridin-4-yl, 6-chloropyridin-3-yl, 2-chloropyridin-3-yl, 2-ethylsulfanylpyridin-3-yl, 2-phenoxypyridin-3-yl, 2-methylsulfanylpyridin-3-yl, 2-methyl-6-trifluoromethylpyridin-3-yl, isoxazol-5-yl, 5-methylisoxazol-3-yl, 3-(2-chloro-6-fluorophenyl)-5-methylisoxazol-4-yl, 3-(2-chlorophenyl)-5-methylisoxazol-4-yl, 3-(2,6-dichlorophenyl)-5-methylisoxazol-4-yl, 5-tert-butyl-2-methyl-2H-pyrazol-3-yl, 1-phenyl-5-n-propyl-1H-pyrazol-4-yl, 1-(4-chlorophenyl)-5-trifluoromethyl-1H-pyrazol-4-yl, 2-tert-butyl-5-methyl-2H-pyrazol-3-yl, 5-methyl-2-phenyl-2H-[1,2,3]triazol-4-yl, 4-methyl[1,2,3]thiadiazol-5-yl, 2-chloro-4-trifluoromethylpyrimidin-5-yl, 2-chloro-4-trifluoromethylpyrimidin-5-yl, benzo[1,2,5]oxadiazol-5-yl, benzo[1.3]dioxol-5-yl, 6-chloro-2H-chroman-3-yl, imidazolidin-2,4-dion-5-ylmethyl, cyclopropyl, cyclobutyl, and—optionally bonded via a —$(CH_2)$— bridge or a —$(CH_2)_2$ bridge—cyclopentyl cyclohexyl, 4,7,7-trimethyl-3-oxo-2-oxa-bicyclo[2,2,1]heptyl, and adamantyl.

11. The compound of claim 1, wherein
I)
$R^1$ represents
a substituted six-membered or ten-membered aryl group;
a five-membered to fourteen-membered heteroaryl group which may be substituted;
—$(CH_2)_m$—O—C(=O)—$R^5$, where m is 1, 2, 3, 4, or 5;
—$(CH_2)_n$—C(=O)—O—$R^6$, where n is 1, 2, 3, 4, or 5;
—$(CH_2)$—$R^{22}$; or
—$(CH_2)$—$(CH_2)_c$—U—$(CH_2)_d$—$R^{23}$, where c is 0 or 1 and d is 0 or 1 and wherein U represents O, S, NH, N—$(CH_3)$, or $N(C_2H_5)$;
$R^2$ represents
hydrogen;
—$(CH_2)$—$(CH_2)_e$—$V_f$—$(CH_2)_g$—$R^{24}$, where e is 0 or 1, f is 0 or 1, and g is 0 or 1, and wherein V represents O, S, NH, N—$(CH_3)$, or $N(C_2H_5)$;
a linear or branched $C_{1-10}$ alkyl group, a linear or branched $C_{2-10}$ alkenyl group, or a linear or branched $C_{2-10}$ alkynyl group, any of which may be substituted; or
a five-membered to fourteen-membered aryl group or heteroaryl group which may be substituted;
$R^3$ represents —C(=O)—$R^4$; and
$R^4$ represents
—$(CHR^{10})$—$P_s$—$(CH_2)_t$—$(CH_2)_u$-$Q_v$-$R^{11}$, where s is 0 or 1, t is 0 or 1, u is 0 or 1, and V is 0 or 1 and in wherein P and Q each independently represent O, S, NH, N—$(CH_3)$, or $N(C_2H_5)$ and the sum of s and v is equal to 1;
—$(CR^{12}R^{13})$—$(CH_2)_w$—$(CH_2)_x$—C(=O)—O—$R^7$, where w is 0 or 1 and x is 0 or 1;

96

—$(CR^{14}R^{15})$—$(CH_2)_y$—O—C(=O)—$R^8$, where y is 0 or 1;
—$(CHR^{16})$—$(CH_2)_z$—C(=O)—$R^9$, where z is 0 or 1;
—CH[$(CH_2)$-$T_a$-$(CH_2)_b$—$R^{17}$]—[NH—C(=O)—O—$R^{18}$], where a is 0 or 1 and b is 0 or 1 wherein T represents O, S, NH, N—$(CH_3)$, or $N(C_2H_5)$;
—$CHR^{19}R^{20}$ or —$(CH_2)$—$CHR^{19}R^{20}$;
—(CH=CH)—$R^{21}$;
a linear or branched $C_{1-10}$ alkyl group, a linear or branched $C_{2-10}$ alkenyl group, or a linear or branched, $C_{2-10}$ alkynyl group, any of which may be substituted;
an unsaturated or saturated three-membered, four-membered, five-membered, six-membered, seven-membered, eight-membered or nine-membered cycloaliphatic group, which may be substituted and which may be condensed with a saturated or unsaturated, monocyclic ring system which may be aromatic and which may be substituted and which may be bridged by one or two linear or branched, $C_{1-5}$ alkylene groups, which groups may be substituted; or
a five-membered to fourteen-membered aryl group or heteroaryl group which may be substituted and which may be condensed with a saturated or unsaturated, monocyclic ring system which ring system may be substituted;
or II)
$R^1$ represents
hydrogen;
a linear or branched unsubstituted $C_{1-10}$ alkyl group, a linear or branched unsubstituted $C_{2-10}$ alkenyl group, or a linear or branched unsubstituted $C_{2-10}$ alkynyl group; or
an unsubstituted phenyl group or an unsubstituted benzyl group;
$R^2$ represents
hydrogen;
—$(CH_2)$—$(CH_2)_e$—$V_f$—$(CH_2)_g$—$R^{24}$, where e is 0 or 1, f is 0 or 1, and g is 0 or 1, wherein V represents O, S, NH, N—$(CH_3)$, or $N(C_2H_5)$;
a linear or branched $C_{1-10}$ alkyl group, a linear or branched $C_{2-10}$ alkenyl group, or a linear or branched $C_{2-10}$ alkynyl group, any of which may be substituted; or
a five-membered to fourteen-membered aryl or heteroaryl group which may be substituted;
$R^3$ represents a —C(=O)—$R^4$ group; and
$R^4$ represents
—$(CHR^{10})$—$P_s$—$(CH_2)_t$—$(CH_2)_u$-$Q_v$-$R^{11}$, where s is 0 or 1, t is 0 or 1, u is 0 or 1, and v is 0 or 1, wherein P and Q each independently represent O, S, NH, N—$(CH_3)$, or $N(C_2H_5)$, and the sum of s and v is equal to 1;
—$(CR^{12}R^{13})$—$(CH_2)_w$—$(CH_2)_x$—C(=O)—O—$R^7$, where w is 0 or 1 and x is 0 or 1;
—$(CR^{14}R^{15})$—$(CH_2)_y$—O—C(=O)—$R^8$, where y is 0 or 1;
—$(CHR^{16})$—$(CH_2)_z$—C(=O)—$R^9$, where z is 0 or 1;
—CH[$(CH_2)$-$T_a$-$(CH_2)_b$—$R^{17}$]-[NH—C(=O)—O—$R^{18}$], where a is 0 or 1 and b is 0 or 1 wherein T represents O, S, NH, N—$(CH_3)$, or $N(C_2H_5)$;
—$CHR^{19}R^{20}$ or —$(CH_2)$—$CHR^{19}R^{20}$;
—(CH=CH)—$R^{21}$;
a linear or branched, substituted $C_{1-10}$ alkyl group;
a linear or branched, $C_{2-10}$ alkenyl group which may be substituted;
a linear or branched, $C_{2-10}$ alkynyl group which may be substituted;

an unsaturated or saturated, three-membered, four-membered, five-membered, six-membered, seven-membered, eight-membered or nine-membered cycloaliphatic group, which may be substituted and which may be condensed with a saturated or unsaturated monocyclic ring system which may be substituted and which may be aromatic which may be substituted bridged by one or two linear or branched, $C_{1-5}$ alkylene groups which may be substituted;

a phenyl group, which is substituted by 1, 2, 3, 4, or 5 substituents independently selected from the group consisting of —CN, —SF$_5$, —NH$_2$, —NO$_2$, —O—CF$_3$, —O—CHF$_2$, —O—CH$_2$F, —S—CF$_3$, —S—CHF$_2$, —S—CH$_2$F, —SH, —S—$C_{1-5}$ alkyl, —C(=O)—OH, —C(=O)—O—$C_{1-5}$ alkyl, —O—C(=O)—$C_{1-5}$ alkyl, —O—C(=O)-phenyl, —(CH$_2$)—O—C(=O)—$C_{1-5}$ alkyl, —(CH$_2$)—O—C(=O)-phenyl, —NH—$C_{1-5}$ alkyl, —N($C_{1-5}$ alkyl)$_2$, —NH—C(=O)—O—$C_{1-5}$ alkyl, —NH—C(=O)—$C_{1-5}$ alkyl, —C(=O)—H, —C(=O)—$C_{1-5}$ alkyl, —C(=O)—NH$_2$, —C(=O)—NH—$C_{1-5}$ alkyl, C(=O)—N—($C_{1-5}$ alkyl)$_2$, —S(=O)$_2$—NH$_2$, —S(=O)$_2$—NH—$C_{1-5}$ alkyl, —S(=O)$_2$—NH-phenyl, —(CH$_2$)benzo[b]furanyl, —O-phenyl, —S-phenyl, —S-benzyl, —O-benzyl, phenyl, and benzyl, wherein in each case the cyclic moiety of the groups —O—C(=O)-phenyl, —(CH$_2$)—O—C(=O)-phenyl, —S(=O)$_2$—NH-phenyl, —O-phenyl, —S-phenyl, —S-benzyl, —O-benzyl, phenyl, —(CH$_2$)benzo[b]furanyl, and benzyl may be substituted by 1, 2, 3, 4, or 5 substituents independently selected from the group consisting of F, Cl, Br, —OH, —CF$_3$, —SF$_5$, —CN, —NO$_2$, —O—$C_{1-5}$:

a group selected from 1,2,3,4,5-pentafluorophenyl, 1,2,3,4-tetrafluorophenyl, 4-methyl-3-nitrophenyl, 5-methyl-3-nitrophenyl, 6-methyl-3-nitrophenyl, and 2-methyl-3-nitrophenyl;

an unsubstituted naphthyl group;

a six-membered or ten-membered aryl group, which may be substituted and which is condensed with a saturated or unsaturated, monocyclic ring system which may be substituted; or an optionally substituted five-membered to fourteen-membered heteroaryl group, which may be condensed with a saturated or unsaturated, optionally substituted monocyclic ring system;

or III)

$R^1$ represents hydrogen;

a linear or branched unsubstituted $C_{1-10}$ alkyl, $C_{2-10}$ alkenyl, or $C_{2-10}$ alkynyl group;

a five-membered to fourteen-membered aryl or heteroaryl group which may be substituted;

—(CH$_2$)$_m$—O—C(=O)—$R^5$, where m is 1, 2, 3, 4, or 5;

—(CH$_2$)$_n$—C(=O)—O—$R^6$, where n is 1, 2, 3, 4, or 5;

an unsubstituted benzyl group;

—(CH$_2$)—$R^{22}$; or

—(CH$_2$)—(CH$_2$)$_c$—U—(CH$_2$)$_d$—$R^{23}$, where c is 0 or 1 and d is 0 or 1 wherein U represents O, S, NH, N—(CH$_3$), or N(C$_2$H$_5$);

$R^2$ represents —(CH$_2$)—(CH$_2$)$_e$—V—(CH$_2$)$_g$—$R^{24}$ where e is 0 or 1 and g is 0 or 1 and wherein V represents S, NH, N—(CH$_3$), or N(C$_2$H$_5$);

$R^3$ represents a —C(=O)—$R^4$ group; and $R^4$ represents

—(CHR$^{10}$)—P$_s$—(CH$_2$)$_t$—(CH$_2$)$_u$-Q$_v$-$R^{11}$ where s is 0 or 1, t is 0 or 1, u is 0 or 1, and v is 0 or 1, wherein P and Q each independently represent O, S, NH, N—(CH$_3$), or N(C$_2$H$_5$) and the sum of s and v is equal to 1;

—(CR$^{12}$R$^{13}$)—(CH$_2$)$_w$—(CH$_2$)$_x$—C(=O)—O—$R^7$, where w is 0 or 1 and x is 0 or 1;

—(CR$^{14}$R$^{15}$)—(CH$_2$)$_y$—O—C(=O)—$R^8$, where y is 0 or 1;

—(CHR$^{16}$)—(CH$_2$)$_z$—C(=O)—$R^9$, where z is 0 or 1;

—CH[(CH$_2$)-T$_a$-(CH$_2$)$_b$—$R^{17}$]—[NH—C(=O)—O—$R^{18}$], where a is 0 or 1 and b is 0 or 1, wherein T represents O, S, NH, N—(CH$_3$), or N(C$_2$H$_5$);

—CHR$^{19}$R$^{20}$ or —(CH$_2$)—CHR$^{19}$R$^{20}$;

—(CH=CH)—$R^{21}$;

a linear or branched $C_{1-10}$ alkyl group, a linear or branched $C_{2-10}$ alkenyl group, or a linear or branched $C_{2-10}$ alkynyl group, any of which may be substituted;

an unsaturated or saturated, three-membered, four-membered, five-membered, six-membered, seven-membered, eight-membered or nine-membered cycloaliphatic group which may be substituted, and which may be condensed with a saturated or unsaturated, monocyclic ring system, which may be substituted and which may be aromatic and which may be bridged by one or two linear or branched, $C_{1-5}$ alkylene groups which may be substituted; or a five-membered to fourteen-membered aryl group or heteroaryl group, which may be substituted and which may be condensed with a saturated or unsaturated, monocyclic ring system which ring system which may be substituted;

and in each case, if present, in the aforementioned groups I) II) and III), $R^5$, $R^6$, and $R^9$, and $R^{18}$ each independently represent $C_{1-10}$ alkyl, $C_{2-10}$ alkenyl, or $C_{2-10}$ alkynyl, any of which may be linear or branched and which may be substituted;

$R^7$ represents hydrogen; $C_{1-10}$ alkyl, $C_{2-10}$ alkenyl, or $C_{2-10}$ alkynyl, any of which may be linear or branched and which may be substituted; or a five-membered to fourteen-membered aryl group which may be substituted or a five-membered to fourteen-membered heteroaryl group which may be substituted;

$R^8$, $R^{16}$, and $R^{24}$ each independently represent $C_{1-10}$ alkyl, $C_{2-10}$ alkenyl, or $C_{2-10}$ alkynyl, any of which may be linear or branched and which may be substituted; or a five-membered to fourteen-membered aryl group which may be substituted or a five-membered to fourteen-membered heteroaryl group which may be substituted;

$R^{10}$, $R^{12}$, and $R^{13}$ each independently represent hydrogen; $C_{1-10}$ alkyl, $C_{2-10}$ alkenyl, or $C_{2-10}$ alkynyl, any of which may be linear or branched and which may be substituted;

$R^{11}$ represents $C_{1-10}$ alkyl, $C_{2-10}$ alkenyl, or $C_{2-10}$ alkynyl, any of which may be linear or branched and which may be substituted; an unsaturated or saturated, three-membered, four-membered, five-membered, six-membered, seven-membered, eight-membered, or nine-membered cycloaliphatic group which may be substituted; or a six-membered or ten-membered aryl group which may be substituted;

$R^{14}$, $R^{15}$, and $R^{19}$ each independently represent hydrogen; $C_{1-10}$ alkyl, $C_{2-10}$ alkenyl, or $C_{2-10}$ alkynyl, any of which may be linear or branched and which may be substituted; or a six-membered or ten-membered aryl group which may be substituted;

$R^{17}$ and $R^{21}$ each independently represent a six-membered or ten-membered aryl group which may be substituted;

$R^{20}$ represents an unsaturated or saturated, three-membered, four-membered, five-membered, six-membered, seven-membered, eight-membered or nine-membered cycloaliphatic group which may be substituted; or a six-membered or ten-membered aryl group which may be substituted;

$R^{22}$ represents a substituted six-membered aryl group; a ten-membered aryl group, which may be substituted; or a heteroaryl group, which may be substituted; and $R^{23}$ represents a five-membered to fourteen-membered aryl group which may be substituted or a five-membered to fourteen-membered heteroaryl group which may be substituted;

wherein the $C_{1-10}$ alkyl groups may be unsubstituted or each may be substituted by 1, 2, 3, 4 or 5 substituents independently selected from the group consisting of F, Cl, Br, I, —CN, —NO$_2$, —OH, —SH, —NH$_2$, and —N(C$_{1-5}$ alkyl)-(C$_{1-5}$ alkyl);

the $C_{2-10}$ alkenyl groups may be unsubstituted or each may be substituted by 1, 2, 3, 4 or 5 substituents independently selected from the group consisting of F, Cl, Br, I, —CN, —NO$_2$, —OH, —SH, —NH$_2$, and —N(C$_{1-5}$ alkyl)-(C$_{1-5}$ alkyl);

the $C_{2-10}$ alkynyl groups may be unsubstituted or each may be substituted by 1, 2, 3, 4 or 5 substituents independently selected from the group consisting of F, Cl, Br, I, —CN, —NO$_2$, —OH, —SH, —NH$_2$, and —N(C$_{1-5}$ alkyl)-(C$_{1-5}$ alkyl);

the $C_{1-5}$ alkylene groups may be unsubstituted or each may be substituted by 1, 2, 3, 4 or 5 substituents independently selected from the group consisting of F, Cl, Br, —OH, —SH, —NH$_2$, —CN, NO$_2$, and phenyl;

the cycloaliphatic groups may be unsubstituted or in each case substituted by 1, 2, 3, 4, or 5 substituents independently selected from the group consisting of oxo (=O), thioxo (=S), F, Cl, Br, I, —CN, —CF$_3$, —SF$_5$, —OH, —O—C$_{1-5}$ alkyl, —NH$_2$, —NO$_2$, —O—CF$_3$, —S—CF$_3$, —SH, —S—C$_{1-5}$ alkyl, —C$_{1-5}$ alkyl, —C(=O)—H, —C(=O)—C$_{1-5}$ alkyl, —C(=O)—OH, —C(=O)—O—C$_{1-5}$ alkyl, —(CH$_2$)—C(=O)—OH, —(CH$_2$)—C(=O)—O—C$_{1-5}$ alkyl, —NH—C$_{1-5}$ alkyl, —N(C$_{1-5}$ alkyl)$_2$, —(CH$_2$)benzo[b]furanyl, —O-phenyl, —O-benzyl, phenyl, benzyl, naphthyl, and —(CH$_2$) naphthyl, wherein in each case the cyclic moiety of the groups —O-phenyl, —O-benzyl, phenyl, —(CH$_2$)benzo[b]furanyl, benzyl, naphthyl, and —(CH$_2$)-naphthyl may be substituted by 1, 2, 3, 4, or 5 substituents independently selected from the group consisting of F, Cl, Br, —OH, —CF$_3$, —SF$_5$, —CN, —NO$_2$, —O—C$_{1-5}$ alkyl, —C$_{1-5}$ alkyl, —O—CF$_3$, —S—CF$_3$, phenyl, and —O-benzyl; and the cycloaliphatic groups may comprise 1, 2, 3, 4, or 5 heteroatoms independently selected from the group consisting of oxygen, nitrogen, and sulfur;

the ring of the monocyclic ring systems may be unsubstituted or may be substituted by 1, 2, 3, 4, or 5 substituents independently selected from the group consisting of oxo (=O), thioxo (=S), F, Cl, Br, I, —CN, —CF$_3$, —SF$_5$, —OH, —O—C$_{1-5}$ alkyl, —O—C$_{2-5}$ alkenyl, —NH$_2$, —NO$_2$, —O—CF$_3$, —O—CHF$_2$, —O—CH$_2$F, —S—CF$_3$, —S—CHF$_2$, —S—CH$_2$F, —SH, —S—C$_{1-5}$ alkyl, —C$_{1-5}$ alkyl, —C(=O)—OH, —C(=O)—O—C$_{1-5}$ alkyl, —O—C(=O)—C$_{1-5}$ alkyl, —O—C(=O)-phenyl, —(CH$_2$)—O—C(=O)—C$_{1-5}$ alkyl, —(CH$_2$)—O—C(=O)-phenyl, —NH—C$_{1-5}$ alkyl, —N(C$_{1-5}$ alkyl)$_2$, —NH—C(=O)—O—C$_{1-5}$ alkyl, —NH—C(=O)—C$_{1-5}$ alkyl, —C(=O)—H, —C(=O)—C$_{1-5}$ alkyl, —C(=O)—NH$_2$, —C(=O)—NH—C$_{1-5}$ alkyl, C(=O)—N—(C$_{1-5}$ alkyl)$_2$, —S(=O)$_2$—NH$_2$, —S(=O)$_2$—NH—C$_{1-5}$ alkyl, —S(=O)$_2$—NH-phenyl, —(CH$_2$)benzo[b]furanyl, —O-phenyl, —S-phenyl, —S-benzyl, —O-benzyl, phenyl, and benzyl, wherein in each case the cyclic moiety of the groups —O—C(=O)-phenyl, —(CH$_2$)—O—C(=O)-phenyl, —S(=O)$_2$—NH-phenyl, —O-phenyl, —S-phenyl, —S-benzyl, —O-benzyl, phenyl, —(CH$_2$)benzo[b]furanyl, and benzyl may be substituted by 1, 2, 3, 4 or 5 substituents independently selected from the group consisting of F, Cl, Br, —OH, —CF$_3$, —SF$_5$, —CN, —NO$_2$, —O—C$_{1-5}$-alkyl, —C$_{1-5}$-alkyl, —O—CF$_3$, —S—CF$_3$, phenyl und —O-benzyl; and the ring of the aforementioned monocyclic ring systems is in each case five-membered, six-membered, or seven-membered and may comprise 1, 2, 3, 4, or 5 heteroatoms as ring members, which are independently selected from the group consisting of oxygen, nitrogen, and sulfur; and unless otherwise stated, the aforementioned aryl groups or heteroaryl groups may be unsubstituted or in each case substituted by 1, 2, 3, 4, or 5 substituents independently selected from the group consisting of F, Cl, Br, I, —CN, —CF$_3$, —SF$_5$, —OH, —O—C$_{1-5}$ alkyl, —O—C$_{2-5}$ alkenyl, —NH$_2$, —NO$_2$, —O—CF$_3$, —O—CHF$_2$, —O—CH$_2$F, —S—CF$_3$, —S—CHF$_2$, —S—CH$_2$F, —SH, —S—C$_{1-5}$ alkyl, —C$_{1-5}$ alkyl, —C(=O)—OH, —C(=O)—O—C$_{1-5}$ alkyl, —O—C(=O)—C$_{1-5}$ alkyl, —O—C(=O)-phenyl, —(CH$_2$)—O—C(=O)—C$_{1-5}$ alkyl, —(CH$_2$)—O—C(=O)-phenyl, —NH—C$_{1-5}$ alkyl, —N(C$_{1-5}$ alkyl)$_2$, —NH—C(=O)—O—C$_{1-5}$ alkyl, —NH—C(=O)—C$_{1-5}$ alkyl, —C(=O)—H, —C(=O)—C$_{1-5}$ alkyl, —C(=O)—NH$_2$, —C(=O)—NH—C$_{1-5}$ alkyl, C(=O)—N—(C$_{1-5}$ alkyl)$_2$, —S(=O)$_2$—NH$_2$, —S(=O)$_2$—NH—C$_{1-5}$ alkyl, —S(=O)$_2$—NH-phenyl, —(CH$_2$)benzo[b]furanyl, —O-phenyl, —S-phenyl, —S-benzyl, —O-benzyl, phenyl, and benzyl, wherein in each case the cyclic moiety of the groups —O—C(=O)-phenyl, —(CH$_2$)—O—C(=O)-phenyl, —S(=O)$_2$—NH-phenyl, —O-phenyl, —S-phenyl, —S-benzyl, —O-benzyl, phenyl, —(CH$_2$)benzo[b]furanyl und benzyl may be substituted by 1, 2, 3, 4 or 5 substituents independently selected from the group consisting of F, Cl, Br, —OH, —CF$_3$, —SF$_5$, —CN, —NO$_2$, —O—C$_{1-5}$-alkyl, —C$_{1-5}$-alkyl, —O—CF$_3$, —S—CF$_3$, phenyl and —O-benzyl; and the aforementioned heteroaryl groups may in each case comprise 1, 2, 3, 4, or 5 heteroatoms independently selected from the group consisting of oxygen, nitrogen, and sulfur, as ring members.

12. The compound of claim 11, wherein,

I)

$R^1$ represents a phenyl or naphthyl group, which is in each case substituted by 1, 2, 3, 4, or 5 substituents independently selected from the group consisting of F, Cl, Br, I, —CN, —CF$_3$, —SF$_5$, —OH, —O—CH$_3$, —O—C$_2$H$_5$, —O—CH(CH$_3$)$_2$, —O—C(CH$_3$)$_3$, —O—CH$_2$—CH$_2$—CH$_2$—CH$_3$, —O—CH$_2$—CH=CH$_2$, —NH$_2$, —NO$_2$, —O—CF$_3$, —O—CHF$_2$, —O—CH$_2$F, —S—CF$_3$, —S—CHF$_2$, —S—CH$_2$F, —SH, —S—CH$_3$, —S—C$_2$H$_5$, —S—CH(CH$_3$)$_2$, —S—C(CH$_3$)$_3$, —S—CH$_2$—

$CH_2$—$CH_2$—$CH_3$, methyl, ethyl, n-propyl, isopropyl, n-butyl, sec-butyl, isobutyl, tert-butyl, —C(=O)—OH, —C(=O)—O—$CH_3$, —C(=O)—O—$C_2H_5$, —C(=O)—O—C($CH_3$)$_3$, —O—C(=O)—$CH_3$, —O—C(=O)—$C_2H_5$, —O—C(=O)-phenyl, —($CH_2$)—O—C(=O)—$CH_3$, —($CH_2$)—O—C(=O)—$C_2H_5$, —($CH_2$)—O—C(=O)-phenyl, —N($CH_3$)$_2$, —N(C—O—C(=O)-phenyl, —($CH_2$)—O—C(=O)-phenyl, —S(=O)$_2$—NH-phenyl, —O-phenyl, —S-phenyl, —S-benzyl, —O-benzyl, phenyl, —($CH_2$)benzo[b]furanyl, and benzyl, wherein in each case the cyclic moieties of the groups O—C(=O)-phenyl, —($CH_2$)—O—C(=O)-phenyl, —S(=O)$_2$—NH-phenyl, —O-phenyl, —S-phenyl, —S-benzyl, —O-benzyl, phenyl, —($CH_2$)-benzo[b]furanyl, and benzyl may be substituted by 1, 2, 3, 4, or 5 substituents independently selected from the group consisting of F, Cl, Br, —OH, —$CF_3$, —$SF_5$, —CN, —$NO_2$, —O—$CH_3$, —O—$C_2H_5$, —O—CH($CH_3$)$_2$, —O—C($CH_3$)$_3$, methyl, ethyl, n-propyl, isopropyl, n-butyl, sec-butyl, isobutyl, tert-butyl, —O—$CF_3$, —S—$CF_3$, phenyl, and —O-benzyl;

a heteroaryl group selected from the group consisting of thiophenyl, furanyl, pyrrolyl, pyrazolyl, pyrazynyl, pyranyl, triazolyl, pyridynyl, imidazolyl, indolyl, isoindolyl, benzo[b]furanyl, benzo[b]thiophenyl, thiazolyl, oxazolyl, isoxazolyl, pyridazynyl, pyrimidynyl, indazolyl, quinazolynyl, quinolynyl, and isoquinolynyl, wherein said heteroaryl group may in each case be substituted by 1, 2, 3, 4, or 5 substituents independently selected from the group consisting of F, Cl, Br, I, —CN, —$CF_3$, —$SF_5$, —OH, —O—$CH_3$, —O—$C_2H_5$, —O—CH($CH_3$)$_2$, —O—C($CH_3$)$_3$, —O—$CH_2$—$CH_2$—$CH_2$—$CH_3$, —O—$CH_2$—CH=$CH_2$, —$NH_2$, —$NO_2$, —O—$CF_3$, —O—$CHF_2$, —O—$CH_2$F, —S—$CF_3$, —S—$CHF_2$, —S—$CH_2$F, —SH, —S—$CH_3$, —S—$C_2H_5$, —S—CH($CH_3$)$_2$, —S—C($CH_3$)$_3$, —S—$CH_2$—$CH_2$—$CH_2$—$CH_3$, methyl, ethyl, n-propyl, isopropyl, n-butyl, sec-butyl, isobutyl, tert-butyl, —C(=O)—OH, —C(=O)—O—$CH_3$, —C(=O)—O—$C_2H_5$, —C(=O)—O—C($CH_3$)$_3$, —O—C(=O)—$CH_3$, —O—C(=O)—$C_2H_5$, —O—C(=O)-phenyl, —(—($CH_2$)—O—C(=O)—$C_2H_5$, —($CH_2$)—O—C(=O)-phenyl, —N($CH_3$)$_2$, —N($C_2H_5$)$_2$, —N(H)($CH_3$), —N(H)($C_2H_5$), —NH—C(=O)—O—$CH_3$, —NH—C(=O)—O—$C_2H_5$, —NH—C(=O)—$CH_3$, —NH—C(=O)—$C_2H_5$, —C(=O)—H, —C(=O)—$CH_3$, —C(=O)—$C_2H_5$, —C(=O)—$NH_2$, —C(=O)—NH—$CH_3$, —C(=O)—NH—$C_2H_5$, —S(=O)$_2$—$NH_2$, —S(=O)$_2$—NH—$CH_3$, —S(=O)$_2$—NH—$C_2H_5$, —S(=O)$_2$—NH-phenyl, —($CH_2$)benzo[b]furanyl, —O-phenyl, —S-phenyl, —S-benzyl, —O-benzyl, phenyl, and benzyl, and each cyclic moiety of the groups —O—C(=O)-phenyl, —($CH_2$)—O—C(=O)-phenyl, —S(=O)$_2$—NH-phenyl, —O-phenyl, —S-phenyl, —S-benzyl, —O-benzyl, phenyl, —($CH_2$)benzo[b]furanyl, and benzyl may be substituted by 1, 2, 3, 4, or 5 substituents independently selected from the group consisting of F, Cl, Br, —OH, —$CF_3$, —$SF_5$, —CN, —$NO_2$, —O—$CH_3$, —O—$C_2H_5$, —O—CH($CH_3$)$_2$, —O—C($CH_3$)$_3$, methyl, ethyl, n-propyl, isopropyl, n-butyl, sec-butyl, isobutyl, tert-butyl, —O—$CF_3$, —S—$CF_3$, phenyl, and —O-benzyl;

—($CH_2$)$_m$—O—C(=O)—$R^5$, where m is 1, 2, 3, 4, or 5;
—($CH_2$)$_n$—C(=O)—O—$R^6$, where n is 1, 2, 3, 4, or 5;
—($CH_2$)—$R^{22}$; —($CH_2$)—O—$R^{23}$, —($CH_2$)—S—$R^{23}$, —($CH_2$)—N($CH_3$)—$R^{23}$, —($CH_2$)—($CH_2$)—O—$R^{23}$, —($CH_2$)—($CH_2$)—S—$R^{23}$, —($CH_2$)—($CH_2$)—NH—$R^{23}$, —($CH_2$)—($CH_2$)—N($CH_3$)—$R^{23}$, —($CH_2$)—($CH_2$)—O—($CH_2$)—$R^{23}$, —($CH_2$)—($CH_2$)—S—($CH_2$)—$R^{23}$, or —($CH_2$)—($CH_2$)—N($CH_3$)—$R^{23}$;

$R^2$ represents hydrogen;

—($CH_2$)—$R^{24}$, —($CH_2$)—O—$R^{24}$, —($CH_2$)—S—$R^{24}$, —($CH_2$)—N($CH_3$)—$R^{24}$, —($CH_2$)—($CH_2$)—$R^{24}$, —($CH_2$)—($CH_2$)—O—$R^{24}$, —($CH_2$)—($CH_2$)—S—$R^{24}$, —($CH_2$)—($CH_2$)—NH—$R^{24}$, —($CH_2$)—($CH_2$)—N($CH_3$)—$R^{24}$, —($CH_2$)—($CH_2$)—($CH_2$)—$R^{24}$, —($CH_2$)—($CH_2$)—O—($CH_2$)—$R^{24}$, —($CH_2$)—($CH_2$)—S—($CH_2$)—$R^{24}$, or —($CH_2$)—($CH_2$)—N($CH_3$)—$R^{24}$; or is selected from the group consisting of methyl, ethyl, n-propyl, isopropyl, n-butyl, sec-butyl, isobutyl, tert-butyl, n-pentyl, sec-pentyl, —($CH_2$)—($CH_2$)—(C($CH_3$)$_3$), n-hexyl, n-heptyl, n-octyl, —($CH_2$)—(CH)—($C_2H_5$)—($CH_2$)—($CH_2$)—($CH_2$)—($CH_3$), vinyl, 1-propenyl, 2-propenyl, 1-butenyl, 2-butenyl, 3-butenyl, 2-methyl-2-butenyl, 1-propynyl, 2-propynyl, 1-butynyl, 2-butynyl, and 3-butynyl, and, in each case, may be substituted by 1, 2, 3, 4, or 5 substituents independently selected from the group consisting of F, Cl, Br, I, —CN, —$NO_2$, —OH, —SH, —$NH_2$, —N($CH_3$)$_2$, —N($C_2H_5$)$_2$, and —N—($CH_3$)—($C_2H_5$); or is selected from the group consisting of phenyl, naphthyl, thiophenyl, furanyl, pyrrolyl, pyrazolyl, pyrazynyl, pyranyl, triazolyl, pyridynyl, imidazolyl, indolyl, isoindolyl, benzo[b]furanyl, benzo[b]thiophenyl, thiazolyl, oxazolyl, isoxazolyl, pyridazynyl, pyrimidynyl, indazolyl, quinazolynyl, quinolynyl, and isoquinolynyl, and in each case may be substituted by 1, 2, 3, 4, or 5 substituents independently selected from the group consisting of F, Cl, Br, I, —CN, —$CF_3$, —$SF_5$, —OH, —O—$CH_3$, —O—$C_2H_5$, —O—CH($CH_3$)$_2$, —O—C($CH_3$)$_3$, —O—$CH_2$—$CH_2$—$CH_2$—$CH_3$, —O—$CH_2$—CH=$CH_2$, —$NH_2$, —$NO_2$, —O—$CF_3$, —O—$CHF_2$, —O—$CH_2$F, —S—$CF_3$, —S—$CHF_2$, —S—$CH_2$F, —SH, —S—$CH_3$, —S—$C_2H_5$, —S—CH($CH_3$)$_2$, —S—C($CH_3$)$_3$, —S—$CH_2$—$CH_2$—$CH_2$—$CH_3$, methyl, ethyl, n-propyl, isopropyl, n-butyl, sec-butyl, isobutyl, tert-butyl, —C(=O)—OH, —C(=O)—O—$CH_3$, —C(=O)—O—$C_2H_5$, —C(=O)—O—C($CH_3$)$_3$, —O—C(=O)—$CH_3$, —O—C(=O)—$C_2H_5$, —O—C(=O)-phenyl, —(CH—($CH_2$)—O—C(=O)—$C_2H_5$, —($CH_2$)—O—C(=O)-phenyl, —N($CH_3$)$_2$, —N($C_2H_5$)$_2$, —N(H)($CH_3$), —N(H)($C_2H_5$), —NH—C(=O)—O—$CH_3$, —NH—C(=O)—O—$C_2H_5$, —NH—C(=O)—$CH_3$, —NH—C(=O)—$C_2H_5$, —C(=O)—H, —C(=O)—$CH_3$, —C(=O)—$C_2H_5$, —C(=O)—$NH_2$, —C(=O)—NH—$CH_3$, —C(=O)—NH—$C_2H_5$, —S(=O)$_2$—$NH_2$, —S(=O)$_2$—NH—$CH_3$, —S(=O)$_2$—NH—$C_2H_5$, —S(=O)$_2$—NH-phenyl, —($CH_2$)benzo[b]furanyl, —O-phenyl, —S-phenyl, —S-benzyl, —O-benzyl, phenyl, and benzyl, wherein in each case the cyclic moiety of the groups —O—C(=O)-phenyl, —($CH_2$)—O—C(=O)-phenyl, —S(=O)$_2$—NH-phenyl, —O-phenyl, —S-phenyl, —S-benzyl, —O-benzyl, phenyl, —(CH₂)benzo[b]furanyl, and benzyl may be substituted by 1, 2, 3, 4, or 5 substituents independently selected from the group consisting of F, Cl, Br, —OH, —CF₃, —SF₅, —CN, —NO₂, —O—CH₃, —O—C₂H₅, —O—CH(CH₃)₂, —O—C(CH₃)₃, methyl, ethyl, n-propyl, isopropyl, n-butyl, sec-butyl, isobutyl, —O—CF₃, —S—CF₃, phenyl, and —O-benzyl;

R³ represents a —C(=O)—R⁴ group; and
R⁴ represents
—(CHR¹⁰)—O—R¹¹, —(CHR¹⁰)—S—R¹¹, —(CHR¹⁰)—NH—R¹¹, —(CHR¹⁰)—O—(CH₂)—R¹¹, —(CHR¹⁰)—S—(CH₂)—R¹¹, —(CHR¹⁰)—NH—(CH₂)—R¹¹, —(CHR¹⁰)—N(CH₃)—(CH₂)—R¹¹, —(CHR¹⁰)—(CH₂)—(CH₂)—O—R¹¹, —(CHR¹⁰)—(CH₂)—(CH₂)—S—R¹¹, —(CHR¹⁰)—(CH₂)—(CH₂)—NH—R¹¹ —(CHR¹⁰)—(CH₂)—(CH₂)—N(C₂H₅)—R¹¹, —(CHR¹⁰)—O—(CH₂)—(CH₂)—O—R¹¹, —(CHR¹⁰)—S—(CH₂)—(CH₂)—S—R¹¹, —(CHR¹⁰)—O—(CH₂)—(CH₂)—S—R¹¹ or —(CHR¹⁰)—S—(CH₂)—(CH₂)—O—R¹¹;
—(CR¹²R¹³)—C(=O)—O—R⁷, —(CR¹²R¹³)—(CH₂)—C(=O)—O—R⁷, or —(CR¹²R¹³)—(CH₂)—(CH₂)—C(=O)—O—R⁷;
—(CR¹⁴R¹⁵)—O—C(=O)—R⁸ or —(CR¹⁴R¹⁵)—(CH₂), and —O—C(=O)—R⁸;
—(CHR¹⁶)—C(=O)—R⁹ or —(CHR¹⁶)—(CH₂)—C(=O)—R⁹;
—CH[(CH₂)—O—(CH₂)—R¹⁷]—[NH—C(=O)—O—R¹⁸] or —CH[(CH₂)—S—(CH₂)—R¹⁷]—[NH—C(=O)—O—R¹⁸];
CHR¹⁹R²⁰ or —(CH₂)—CHR¹⁹R²⁰;
—(CH=CH)—R²¹; or is selected from the group consisting of methyl, ethyl, n-propyl, isopropyl, n-butyl, sec-butyl, isobutyl, tert-butyl, n-pentyl, 2-pentyl, 3-pentyl, —(CH₂)—(C(CH₃)₃), n-hexyl, 3-hexyl, —(CH₂)—(CH₂)—(C(CH₃)₃), n-heptyl, 3-heptyl, 4-heptyl, n-octyl, —(CH₂)—(CH)—(C₂H₅)—(CH₂)—(CH₂)—(CH₂)—(CH₃), vinyl, 1-propenyl, 2-propenyl, 1-butenyl, 2-butenyl, and 3-butenyl, and in each case may be substituted by 1, 2, 3, 4, or 5 substituents independently selected from the group consisting of F, Cl, Br, I, —CN, —NO₂, —OH, —SH, —NH₂, —N(CH₃)₂, —N(C₂H₅)₂, and N—(CH₃)—(C₂H₅); or is a (hetero)cycloaliphatic group selected from the group consisting of cyclopropyl, cyclobutyl, cyclopentyl, cyclohexyl, cycloheptyl, cyclopentenyl, cyclohexenyl, cycloheptenyl, imidazolidynyl, tetrahydrofuranyl, tetrahydrothiophenyl, pyrrolidynyl, piperidynyl, morpholynyl, piperazynyl, thiomorpholynyl, tetrahydropyranyl, azepanyl, diazepanyl, dithiolanyl, adamantyl, and 7,7-dimethyl-2-oxa-bicyclo[2,2,1]heptyl, which (hetero)cycloaliphatic group may in each case be substituted by 1, 2, 3, 4, or 5 substituents independently selected from the group consisting of oxo (=O), thioxo (=S), F, Cl, Br, I, —CN, —CF₃, —SF₅, —OH, —O—CH₃, —O—C₂H₅, —O—C(CH₃)₃, —NH₂, —NO₂, —O—CF₃, —S—CF₃, —SH, S—CH₃, —S—C₂H₅, —S—C(CH₃)₃, methyl, ethyl, n-propyl, isopropyl, n-butyl, sec-butyl, isobutyl, tert-butyl, —C(=O)—H, —C(=O)—CH₃, —C(=O)—C₂H₅, —C(=O)—OH, —C(=O)—O—CH₃, —C(=O)—O—C₂H₅, —C(=O)—O—C(CH₃)₃, —(CH₂)—C(=O)—OH, —(CH₂)—C(=O)—O—CH₃, —(CH₂)—C(=O)—O—C₂H₅, —N(CH₃)₂, —N(C₂H₅)₂, —N(H)(CH₃), —N(H)(C₂H₅), —(CH₂)-benzo[b]furanyl, —O-phenyl, —O-benzyl, phenyl, benzyl, naphthyl, and —(CH₂)-naphthyl be substituted can, and in each case the cyclic moiety of the groups —O-phenyl, —O-benzyl, phenyl, —(CH₂)benzo[b]furanyl, benzyl, naphthyl, and —(CH₂)-naphthyl may be substituted by 1, 2, 3, 4, or 5 substituents independently selected from the group consisting of F, Cl, Br, —OH, —CF₃, —SF₅, —CN, —NO₂, —O—CH₃, —O—C₂H₅, methyl, ethyl, n-propyl, isopropyl, n-butyl, sec-butyl, isobutyl, tert-butyl, —O—CF₃, —S—CF₃, phenyl, and —O-benzyl; or is selected from the group consisting of phenyl, naphthyl, (1,3)-benzodioxolyl, (1,4)-benzodioxanyl, thiophenyl, furanyl, pyrrolyl, pyrazolyl, pyrazynyl, pyranyl, triazolyl, pyridynyl, imidazolyl, indolyl, isoindolyl, benzo[b]furanyl, benzo[b]thiophenyl, thiazolyl, thiadiazolyl, oxazolyl, isoxazolyl, pyridazynyl, pyrimidynyl, indazolyl, quinazolynyl, quinolynyl, isoquinolynyl, phenazynyl, phenothiazynyl, oxadiazolyl, benzo[1,2,5]oxadiazolyl, and chromanyl, and in each case may be substituted by 1, 2, 3, 4, or 5 substituents independently selected from the group consisting of F, Cl, Br, I, —CN, —CF₃, —SF₅, —OH, —O—CH₃, —O—C₂H₅, —O—CH(CH₃)₂, —O—C(CH₃)₃, —O—CH₂—CH₂—CH₂—CH₃, —O—CH₂—CH=CH₂, —NH₂, —NO₂, —O—CF₃, —O—CHF₂, —O—CH₂F, —S—CF₃, —S—CHF₂, —S—CH₂F, —SH, —S—CH₃, —S—C₂H₅, —S—CH(CH₃)₂, —S—C(CH₃)₃, —S—CH₂—CH₂—CH₂—CH₃, methyl, ethyl, n-propyl, isopropyl, n-butyl, sec-butyl, isobutyl, tert-butyl, —C(=O)—OH, —C(=O)—O—CH₃, —C(=O)—O—C₂H₅, —C(=O)—O—C(CH₃)₃, —O—C(=O)—CH₃, —O—C(=O)—C₂H₅, —O—C(=O)-phenyl, —(CH₂)—O—C(=O)—CH₃, —(CH₂)—O—C(=O)—C₂H₅, —(CH₂)—O—C(=O)-phenyl, —N(CH₃)₂, —N(C₂H₅)₂, —N(H)(CH₃), —N(H)(C₂H₅), —NH—C(=O)—O—CH₃, —NH—C(=O)—O—C₂H₅, —NH—C(=O)—CH₃, —NH—C(=O)—C₂H₅, —C(=O)—H, —C(=O)—CH₃, —C(=O)—C₂H₅, —C(=O)—NH₂, —C(=O)—NH—CH₃, —C(=O)—NH—C₂H₅, —S(=O)₂—NH₂, —S(=O)₂—NH—CH₃, —S(=O)₂—NH—C₂H₅, —S(=O)₂—NH-phenyl, —(CH₂)benzo[b]furanyl, —O-phenyl, —S-phenyl, —S-benzyl, —O-benzyl, phenyl, and benzyl, and in each case the cyclic moiety of the groups —O—C(=O)-phenyl, —(CH₂)—O—C(=O)-phenyl, —S(=O)₂—NH-phenyl, —O-phenyl, —S-phenyl, —S-benzyl, —O-benzyl, phenyl, —(CH₂)benzo[b]furanyl, and benzyl may be substituted by 1, 2, 3, 4, or 5 substituents selected independently from the group consisting of F, Cl, Br, —OH, —CF₃, —SF₅, —CN, —NO₂, —O—CH₃, —O—C₂H₅, —O—CH(CH₃)₂, —O—C(CH₃)₃, methyl, ethyl, n-propyl, isopropyl, n-butyl, sec-butyl, isobutyl, tert-butyl, —O—CF₃, —S—CF₃, phenyl, and —O-benzyl;

or II)

R¹ represents hydrogen; or is selected from the group consisting of methyl, ethyl, n-propyl, isopropyl, n-butyl, sec-butyl, isobutyl, tert-butyl, n-pentyl, sec-pentyl, —(CH₂)—(CH₂)—(C(CH₃)₃), n-hexyl, n-heptyl, n-octyl, —(CH₂)—(CH)—(C₂H₅)—(CH₂)—(CH₂)—(CH₂)—(CH₃), vinyl, 1-propenyl, 2-propenyl, 1-butenyl, 2-butenyl, 3-butenyl, 2-methyl-2-butenyl, 1-propynyl, 2-propynyl, 1-butynyl, 2-butynyl, and 3-butynyl; or is an unsubstituted phenyl group or benzyl group;

$R^2$ represents hydrogen;

—$(CH_2)$—$R^{24}$, —$(CH_2)$—O—$R^{24}$, —$(CH_2)$—S—$R^{24}$, —$(CH_2)$—N$(CH_3)$—$R^{24}$, —$(CH_2)$—$(CH_2)$—$R^{24}$, —$(CH_2)$—$(CH_2)$—O—$R^{24}$, —$(CH_2)$—$(CH_2)$—S—$R^{24}$, —$(CH_2)$—$(CH_2)$—NH—$R^{24}$, —$(CH_2)$—$(CH_2)$—N$(CH_3)$—$R^{24}$, —$(CH_2)$—$(CH_2)$—$(CH_2)$—$R^{24}$, —$(CH_2)$—$(CH_2)$—O—$(CH_2)$—$R^{24}$, —$(CH_2)$—$(CH_2)$—S—$(CH_2)$—$R^{24}$, or —$(CH_2)$—$(CH_2)$—N$(CH_3)$—$R^{24}$; or is selected from the group consisting of methyl, ethyl, n-propyl, isopropyl, n-butyl, sec-butyl, isobutyl, tert-butyl, n-pentyl, sec-pentyl, —$(CH_2)$—$(CH_2)$—$(C(CH_3)_3)$, n-hexyl, n-heptyl, n-octyl, —$(CH_2)$—$(CH)$—$(C_2H_5)$—$(CH_2)$—$(CH_2)$—$(CH_2)$—$(CH_3)$, vinyl, 1-propenyl, 2-propenyl, 1-butenyl, 2-butenyl, 3-butenyl, 2-methyl-2-butenyl, 1-propynyl, 2-propynyl, 1-butynyl, 2-butynyl, and 3-butynyl, which may in each case be substituted by 1, 2, 3, 4, or 5 substituents independently selected from the group consisting of F, Cl, Br, I, —CN, —$NO_2$, —OH, —SH, —$NH_2$, —N$(CH_3)_2$, —N$(C_2H_5)_2$, and —N—$(CH_3)$—$(C_2H_5)$; or is selected from the group consisting of phenyl, naphthyl, thiophenyl, furanyl, pyrrolyl, pyrazolyl, pyrazynyl, pyranyl, triazolyl, pyridynyl, imidazolyl, indolyl, isoindolyl, benzo[b]furanyl, benzo[b]thiophenyl, thiazolyl, oxazolyl, isoxazolyl, pyridazynyl, pyrimidynyl, indazolyl, quinazolynyl, quinolynyl, and isoquinolynyl, and which may in each case be substituted by 1, 2, 3, 4, or 5 substituents independently selected from the group consisting of F, Cl, Br, I, —CN, —$CF_3$, —$SF_5$, —OH, —O—$CH_3$, —O—$C_2H_5$, —O—CH$(CH_3)_2$, —O—C$(CH_3)_3$, —O—$CH_2$—$CH_2$—$CH_2$—$CH_3$, —O—$CH_2$—CH=$CH_2$, —$NH_2$, —$NO_2$, —O—$CF_3$, —O—$CHF_2$, —O—$CH_2F$, —S—$CF_3$, —S—$CHF_2$, —S—$CH_2F$, —SH, —S—$CH_3$, —S—$C_2H_5$, —S—CH$(CH_3)_2$, —S—C$(CH_3)_3$, —S—$CH_2$—$CH_2$—$CH_2$—$CH_3$, methyl, ethyl, n-propyl, isopropyl, n-butyl, sec-butyl, isobutyl, tert-butyl, —C(=O)—OH, —C(=O)—O—$CH_3$, —C(=O)—O—$C_2H_5$, —C(=O)—O—C$(CH_3)_3$, —O—C(=O)—$CH_3$, —O—C(=O)—$C_2H_5$, —O—C(=O)-phenyl, —$(CH_2)$—O—C(=O)—$CH_3$, —$(CH_2)$—O—C(=O)—$C_2H_5$, —$(CH_2)$—O—C(=O)-phenyl, —N$(CH_3)_2$, —N$(C_2H_5)_2$, —N(H)$(CH_3)$, —N(H)$(C_2H_5)$, —NH—C(=O)—O—$CH_3$, —NH—C(=O)—O—$C_2H_5$, —NH—C(=O)—$CH_3$, —NH—C(=O)—$C_2H_5$, —C(=O)—H, —C(=O)—$CH_3$, —C(=O)—$C_2H_5$, —C(=O)—$NH_2$, —C(=O)—NH—$CH_3$—C(=O)—NH—$C_2H_5$, —S(=O)$_2$—$NH_2$, —S(=O)$_2$—NH—$CH_3$, —S(=O)$_2$—NH—$C_2H_5$, —S(=O)$_2$—NH-phenyl, —$(CH_2)$benzo[b]furanyl, —O-phenyl, —S-phenyl, —S-benzyl, —O-benzyl, phenyl, and benzyl, and in each case the cyclic moiety of the groups —O—C(=O)-phenyl, —$(CH_2)$—O—C(=O)-phenyl, —S(=O)$_2$—NH-phenyl, —O-phenyl, —S-phenyl, —S-benzyl, —O-benzyl, phenyl, —$(CH_2)$benzo[b]furanyl, and benzyl may be substituted by 1, 2, 3, 4, or 5 substituents selected independently of the group consisting of F, Cl, Br, —OH, —$CF_3$, —$SF_5$, —CN, —$NO_2$, —O—$CH_3$, —O—$C_2H_5$, —O—CH$(CH_3)_2$, —O—C$(CH_3)_3$, methyl, ethyl, n-propyl, isopropyl, n-butyl, sec-butyl, isobutyl, tert-butyl, —O—$CF_3$, —S—$CF_3$, phenyl, and —O-benzyl;

$R^3$ represents a —C(=O)—$R^4$ group; and $R^4$ represents

—$(CHR^{10})$—O—$R^{11}$, —$(CHR^{10})$—S—$R^{11}$, —$(CHR^{10})$—NH—$R^{11}$, —$(CHR^{10})$—O—$(CH_2)$—$R^{11}$, —$(CHR^{10})$—S—$(CH_2)$—$R^{11}$, —$(CHR^{10})$—NH—$(CH_2)$—$R^{11}$, —$(CHR^{10})$—N$(CH_3)$—$(CH_2)$—$R^{11}$, —$(CHR^{10})$—$(CH_2)$—$(CH_2)$—O—$R^{11}$, —$(CHR^{10})$—$(CH_2)$—$(CH_2)$—S—$R^{11}$, —$(CHR^{10})$—$(CH_2)$—$(CH_2)$—NH—$R^{11}$— $(CHR^{10})$—$(CH_2)$—$(CH_2)$—N$(C_2H_5)$—$R^{11}$, —$(CHR^{10})$—O—$(CH_2)$—$(CH_2)$—O—$R^{11}$, —$(CHR^{10})$—S—$(CH_2)$—$(CH_2)$—S—$R^{11}$, —$(CHR^{10})$—O—$(CH_2)$—$(CH_2)$—S—$R^{11}$, or —$(CHR^{10})$—S—$(CH_2)$—$(CH_2)$—O—$R^{11}$, —$(CR^{12}R^{13})$—C(=O)—O—$R^7$, —$(CR^{12}R^{13})$—$(CH_2)$—C(=O)—O—$R^7$, or —$(CR^{12}R^{13})$—$(CH_2)$—$(CH_2)$—C(=O)—O—$R^7$;

—$(CR^{14}R^{15})$—O—C(=O)—$R^8$ or —$(CR^{14}R^{15})$—$(CH_2)$, and —O—C(=O)—$R^8$;

—$(CHR^{16})$—C(=O)—$R^9$ or —$(CHR^{16})$—$(CH_2)$—C(=O)—$R^9$;

—CH[$(CH_2)$—O—$(CH_2)$—$R^{17}$]—[NH—C(=O)—O—$R^{18}$] or —CH[$(CH_2)$—S—$(CH_2)$—$R^{17}$]—[NH—C(=O)—OR];

—$CHR^{19}R^{20}$ or —$(CH_2)$—$CHR^{19}R^{20}$;

—(CH=CH)—$R^{21}$;

an alkyl group selected from the group consisting of methyl, ethyl, n-propyl, isopropyl, n-butyl, sec-butyl, isobutyl, tert-butyl, n-pentyl, 2-pentyl, 3-pentyl, —$(CH_2)$—$(C(CH_3)_3)$, n-hexyl, 3-hexyl, —$(CH_2)$—$(CH_2)$—$(C(CH_3)_3)$, n-heptyl, 3-heptyl, 4-heptyl, n-octyl, and —$(CH_2)$—$(CH)$—$(C_2H_5)$—$(CH_2)$—$(CH_2)$—$(CH_2)$—$(CH_3)$, wherein the alkyl group is in each case substituted by 1, 2, 3, 4, or 5 substituents independently selected from the group consisting of F, Cl, Br, I, —CN, —$NO_2$, —OH, —SH, —$NH_2$, —N$(CH_3)_2$, —N$(C_2H_5)_2$, and —N—$(CH_3)$—$(C_2H_5)$; or is selected from the group consisting of vinyl, 1-propenyl, 2-propenyl, 1-butenyl, 2-butenyl, 3-butenyl, 1-propynyl, 2-propynyl, 1-butynyl, 2-butynyl, and 3-butynyl, and may in each case be substituted by 1, 2, 3, 4, or 5 substituents independently selected from the group consisting of F, Cl, Br, I, —CN, —$NO_2$, —OH, —SH, —$NH_2$, —N—$(CH_3)_2$, —N$(C_2H_5)_2$, and —N—$(CH_3)$—$(C_2H_5)$; or is a (hetero)cycloaliphatic moiety selected from the group consisting of cyclopropyl, cyclobutyl, cyclopentyl, cyclohexyl, cycloheptyl, cyclopentenyl, cyclohexenyl, cycloheptenyl, imidazolidynyl, tetrahydrofuranyl, tetrahydrothiophenyl, pyrrolidynyl, piperidynyl, morpholynyl, piperazynyl, thiomorpholynyl, tetrahydropyranyl, azepanyl, diazepanyl, dithiolanyl, adamantyl, and 7,7-dimethyl-2-oxa-bicyclo[2,2,1]heptyl, which (hetero)cycloaliphatic moiety may, in each case be substituted by 1, 2, 3, 4, or 5 substituents independently selected from the group consisting of oxo (=O), thioxo (=S), F, Cl, Br, I, —CN, —$CF_3$, —$SF_5$, —OH, —O—$CH_3$, —O—$C_2H_5$, —O—C$(CH_3)_3$, —$NH_2$, —$NO_2$, —O—$CF_3$, —S—$CF_3$, —SH, S—$CH_3$, —S—$C_2H_5$, —S—C$(CH_3)_3$, methyl, ethyl, n-propyl, isopropyl, n-butyl, sec-butyl, isobutyl, tert-butyl, —C(=O)—

H, —C(=O)—CH$_3$, —C(=O)—C$_2$H$_5$, —C(=O)—OH, —C(=O)—O—CH$_3$, —C(=O)—O—C$_2$H$_5$, —C(=O)—O—C(CH$_3$)$_3$, —(CH$_2$)—C(=O)—OH, —(CH$_2$)—C(=O)—O—CH$_3$, —(CH$_2$)—C(=O)—O—C$_2$H$_5$, —N(CH$_3$)$_2$, —N(C$_2$H$_5$)$_2$, —N(H)(CH$_3$), —N(H)(C$_2$H$_5$), —(CH$_2$)—benzo[b]furanyl, —O-phenyl, —O-benzyl, phenyl, benzyl, naphthyl, and —(CH$_2$)-naphthyl, and in each case the cyclic moiety of the groups —O-phenyl, —O-benzyl, phenyl, —(CH$_2$)benzo[b]furanyl, benzyl, naphthyl and —(CH$_2$)—naphthyl may be substituted by 1, 2, 3, 4, or 5 substituents independently selected from the group consisting of F, Cl, Br, —OH, —CF$_3$, —SF$_5$, —CN, —NO$_2$, —O—CH$_3$, —O—C$_2$H$_5$, methyl, ethyl, n-propyl, isopropyl, n-butyl, sec-butyl, isobutyl, tert-butyl, —O—CF$_3$, —S—CF$_3$, phenyl, and —O-benzyl, or is a phenyl group, which phenyl groups may be substituted by 1, 2, 3, 4 or 5 substituents independently selected from the group consisting of —CN, —SF$_5$, —NH$_2$, —NO$_2$, —O—CF$_3$, —O—CHF$_2$, —O—CH$_2$F, —S—CF$_3$, —S—CHF$_2$, —S—CH$_2$F, —SH, —S—CH$_3$, —S—C$_2$H$_5$, —S—CH(CH$_3$)$_2$, —S—C(CH$_3$)$_3$, —S—CH$_2$—CH$_2$—CH$_2$—CH$_3$, —C(=O)—OH, —C(=O)—O—CH$_3$, —C(=O)—O—C$_2$H$_5$, —C(=O)—O—C(CH$_3$)$_3$, —O—C(=O)—CH$_3$, —O—C(=O)—C$_2$H$_5$, —O—C(=O)-phenyl, —(CH$_2$)—O—C(=O)—CH$_3$, —(CH$_2$)—O—C(=O)—C$_2$H$_5$, —(CH$_2$)—O—C(=O)-phenyl, —N(CH$_3$)$_2$, —N(C$_2$H$_5$)$_2$, —N(H)(CH$_3$), —N(H)(C$_2$H$_5$), —NH—C(=O)—O—CH$_3$, —NH—C(=O)—O—C$_2$H$_5$, —NH—C(=O)—CH$_3$, —NH—C(=O)—C$_2$H$_5$, —C(=O)—H, —C(=O)—CH$_3$, —C(=O)—C$_2$H$_5$, —C(=O)—NH$_2$, —C(=O)—NH—CH$_3$, —C(=O)—NH—C$_2$H$_5$, —S(=O)$_2$—NH$_2$, —S(=O)$_2$—NH—CH$_3$, —S(=O)$_2$—NH—C$_2$H$_5$, —(CH$_2$)benzo[b]furanyl, —O-phenyl, —S-phenyl, —S-benzyl, —O-benzyl, phenyl, and benzyl, and in each case the cyclic moiety of the groups —O—C(=O)—phenyl, —(CH$_2$)—O—C(=O)-phenyl, —S(=O)$_2$—NH-phenyl, —O-phenyl, —S-phenyl, —S-benzyl, —O-benzyl, phenyl, —(CH$_2$)-benzo[b]furanyl and benzyl may be substituted by 1, 2, 3, 4 or 5 substituents independently selected from the group consisting of F, Cl, Br, —OH, —CF$_3$, —SF$_5$, —CN, —NO$_2$, —O—CH$_3$, —O—C$_2$H$_5$, —O—CH(CH$_3$)$_2$, —O—C(CH$_3$)$_3$, methyl, ethyl, n-propyl, isopropyl, n-butyl, sec-butyl, isobutyl, tert-butyl, —O—CF$_3$, —S—CF$_3$, phenyl and —O-benzyl, or is selected from the group consisting of 1,2,3,4,5-pentafluorophenyl, 1,2,3,4-tetrafluorophenyl, 4-methyl-3-nitrophenyl, 5-methyl-3-nitrophenyl, 6-methyl-3-nitrophenyl, and 2-methyl-3-nitrophenyl;

unsubstituted naphthyl; or is selected from the group consisting of (1,3)-benzodioxolyl and (1,4)-benzodioxanyl, which may be substituted by 1, 2, 3, 4, or 5 substituents selected from the group consisting of F, Cl, Br, I, —CN, —CF$_3$, —SF$_5$, —OH, —O—CH$_3$, —O—C$_2$H$_5$, —O—CH(CH$_3$)$_2$, —O—C(CH$_3$)$_3$, —O—CH$_2$—CH$_2$—CH$_3$, —O—CH$_2$—CH=CH$_2$, —NH$_2$, —NO$_2$, —O—CF$_3$, —O—CHF$_2$, —O—CH$_2$F, —S—CF$_3$, —S—CHF$_2$, —S—CH$_2$F, —SH, —S—CH$_3$, —S—C$_2$H$_5$, —S—CH(CH$_3$)$_2$, —S—C(CH$_3$)$_3$, —S—CH$_2$—CH$_2$—CH$_2$—CH$_3$, methyl, ethyl, n-propyl, isopropyl, n-butyl, sec-butyl, isobutyl, tert-butyl; or is a heteroaryl group selected from the group consisting of thiophenyl, furanyl, pyrrolyl, pyrazolyl, pyrazynyl, pyranyl, triazolyl, pyridynyl, imidazolyl, indolyl, isoindolyl, benzo[b]furanyl, benzo[b]thiophenyl, thiazolyl, thiadiazolyl, oxazolyl, isoxazolyl, pyridazynyl, pyrimidynyl, indazolyl, quinazolynyl, quinolynyl, isoquinolynyl, phenazynyl, phenothiazynyl, oxadiazolyl, benzo[1,2,5]oxadiazolyl, and chromanyl, which heteroaryl group may in each case be substituted by 1, 2, 3, 4, or 5 substituents independently selected from the group consisting of F, Cl, Br, I, —CN, —CF$_3$, —SF$_5$, —OH, —O—CH$_3$, —O—C$_2$H$_5$, —O—CH(CH$_3$)$_2$, —O—C(CH$_3$)$_3$, —O—CH$_2$—CH$_2$—CH$_2$—CH$_3$, —O—CH$_2$—CH=CH$_2$, —NH$_2$, —NO$_2$, —O—CF$_3$, —O—CHF$_2$, —O—CH$_2$F, —S—CF$_3$, —S—CHF$_2$, —S—CH$_2$F, —SH, —S—CH$_3$, —S—C$_2$H$_5$, —S—CH(CH$_3$)$_2$, —S—C(CH$_3$)$_3$, —S—CH$_2$—CH$_2$—CH$_2$—CH$_3$, methyl, ethyl, n-propyl, isopropyl, n-butyl, sec-butyl, isobutyl, tert-butyl, —C(=O)—OH, —C(=O)—O—CH$_3$, —C(=O)—O—C$_2$H$_5$, —C(=O)—O—C(CH$_3$)$_3$, —O—C(=O)—CH$_3$, —O—C(=O)—C$_2$H$_5$, —O—C(=O)-phenyl, —(CH$_2$)—O—C(=O)—CH$_3$, —(CH$_2$)—O—C(=O)—C$_2$H$_5$, —(CH$_2$)—O—C(=O)-phenyl, —N(CH$_3$)$_2$, —N(C$_2$H$_5$)$_2$, —N(H)(CH$_3$), —N(H)(C$_2$H$_5$), —NH—C(=O)—O—CH$_3$, —NH—C(=O)—O—C$_2$H$_5$, —NH—C(=O)—CH$_3$, —NH—C(=O)—C$_2$H$_5$, —C(=O)—H, —C(=O)—CH$_3$, —C(=O)—C$_2$H$_5$, —C(=O)—NH$_2$, —C(=O)—NH—CH$_3$, —C(=O)—NH—C$_2$H$_5$, —S(=O)$_2$—NH$_2$, —S(=O)$_2$—NH—CH$_3$, —S(=O)$_2$—NH—C$_2$H$_5$, —S(=O)$_2$—NH-phenyl, —(CH$_2$)benzo[b]furanyl, —O-phenyl, —S-phenyl, —S-benzyl, —O-benzyl, phenyl, and benzyl, and in each case the cyclic moiety of the groups —O—C(=O)-phenyl, —(CH$_2$)—O—C(=O)-phenyl, —S(=O)$_2$—NH-phenyl, —O-phenyl, —S-phenyl, —S-benzyl, —O-benzyl, phenyl, —(CH$_2$)benzo[b]furanyl, and benzyl may be substituted by 1, 2, 3, 4, or 5 substituents independently selected from the group consisting of F, Cl, Br, —OH, —CF$_3$, —SF$_5$, —CN, —NO$_2$, —O—CH$_3$, —O—C$_2$H$_5$, —O—CH(CH$_3$)$_2$, —O—C(CH$_3$)$_3$, methyl, ethyl, n-propyl, isopropyl, n-butyl, sec-butyl, isobutyl, tert-butyl, —O—CF$_3$, —S—CF$_3$, phenyl, and —O-benzyl, or III)

$R^1$ represents hydrogen; or is selected from the group consisting of methyl, ethyl, n-propyl, isopropyl, n-butyl, sec-butyl, isobutyl, tert-butyl, n-pentyl, sec-pentyl, —(CH$_2$)—(CH$_2$)—(C(CH$_3$)$_3$), n-hexyl, n-heptyl, n-octyl, —(CH$_2$)—(CH)—(C$_2$H$_5$)—(CH$_2$)—(CH$_2$)—(CH$_2$)—(CH$_3$), vinyl, 1-propenyl, 2-propenyl, 1-butenyl, 2-butenyl, 3-butenyl, 2-methyl-2-butenyl, 1-propynyl, 2-propynyl, 1-butynyl, 2-butynyl, and 3-butynyl; or is selected from the group consisting of phenyl, naphthyl, thiophenyl, furanyl, pyrrolyl, pyrazolyl, pyrazynyl, pyranyl, triazolyl, pyridynyl, imidazolyl, indolyl, isoindolyl, benzo[b]furanyl, benzo[b]thiophenyl, thiazolyl, oxazolyl, isoxazolyl, pyridazynyl, pyrimidynyl, indazolyl, quinazolynyl, quinolynyl, and isoquinolynyl, which in each case may be substituted by 1, 2, 3, 4, or 5 substituents selected independently of the group consisting of F, Cl, Br, I, —CN, —CF$_3$, —SF$_5$, —OH, —O—CH$_3$, —O—C$_2$H$_5$, —O—CH(CH$_3$)$_2$, —O—C(CH$_3$)$_3$, —O—CH$_2$—CH$_2$—CH$_2$—CH$_3$, —O—CH$_2$—CH=CH$_2$, —NH$_2$, —NO$_2$, —O—CF$_3$, —O—CHF$_2$, —O—CH$_2$F, —S—CF$_3$, —S—CHF$_2$, —S—CH$_2$F, —SH, —S—CH$_3$, —S—C$_2$H$_5$, —S—CH(CH$_3$)$_2$, —S—C(CH$_3$)$_3$, —S—CH$_2$—CH$_2$—CH$_2$—CH$_3$, methyl, ethyl, n-propyl, isopropyl, n-butyl, sec-butyl, isobutyl, tert-butyl, —C(=O)—OH, —C(=O)—O—CH$_3$, —C(=O)—O—C$_2$H$_5$, —C(=O)—O—C(CH$_3$)$_3$, —O—C(=O)—CH$_3$, —O—C(=O)—C$_2$H$_5$, —O—C(=O)-phenyl, —(CH$_2$)—O—C(=O)—CH$_3$, —(CH$_2$)—O—C(=O)—C$_2$H$_5$, —(CH$_2$)—O—C(=O)-phenyl, —N(CH$_3$)$_2$, —N(C$_2$H$_5$)$_2$, —N(H)(CH$_3$), —N(H)(C$_2$H$_5$), —NH—C(=O)—O—CH$_3$, —NH—C(=O)—O—C$_2$H$_5$, —NH—C(=O)—CH$_3$, —NH—C(=O)—C$_2$H$_5$, —C(=O)—H, —C(=O)—CH$_3$, —C(=O)—C$_2$H$_5$, —C(=O)—NH$_2$, —C(=O)—NH—CH$_3$, —C(=O)—NH—C$_2$H$_5$, —S(=O)$_2$—NH$_2$, —S(=O)$_2$—NH—CH$_3$, —S(=O)$_2$—NH—C$_2$H$_5$, —S(=O)$_2$—NH-phenyl, —(CH$_2$)-Benzo[b]furanyl, —O-phenyl, —S-phenyl, —S-benzyl, —O-benzyl, phenyl, and benzyl, wherein in each case the cyclic moiety of the groups —O—C(=O)-phenyl, —(CH$_2$)—O—C(=O)-phenyl, —S(=O)$_2$—NH-phenyl, —O-phenyl, —S-phenyl, —S-benzyl, —O-benzyl, phenyl, —(CH$_2$)benzo[b]furanyl, and benzyl may be substituted by 1, 2, 3, 4, or 5 substituents independently selected from the group consisting of F, Cl, Br, —OH, —CF$_3$, —SF$_5$, —CN, —NO$_2$, —O—CH$_3$, —O—C$_2$H$_5$, —O—CH(CH$_3$)$_2$, —O—C(CH$_3$)$_3$, methyl, ethyl, n-propyl, isopropyl, n-butyl, sec-butyl, isobutyl, tert-butyl, —O—CF$_3$, —S—CF$_3$, phenyl, and —O-benzyl, —(CH$_2$)$_m$—O—C(=O)—R$^5$, where m is 1, 2, 3, 4, or 5;
—(CH$_2$)$_n$—C(=O)—O—R$^6$, where n is 1, 2, 3, 4, or 5;
an unsubstituted benzyl group;
—(CH$_2$)—R$^{22}$; or
—(CH$_2$)—O—R$^{23}$, —(CH$_2$)—S—R$^{23}$, —(CH$_2$)—N(CH$_3$)—R$^{23}$, —(CH$_2$)—(CH$_2$)—O—R$^{23}$, —(CH$_2$)—(CH$_2$)—S—R$^{23}$, —(CH$_2$)—(CH$_2$)—NH—R$^{23}$, —(CH$_2$)—(CH$_2$)—N(CH$_3$)—R$^{23}$, —(CH$_2$)—(CH$_2$)—O—(CH$_2$)—R$^{23}$, —(CH$_2$)—(CH$_2$)—S—(CH$_2$)—R$^{23}$, or —(CH$_2$)—(CH$_2$)—N(CH$_3$)—R$^{23}$;

R$^2$ represents —(CH$_2$)—S—R$^{24}$, —(CH$_2$)—N(CH$_3$)—R$^{24}$, —(CH$_2$)—(CH$_2$)—S—R$^{24}$, —(CH$_2$)—(CH$_2$)—NH—R$^{24}$, —(CH$_2$)—(CH$_2$)—N(CH$_3$)—R$^{24}$, —(CH$_2$)—(CH$_2$)—S—(CH$_2$)—R$^{24}$, or —(CH$_2$)—(CH$_2$)—N(CH$_3$)—R$^{24}$;

R$^3$ represents a —C(=O)—R$^4$ group; and

R$^4$ represents —(CHR$^{10}$)—O—R$^{11}$, —(CHR$^{10}$)—S—R$^{11}$, —(CHR$^{10}$)—O—(CH$_2$)—R$^{11}$, —(CHR$^{10}$)—S—(CH$_2$)—R$^{11}$, —(CHR$^{10}$)—(CH$_2$)—(CH$_2$)—O—R$^{11}$, —(CHR$^{10}$)—(CH$_2$)—(CH$_2$)—S—R$^{11}$, or —(CHR$^{10}$)—O—(CH$_2$)—(CH$_2$)—O—R$^{11}$, —(CR$^{12}$R$^{13}$)—C(=O)—O—R$^7$ or —(CR$^{12}$R$^{13}$)—(CH$_2$)—C(=O)—O—R$^7$;
—(CR$^{14}$R$^{15}$)—O—C(=O)—R$^8$ or —(CR$^{14}$R$^{15}$)—(CH$_2$)—and —O—C(=O)—R$^8$;
—(CHR$^{16}$)—C(=O)—R$^9$;
—CH[(CH$_2$)—O—(CH$_2$)—R$^{17}$]—[NH—C(=O)—O—R$^{18}$];
—CHR$^{19}$R$^{20}$ or —(CH$_2$)—CHR$^{19}$R$^{20}$;

—(CH=CH)—R$^{21}$; or is selected from the group consisting of methyl, ethyl, n-propyl, isopropyl, n-butyl, sec-butyl, isobutyl, tert-butyl, n-pentyl, 2-pentyl, 3-pentyl, —(CH$_2$)—(C(CH$_3$)$_3$), n-hexyl, 3-hexyl, —(CH$_2$)—(CH$_2$)—(C(CH$_3$)$_3$), n-heptyl, 3-heptyl, 4-heptyl, n-octyl, —(CH$_2$)—(CH)—(C$_2$H$_5$)—(CH$_2$)—(CH$_2$)—(CH$_2$)—(CH$_3$), vinyl, 1-propenyl, 2-propenyl, 1-butenyl, 2-butenyl, and 3-butenyl, and in each case may be substituted by 1, 2, 3, 4, or 5 substituents independently selected from the group consisting of F, Cl, Br, I, —CN, —NO$_2$, —OH, —SH, —NH$_2$, —N(CH$_3$)$_2$, —N(C$_2$H$_5$)$_2$, and N—(CH$_3$)—(C$_2$H$_5$);

a (hetero)cycloaliphatic group selected from the group consisting of cyclopropyl, cyclobutyl, cyclopentyl, cyclohexyl, cycloheptyl, cyclopentenyl, cyclohexenyl, cycloheptenyl, imidazolidynyl, tetrahydrofuranyl, tetrahydrothiophenyl, pyrrolidynyl, piperidynyl, morpholynyl, piperazynyl, thiomorpholynyl, tetrahydropyranyl, azepanyl, diazepanyl, dithiolanyl, adamantyl, and 7,7-dimethyl-2-oxa-bicyclo[2,2,1]heptyl, which (hetero)cycloaliphatic group may in each case be substituted by 1, 2, 3, 4, or 5 substituents independently selected from the group consisting of oxo (=O), thioxo (=S), F, Cl, Br, I, —CN, —CF$_3$, —SF$_5$, —OH, —O—CH$_3$, —O—C$_2$H$_5$, —O—C(CH$_3$)$_3$, —NH$_2$, —NO$_2$, —O—CF$_3$, —S—CF$_3$, —SH, S—CH$_3$, —S—C$_2$H$_5$, —S—C(CH$_3$)$_3$, methyl, ethyl, n-propyl, isopropyl, n-butyl, sec-butyl, isobutyl, tert-butyl, —C(=O)—H, —C(=O)—CH$_3$, —C(=O)—C$_2$H$_5$, —C(=O)—OH, —C(=O)—O—CH$_3$, —C(=O)—O—C$_2$H$_5$, —C(=O)—O—C(CH$_3$)$_3$, —(CH$_2$)—C(=O)—OH, —(CH$_2$)—C(=O)—O—CH$_3$, —(CH$_2$)—C(=O)—O—C$_2$H$_5$, —N(CH$_3$)$_2$, —N(C$_2$H$_5$)$_2$, —N(H)(CH$_3$), —N(H)(C$_2$H$_5$), —(CH$_2$)benzo[b]furanyl, —O-phenyl, —O-benzyl, phenyl, benzyl, naphthyl, and —(CH$_2$)-naphthyl, and in each case the cyclic moiety of the groups —O-phenyl, —O-benzyl, phenyl, —(CH$_2$)benzo[b]furanyl, benzyl, naphthyl, and —(CH$_2$)-naphthyl may be substituted by 1, 2, 3, 4, or 5 substituents independently selected from the group consisting of F, Cl, Br, —OH, —CF$_3$, —SF$_5$, —CN, —NO$_2$, —O—CH$_3$, —O—C$_2$H$_5$, methyl, ethyl, n-propyl, isopropyl, n-butyl, sec-butyl, isobutyl, tert-butyl, —O—CF$_3$, —S—CF$_3$, phenyl, and —O-benzyl, or is selected from the group consisting of phenyl, naphthyl, (1,3)-benzodioxolyl, (1,4)-benzodioxanyl, thiophenyl, furanyl, pyrrolyl, pyrazolyl, pyrazynyl, pyranyl, triazolyl, pyridynyl, imidazolyl, indolyl, isoindolyl, benzo[b]furanyl, benzo[b]thiophenyl, thiazolyl, thiadiazolyl, oxazolyl, isoxazolyl, pyridazynyl, pyrimidynyl, indazolyl, chinazolynyl, chinolynyl, isochinolynyl, phenazynyl, phenothiazynyl, oxadiazolyl, benzo[1,2,5]oxadiazolyl und chromanyl, which may in each case be substituted by 1, 2, 3, 4 or 5 substituents independently selected from the group consisting of F, Cl, Br, I, —CN, —CF$_3$, —SF$_5$, —OH, —O—CH$_3$, —O—C$_2$H$_5$, —O—CH(CH$_3$)$_2$, —O—C(CH$_3$)$_3$, —O—CH$_2$—CH$_2$—CH$_2$—CH$_3$, —O—CH$_2$—CH=CH$_2$, —NH$_2$, —NO$_2$, —O—CF$_3$, —O—CHF$_2$, —O—CH$_2$F, —S—CF$_3$, —S—CHF$_2$, —S—CH$_2$F, —SH, —S—CH$_3$, —S—C$_2$H$_5$, —S—CH(CH$_3$)$_2$, —S—C(CH$_3$)$_3$, —S—CH$_2$—CH$_2$—CH$_2$—CH$_3$, methyl, ethyl, n-propyl, isopropyl, n-butyl, sec-butyl, isobutyl, tert-butyl, —C(=O)—OH, —C(=O)—O—CH$_3$, —C(=O)—O—C₂H₅, —C(=O)—O—C(CH₃)₃, —O—C(=O)—CH₃, —O—C(=O)—C₂H₅, —O—C(=O)-phenyl, —(CH₂)—O—C(=O)—CH₃, —(CH₂)—O—C(=O)—C₂H₅, —(CH₂)—O—C(=O)-phenyl, —N(CH₃)₂, —N(C₂H₅)₂, —N(H)(CH₃), —N(H)(C₂H₅), —NH—C(=O)—O—CH₃, —NH—C(=O)—O—C₂H₅, —NH—C(=O)—CH₃, —NH—C(=O)—C₂H₅, —C(=O)—H, —C(=O)—CH₃, —C(=O)—C₂H₅, —C(=O)—NH₂, —C(=O)—NH—CH₃, —C(=O)—NH—C₂H₅, —S(=O)₂—NH₂, —S(=O)₂—NH—CH₃, —S(=O)₂—NH—C₂H₅, —S(=O)₂—NH-phenyl, —(CH₂)—benzo[b]furanyl, —O-phenyl, —S-phenyl, —S-benzyl, —O-benzyl, phenyl und benzyl, and in each case the cyclic moiety of the groups —O—C(=O)-phenyl, —(CH₂)—O—C(=O)-phenyl, —S(=O)₂—NH-phenyl, —O-phenyl, —S-phenyl, —S-benzyl, —O-benzyl, phenyl, —(CH₂)benzo[b]furanyl, and benzyl may be substituted by 1, 2, 3, 4, or 5 substituents independently selected from the group consisting of F, Cl, Br, —OH, —CF₃, —SF₅, —CN, —NO₂, —O—CH₃, —O—C₂H₅, —O—CH(CH₃)₂, —O—C(CH₃)₃, methyl, ethyl, n-propyl, isopropyl, n-butyl, sec-butyl, isobutyl, tert-butyl, —O—CF₃, —S—CF₃, phenyl, and —O-benzyl, and in each case, if present, in the aforementioned groups I) II) and III)

R⁵, R⁶, R⁹ and R¹⁸ each independently represent a moiety selected from the group consisting of methyl, ethyl, n-propyl, isopropyl, n-butyl, sec-butyl, isobutyl, tert-butyl, n-pentyl, 2-pentyl, 3-pentyl, —(CH₂)—(C(CH₃)₃), n-hexyl, 3-hexyl, —(CH₂)—(CH₂)—(C(CH₃)₃), n-heptyl, 3-heptyl, 4-heptyl, n-octyl, —(CH₂)—(CH)—(C₂H₅)—(CH₂)—(CH₂)—(CH₂)—(CH₃), vinyl, 1-propenyl, 2-propenyl, 1-butenyl, 2-butenyl, and 3-butenyl, which may in each case be substituted by 1, 2, 3, 4, or 5 substituents independently selected from the group consisting of F, Cl, Br, I, —CN, —NO₂, —OH, —SH, —NH₂, —N(CH₃)₂, —N(C₂H₅)₂, and N—(CH₃)—(C₂H₅);

R⁷ represents hydrogen; or is selected from the group consisting of methyl, ethyl, n-propyl, isopropyl, n-butyl, sec-butyl, isobutyl, tert-butyl, n-pentyl, 2-pentyl, 3-pentyl, —(CH₂)—(C(CH₃)₃), n-hexyl, 3-hexyl, —(CH₂)—(CH₂)—(C(CH₃)₃), n-heptyl, 3-heptyl, 4-heptyl, n-octyl, —(CH₂)—(CH)—(C₂H₅)—(CH₂)—(CH₂)—(CH₂)—(CH₃), vinyl, 1-propenyl, 2-propenyl, 1-butenyl, 2-butenyl, and 3-butenyl, and may be substituted by 1, 2, 3, 4, or 5 substituents independently selected from the group consisting of F, Cl, Br, I, —CN, —NO₂, —OH, —SH, —NH₂, —N(CH₃)₂, —N(C₂H₅)₂, and N—(CH₃)—(C₂H₅); or is selected from the group consisting of phenyl, naphthyl, thiophenyl, furanyl, pyrrolyl, pyrazolyl, pyrazynyl, pyranyl, triazolyl, pyridynyl, imidazolyl, indolyl, isoindolyl, benzo[b]furanyl, benzo[b]thiophenyl, thiazolyl, thiadiazolyl, oxazolyl, isoxazolyl, pyridazynyl, pyrimidynyl, indazolyl, quinazolynyl, quinolynyl, isoquinolynyl, phenazynyl, phenothiazynyl, oxadiazolyl, benzo[1,2,5]oxadiazolyl, and chromanyl, and in each case may be substituted by 1, 2, 3, 4, or 5 substituents independently selected from the group consisting of F, Cl, Br, I, —CN, —CF₃, —SF₅, —OH, —O—CH₃, —O—C₂H₅, —O—CH(CH₃)₂, —O—C(CH₃)₃, —O—CH₂—CH₂—CH₂—CH₃, —O—CH₂—CH=CH₂, —NH₂, —NO₂, —O—CF₃, —O—CHF₂, —O—CH₂F, —S—CF₃, —S—CHF₂, —S—CH₂F, —SH, —S—CH₃, —S—C₂H₅, —S—CH(CH₃)₂, —S—C(CH₃)₃, —S—CH₂—CH₂—CH₂—CH₃, methyl, ethyl, n-propyl, isopropyl, n-butyl, sec-butyl, isobutyl, tert-butyl, —C(=O)—OH, —C(=O)—O—CH₃, —C(=O)—O—C₂H₅, —C(=O)—O—C(CH₃)₃, —O—C(=O)—CH₃, —O—C(=O)—C₂H₅, —O—C(=O)-phenyl, —(CH₂)—O—C(=O)—CH₃, —(CH₂)—O—C(=O)—C₂H₅, —(CH₂)—O—C(=O)-phenyl, —N(CH₃)₂, —N(C₂H₅)—S(=O)₂—NH—CH₃, —S(=O)₂—NH—C₂H₅, —S(=O)₂—NH-phenyl, —(CH₂)benzo[b]furanyl, —O-phenyl, —S-phenyl, —S-benzyl, —O-benzyl, phenyl, and benzyl, wherein in each case the cyclic moiety of the groups —O—C(=O)-phenyl, —(CH₂)—O—C(=O)-phenyl, —S(=O)₂—NH-phenyl, —O-phenyl, —S-phenyl, —S-benzyl, —O-benzyl, phenyl, —(CH₂)benzo[b]furanyl, and benzyl may be substituted by 1, 2, 3, 4, or 5 substituents independently selected from the group consisting of F, Cl, Br, —OH, —CF₃, —SF₅, —CN, —NO₂, —O—CH₃, —O—C₂H₅, —O—CH(CH₃)₂, —O—C(CH₃)₃, methyl, ethyl, n-propyl, isopropyl, n-butyl, sec-butyl, isobutyl, tert-butyl, —O—CF₃, —S—CF₃, phenyl, and —O-benzyl, R⁸, R¹⁶, and R²⁴ each independently are selected from the group consisting of methyl, ethyl, n-propyl, isopropyl, n-butyl, sec-butyl, isobutyl, tert-butyl, n-pentyl, 2-pentyl, 3-pentyl, —(CH₂)—(C(CH₃)₃), n-hexyl, 3-hexyl, —(CH₂)—(CH₂)—(C(CH₃)₃), n-heptyl, 3-heptyl, 4-heptyl, n-octyl, —(CH₂)—(CH)—(C₂H₅)—(CH₂)—(CH₂)—(CH₂)—(CH₃), vinyl, 1-propenyl, 2-propenyl, 1-butenyl, 2-butenyl, and 3-butenyl, and may in each case be substituted by 1, 2, 3, 4, or 5 substituents independently selected from the group consisting of F, Cl, Br, I, —CN, —NO₂, —OH, —SH, —NH₂, —N(CH₃)₂, —N(C₂H₅)₂, and N—(CH₃)—(C₂H₅);

are selected from the group consisting of phenyl, naphthyl, thiophenyl, furanyl, pyrrolyl, pyrazolyl, pyranyl, triazolyl, pyridynyl, imidazolyl, indolyl, isoindolyl, benzo[b]furanyl, benzo[b]thiophenyl, thiazolyl, thiadiazolyl, oxazolyl, isoxazolyl, pyridazynyl, pyrazynyl, pyrimidynyl, indazolyl, quinazolynyl, quinolynyl, isoquinolynyl, phenazynyl, phenothiazynyl, oxadiazolyl, benzo[1,2,5]oxadiazolyl, and chromanyl, and may in each case be substituted by 1, 2, 3, 4, or 5 substituents selected independently of the group consisting of F, Cl, Br, I, —CN, —CF₃, —SF₅, —OH, —O—CH₃, —O—C₂H₅, —O—CH(CH₃)₂, —O—C(CH₃)₃, —O—CH₂—CH₂—CH₂—CH₃, —O—CH₂—CH=CH₂, —NH₂, —NO₂, —O—CF₃, —O—CHF₂, —O—CH₂F, —S—CF₃, —S—CHF₂, —S—CH₂F, —SH, —S—CH₃, —S—C₂H₅, —S—CH(CH₃)₂, —S—C(CH₃)₃, —S—CH₂—CH₂—CH₂—CH₃, methyl, ethyl, n-propyl, isopropyl, n-butyl, sec-butyl, isobutyl, tert-butyl, —C(=O)—OH, —C(=O)—O—CH₃, —C(=O)—O—C₂H₅, —C(=O)—O—C(CH₃)₃, —O—C(=O)—CH₃, —O—C(=O)—C₂H₅, —O—C(=O)-phenyl, —(CH₂)—O—C(=O)—CH₃, —(CH₂)—O—C(=O)—C₂H₅, —(CH₂)—O—C(=O)-phenyl, —N(CH₃)₂, —N(C₂H₅)—S(=O)₂—NH—C₂H₅, —S(=O)₂—NH-phenyl, —(CH₂)benzo[b]furanyl, —O-phenyl, —S-phenyl, —S-benzyl, —O-benzyl, phenyl, and benzyl, and in each case the cyclic moiety of the groups —O—C(=O)-phenyl, —(CH$_2$)—O—C(=O)-phenyl, —S(=O)$_2$—NH-phenyl, —O-phenyl, —S-phenyl, —S-benzyl, —O-benzyl, phenyl, —(CH$_2$)benzo[b]furanyl, and benzyl may be substituted by 1, 2, 3, 4, or 5 substituents independently selected from the group consisting of F, Cl, Br, —OH, —CF$_3$, —SF$_5$, —CN, —NO$_2$, —O—CH$_3$, —O—C$_2$H$_5$, —O—CH(CH$_3$)$_2$, —O—C(CH$_3$)$_3$, methyl, ethyl, n-propyl, isopropyl, n-butyl, sec-butyl, isobutyl, tert-butyl, —O—CF$_3$, —S—CF$_3$, phenyl, and —O-benzyl;

$R^{10}$, $R^{12}$, and $R^{13}$ each independently reprepent hydrogen; or are selected from the group consisting of methyl, ethyl, n-propyl, isopropyl, n-butyl, sec-butyl, isobutyl, tert-butyl, n-pentyl, 2-pentyl, 3-pentyl, —(CH$_2$)—(C(CH$_3$)$_3$), n-hexyl, 3-hexyl, —(CH$_2$)—(CH$_2$)—(C(CH$_3$)$_3$), n-heptyl, 3-heptyl, 4-heptyl, n-octyl, —(CH$_2$)—(CH)—(C$_2$H$_5$)—(CH$_2$)—(CH$_2$)—(CH$_2$)—(CH$_3$), vinyl, 1-propenyl, 2-propenyl, 1-butenyl, 2-butenyl, and 3-butenyl, which may in each case be substituted by 1, 2, 3, 4, or 5 substituents independently selected from the group consisting of F, Cl, Br, I, —CN, —NO$_2$, —OH, —SH, —NH$_2$, —N(CH$_3$)$_2$, —N(C$_2$H$_5$)$_2$, and —N—(CH$_3$)—(C$_2$H$_5$); or are selected from the group consisting of methyl, ethyl, n-propyl, isopropyl, n-butyl, sec-butyl, isobutyl, tert-butyl, n-pentyl, 11-pentyl, 3-pentyl, —(CH$_2$)—(C(CH$_3$)$_3$), n-hexyl, 3-hexyl, —(CH$_2$)—(CH$_2$)—(C(CH$_3$)$_3$), n-heptyl, 3-heptyl, 4-heptyl, n-octyl, —(CH$_2$)—(CH)—(C$_2$H$_5$)—(CH$_2$)—(CH$_2$)—(CH$_2$)—(CH$_3$), vinyl, 1-propenyl, 2-propenyl, 1-butenyl, 2-butenyl, and 3-butenyl, which may in each case be substituted by 1, 2, 3, 4, or 5 substituents independently selected from the group consisting of F, Cl, Br, I, —CN, —NO$_2$, —OH, —SH, —NH$_2$, —N(CH$_3$)$_2$, —N(C$_2$H$_5$)$_2$, and N—(CH$_3$)—(C$_2$H$_5$);

$R^{11}$ is selected from the group consisting of ethyl, n-propyl, isopropyl, n-butyl, sec-butyl, isobutyl, tert-butyl, n-pentyl, 2-pentyl, 3-pentyl, —(CH$_2$)—(C(CH$_3$)$_3$), n-hexyl, 3-hexyl, —(CH$_2$)—(CH$_2$)—(C(CH$_3$)$_3$), n-Heptyl, 3-heptyl, 4-heptyl, n-octyl, —(CH$_2$)—(CH)—(C$_2$H$_5$)—(CH$_2$)—(CH$_2$)—(CH$_2$)—(CH$_3$), vinyl, 1-propenyl, 2-propenyl, 1-butenyl, 2-butenyl and 3-butenyl, and may be substituted in each case by 1, 2, 3, 4 or 5 substituents independently selected from the group consisting of F, Cl, Br, I, —CN, —NO$_2$, —OH, —SH, —NH$_2$, —N(CH$_3$)$_2$, —N(C$_2$H$_5$)$_2$ und —N(CH$_3$)—(C$_2$H$_5$); or is a (hetero)cycloaliphatic group selected from the group consisting of cyclopropyl, cyclobutyl, cyclopentyl, cyclohexyl, cycloheptyl, cyclopentenyl, cyclohexenyl, cycloheptenyl, imidazolidynyl, pyrrolidynyl, piperidynyl, morpholynyl, piperazynyl, azepanyl, and diazepanyl, which (hetero)cycloaliphatic group may in each case be substituted by 1, 2, 3, 4, or 5 substituents independently selected from the group consisting of oxo (=O), thioxo (=S), F, Cl, Br, I, —CN, —CF$_3$, —SF$_5$, —OH, —O—CH$_3$, —O—C$_2$H$_5$, —O—C(CH$_3$)$_3$, —NH$_2$, —NO$_2$, —O—CF$_3$, —S—CF$_3$, —SH, S—CH$_3$, —S—C$_2$H$_5$, —S—C(CH$_3$)$_3$, methyl, ethyl, n-propyl, isopropyl, n-butyl, sec-butyl, isobutyl, tert-butyl, —C(=O)—H, —C(=O)—CH$_3$, —C(=O)—C$_2$H$_5$, —C(=O)—OH, —C(=O)—O—CH$_3$, —C(=O)—O—C$_2$H$_5$, and —C(=O)—O—C(CH$_3$)$_3$; or is a phenyl or naphthyl group, which may in each case be substituted by 1, 2, 3, 4, or 5 substituents independently selected from the group consisting of F, Cl, Br, I, —CN, —CF$_3$, —SF$_5$, —OH, —O—CH$_3$, —O—C$_2$H$_5$, —O—CH(CH$_3$)$_2$, —O—C(CH$_3$)$_3$, —O—CH$_2$—CH$_2$—CH$_2$—CH$_3$, —O—CH$_2$—CH=CH$_2$, —NH$_2$, —NO$_2$, —O—CF$_3$, —O—CHF$_2$, —O—CH$_2$F, —S—CF$_3$, —S—CHF$_2$, —S—CH$_2$F, —SH, —S—CH$_3$, —S—C$_2$H$_5$, —S—CH(CH$_3$)$_2$, —S—C(CH$_3$)$_3$, —S—CH$_2$—CH$_2$—CH$_2$—CH$_3$, methyl, ethyl, n-propyl, isopropyl, n-butyl, sec-butyl, isobutyl, tert-butyl, and phenyl;

$R^{14}$, $R^{15}$, and $R^{19}$ each independently represent hydrogen; or are selected from the group consisting of methyl, ethyl, n-propyl, isopropyl, n-butyl, sec-butyl, isobutyl, tert-butyl, n-pentyl, 2-pentyl, 3-pentyl, —(CH$_2$)—(C(CH$_3$)$_3$), n-hexyl, 3-hexyl, —(CH$_2$)—(CH$_2$)—(C(CH$_3$)$_3$), n-heptyl, 3-heptyl, 4-heptyl, n-octyl, —(CH$_2$)—(CH)—(C$_2$H$_5$)—(CH$_2$)—(CH$_2$)—(CH$_2$)—(CH$_3$), vinyl, 1-propenyl, 2-propenyl, 1-butenyl, 2-butenyl, and 3-butenyl, which may in each case be substituted by 1, 2, 3, 4, or 5 substituents independently selected from the group consisting of F, Cl, Br, I, —CN, —NO$_2$, —OH, —SH, —NH$_2$, —N(CH$_3$)$_2$, —N(C$_2$H$_5$)$_2$, and N—(CH$_3$)—(C$_2$H$_5$); or a phenyl group or naphthyl group, which may in each case be substituted by 1, 2, 3, 4, or 5 substituents independently selected from the group consisting of F, Cl, Br, I, —CN, —CF$_3$, —SF$_5$, —OH, —O—CH$_3$, —O—C$_2$H$_5$, —O—CH(CH$_3$)$_2$, —O—C(CH$_3$)$_3$, —O—CH$_2$—CH$_2$—CH$_2$—CH$_3$, —O—CH$_2$—CH=CH$_2$, —NH$_2$, —NO$_2$, —O—CF$_3$, —O—CHF$_2$, —O—CH$_2$F, —S—CF$_3$, —S—CHF$_2$, —S—CH$_2$F, —SH, —S—CH$_3$, —S—C$_2$H$_5$, —S—CH(CH$_3$)$_2$, —S—C(CH$_3$)$_3$, —S—CH$_2$—CH$_2$—CH$_2$—CH$_3$, methyl, ethyl, n-propyl, isopropyl, n-butyl, sec-butyl, isobutyl, and tert-butyl;

$R^{20}$ represents a (hetero)cycloaliphatic moiety selected from the group consisting of cyclopropyl, cyclobutyl, cyclopentyl, cyclohexyl, cycloheptyl, cyclopentenyl, cyclohexenyl, cycloheptenyl, imidazolidynyl, pyrrolidynyl, piperidynyl, morpholynyl, piperazynyl, azepanyl, and diazepanyl, which (hetero)cycloaliphatic moiety may in each case be substituted by 1, 2, 3, 4, or 5 substituents independently selected from the group consisting of oxo (=O), thioxo (=S), F, Cl, Br, I, —CN, —CF$_3$, —SF$_5$, —OH, —O—CH$_3$, —O—C$_2$H$_5$, —O—C(CH$_3$)$_3$, —NH$_2$, —NO$_2$, —O—CF$_3$, —S—CF$_3$, —SH, S—CH$_3$, —S—C$_2$H$_5$, —S—C(CH$_3$)$_3$, methyl, ethyl, n-propyl, isopropyl, n-butyl, sec-butyl, isobutyl, tert-butyl, —C(=O)—H, —C(=O)—CH$_3$, —C(=O)—C$_2$H$_5$, —C(=O)—OH, —C(=O)—O—CH$_3$, —C(=O)—O—C$_2$H$_5$, and —C(=O)—O—C(CH$_3$)$_3$; or a phenyl or naphthyl group, which may in each case be substituted by 1, 2, 3, 4, or 5 substituents independently selected from the group consisting of F, Cl, Br, I, —CN, —CF$_3$, —SF$_5$, —OH, —O—CH$_3$, —O—C$_2$H$_5$, —O—CH(CH$_3$)$_2$, —O—C(CH$_3$)$_3$, —O—CH$_2$—CH$_2$—CH$_2$—CH$_3$, —O—CH$_2$—CH=CH$_2$, —NH$_2$, —NO$_2$, —O—CF$_3$, —O—CHF$_2$, —O—CH$_2$F, —S—CF$_3$, —S—CHF$_2$, —S—CH$_2$F, —SH, —S—CH$_3$, —S—C$_2$H$_5$, —S—CH(CH$_3$)$_2$, —S—C(CH$_3$)$_3$, —S—CH$_2$—CH$_2$—CH$_2$—CH$_3$, methyl, ethyl, n-propyl, isopropyl, n-butyl, sec-butyl, isobutyl, tert-butyl, and phenyl;

$R^{17}$ and $R^{21}$ each independently represent a phenyl or naphthyl group, which may in each case be substituted by 1, 2, 3, 4, or 5 substituents independently selected from the group consisting of F, Cl, Br, I, —CN, —CF$_3$, —SF$_5$, —OH, —O—CH$_3$, —O—C$_2$H$_5$, —O—CH(CH$_3$)$_2$, —O—C(CH$_3$)$_3$, —O—CH$_2$—CH$_2$—CH$_2$—CH$_3$, —O—CH$_2$—CH=CH$_2$, —NH$_2$, —NO$_2$, —O—CF$_3$, —O—CHF$_2$, —O—CH$_2$F, —S—CF$_3$, —S—CHF$_2$, —S—CH$_2$F, —SH, —S—CH$_3$, —S—C$_2$H$_5$, —S—CH(CH$_3$)$_2$, —S—C(CH$_3$)$_3$, —S—CH$_2$—CH$_2$—CH$_2$—CH$_3$, methyl, ethyl, n-propyl, isopropyl, n-butyl, sec-butyl, isobutyl, and tert-butyl;

$R^{22}$ represents
 a phenyl group, which phenyl group is in each case substituted by 1, 2, 3, 4, or 5 substituents independently selected from the group consisting of F, Cl, Br, I, —CN, —CF$_3$, —SF$_5$, —OH, —O—CH$_3$, —O—C$_2$H$_5$, —O—CH(CH$_3$)$_2$, —O—C(CH$_3$)$_3$, —O—CH$_2$—CH$_2$—CH$_2$—CH$_3$, —O—CH$_2$—CH=CH$_2$, —NH$_2$, —NO$_2$, —O—CF$_3$, —O—CHF$_2$, —O—CH$_2$F, —S—CF$_3$, —S—CHF$_2$, —S—CH$_2$F, —SH, —S—CH$_3$, —S—C$_2$H$_5$, —S—CH(CH$_3$)$_2$, —S—C(CH$_3$)$_3$, —S—CH$_2$—CH$_2$—CH$_2$—CH$_3$, methyl, ethyl, n-propyl, isopropyl, n-butyl, sec-butyl, isobutyl, tert-butyl, —C(=O)—OH, —C(=O)—O—CH$_3$, —C(=O)—O—C$_2$H$_5$, —C(=O)—O—C(CH$_3$)$_3$, —O—C(=O)—CH$_3$, —O—C(=O)—C$_2$H$_5$, —N(CH$_3$)$_2$, —N(C$_2$H$_5$)$_2$, —N(H)(CH$_3$), —N(H)(C$_2$H$_5$), —NH—C(=O)—O—CH$_3$;
 a naphthyl group, which naphthyl group may be substituted by 1, 2, 3, 4, or 5 substituents selected independently of the group consisting of F, Cl, Br, I, —CN, —CF$_3$, —SF$_5$, —OH, —O—CH$_3$, —O—C$_2$H$_5$, —O—CH(CH$_3$)$_2$, —O—C(CH$_3$)$_3$, —O—CH$_2$—CH$_2$—CH$_2$—CH$_3$, —O—CH$_2$—CH=CH$_2$, —NH$_2$, —NO$_2$, —O—CF$_3$, —O—CHF$_2$, —O—CH$_2$F, —S—CF$_3$, —S—CHF$_2$, —S—CH$_2$F, —SH, —S—CH$_3$, —S—C$_2$H$_5$, —S—CH(CH$_3$)$_2$, —S—C(CH$_3$)$_3$, —S—CH$_2$—CH$_2$—CH$_2$—CH$_3$, methyl, ethyl, n-propyl, isopropyl, n-butyl, sec-butyl, isobutyl, and tert-butyl;
 a heteroaryl group selected from the group consisting of thiophenyl, furanyl, pyrrolyl, pyrazolyl, pyranyl, triazolyl, pyridynyl, imidazolyl, indolyl, isoindolyl, benzo[b]furanyl, benzo[b]thiophenyl, thiazolyl, thiadiazolyl, oxazolyl, isoxazolyl, pyridazynyl, pyrazynyl, pyrimidynyl, indazolyl, quinazolynyl, and quinolynyl, which heteroaryl group may in each case be substituted by 1, 2, 3, 4, or 5 substituents independently selected from the group consisting of F, Cl, Br, I, —CN, —CF$_3$, —SF$_5$, —OH, —O—CH$_3$, —O—C$_2$H$_5$, —O—CH(CH$_3$)$_2$, —O—C(CH$_3$)$_3$, —O—CH$_2$—CH$_2$—CH$_2$—CH$_3$, —O—CH$_2$—CH=CH$_2$, —NH$_2$, —NO$_2$, —O—CF$_3$, —O—CHF$_2$, —O—CH$_2$F, —S—CF$_3$, —S—CHF$_2$, —S—CH$_2$F, —SH, —S—CH$_3$, —S—C$_2$H$_5$, —S—CH(CH$_3$)$_2$, —S—C(CH$_3$)$_3$, —S—CH$_2$—CH$_2$—CH$_2$—CH$_3$, methyl, ethyl, n-propyl, isopropyl, n-butyl, sec-butyl, isobutyl, tert-butyl, —C(=O)—OH, —C(=O)—O—CH$_3$, —C(=O)—O—C$_2$H$_5$, and —C(=O)—O—C(CH$_3$)$_3$, and $R^{23}$ is selected from the group consisting of phenyl, naphthyl, thiophenyl, furanyl, pyrrolyl, pyrazolyl, pyranyl, triazolyl, pyridynyl, imidazolyl, indolyl, isoindolyl, benzo[b]furanyl, benzo[b]thiophenyl, thiazolyl, thiadiazolyl, oxazolyl, isoxazolyl, pyridazynyl, pyrazynyl, pyrimidynyl, indazolyl, quinazolynyl, and quinolynyl, each of which may be substituted by 1, 2, 3, 4, or 5 substituents independently selected from the group consisting of F, Cl, Br, I, —CN, —CF$_3$, —SF$_5$, —OH, —O—CH$_3$, —O—C$_2$H$_5$, —O—CHs(CH$_3$)$_2$, —O—C(CH$_3$)$_3$, —O—CH$_2$—CH$_2$—CH$_2$—CH$_3$, —O—CH$_2$—CH=CH$_2$, —NH$_2$, —NO$_2$, —O—CF$_3$, —O—CHF$_2$, —O—CH$_2$F, —S—CF$_3$, —S—CHF$_2$, —S—CH$_2$F, —SH, —S—CH$_3$, —S—C$_2$H$_5$, —S—CH(CH$_3$)$_2$, —S—C(CH$_3$)$_3$, —S—CH$_2$—CH$_2$—CH$_2$—CH$_3$, methyl, ethyl, n-propyl, isopropyl, n-butyl, sec-butyl, isobutyl, tert-butyl, —C(=O)—OH, —C(=O)—O—CH$_3$, —C(=O)—O—C$_2$H$_5$, and —C(=O)—O—C(CH$_3$)$_3$.

13. The compound of claim 11, wherein,

I)
$R^1$ represents
 —(CH$_2$)$_m$—O—C(=O)—R$^5$ where m is 1, 2, 3, or 4;
 —(CH$_2$)$_n$—C(=O)—O—R$^6$, where n is 1, 2 or 3;
 —(CH$_2$)—R$^{22}$; or
 —(CH$_2$)—(CH$_2$)—O—R$^{23}$, —(CH$_2$)—(CH$_2$)—S—R$^{23}$, —(CH$_2$)—(CH$_2$)—NH—R$^{23}$, or —(CH$_2$)—(CH$_2$)—N(CH$_3$)—R$^{23}$;

$R^2$ represents
 hydrogen;
 —(CH$_2$)—R$^{24}$, —(CH$_2$)—(CH$_2$)—R$^{24}$, —(CH$_2$)—(CH$_2$)—O—R$^{24}$, —(CH$_2$)—(CH$_2$)—S—R$^{24}$, or —(CH$_2$)—(CH$_2$)—(CH$_2$)—R$^{24}$; or
 an alkyl group which is selected from the group consisting of methyl, ethyl, n-propyl, isopropyl, n-butyl, sec-butyl, isobutyl, tert-butyl, n-pentyl, and sec-pentyl;

$R^3$ represents a —C(=O)—R$^4$ group; and $R^4$ represents
 —(CHR$^{10}$)—O—R$^{11}$, —(CHR$^{10}$)—S—R$^{11}$, —(CHR$^{10}$)—O—(CH$_2$)—R$^{11}$, —(CHR$^{10}$)—S—(CH$_2$)—R$^{11}$, —(CHR$^{10}$)—(CH$_2$)—(CH$_2$)—O—R$^{11}$, —(CHR$^{10}$)—(CH$_2$)—(CH$_2$)—S—R$^{11}$, or —(CHR$^{10}$)—O—(CH$_2$)—(CH$_2$)—O—R$^{11}$;
 —(CR$^{12}$R$^{13}$)—C(=O)—O—R$^7$ or —(CR$^{12}$R$^{13}$)—(CH$_2$)—C(=O)—O—R$^7$;
 —(CR$^{14}$R$^{15}$)—O—C(=O)—R$^8$ or —(CR$^{14}$R$^{15}$)—(CH$_2$), and —O—C(=O)—R$^8$;
 —(CHR$^{16}$)—C(=O)—R$^9$;
 —CH[(CH$_2$)—O—(CH$_2$)—R$^{17}$]—[NH—C(=O)—O—R$^{18}$];
 —CHR$^{19}$R$^{20}$ or —(CH$_2$)—CHR$^{19}$R$^{20}$;
 —(CH=CH)—R$^{21}$; or
 is selected from the group consisting of methyl, ethyl, n-propyl, isopropyl, n-butyl, sec-butyl, isobutyl, tert-butyl, n-pentyl, 2-pentyl, 3-pentyl, —(CH$_2$)—(C(CH$_3$)$_3$), n-hexyl, 3-hexyl, —(CH$_2$)—(CH$_2$)—(C(CH$_3$)$_3$), n-heptyl, 3-heptyl, 4-heptyl, —(CH$_2$)—N(CH$_3$)$_2$, —(CH$_2$)—(CH$_2$)—N(CH$_3$)$_2$, 1-butenyl, 2-butenyl, and 3-butenyl; or
 is a (hetero)cycloaliphatic group selected from the group consisting of cyclopropyl, cyclobutyl, cyclopentyl, cyclohexyl, cycloheptyl, cyclopentenyl, cyclohexenyl, cycloheptenyl, adamantyl, and 7,7-dimethyl-3-oxo-2-oxa-bicyclo[2,2,1]heptyl, and the cycloaliphatic group may in each case be substituted by 1, 2, 3, 4, or 5 substituents independently selected from the group consisting of methyl, ethyl, and n-propyl; or is selected from the group consisting of phenyl, naphthyl, (1,3)-benzodioxolyl, (1,4)-benzodioxanyl, thiophenyl, furanyl, pyrazolyl, triazolyl, pyridynyl, imidazolyl, indolyl, thiazolyl, thiadiazolyl, oxazolyl, isoxazolyl, pyrimidynyl, oxadiazolyl, benzo[1,2,5]oxadiazolyl, and chromanyl, which may in each case be substituted by 1, 2, 3, 4, or 5 substituents independently selected from the group consisting of F, Cl, Br, I, —CN, —CF$_3$, —O—CH$_3$, —O—C$_2$H$_5$, —NO$_2$, —O—CF$_3$, —O—CHF$_2$, —O—CH$_2$F, —S—CF$_3$, —S—CHF$_2$, —S—CH$_2$F, —S—CH$_3$, —S—C$_2$H$_5$, —S—CH(CH$_3$)$_2$, —S—C(CH$_3$)$_3$, methyl, ethyl, n-propyl, isopropyl, n-butyl, sec-butyl, isobutyl, tert-butyl, —(CH$_2$)—O—C(=O)—CH$_3$, —(CH$_2$)—O—C(=O)—C$_2$H$_5$, —(CH$_2$)—O—C(=O)-phenyl, —N(CH$_3$)$_2$, —N(C$_2$H$_5$)$_2$, —NH—C(=O)—CH$_3$, —NH—C(=O)—C$_2$H$_5$, —S(=O)$_2$—NH$_2$, —O-phenyl, and phenyl, and the cyclic moiety of the groups —O—phenyl and phenyl may in each case be substituted by 1, 2, 3, 4, or 5 substituents independently selected from the group consisting of F, Cl, Br, methyl, ethyl, n-propyl, and isopropyl;

or II)

$R^1$ represents hydrogen; or is selected from the group consisting of methyl, ethyl, n-propyl, isopropyl, n-butyl, sec-butyl, isobutyl, tert-butyl, 1-propenyl, 2-propenyl, 1-butenyl, 2-butenyl, 3-butenyl, 2-methyl-2-butenyl, 1-propynyl, and 2-propynyl; or is an unsubstituted benzyl group;

$R^2$ represents hydrogen; or
—(CH$_2$)—R$^{24}$, —(CH$_2$)—(CH$_2$)—R$^{24}$, —(CH$_2$)—(CH$_2$)—O—R$^{24}$, —(CH$_2$)—(CH$_2$)—S—R$^{24}$, or —(CH$_2$)—(CH$_2$)—(CH$_2$)—R$^{24}$; or an alkyl group selected from the group consisting of methyl, ethyl, n-propyl, isopropyl, n-butyl, sec-butyl, isobutyl, tert-butyl, n-pentyl, and sec-pentyl;

$R^3$ represents a —C(=O)—R$^4$ group; and $R^4$ represents
—(CHR$^{10}$)—O—R$^{11}$, —(CHR$^{10}$)—S—R$^{11}$, —(CHR$^{10}$)—O—(CH$_2$)—R$^{11}$, —(CHR$^{10}$)—S—(CH$_2$)—R$^{11}$, —(CHR$^{10}$)—(CH$_2$)—(CH$_2$)—O—R$^{11}$, —(CHR$^{10}$)—(CH$_2$)—(CH$_2$)—S—R$^{11}$, or —(CHR$^{10}$)—O—(CH$_2$)—(CH$_2$)—O—R$^{11}$,
—(CR$^{12}$R$^{13}$)—C(=O)—O—R$^7$ or —(CR$^{12}$R$^{13}$)—(CH$_2$)—C(=O)—O—R$^7$;
—(CR$^{14}$R$^{15}$)—O—C(=O)—R$^8$ or —(CR$^{14}$R$^{15}$)—(CH$_2$), and —O—C(=O)—R$^8$;
—(CHR$^{16}$)—C(=O)—R$^9$;
—CH[(CH$_2$)—O—(CH$_2$)—R$^{17}$]—[NH—C(=O)—O—R$^{18}$];
—CHR$^{19}$R$^{20}$ or —(CH$_2$)—CHR$^{19}$R$^{20}$;
—(CH=CH)—R$^{21}$; or is selected from the group consisting of —(CH$_2$)—N(CH$_3$)$_2$, —(CH$_2$)—(CH$_2$)—N(CH$_3$)$_2$, 1-butenyl, 2-butenyl, and 3-butenyl; or is a (hetero)cycloaliphatic group selected from the group consisting of cyclopropyl, cyclobutyl, cyclopentyl, cyclohexyl, cycloheptyl, cyclopentenyl, cyclohexenyl, cycloheptenyl, adamantyl, and 7,7-dimethyl-3-oxo-2-oxa-bicyclo[2,2,1]heptyl, and the cycloaliphatic group may in each case be substituted by 1, 2, 3, 4, or 5 substituents selected from the group consisting of methyl, ethyl, and n-propyl; or is a phenyl group, which phenyl group is in each case substituted by 1, 2, 3, 4, or 5 substituents independently selected from the group consisting of —CN, —NO$_2$, —O—CF$_3$, —O—CHF$_2$, —O—CH$_2$F, —S—CF$_3$, —S—CHF$_2$, —S—CH$_2$F, —(CH$_2$)—O—C(=O)—CH$_3$, —(CH$_2$)—O—C(=O)—C$_2$H$_5$, —(CH$_2$)—O—C(=O)-phenyl, —N(CH$_3$)$_2$, —N(C$_2$H$_5$)$_2$, —N(H)(CH$_3$), —N(H)(C$_2$H$_5$), —NH—C(=O)—CH$_3$, —NH—C(=O)—C$_2$H$_5$, —S(=O)$_2$—NH$_2$, —S(=O)$_2$—NH—CH$_3$, —S(=O)$_2$—NH—C$_2$H$_5$, and phenyl, and the cyclic moiety of the groups —(CH$_2$)—O—C(=O)-phenyl and phenyl may in each case be substituted by 1, 2, 3, 4, or 5 substituents independently selected from the group consisting of F, Cl, Br, methyl, ethyl, n-propyl, isopropyl, n-butyl, sec-butyl, isobutyl, and tert-butyl, or is selected from the group consisting of 1,2,3,4,5-pentafluorophenyl, 1,2,3,4-tetrafluorophenyl, 4-methyl-3-nitrophenyl, 5-methyl-3-nitrophenyl, 6-methyl-3-nitrophenyl, and 2-methyl-3-nitrophenyl;

an unsubstituted naphthyl group;

an unsubstituted group selected from (1,3)-benzodioxolyl and (1,4)-benzodioxanyl; or is a heteroaryl group selected from the group consisting of thiophenyl, furanyl, pyrazolyl, triazolyl, pyridynyl, imidazolyl, indolyl, thiazolyl, thiadiazolyl, oxazolyl, isoxazolyl, pyrimidynyl, oxadiazolyl, benzo[1,2,5]oxadiazolyl, and chromanyl, which heteroaryl group may in each case be substituted by 1, 2, 3, 4, or 5 substituents independently selected from the group consisting of F, Cl, Br, I, —CN, —CF$_3$, —O—CH$_3$, —O—C$_2$H$_5$, —NO$_2$, —O—CF$_3$, —O—CHF$_2$, —O—CH$_2$F, —S—CF$_3$, —S—CHF$_2$, —S—CH$_2$F, —S—CH$_3$, —S—C$_2$H$_5$, —S—CH(CH$_3$)$_2$, —S—C(CH$_3$)$_3$, methyl, ethyl, n-propyl, isopropyl, n-butyl, sec-butyl, isobutyl, tert-butyl, —O-phenyl, and phenyl, and the cyclic moiety of the groups —O-phenyl and phenyl may in each case be substituted by 1, 2, 3, 4, or 5 substituents independently selected from the group consisting of F, Cl, Br, methyl, ethyl, n-propyl, and isopropyl;

or III)

$R^1$ represents
hydrogen;
is selected from the group consisting of methyl, ethyl, n-propyl, isopropyl, n-butyl, sec-butyl, isobutyl, tert-butyl, 1-propenyl, 2-propenyl, 1-butenyl, 2-butenyl, 3-butenyl, 2-methyl-2-butenyl, 1-propynyl, and 2-propynyl;
—(CH$_2$)$_m$—O—C(=O)—R$^5$, where m is 1, 2, 3, or 4;
—(CH$_2$)$_n$—C(=O)—O—R$^6$, where n is 1, 2 or 3;
—(CH$_2$)$_n$—C(=O)—O—R$^6$, where n is 1, 2 or 3;
an unsubstituted benzyl group;
—(CH$_2$)—R$^{22}$; or
—(CH$_2$)—(CH$_2$)—O—R$^{23}$, —(CH$_2$)—(CH$_2$)—S—R$^{23}$, —(CH$_2$)—(CH$_2$)—NH—R$^{23}$, or —(CH$_2$)—(CH$_2$)—N(CH$_3$)—R$^{23}$;

$R^2$ represents —(CH$_2$)—(CH$_2$)—S—R$^{24}$;

$R^3$ represents a —C(=O)—R$^4$ group; and $R^4$ represents
—(CHR$^{10}$)—O—R$^{11}$, —(CHR$^{10}$)—S—R$^{11}$, —(CHR$^{10}$)—O—(CH$_2$)—R$^{11}$, —(CHR$^{10}$)—S—(CH$_2$)—R$^{11}$, —(CHR$^{10}$)—(CH$_2$)—(CH$_2$)—O—R$^{11}$, —(CHR$^{10}$)—(CH$_2$)—(CH$_2$)—S—R$^{11}$, or —(CHR$^{10}$)—O—(CH$_2$)—(CH$_2$)—O—R$^{11}$;

—(CR$^{12}$R$^{13}$)—C(=O)—O—R$^7$ or —(CR$^{12}$R$^{13}$)—(CH$_2$)—C(=O)—O—R$^7$;
—(CR$^{14}$R$^{15}$)—O—C(=O)—R$^8$ or —(CR$^{14}$R$^{15}$)—(CH$_2$), and —O—C(=O)—R$^8$;
—(CHR$^{16}$)—C(=O)—R$^9$;
—CH[(CH$_2$)—O—(CH$_2$)—R$^{17}$]—[NH—C(=O)—O—R$^{18}$];
—CHR$^{19}$R$^{20}$ or —(CH$_2$)—CHR$^{19}$R$^{20}$;
—(CH=CH)—R$^{21}$; or is selected from the group consisting of methyl, ethyl, n-propyl, isopropyl, n-butyl, sec-butyl, isobutyl, tert-butyl, n-pentyl, 2-pentyl, 3-pentyl, —(CH$_2$)—(C(CH$_3$)$_3$), n-hexyl, 3-hexyl, —(CH$_2$)—(CH$_2$)—(C(CH$_3$)$_3$), n-heptyl, 3-heptyl, 4-heptyl, —(CH$_2$)—N(CH$_3$)$_2$, —(CH$_2$)—(CH$_2$)—N(CH$_3$)$_2$, 1-butenyl, 2-butenyl, and 3-butenyl; or is a (hetero)cycloaliphatic group selected from the group consisting of cyclopropyl, cyclobutyl, cyclopentyl, cyclohexyl, cycloheptyl, cyclopentenyl, cyclohexenyl, cycloheptenyl, adamantyl, and 7,7-dimethyl-3-oxo-2-oxa-bicyclo[2,2,1]heptyl, and the cycloaliphatic group may in each case be substituted by 1, 2, 3, 4, or 5 substituents methyl, ethyl, and n-propyl; or is selected from the group consisting of phenyl, naphthyl, (1,3)-benzodioxolyl, (1,4)-benzodioxanyl, thiophenyl, furanyl, pyrazolyl, triazolyl, pyridynyl, imidazolyl, indolyl, thiazolyl, thiadiazolyl, oxazolyl, isoxazolyl, pyrimidynyl, oxadiazolyl, benzo[1,2,5]oxadiazolyl, and chromanyl, and may in each case be substituted by 1, 2, 3, 4, or 5 substituents independently selected from the group consisting of F, Cl, Br, I, —CN, —CF$_3$, —O—CH$_3$, —O—C$_2$H$_5$, —NO$_2$, —O—CF$_3$, —O—CHF$_2$, —O—CH$_2$F, —S—CF$_3$, —S—CHF$_2$, —S—CH$_2$F, —S—CH$_3$, —S—C$_2$H$_5$, —S—CH(CH$_3$)$_2$, —S—C(CH$_3$)$_3$, methyl, ethyl, n-propyl, isopropyl, n-butyl, sec-butyl, isobutyl, tert-butyl, —(CH$_2$)—O—C(=O)—CH$_3$, —(CH$_2$)—O—C(=O)—C$_2$H$_5$, —(CH$_2$)—O—C(=O)-phenyl, —N(CH$_3$)$_2$, —N(C$_2$H$_5$)$_2$, —NH—C(=O)—CH$_3$, —NH—C(=O)—C$_2$H$_5$, —S(=O)$_2$—NH$_2$, —O-phenyl, and phenyl, and the cyclic moiety of the groups —O-phenyl and phenyl may in each case be substituted by 1, 2, 3, 4, or 5 substituents independently selected from the group consisting of F, Cl, Br, methyl, ethyl, n-propyl, and isopropyl;

and in each case, if present, in the aforementioned groups I) II) and III)

R$^5$ represents a methyl or ethyl group;
R$^6$ represents a methyl or ethyl group;
R$^7$ represents hydrogen; or a methyl or ethyl group;
R$^8$ represents a methyl or ethyl group or an unsubstituted phenyl group;
R$^9$ represents a methyl or ethyl group;
R$^{10}$ represents a hydrogen group; or a methyl or ethyl group;
R$^{11}$ represents methyl or ethyl group; a phenyl group, which may be substituted by 1, 2, 3, 4, or 5 substituents independently selected from the group consisting of F, Cl, Br, —O—CH$_3$, —O—C$_2$H$_5$, —O—CH(CH$_3$)$_2$, —O—C(CH$_3$)$_3$, and phenyl;
R$^{12}$ represents hydrogen; or a methyl group;
R$^{13}$ represents hydrogen; or a methyl group;
R$^{14}$ represents hydrogen; a methyl or ethyl group; or an unsubstituted phenyl group;
R$^{15}$ represents hydrogen; or a methyl group;

R$^{16}$ a methyl or ethyl group; or an unsubstituted phenyl group;
R$^{17}$ represents an unsubstituted phenyl group;
R$^{18}$ represents an alkyl group which is selected from the group consisting of methyl, ethyl, n-propyl, isopropyl, n-butyl, isobutyl, and tert-butyl;
R$^{19}$ represents hydrogen; a methyl or ethyl group; or an unsubstituted phenyl group;
R$^{20}$ is selected from the group consisting of cyclopentyl, cyclohexyl, and hydantoin; or is a phenyl group, which may be substituted by 1, 2, 3, 4, or 5 substituents independently selected from the group consisting of F, Cl, Br, —O—CH$_3$, —O—C$_2$H$_5$, —O—CH(CH$_3$)$_2$, —O—C(CH$_3$)$_3$, and phenyl;
R$^{21}$ represents a phenyl group, which may be substituted by 1, 2, 3, 4, or 5 substituents independently selected from the group consisting of F, Cl, Br, and CF$_3$;
R$^{22}$ represents a phenyl group, which phenyl group is in each case substituted by 1, 2, 3, 4, or 5 substituents independently selected from the group consisting of F, Cl, Br, —CN, —CF$_3$, —NO$_2$, —O—CF$_3$, —S—CF$_3$, methyl, ethyl, n-propyl, isopropyl, n-butyl, sec-butyl, isobutyl, tert-butyl, —C(=O)—OH, and —C(=O)—O—CH$_3$—C(=O)—O—C$_2$H$_5$; or is an unsubstituted naphthyl group;
R$^{23}$ represents an unsubstituted phenyl group; and
R$^{24}$ represents a methyl or ethyl group; or an unsubstituted phenyl group.

14. The compound of claim 1, selected from the group consisting of
(1) 3-(S)-Benzyl-8-(2-ethylbutyryl)-1,4,8-triazaspiro[4,5]decan-2-one,
(2) 8-(2,4-Dimethoxybenzoyl)-3-(S)-(2-methylsulfanylethyl)-1,4,8-triazaspiro[4,5]decan-2-one,
(3) 3-(S,R)-Benzyl-8-(2-ethylbutyryl)-1,4,8-triazaspiro[4,5]decan-2-one,
(4) 8-Acetyl-3-(S)-benzyl-1,4,8-triazaspiro[4,5]decan-2-one,
(5) 3-(S,R)-Benzyl-8-(4-chlorobenzoyl)-1,4,8-triazaspiro[4,5]decan-2-one,
(6) 3-(S)-Benzyl-8-(4-chlorobenzoyl)-1,4,8-triazaspiro[4,5]decan-2-one,
(7) 8-(2-ethylbutyryl)-3-(S)-(2-methylsulfanylethyl)-1,4,8-triazaspiro[4,5]decan-2-one,
(8) 1,3-(S)-Dibenzyl-8-(2-ethylbutyryl)-1,4,8-triazaspiro[4,5]decan-2-one,
(9) 8-Acetyl-1,3-(S)-dibenzyl-1,4,8-triazaspiro[4,5]decan-2-one,
(10) 3-(S,R)-Benzyl-8-(4-chlorobenzoyl)-1-(4-methoxybenzyl)-1,4,8-triazaspiro[4,5]decan-2-one,
(11) 3-(S,R)-Benzyl-8-(4-chlorobenzoyl)-1-(4-fluorobenzyl)-1,4,8-triazaspiro[4,5]decan-2-one,
(12) 1,3-(S,R)-Dibenzyl-8-(4-chlorobenzoyl)-1,4,8-triazaspiro[4,5]decan-2-one,
(13) 3-(S,R)-Benzyl-8-(2-ethylbutyryl)-1-(4-methoxybenzyl)-1,4,8-triazaspiro[4,5]decan-2-one,
(14) 3-(S,R)-Benzyl-8-(2-ethylbutyryl)-1-(4-fluorobenzyl)-1,4,8-triazaspiro[4,5]decan-2-one,
(15) 1,3-(S,R)-Dibenzyl-8-(2-ethylbutyryl)-1,4,8-triazaspiro[4,5]decan-2-one,
(16) 1-Benzyl-8-(2-ethylbutyryl)-3-(S)-(2-methylsulfanylethyl)-1,4,8-triazaspiro[4,5]decan-2-one,
(17) 1,3-(S)-Dibenzyl-8-(4-chlorobenzoyl)-1,4,8-triazaspiro[4,5]decan-2-one,
(18) 1,3-(S)-Dibenzyl-8-(2-ethylbutyryl)-1,4,8-triazaspiro[4,5]decan-2-one,

(19) 8-Acetyl-1,3-(S)-dibenzyl-1,4,8-triazaspiro[4,5]decan-2-one,
(20) 3-(S,R)-Benzyl-8-(4-chlorobenzoyl)-1-(4-methoxybenzyl)-1,4,8-triazaspiro[4,5]decan-2-one,
(21) 3-(S,R)-Benzyl-8-(4-chlorobenzoyl)-1-(4-fluorobenzyl)-1,4,8-triazaspiro[4,5]decan-2-one,
(22) 1,3-(S,R)-Dibenzyl-8-(4-chlorobenzoyl)-1,4,8-triazaspiro[4,5]decan-2-one,
(23) 3-(S,R)-Benzyl-8-(2-ethylbutyryl)-1-(4-methoxybenzyl)-1,4,8-triazaspiro[4,5]decan-2-one,
(24) 3-(S,R)-Benzyl-8-(2-ethylbutyryl)-1-(4-fluorobenzyl)-1,4,8-triazaspiro[4,5]decan-2-one,
(25) 1,3-(S,R)-Dibenzyl-8-(2-ethylbutyryl)-1,4,8-triazaspiro[4,5]decan-2-one,
(26) 1-Benzyl-8-(2-ethylbutyryl)-3-(S)-(2-methylsulfanylethyl)-1,4,8-triazaspiro[4,5]decan-2-one,
(27) 1,3-(S)-Dibenzyl-8-(4-chlorobenzoyl)-1,4,8-triazaspiro[4,5]decan-2-one,
(28) 1-Benzyl-8-(2,4-Dimethoxybenzoyl)-3-(S)-(2-methylsulfanylethyl)-1,4,8-triazaspiro[4,5]decan-2-one,
(29) 1,3-(S)-Dibenzyl-1,4,8-triazaspiro[4,5]decan-2-one,
(30) 1-Benzyl-3-(S)-(2-methylsulfanylethyl)-1,4,8-triazaspiro[4,5]decan-2-one,
(31) 1,3-(S)-Dibenzyl-8-butynyl-1,4,8-triazaspiro[4,5]decan-2-one,
(32) 1,3-(S)-Dibenzyl-8-(3-fluoro-4-trifluoromethylbenzyl)-1,4,8-triazaspiro[4,5]decan-2-one,
(33) 1,3-(S)-Dibenzyl-8-(2,3-difluorobenzoyl)-1,4,8-triazaspiro[4,5]decan-2-one,
(34) 1,3-(S)-Dibenzyl-8-[2-(4-chlorophenoxy)-acetyl]-1,4,8-triazaspiro[4,5]decan-2-one,
(35) 1,3-(S)-Dibenzyl-8-diphenylacetyl-1,4,8-triazaspiro[4,5]decan-2-one,
(36) 1,3-(S)-Dibenzyl-8-(2-phenoxyacetyl)-1,4,8-triazaspiro[4,5]decan-2-one,
(37) 1,3-(S)-Dibenzyl-8-(3-phenylpropionyl)-1,4,8-triazaspiro[4,5]decan-2-one,
(38) 1,3-(S)-Dibenzyl-8-(naphthalin-2-carbonyl)-1,4,8-triazaspiro[4,5]decan-2-one,
(39) 1,3-(S)-Dibenzyl-8-(furan-2-carbonyl)-1,4,8-triazaspiro[4,5]decan-2-one,
(40) 1,3-(S)-Dibenzyl-8-(3-methoxybenzoyl)-1,4,8-triazaspiro[4,5]decan-2-one,
(41) 1,3-(S)-Dibenzyl-8-(4-fluorobenzoyl)-1,4,8-triazaspiro[4,5]decan-2-one,
(42) 1-Benzyl-8-(4-fluorobenzoyl)-3-(S)-(2-methylsulfanylethyl)-1,4,8-triazaspiro[4,5]decan-2-one,
(43) 1,3-(S)-Dibenzyl-8-butyryl-1,4,8-triazaspiro[4,5]decan-2-one,
(44) 1,3-(S)-Dibenzyl-8-(3-fluoro-4-trifluoromethylbenzoyl)-1,4,8-triazaspiro[4,5]decan-2-one,
(45) 1,3-(S)-Dibenzyl-8-(2,3-difluorobenzoyl)-1,4,8-triazaspiro[4,5]decan-2-one,
(46) 1,3-(S)-Dibenzyl-8-[2-(4-chlorophenoxy)-acetyl]-1,4,8-triazaspiro[4,5]decan-2-one,
(47) 1,3-(S)-Dibenzyl-8-diphenylacetyl-1,4,8-triazaspiro[4,5]decan-2-one,
(48) 1,3-(S)-Dibenzyl-8-(2-phenoxyacetyl)-1,4,8-triazaspiro[4,5]decan-2-one,
(49) 1,3-(S)-Dibenzyl-8-(3-phenylpropionyl)-1,4,8-triazaspiro[4,5]decan-2-one,
(50) 1,3-(S)-Dibenzyl-8-(naphthalin-2-carbonyl)-1,4,8-triazaspiro[4,5]decan-2-one,
(51) 1,3-(S)-Dibenzyl-8-(furan-2-carbonyl)-1,4,8-triazaspiro[4,5]decan-2-one,
(52) 1,3-(S)-Dibenzyl-8-(3-methoxybenzoyl)-1,4,8-triazaspiro[4,5]decan-2-one,
(53) 1,3-(S)-Dibenzyl-8-(4-fluorobenzoyl)-1,4,8-triazaspiro[4,5]decan-2-one,
(54) 1-Benzyl-8-(4-fluorobenzoyl)-3-(S)-(2-methylsulfanylethyl)-1,4,8-triazaspiro[4,5]decan-2-one,
(55) N-[4-(3-Isobutyl-2-oxo-1-prop-2-ynyl-1,4,8-triazaspiro[4,5]decan-8-carbonyl)-phenyl]acetamide,
(56) 1-(2-Phenoxyethyl)-8-(thiophene-2-carbonyl)-1,4,8-triazaspiro[4,5]decan-2-one,
(57) 2-(2-Oxo-8-pent-4-enoyl-1,4,8-triazaspiro[4,5]dec-1-ylmethyl)-benzonitrile,
(58) 8-(2,4-Dimethoxybenzoyl)-1-methyl-3-(2-methylsulfanylethyl)-1,4,8-triazaspiro[4,5]decan-2-one,
(59) 2-[8-(2-Ethylbutyryl)-2-oxo-1,4,8-triazaspiro[4,5]dec-1-ylmethyl]-benzonitrile,
(60) 4-(2-Isobutyl-3-oxo-1,4,8-triazaspiro[4,5]decan-8-carbonyl)-benzonitrile,
(61) 8-(6-Chloropyridin-3-carbonyl)-3-isobutyl-1,4,8-triazaspiro[4,5]decan-2-one,
(62) 2-[8-(2-Methylpentanoyl)-2-oxo-1,4,8-triazaspiro[4,5]dec-1-ylmethyl]-benzonitrile,
(63) 1-Benzyl-8-(biphenyl-4-carbonyl)-1,4,8-triazaspiro[4,5]decan-2-one,
(64) 3-Isobutyl-8-(5-methylisoxazole-3-carbonyl)-1,4,8-triazaspiro[4,5]decan-2-one,
(65) Ethyl 3-oxo-3-[2-oxo-1-(2-phenoxyethyl)-1,4,8-triazaspiro[4,5]dec-8-yl]-propionate,
(66) 8-(2-Chlorobenzoyl)-3-isopropyl-1,4,8-triazaspiro[4,5]decan-2-one,
(67) 8-Cyclopentanecarbonyl-3-isopropyl-1,4,8-triazaspiro[4,5]decan-2-one,
(68) 8-(Furan-2-carbonyl)-1-methyl-3-(2-methylsulfanylethyl)-1,4,8-triazaspiro[4,5]decan-2-one,
(69) 3-Benzyl-8-(2-ethylsulfanylpyridin-3-carbonyl)-1-methyl-1,4,8-triazaspiro[4,5]decan-2-one,
(70) 3-Benzyl-8-(4-chlorobenzoyl)-1,4,8-triazaspiro[4,5]decan-2-one,
(71) 8-(2-Benzyloxyacetyl)-3-isobutyl-1,4,8-triazaspiro[4,5]decan-2-one,
(72) 3-Benzyl-8-(2-methoxyacetyl)-1-prop-2-ynyl-1,4,8-triazaspiro[4,5]decan-2-one,
(73) 8-(5-tert-Butyl-2-methyl-2H-pyrazole-3-carbonyl)-3-isobutyl-1,4,8-triazaspiro[4,5]decan-2-one,
(74) 2-{8-[3-(2-chloro-6-fluorophenyl)-5-methylisoxazole-4-carbonyl]-2-oxo-1,4,8-triazaspiro[4,5]dec-1-ylmethyl}-benzonitrile,
(75) 3-Benzyl-8-(2-chlorobenzoyl)-1,4,8-triazaspiro[4,5]decan-2-one,
(76) 3-Benzyl-8-(3-dimethylaminobenzoyl)-1-methyl-1,4,8-triazaspiro[4,5]decan-2-one,
(77) 8-(3-Methylbenzoyl)-1-(2-phenoxyethyl)-1,4,8-triazaspiro[4,5]decan-2-one,
(78) 3-Isopropyl-1-(3-methylbut-2-enyl)-8-(pyridin-4-carbonyl)-1,4,8-triazaspiro[4,5]decan-2-one,
(79) 1-Benzyl-8-(4-methyl[1,2,3]thiadiazole-5-carbonyl)-1,4,8-triazaspiro[4,5]decan-2-one,
(80) 2-{8-[3-(2-chlorophenyl)-acryloyl]-2-oxo-1,4,8-triazaspiro[4,5]dec-1-ylmethyl}-benzonitrile,
(81) 8-(3-Chlorobenzoyl)-3-isobutyl-1,4,8-triazaspiro[4,5]decan-2-one,
(82) Ethyl 2-(2-benzyl-3-oxo-1,4,8-triazaspiro[4,5]dec-8-yl)-2-oxo-1-phenylacetate,
(83) 8-(3,5-Dimethoxybenzoyl)-3-isobutyl-1,4,8-triazaspiro[4,5]decan-2-one,
(84) 3-Benzyl-8-(isoxazole-5-carbonyl)-1,4,8-triazaspiro[4,5]decan-2-one,
(85) 8-(3-Chlorothiophene-2-carbonyl)-3-isobutyl-1,4,8-triazaspiro[4,5]decan-2-one,

(86) 3-Isopropyl-8-pentafluorobenzoyl-1,4,8-triazaspiro[4,5]decan-2-one,
(87) 8-(2,5-Dimethylfuran-3-carbonyl)-3-isobutyl-1,4,8-triazaspiro[4,5]decan-2-one,
(88) 1-Butyl-8-[2-(3,4-dimethoxyphenyl)-acetyl]-3-(2-methylsulfanylethyl)-1,4,8-triazaspiro[4,5]decan-2-one,
(89) 1-Benzyl-3-isopropyl-8-(pyridin-4-carbonyl)-1,4,8-triazaspiro[4,5]decan-2-one,
(90) 1,3-Dibenzyl-8-(3-dimethylaminobenzoyl)-1,4,8-triazaspiro[4,5]decan-2-one,
(91) 5-{2-[1-(4-Fluorobenzyl)-3-(2-methylsulfanylethyl)-2-oxo-1,4,8-triazaspiro[4,5]dec-8-yl]-2-oxoethyl}-imidazolidine-2,4-dione,
(92) 8-(Biphenyl-4-carbonyl)-1-(fluorobenzyl)-3-isobutyl-1,4,8-triazaspiro[4,5]decan-2-one,
(93) 2-[2-Oxo-8-(2-propylpentanoyl)-1,4,8-triazaspiro[4,5]dec-1-ylmethyl]-benzonitrile,
(94) 2-[8-(Furan-2-carbonyl)-3-isopropyl-2-oxo-1,4,8-triazaspiro[4,5]dec-1-ylmethyl]-benzonitrile,
(95) 8-[2-(4-Chlorophenoxy)-acetyl]-3-isobutyl-1-prop-2-ynyl-1,4,8-triazaspiro[4,5]decan-2-one,
(96) 1,3-Dibenzyl-8-(4-bromobenzoyl)-1,4,8-triazaspiro[4,5]decan-2-one,
(97) 8-(3-Difluoromethylsulfanylbenzoyl)-3-isobutyl-1,4,8-triazaspiro[4,5]decan-2-one,
(98) 8-(2,3-Dimethylbenzoyl)-3-isopropyl-1,4,8-triazaspiro[4,5]decan-2-one,
(99) 3-Benzyl-8-(2,3-dimethylbenzoyl)-1,4,8-triazaspiro[4,5]decan-2-one,
(100) 1-(4-Fluorobenzyl)-3-(2-methylsulfanylethyl)-8-(pyridin-2-carbonyl)-1,4,8-triazaspiro[4,5]decan-2-one,
(101) 3-Benzyl-8-(3,3-dimethylbutyryl)-1,4,8-triazaspiro[4,5]decan-2-one,
(102) 2-[8-(3-Dimethylaminobenzoyl)-3-isobutyl-2-oxo-1,4,8-triazaspiro[4,5]dec-1-ylmethyl]-benzonitrile,
(103) 3-[8-(2-Methoxyacetyl)-3-(2-methylsulfanylethyl)-2-oxo-1,4,8-triazaspiro[4,5]dec-1-ylmethyl]-benzonitrile,
(104) Ethyl 2-(3-benzyl-1-methyl-2-oxo-1,4,8-triazaspiro[4,5]dec-8-yl)-2-oxo-1-phenylacetate,
(105) 2-[8-[2-(2-Methoxyethoxy)-acetyl]-3-(2-methylsulfanylethyl)-2-oxo-1,4,8-triazaspiro[4,5]dec-1-ylmethyl]-benzonitrile,
(106) 3-Benzyl-8-[3-(2-chloro-6-fluorophenyl)-5-methylisoxazole-4-carbonyl]-1,4,8-triazaspiro[4,5]decan-2-one,
(107) 8-(2-Chloro-6-fluorobenzoyl)-3-isopropyl-1,4,8-triazaspiro[4,5]decan-2-one,
(108) 1-Methyl-3-(2-methylsulfanylethyl)-8-(2-phenoxyacetyl)-1,4,8-triazaspiro[4,5]decan-2-one,
(109) 8-(2-Chloropyridin-3-carbonyl)-1-(4-fluorobenzyl)-3-isobutyl-1,4,8-triazaspiro[4,5]decan-2-one,
(110) 8-(2-Ethylbutyryl)-1-methyl-3-(2-methylsulfanylethyl)-1,4,8-triazaspiro[4,5]decan-2-one,
(111) 1-Methyl-3-(2-methylsulfanylethyl)-8-(2-phenoxypyridin-3-carbonyl)-1,4,8-triazaspiro[4,5]decan-2-one,
(112) 8-(3-Fluorobenzoyl)-1-methyl-3-(2-methylsulfanylethyl)-1,4,8-triazaspiro[4,5]decan-2-one,
(113) 3-Benzyl-8-(naphthalin-2-carbonyl)-1,4,8-triazaspiro[4,5]decan-2-one,
(114) 8-Cyclohexanecarbonyl-1-(2-phenoxyethyl)-1,4,8-triazaspiro[4,5]decan-2-one,
(115) 8-(2-Phenoxyacetyl)-1-(2-phenoxyethyl)-1,4,8-triazaspiro[4,5]decan-2-one,
(116) 4-[1-Butyl-3-(2-methylsulfanylethyl)-2-oxo-1,4,8-triazaspiro[4,5]decan-8-carbonyl]-benzonitrile,
(117) 3-Benzyl-8-(3,3-dimethylbutyryl)-1-methyl-1,4,8-triazaspiro[4,5]decan-2-one,
(118) 3-Benzyl-8-(4-propylbenzoyl)-1,4,8-triazaspiro[4,5]decan-2-one,
(119) 3-Isopropyl-8-(2-phenoxypropionyl)-1,4,8-triazaspiro[4,5]decan-2-one,
(120) 1-Butyl-8-hexanoyl-3-isopropyl-1,4,8-triazaspiro[4,5]decan-2-one,
(121) 8-(4-Bromo-3-methylbenzoyl)-3-isopropyl-1,4,8-triazaspiro[4,5]decan-2-one,
(122) 8-[3-(2-Chloro-6-fluorophenyl)-5-methylisoxazole-4-carbonyl]-3-isopropyl-1-(2-phenoxyethyl)-1,4,8-triazaspiro[4,5]decan-2-one,
(123) 1-(2-Fluorobenzyl)-3-isobutyl-8-(3-methylbenzoyl)-1,4,8-triazaspiro[4,5]decan-2-one,
(124) 8-(2-Ethylhexanoyl)-1-(2-phenoxyethyl)-1,4,8-triazaspiro[4,5]decan-2-one,
(125) 3-Benzyl-8-(3,4-difluorobenzoyl)-1,4,8-triazaspiro[4,5]decan-2-one,
(126) 3-Benzyl-8-(4-ethoxybenzoyl)-1-methyl-1,4,8-triazaspiro[4,5]decan-2-one,
(127) 1-Benzyl-8-(6-chloropyridin-3-carbonyl)-1,4,8-triazaspiro[4,5]decan-2-one,
(128) 8-(3-Dimethylaminobenzoyl)-1-(3,5-dimethylbenzyl)-3-(2-methylsulfanylethyl)-1,4,8-triazaspiro[4,5]decan-2-one,
(129) 3-[8-(Benzo[1,3]dioxol-5-carbonyl)-3-(2-methylsulfanylethyl)-2-oxo-1,4,8-triazaspiro[4,5]dec-1-ylmethyl]-benzonitrile,
(130) 3-Benzyl-1-methyl-8-pent-4-enoyl-1,4,8-triazaspiro[4,5]decan-2-one,
(131) 8-(4-Ethoxybenzoyl)-1-methyl-3-(2-methylsulfanylethyl)-1,4,8-triazaspiro[4,5]decan-2-one,
(132) 3-Benzyl-8-(2-benzyloxyacetyl)-1-methyl-1,4,8-triazaspiro[4,5]decan-2-one,
(133) 8-(3,4-Difluorobenzoyl)-1-(2-phenoxyethyl)-1,4,8-triazaspiro[4,5]decan-2-one,
(134) 3-Benzyl-1-methyl-8-(2-methylsulfanylpyridin-3-carbonyl)-1,4,8-triazaspiro[4,5]decan-2-one,
(135) 1-Butyl-8-(4-methoxybenzoyl)-3-(2-methylsulfanylethyl)-1,4,8-triazaspiro[4,5]decan-2-one,
(136) 1,3-Dibenzyl-8-(2-ethylsulfanylpyridin-3-carbonyl)-1,4,8-triazaspiro[4,5]decan-2-one,
(137) 3-Benzyl-8-(3-difluoromethylsulfanylbenzoyl)-1,4,8-triazaspiro[4,5]decan-2-one,
(138) 1-(4-Fluorobenzyl)-8-(furan-2-carbonyl)-3-(2-methylsulfanylethyl)-1,4,8-triazaspiro[4,5]decan-2-one,
(139) 3-Benzyl-8-(3-fluoro-4-methylbenzoyl)-1-methyl-1,4,8-triazaspiro[4,5]decan-2-one,
(140) 8-[3-(2-Chloro-6-fluorophenyl)-5-methylisoxazole-4-carbonyl]-3-isopropyl-1,4,8-triazaspiro[4,5]decan-2-one,
(141) 1-Butyl-8-(6-Chloro-2H-chroman-3-carbonyl)-3-(2-methylsulfanylethyl)-1,4,8-triazaspiro[4,5]decan-2-one,
(142) 3-[8-(3-Methoxybenzoyl)-3-(2-methylsulfanylethyl)-2-oxo-1,4,8-triazaspiro[4,5]dec-1-ylmethyl]-benzonitrile,
(143) 8-Cyclobutanecarbonyl-3-(2-methylsulfanylethyl)-1-prop-2-ynyl-1,4,8-triazaspiro[4,5]decan-2-one,
(144) 3-Benzyl-1-butyl-8-(furan-2-carbonyl)-1,4,8-triazaspiro[4,5]decan-2-one,
(145) 1-Benzyl-8-(3-chlorothiophene-2-carbonyl)-3-isobutyl-1,4,8-triazaspiro[4,5]decan-2-one, (146) 3-Benzyl-8-(2,5-bis-trifluoromethylbenzoyl)-1-butyl-1,4,8-triazaspiro[4,5]decan-2-one,
(147) 8-(3-Chloro-2-fluorobenzoyl)-1-(3,5-dimethylbenzyl)-3-(2-methylsulfanylethyl)-1,4,8-triazaspiro[4,5]decan-2-one,
(148) 1-Benzyl-8-(2-chloropyridin-3-carbonyl)-3-isopropyl-1,4,8-triazaspiro[4,5]decan-2-one,
(149) 3-Isobutyl-8-pentafluorobenzoyl-1-prop-2-ynyl-1,4,8-triazaspiro[4,5]decan-2-one,
(150) 8-(2-Benzyloxyacetyl)-1-butyl-3-(2-methylsulfanylethyl)-1,4,8-triazaspiro[4,5]decan-2-one,
(151) 8-(Furan-2-carbonyl)-3-isobutyl-1-prop-2-ynyl-1,4,8-triazaspiro[4,5]decan-2-one,
(152) 1-Butyl-3-(2-methylsulfanylethyl)-8-(4-phenoxybutyryl)-1,4,8-triazaspiro[4,5]decan-2-one,
(153) 3-Benzyl-8-(6-chloropyridin-3-carbonyl)-1-methyl-1,4,8-triazaspiro[4,5]decan-2-one,
(154) 1-(2-Fluorobenzyl)-3-(2-methylsulfanylethyl)-8-(2-phenoxypyridin-3-carbonyl)-1,4,8-triazaspiro[4,5]decan-2-one,
(155) 1-(2-Fluorobenzyl)-3-isobutyl-8-(2-methyl-6-trifluoromethylpyridin-3-carbonyl)-1,4,8-triazaspiro[4,5]decan-2-one,
(156) 8-[2-(3-Chlorophenoxy)-acetyl]-3-isopropyl-1-(2-phenoxyethyl)-1,4,8-triazaspiro[4,5]decan-2-one,
(157) 8-(2,3-Dimethylbenzoyl)-1-methyl-3-(2-methylsulfanylethyl)-1,4,8-triazaspiro[4,5]decan-2-one,
(158) 3-Isopropyl-8-(2-methyl-6-trifluoromethylpyridin-3-carbonyl)-1-(2-phenoxyethyl)-1,4,8-triazaspiro[4,5]decan-2-one,
(159) 3-Benzyl-1-methyl-8-(5-methyl-2-phenyl-2H-[1,2,3]triazole-4-carbonyl)-1,4,8-triazaspiro[4,5]decan-2-one,
(160) 8-[3-(2-Chlorophenyl)-5-methylisoxazole-4-carbonyl]-1-(3,5-dimethylbenzyl)-3-(2-methylsulfanylethyl)-1,4,8-triazaspiro[4,5]decan-2-one,
(161) 1-(2-Fluorobenzyl)-3-(2-methylsulfanylethyl)-8-(pyridin-2-carbonyl)-1,4,8-triazaspiro[4,5]decan-2-one,
(162) 1-Benzyl-3-(2-methylsulfanylethyl)-8-(2-phenoxypyridin-3-carbonyl)-1,4,8-triazaspiro[4,5]decan-2-one,
(163) 1,3-Dibenzyl-8-(3-chlorothiophene-2-carbonyl)-1,4,8-triazaspiro[4,5]decan-2-one,
(164) 3-Benzyl-8-(4-tert-butylbenzoyl)-1-methyl-1,4,8-triazaspiro[4,5]decan-2-one,
(165) 2-[3-Isobutyl-8-(2-methoxyacetyl)-2-oxo-1,4,8-triazaspiro[4,5]dec-1-ylmethyl]-benzonitrile,
(166) 3-Benzyl-1-butyl-8-(5-fluoro-2-trifluoromethylbenzoyl)-1,4,8-triazaspiro[4,5]decan-2-one,
(167) 3-Benzyl-8-[2-(4-methoxyphenyl)-acetyl]-1-methyl-1,4,8-triazaspiro[4,5]decan-2-one,
(168) 1,3-Dibenzyl-8-(4-methyl[1,2,3]thiadiazole-5-carbonyl)-1,4,8-triazaspiro[4,5]decan-2-one,
(169) 1-Benzyl-3-isopropyl-8-(2-methyl-6-trifluoromethylpyridin-3-carbonyl)-1,4,8-triazaspiro[4,5]decan-2-one,
(170) 1-Benzyl-8-(4-ethoxybenzoyl)-3-isobutyl-1,4,8-triazaspiro[4,5]decan-2-one,
(171) 3-Benzyl-1-butyl-8-cyclohexanecarbonyl-1,4,8-triazaspiro[4,5]decan-2-one,
(172) 3-[8-[3-(2-Chloro-6-fluorophenyl)-5-methylisoxazole-4-carbonyl]-3-(2-methylsulfanylethyl)-2-oxo-1,4,8-triazaspiro[4,5]dec-1-ylmethyl]-benzonitrile,
(173) 1-(2-Fluorobenzyl)-3-isobutyl-8-pent-4-enoyl-1,4,8-triazaspiro[4,5]decan-2-one,
(174) 1-Methyl-3-(2-methylsulfanylethyl)-8-(2-propylpentanoyl)-1,4,8-triazaspiro[4,5]decan-2-one,
(175) 3-Benzyl-1-methyl-8-(2-phenoxyacetyl)-1,4,8-triazaspiro[4,5]decan-2-one,
(176) 3-Isobutyl-1-prop-2-ynyl-8-(3-trifluoromethylbenzoyl)-1,4,8-triazaspiro[4,5]decan-2-one,
(177) 3-Benzyl-8-(furan-2-carbonyl)-1-prop-2-ynyl-1,4,8-triazaspiro[4,5]decan-2-one,
(178) 1-Methyl-3-(2-methylsulfanylethyl)-8-(naphthalin-1-carbonyl)-1,4,8-triazaspiro[4,5]decan-2-one,
(179) 3-Benzyl-1-butyl-8-(3-cyclopentylpropionyl)-1,4,8-triazaspiro[4,5]decan-2-one,
(180) 1-(3,5-Dimethylbenzyl)-3-(2-methylsulfanylethyl)-8-pentanoyl-1,4,8-triazaspiro[4,5]decan-2-one,
(181) 3-Benzyl-1-butyl-8-(2-methoxyacetyl)-1,4,8-triazaspiro[4,5]decan-2-one,
(182) 3-Benzyl-8-(3-fluoro-4-trifluoromethylbenzoyl)-1-methyl-1,4,8-triazaspiro[4,5]decan-2-one,
(183) 1-Benzyl-8-(3-difluoromethylsulfanylbenzoyl)-3-isopropyl-1,4,8-triazaspiro[4,5]decan-2-one,
(184) 8-(2-Chloro-6-fluoro-3-methylbenzoyl)-1-methyl-3-(2-methylsulfanylethyl)-1,4,8-triazaspiro[4,5]decan-2-one,
(185) Methyl 4-[3-Isopropyl-8-(2-methylsulfanylpyridin-3-carbonyl)-2-oxo-1,4,8-triazaspiro[4,5]dec-1-ylmethyl]benzoate,
(186) 8-[2-(2,5-Dimethoxyphenyl)-acetyl]-1-(2-fluorobenzyl)-3-(2-methylsulfanylethyl)-1,4,8-triazaspiro[4,5]decan-2-one,
(187) 8-(5-tert-Butyl-2-methylfuran-3-carbonyl)-3-isopropyl-1-(2-phenoxyethyl)-1,4,8-triazaspiro[4,5]decan-2-one,
(188) 8-(2-Cyclopentylacetyl)-1-(4-fluorobenzyl)-3-isobutyl-1,4,8-triazaspiro[4,5]decan-2-one,
(189) Methyl 4-[8-(3,3-dimethylbutyryl)-3-isopropyl-2-oxo-1,4,8-triazaspiro[4,5]dec-1-ylmethyl]benzoate,
(190) 3-[8-Cyclopropanecarbonyl-3-(2-methylsulfanylethyl)-2-oxo-1,4,8-triazaspiro[4,5]dec-1-ylmethyl]-benzonitrile,
(191) 3-[3-(2-Methylsulfanylethyl)-2-oxo-8-(3-trifluoromethoxybenzoyl)-1,4,8-triazaspiro[4,5]dec-1-ylmethyl]-benzonitrile,
(192) 1-Butyl-8-(2-cyclopentylacetyl)-3-isopropyl-1,4,8-triazaspiro[4,5]decan-2-one,
(193) 3-Benzyl-1-butyl-8-(pyridin-2-carbonyl)-1,4,8-triazaspiro[4,5]decan-2-one,
(194) 3-Benzyl-8-[3-(2-chlorophenyl)-acryloyl]-1-methyl-1,4,8-triazaspiro[4,5]decan-2-one,
(195) Methyl 4-[8-(3-fluoro-4-trifluoromethylbenzoyl)-3-isopropyl-2-oxo-1,4,8-triazaspiro[4,5]dec-1-ylmethyl]benzoate,
(196) 8-[3-(2,6-Dichlorophenyl)-5-methylisoxazole-4-carbonyl]-1-methyl-3-(2-methylsulfanylethyl)-1,4,8-triazaspiro[4,5]decan-2-one,
(197) 1-Butyl-8-cyclohexanecarbonyl-3-(2-methylsulfanylethyl)-1,4,8-triazaspiro[4,5]decan-2-one,
(198) 3-Benzyl-1-butyl-8-(4-iodobenzoyl)-1,4,8-triazaspiro[4,5]decan-2-one
(199) 1-Methyl-3-(2-methylsulfanylethyl)-8-[3-(3-trifluoromethylphenyl)-acryloyl]-1,4,8-triazaspiro[4,5]decan-2-one,
(200) 1,3-Dibenzyl-8-(4-phenoxybutyryl)-1,4,8-triazaspiro[4,5]decan-2-one
(201) 3-Benzyl-8-(2-chloro-6-fluorobenzoyl)-1-prop-2-ynyl-1,4,8-triazaspiro[4,5]decan-2-one,
(202) Methyl 4-[8-(2-chloropyridin-3-carbonyl)-3-isopropyl-2-oxo-1,4,8-triazaspiro[4,5]dec-1-ylmethyl]benzoate, (203) 8-(2,5-Dimethylfuran-3-carbonyl)-3-isopropyl-1-(2-phenoxyethyl)-1,4,8-triazaspiro[4,5]decan-2-one,
(204) 8-(Biphenyl-4-carbonyl)-3-(2-methylsulfanylethyl)-1-prop-2-ynyl-1,4,8-triazaspiro[4,5]decan-2-one,
(205) 8-(3-Chlorothiophene-2-carbonyl)-3-(2-methylsulfanylethyl)-1-prop-2-ynyl-1,4,8-triazaspiro[4,5]decan-2-one,
(206) 1-(4-Fluorobenzyl)-8-[2-(4-methoxyphenyl)-acetyl]-3-(2-methylsulfanylethyl)-1,4,8-triazaspiro[4,5]decan-2-one,
(207) 1-Benzyl-3-isopropyl-8-(4-methyl[1,2,3]thiadiazole-5-carbonyl)-1,4,8-triazaspiro[4,5]decan-2-one,
(208) 2-[3-Isopropyl-8-(2-methylsulfanylpyridin-3-carbonyl)-2-oxo-1,4,8-triazaspiro[4,5]dec-1-ylmethyl]-benzonitrile,
(209) 3-[8-(5-tert-Butyl-2-methyl-2H-pyrazole-3-carbonyl)-3-isobutyl-2-oxo-1,4,8-triazaspiro[4,5]dec-1-ylmethyl]-benzonitrile,
(210) 1-Butyl-8-(2,5-dimethylfuran-3-carbonyl)-3-(2-methylsulfanylethyl)-1,4,8-triazaspiro[4,5]decan-2-one,
(211) 8-(3-Cyclopentylpropionyl)-1-(2-fluorobenzyl)-3-isobutyl-1,4,8-triazaspiro[4,5]decan-2-one,
(212) 1-Benzyl-8-(3-cyclopentylpropionyl)-3-(2-methylsulfanylethyl)-1,4,8-triazaspiro[4,5]decan-2-one,
(213) 3-(2-Methylsulfanylethyl)-8-(4-phenoxybutyryl)-1-prop-2-ynyl-1,4,8-triazaspiro[4,5]decan-2-one,
(214) 1,3-Dibenzyl-8-(3-phenylacryloyl)-1,4,8-triazaspiro[4,5]decan-2-one,
(215) 3-Benzyl-8-(6-chloro-2-fluoro-3-methylbenzoyl)-1-methyl-1,4,8-triazaspiro[4,5]decan-2-one,
(216) 8-[3-(2-Chlorophenyl)-acryloyl]-3-isopropyl-1-(2-phenoxyethyl)-1,4,8-triazaspiro[4,5]decan-2-one,
(217) 2-[3-Isopropyl-2-oxo-8-(3-phenylacryloyl)-1,4,8-triazaspiro[4,5]dec-1-ylmethyl]-benzonitrile,
(218) 3-Benzyl-1-methyl-8-(4-methyl-3-nitrobenzoyl)-1,4,8-triazaspiro[4,5]decan-2-one,
(219) 1-Benzyl-8-(furan-2-carbonyl)-3-isopropyl-1,4,8-triazaspiro[4,5]decan-2-one,
(220) 1-Butyl-8-(3,5-dimethoxybenzoyl)-3-(2-methylsulfanylethyl)-1,4,8-triazaspiro[4,5]decan-2-one,
(221) 1,3-Dibenzyl-8-(3,3-dimethylbutyryl)-1,4,8-triazaspiro[4,5]decan-2-one,
(222) 8-(2,6-Difluoro-3-methylbenzoyl)-1-methyl-3-(2-methylsulfanylethyl)-1,4,8-triazaspiro[4,5]decan-2-one,
(223) 2-[8-(2-Chloro-6-fluorobenzoyl)-3-(2-methylsulfanylethyl)-2-oxo-1,4,8-triazaspiro[4,5]dec-1-ylmethyl]-benzonitrile,
(224) 8-[3-(2-Chloro-6-fluorophenyl)-5-methylisoxazole-4-carbonyl]-3-isopropyl-1-(3-methylbut-2-enyl)-1,4,8-triazaspiro[4,5]decan-2-one,
(225) 3-Isobutyl-1-prop-2-ynyl-8-(4-trifluoromethoxybenzoyl)-1,4,8-triazaspiro[4,5]decan-2-one,
(226) 1-Benzyl-8-(2-chloro-6-fluoro-3-methylbenzoyl)-1,4,8-triazaspiro[4,5]decan-2-one,
(227) Benzyl 2-(1-benzyl-3-isopropyl-2-oxo-1,4,8-triazaspiro[4,5]decan-8-carbonyl)benzoate,
(228) 1,3-Dibenzyl-8-(2-phenylbutyryl)-1,4,8-triazaspiro[4,5]decan-2-one,
(229) 3-Benzyl-1-methyl-8-(4-nitrobenzoyl)-1,4,8-triazaspiro[4,5]decan-2-one,
(230) 3-Benzyl-1-methyl-8-(5-methylisoxazole-3-carbonyl)-1,4,8-triazaspiro[4,5]decan-2-one,
(231) 1-Benzyl-8-(6-chloro-2-fluoro-3-methylbenzoyl)-3-(2-methylsulfanylethyl)-1,4,8-triazaspiro[4,5]decan-2-one,
(232) 1-Benzyl-8-(3-fluoro-4-trifluoromethylbenzoyl)-3-isobutyl-1,4,8-triazaspiro[4,5]decan-2-one,
(233) 3-Benzyl-8-(6-chloro-2H-chroman-3-carbonyl)-1-methyl-1,4,8-triazaspiro[4,5]decan-2-one,
(234) 3-Benzyl-1-butyl-8-(4-methyl[1,2,3]thiadiazole-5-carbonyl)-1,4,8-triazaspiro[4,5]decan-2-one,
(235) 3-Benzyl-8-(4-methyl[1,2,3]thiadiazole-5-carbonyl)-1-prop-2-ynyl-1,4,8-triazaspiro[4,5]decan-2-one,
(236) 2-[8-(6-Chloro-2H-chroman-3-carbonyl)-3-isopropyl-2-oxo-1,4,8-triazaspiro[4,5]dec-1-ylmethyl]-benzonitrile,
(237) 2-[8-(5-Methylisoxazole-3-carbonyl)-3-(2-methylsulfanylethyl)-2-oxo-1,4,8-triazaspiro[4,5]dec-1-ylmethyl]-benzonitrile,
(238) 2-[8-(3-Chloro-2-fluorobenzoyl)-3-isopropyl-2-oxo-1,4,8-triazaspiro[4,5]dec-1-ylmethyl]-benzonitrile,
(239) Methyl 4-[8-(5-tert-butyl-2-methyl-2H-pyrazole-3-carbonyl)-3-isopropyl-2-oxo-1,4,8-triazaspiro[4,5]dec-1-ylmethyl]benzoate,
(240) 3-Benzyl-1-butyl-8-(5-tert-butyl-2-methyl-2H-pyrazole-3-carbonyl)-1,4,8-triazaspiro[4,5]decan-2-one,
(241) 3-Benzyl-1-butyl-8-(2-chloro-4-trifluoromethylpyrimidin-5-carbonyl)-1,4,8-triazaspiro[4,5]decan-2-one,
(242) 3-Benzyl-8-(5-methylisoxazole-3-carbonyl)-1-prop-2-ynyl-1,4,8-triazaspiro[4,5]decan-2-one,
(243) Methyl 4-[8-(2-chloropyridin-3-carbonyl)-2-oxo-1,4,8-triazaspiro[4,5]dec-1-ylmethyl]benzoate,
(244) 8-(2-tert-Butyl-5-methyl-2H-pyrazole-3-carbonyl)-1-(2-fluorobenzyl)-1,4,8-triazaspiro[4,5]decan-2-one,
(245) Methyl 4-[8-(2-methylsulfanylpyridin-3-carbonyl)-2-oxo-1,4,8-triazaspiro[4,5]dec-1-ylmethyl]benzoate,
(246) Butyl 4-[8-(4-acetylaminobenzoyl)-3-isobutyl-2-oxo-1,4,8-triazaspiro[4,5]dec-1-yl]acetate,
(247) Ethyl [8-(4-acetylaminobenzoyl)-3-benzyl-2-oxo-1,4,8-triazaspiro[4,5]dec-1-yl]acetate,
(248) Butyl 4-[8-(2-ethylsulfanylpyridin-3-carbonyl)-3-isobutyl-2-oxo-1,4,8-triazaspiro[4,5]dec-1-yl]acetate,
(249) Methyl 4-[8-(4-methyl[1,2,3]thiadiazole-5-carbonyl)-2-oxo-1,4,8-triazaspiro[4,5]dec-1-ylmethyl]benzoate,
(250) 4-[1-Allyl-3-(2-methylsulfanylethyl)-2-oxo-1,4,8-triazaspiro[4,5]decan-8-carbonyl]-benzolsulfonamide,
(251) Methyl 4-(8-cyclobutanecarbonyl-2-oxo-1,4,8-triazaspiro[4,5]dec-1-ylmethyl)benzoate,
(252) Ethyl 2-[1-allyl-3-(2-methylsulfanylethyl)-2-oxo-1,4,8-triazaspiro[4,5]dec-8-yl]-2-oxo-acetate,
(253) 8-(Biphenyl-4-carbonyl)-1-(2-fluorobenzyl)-1,4,8-triazaspiro[4,5]decan-2-one,
(254) Ethyl [3-(2-Methylsulfanylethyl)-2-oxo-8-propinyl-1,4,8-triazaspiro[4,5]dec-1-yl]acetate,
(255) 8-(Benzo[1,3]dioxole-5-carbonyl)-1-(2,6-dichlorobenzyl)-3-isobutyl-1,4,8-triazaspiro[4,5]decan-2-one,
(256) 1-Allyl-8-(biphenyl-4-carbonyl)-3-isopropyl-1,4,8-triazaspiro[4,5]decan-2-one,
(257) Ethyl [3-benzyl-8-(biphenyl-4-carbonyl)-2-oxo-1,4,8-triazaspiro[4,5]dec-1-yl]acetate,
(258) Ethyl [8-(3-dimethylaminobenzoyl)-3-(2-methylsulfanylethyl)-2-oxo-1,4,8-triazaspiro[4,5]dec-1-yl]acetate,
(259) 3-(2-Oxo-8-pentanoyl-1,4,8-triazaspiro[4,5]dec-1-ylmethyl)-benzonitrile,
(260) Methyl 4-(8-cyclopentanecarbonyl-2-oxo-1,4,8-triazaspiro[4,5]dec-1-ylmethyl)benzoate, (261) Ethyl 4-[1-(2-fluorobenzyl)-2-oxo-1,4,8-triazaspiro[4,5]dec-8-yl]-4-oxo-butanoate,
(262) 1-(2-Fluorobenzyl)-8-(3,4,5-trimethoxybenzoyl)-1,4,8-triazaspiro[4,5]decan-2-one,
(263) Methyl 4-[8-(2-chloropyridin-4-carbonyl)-2-oxo-1,4,8-triazaspiro[4,5]dec-1-ylmethyl]benzoate,
(264) 3-[8-(3,5-Bis-trifluoromethylbenzoyl)-2-oxo-1,4,8-triazaspiro[4,5]dec-1-ylmethyl]-benzonitrile,
(265) 3-Benzyl-1-(2-fluorobenzyl)-8-(2-methoxybenzoyl)-1,4,8-triazaspiro[4,5]decan-2-one,
(266) 8-(Benzo[1,2,5]oxadiazole-5-carbonyl)-1-(2,6-dichlorobenzyl)-3-isobutyl-1,4,8-triazaspiro[4,5]decan-2-one,
(267) Ethyl [3-benzyl-2-oxo-8-(4-sulfamoylbenzoyl)-1,4,8-triazaspiro[4,5]dec-1-yl]acetate,
(268) 3-[2-Oxo-8-(3,4,5-trimethoxybenzoyl)-1,4,8-triazaspiro[4,5]dec-1-ylmethyl]-benzonitrile,
(269) Ethyl 2-[1-(4-acetoxybutyl)-3-isobutyl-2-oxo-1,4,8-triazaspiro[4,5]dec-8-yl]-1,1-dimethyl-2-oxo-acetate,
(270) 8-(6-Chloropyridin-3-carbonyl)-1-(2,6-dichlorobenzyl)-3-isobutyl-1,4,8-triazaspiro[4,5]decan-2-one,
(271) 8-(2-Ethoxybenzoyl)-1-(2-fluorobenzyl)-1,4,8-triazaspiro[4,5]decan-2-one,
(272) 1-Allyl-8-cyclopropanecarbonyl-3-(2-methylsulfanylethyl)-1,4,8-triazaspiro[4,5]decan-2-one,
(273) 3-[3-Isopropyl-8-(2-methoxyacetyl)-2-oxo-1,4,8-triazaspiro[4,5]dec-1-ylmethyl]-benzonitrile,
(274) Methyl 4-(2-oxo-8-phenylacetyl-1,4,8-triazaspiro[4,5]dec-1-ylmethyl)benzoate,
(275) Ethyl 2-[1-(3-cyanobenzyl)-2-oxo-1,4,8-triazaspiro[4,5]dec-8-yl]-2-oxo-1-phenylacetate,
(276) 1-(2-Fluorobenzyl)-8-(4-methoxybenzoyl)-1,4,8-triazaspiro[4,5]decan-2-one,
(277) Methyl 4-(8-cyclohexanecarbonyl-2-oxo-1,4,8-triazaspiro[4,5]dec-1-ylmethyl)benzoate,
(278) 1-(2-Fluorobenzyl)-8-pent-4-enoyl-1,4,8-triazaspiro[4,5]decan-2-one,
(279) Ethyl [3-isobutyl-8-(3-ethylbutyryl)-2-oxo-1,4,8-triazaspiro[4,5]dec-1-yl]acetate,
(280) 1-Allyl-8-(3,3-dimethylbutyryl)-3-(2-methylsulfanylethyl)-1,4,8-triazaspiro[4,5]decan-2-one,
(281) 1-Allyl-3-(2-methylsulfanylethyl)-8-(2-methylsulfanylpyridin-3-carbonyl)-1,4,8-triazaspiro[4,5]decan-2-one,
(282) Ethyl [3-isobutyl-8-(2-Methylpentanoyl)-2-oxo-1,4,8-triazaspiro[4,5]dec-1-yl]acetate,
(283) Methyl 4-[8-(5-tert-butyl-2-methylfuran-3-carbonyl)-2-oxo-1,4,8-triazaspiro[4,5]dec-1-ylmethyl]benzoate,
(284) Ethyl (3-benzyl-8-cyclopropanecarbonyl-2-oxo-1,4,8-triazaspiro[4,5]dec-1-yl)acetate,
(285) Ethyl [3-benzyl-8-(3-methylbutyryl)-2-oxo-1,4,8-triazaspiro[4,5]dec-1-yl]acetate,
(286) 1-(2,6-Dichlorobenzyl)-8-(2,5-dimethylfuran-3-carbonyl)-3-isobutyl-1,4,8-triazaspiro[4,5]decan-2-one,
(287) 1-Allyl-3-isopropyl-8-[2-(3-methoxyphenyl)-acetyl]-1,4,8-triazaspiro[4,5]decan-2-one,
(288) Ethyl [8-(4-tert-butylbenzoyl)-3-(2-methylsulfanylethyl)-2-oxo-1,4,8-triazaspiro[4,5]dec-1-yl]acetate,
(289) 3-(2-Methylsulfanylethyl)-1-(2-nitrobenzoyl)-8-(2-phenoxypyridin-3-carbonyl)-1,4,8-triazaspiro[4,5]decan-2-one,
(290) Ethyl (3-benzyl-2-oxo-8-pentanoyl-1,4,8-triazaspiro[4,5]dec-1-yl)acetate,
(291) 8-(2-Chloropyridin-4-carbonyl)-1-(2-fluorobenzyl)-1,4,8-triazaspiro[4,5]decan-2-one,
(292) Ethyl [8-(3-methylbutyryl)-3-(2-methylsulfanylethyl)-2-oxo-1,4,8-triazaspiro[4,5]dec-1-yl]acetate,
(293) 1-Allyl-3-(2-methylsulfanylethyl)-8-pentafluorobenzoyl-1,4,8-triazaspiro[4,5]decan-2-one,
(294) 1-(2-Fluorobenzyl)-8-(2-trifluoromethylbenzoyl)-1,4,8-triazaspiro[4,5]decan-2-one,
(295) 8-(Benzo[1,2,5]oxadiazole-5-carbonyl)-1-(2-fluorobenzyl)-1,4,8-triazaspiro[4,5]decan-2-one,
(296) Methyl 4-[8-(4-tert-butylbenzoyl)-2-oxo-1,4,8-triazaspiro[4,5]dec-1-ylmethyl]benzoate,
(297) Ethyl [3-benzyl-2-oxo-8-(1-phenyl-5-propyl-1H-pyrazole-4-carbonyl)-1,4,8-triazaspiro[4,5]dec-1-yl]acetate,
(298) 1-Allyl-3-isopropyl-8-pent-4-enoyl-1,4,8-triazaspiro[4,5]decan-2-one,
(299) 3-[2-Oxo-8-(2-trifluoromethylbenzoyl)-1,4,8-triazaspiro[4,5]dec-1-ylmethyl]-benzonitrile,
(300) 8-(2-Dimethylaminoacetyl)-1-(3,5-dimethylbenzyl)-3-isobutyl-1,4,8-triazaspiro[4,5]decan-2-one,
(301) Butyl [8-(2-ethoxybenzoyl)-3-isobutyl-2-oxo-1,4,8-triazaspiro[4,5]dec-1-yl]acetate,
(302) 1-(2-Fluorobenzyl)-8-(3-methoxybenzoyl)-1,4,8-triazaspiro[4,5]decan-2-one,
(303) Ethyl [8-(furan-2-carbonyl)-3-isobutyl-2-oxo-1,4,8-triazaspiro[4,5]dec-1-yl]acetate,
(304) 8-(5-tert-Butyl-2-methyl-2H-pyrazole-3-carbonyl)-1-(2-fluorobenzyl)-1,4,8-triazaspiro[4,5]decan-2-one,
(305) 1-(2-Fluorobenzyl)-8-(thiophene-2-carbonyl)-1,4,8-triazaspiro[4,5]decan-2-one,
(306) Ethyl [3-benzyl-8-(2-fluorobenzoyl)-2-oxo-1,4,8-triazaspiro[4,5]dec-1-yl]acetate,
(307) Ethyl [8-(isoxazole-5-carbonyl)-3-(2-methylsulfanylethyl)-2-oxo-1,4,8-triazaspiro[4,5]dec-1-yl]acetate,
(308) 1-(2,6-Dichlorobenzyl)-3-isobutyl-8-(4-propylbenzoyl)-1,4,8-triazaspiro[4,5]decan-2-one,
(309) Ethyl [8-[2-(2,5-dimethoxyphenyl)-acetyl]-3-(2-methylsulfanylethyl)-2-oxo-1,4,8-triazaspiro[4,5]dec-1-yl]acetate,
(310) Ethyl (3-benzyl-8-cyclobutanecarbonyl-2-oxo-1,4,8-triazaspiro[4,5]dec-1-yl)acetate,
(311) 1-(2-Fluorobenzyl)-8-[2-(4-methoxyphenyl)-acetyl]-1,4,8-triazaspiro[4,5]decan-2-one,
(312) 1-Allyl-3-(2-methylsulfanylethyl)-8-(2-methyl-6-trifluoromethylpyridin-3-carbonyl)-1,4,8-triazaspiro[4,5]decan-2-one,
(313) Ethyl [3-(2-methylsulfanylethyl)-2-oxo-8-(4-trifluoromethylbenzoyl)-1,4,8-triazaspiro[4,5]dec-1-yl]acetate,
(314) 1-Allyl-3-(2-methylsulfanylethyl)-8-(1-phenyl-5-propyl-1H-pyrazole-4-carbonyl)-1,4,8-triazaspiro[4,5]decan-2-one,
(315) 1-(2,6-Dichlorobenzyl)-8-(2,3-difluoro-4-methylbenzoyl)-3-isobutyl-1,4,8-triazaspiro[4,5]decan-2-one,
(316) 1-Allyl-3-isopropyl-8-(2-methylbenzoyl)-1,4,8-triazaspiro[4,5]decan-2-one,
(317) 8-(2-Chloro-5-trifluoromethylbenzoyl)-1-(2,6-dichlorobenzyl)-3-isobutyl-1,4,8-triazaspiro[4,5]decan-2-one,
(318) 1-Allyl-8-[2-(3-methoxyphenyl)-acetyl]-3-(2-methylsulfanylethyl)-1,4,8-triazaspiro[4,5]decan-2-one,
(319) 1-Allyl-3-(2-methylsulfanylethyl)-8-(3-phenylpropionyl)-1,4,8-triazaspiro[4,5]decan-2-one,
(320) Ethyl [3-benzyl-8-(2-benzyloxyacetyl)-2-oxo-1,4,8-triazaspiro[4,5]dec-1-yl]acetate, (321) 1-Allyl-8-(5-tert-butyl-2-methyl-2H-pyrazole-3-carbonyl)-3-(2-methylsulfanylethyl)-1,4,8-triazaspiro[4,5]decan-2-one, (322) Ethyl 1,1-dimethyl-2-[3-(2-methylsulfanylethyl)-1-(2-nitrobenzyl)-2-oxo-1,4,8-triazaspiro[4,5]dec-8-yl]-2-oxo-acetate, (323) Benzyl 2-[1-ethoxycarbonylmethyl-3-(2-methylsulfanylethyl)-2-oxo-1,4,8-triazaspiro[4,5]decan-8-carbonyl]benzoate, (324) 1-Allyl-3-isopropyl-8-(4-methyl[1,2,3]thiadiazole-5-carbonyl)-1,4,8-triazaspiro[4,5]decan-2-one, (325) 1-Allyl-8-(2,5-dimethylfuran-3-carbonyl)-3-(2-methylsulfanylethyl)-1,4,8-triazaspiro[4,5]decan-2-one, (326) 1-Allyl-8-(benzo[1,2,5]oxadiazole-5-carbonyl)-3-(2-methylsulfanylethyl)-1,4,8-triazaspiro[4,5]decan-2-one, (327) 1-(2-Fluorobenzyl)-8-(4-phenoxybutyryl)-1,4,8-triazaspiro[4,5]decan-2-one, (328) 1-Allyl-8-(2-cyclopentylacetyl)-3-(2-methylsulfanylethyl)-1,4,8-triazaspiro[4,5]decan-2-one, (329) Ethyl [3-benzyl-8-(naphthalin-2-carbonyl)-2-oxo-1,4,8-triazaspiro[4,5]dec-1-yl]acetate, (330) 8-[3-(2-Chloro-6-fluorophenyl)-5-methylisoxazole-4-carbonyl]-1-(2-fluorobenzyl)-1,4,8-triazaspiro[4,5]decan-2-one, (331) 3-[8-(3,5-Dimethoxybenzoyl)-3-isopropyl-2-oxo-1,4,8-triazaspiro[4,5]dec-1-ylmethyl]-benzonitrile, (332) 3-(2-Methylsulfanylethyl)-1-(2-nitrobenzyl)-8-(1-phenyl-5-propyl-1H-pyrazole-4-carbonyl)-1,4,8-triazaspiro[4,5]decan-2-one, (333) Ethyl {3-benzyl-8-[3-(2-chloro-6-fluorophenyl)-5-methylisoxazole-4-carbonyl]-2-oxo-1,4,8-triazaspiro[4,5]dec-1-yl}acetate, (334) 1-(2-Fluorobenzyl)-8-(3-fluoro-4-trifluoromethylbenzoyl)-1,4,8-triazaspiro[4,5]decan-2-one, (335) Ethyl [8-[1-(4-chlorophenyl)-5-trifluoromethyl-1H-pyrazole-4-carbonyl]-3-(2-methylsulfanylethyl)-2-oxo-1,4,8-triazaspiro[4,5]dec-1-yl]acetate, (336) 3-[8-(Naphthalin-1-carbonyl)-2-oxo-1,4,8-triazaspiro[4,5]dec-1-ylmethyl]-benzonitrile, (337) Ethyl [8-(3,3-dimethylbutyryl)-3-(2-methylsulfanylethyl)-2-oxo-1,4,8-triazaspiro[4,5]dec-1-yl]acetate, (338) 8-Acetyl-3-(2-methylsulfanylethyl)-1-naphthalin-2-ylmethyl-1,4,8-triazaspiro[4,5]decan-2-one, (339) Ethyl [3-benzyl-8-(3-cyanobenzoyl)-2-oxo-1,4,8-triazaspiro[4,5]dec-1-yl]acetate, (340) 8-(5-tert-Butyl-2-methyl-2H-pyrazole-3-carbonyl)-1-(2,6-dichlorobenzyl)-3-isobutyl-1,4,8-triazaspiro[4,5]decan-2-one, (341) 4-[3-Benzyl-1-(2-fluorobenzyl)-2-oxo-1,4,8-triazaspiro[4,5]decan-8-carbonyl]-benzonitrile, (342) Methyl 4-[3-benzyl-1-(2-fluorobenzyl)-2-oxo-1,4,8-triazaspiro[4,5]dec-8-yl]-4-oxo-butyrate, (343) 3-(2-Methylsulfanylethyl)-1-naphthalin-2-ylmethyl-8-(3,4,5-trimethoxybenzoyl)-1,4,8-triazaspiro[4,5]decan-2-one, (344) Ethyl [3-benzyl-8-(isoxazole-5-carbonyl)-2-oxo-1,4,8-triazaspiro[4,5]dec-1-yl]acetate, (345) 8-(3-Difluoromethylsulfanylbenzoyl)-1-(2-fluorobenzyl)-1,4,8-triazaspiro[4,5]decan-2-one, (346) Ethyl [3-benzyl-8-(2,3-dimethylbenzoyl)-2-oxo-1,4,8-triazaspiro[4,5]dec-1-yl]acetate, (347) 1-(2-Fluorobenzyl)-8-(4-propylbenzoyl)-1,4,8-triazaspiro[4,5]decan-2-one, (348) 3-[8-(4-Iodobenzoyl)-2-oxo-1,4,8-triazaspiro[4,5]dec-1-ylmethyl]-benzonitrile, (349) 1-(2-Fluorobenzyl)-8-(2-propylpentanoyl)-1,4,8-triazaspiro[4,5]decan-2-one, (350) 3-[8-(2,6-Difluoro-3-methylbenzoyl)-3-isopropyl-2-oxo-1,4,8-triazaspiro[4,5]dec-1-ylmethyl]-benzonitrile, (351) 3-(2-Methylsulfanylethyl)-8-(4-methyl[1,2,3]thiadiazole-5-carbonyl)-1-(2-nitrobenzyl)-1,4,8-triazaspiro[4,5]decan-2-one, (352) Butyl 4-[3-isobutyl-8-(4-methyl[1,2,3]thiadiazole-5-carbonyl)-2-oxo-1,4,8-triazaspiro[4,5]dec-1-yl]acetate, (353) 8-[2-(4-Chlorophenoxy)-acetyl]-3-(2-methylsulfanylethyl)-1-naphthalin-2-ylmethyl-1,4,8-triazaspiro[4,5]decan-2-one, (354) Ethyl [3-benzyl-2-oxo-8-(3-trifluoromethylbenzoyl)-1,4,8-triazaspiro[4,5]dec-1-yl]acetate, (355) 8-(4-Bromobenzoyl)-3-(2-methylsulfanylethyl)-1-naphthalin-2-ylmethyl-1,4,8-triazaspiro[4,5]decan-2-one, (356) Ethyl [8-(2-chloropyridin-4-carbonyl)-3-(2-methylsulfanylethyl)-2-oxo-1,4,8-triazaspiro[4,5]dec-1-yl]acetate, (357) 1-Allyl-8-(3,5-dimethoxybenzoyl)-3-(2-methylsulfanylethyl)-1,4,8-triazaspiro[4,5]decan-2-one, (358) 3-[8-(4-Methyl-3-nitrobenzoyl)-2-oxo-1,4,8-triazaspiro[4,5]dec-1-ylmethyl]-benzonitrile, (359) 8-(4-tert-Butylbenzoyl)-1-(2-fluorobenzyl)-1,4,8-triazaspiro[4,5]decan-2-one, (360) 1-Allyl-3-isopropyl-8-(5-methylisoxazole-3-carbonyl)-1,4,8-triazaspiro[4,5]decan-2-one, (361) 1-Allyl-3-(2-methylsulfanylethyl)-8-(2-trifluoromethylbenzoyl)-1,4,8-triazaspiro[4,5]decan-2-one, (362) Ethyl [3-benzyl-8-(3-cyclopentylpropionyl)-2-oxo-1,4,8-triazaspiro[4,5]dec-1-yl]acetate, (363) 3-Benzyl-8-(3,5-difluorobenzoyl)-1-(2-fluorobenzyl)-1,4,8-triazaspiro[4,5]decan-2-one, (364) Ethyl [3-benzyl-8-(5-fluoro-2-trifluoromethylbenzoyl)-2-oxo-1,4,8-triazaspiro[4,5]dec-1-yl]acetate, (365) Ethyl [3-benzyl-2-oxo-8-(3,4,5-trimethoxybenzoyl)-1,4,8-triazaspiro[4,5]dec-1-yl]acetate, (366) Benzyl 2-[1-(2-fluorobenzyl)-2-oxo-1,4,8-triazaspiro[4,5]decan-8-carbonyl]benzoate, (367) 1-(2-Fluorobenzyl)-8-(2-methylbenzoyl)-1,4,8-triazaspiro[4,5]decan-2-one, (368) 1-(2-Fluorobenzyl)-8-(2-phenylbutyryl)-1,4,8-triazaspiro[4,5]decan-2-one, (369) 1-Allyl-8-(6-chloropyridin-3-carbonyl)-3-isopropyl-1,4,8-triazaspiro[4,5]decan-2-one, (370) Ethyl [8-(2,5-dimethylfuran-3-carbonyl)-3-(2-methylsulfanylethyl)-2-oxo-1,4,8-triazaspiro[4,5]dec-1-yl]acetate, (371) Ethyl [8-(5-tert-butyl-2-methyl-2H-pyrazole-3-carbonyl)-3-(2-methylsulfanylethyl)-2-oxo-1,4,8-triazaspiro[4,5]dec-1-yl]acetate, (372) Benzyl 2-[1-allyl-3-(2-methylsulfanylethyl)-2-oxo-1,4,8-triazaspiro[4,5]decan-8-carbonyl]benzoate, (373) Ethyl 2-[1-allyl-3-(2-methylsulfanylethyl)-2-oxo-1,4,8-triazaspiro[4,5]dec-8-yl]-2-oxo-1-phenylacetate, (374) 3-[8-(2-Chloro-6-fluorobenzoyl)-3-isopropyl-2-oxo-1,4,8-triazaspiro[4,5]dec-1-ylmethyl]-benzonitrile, (375) 3-(2-Methylsulfanylethyl)-1-(2-nitrobenzyl)-8-(3-phenylpropionyl)-1,4,8-triazaspiro[4,5]decan-2-one, (376) 3-[8-(2,3-Dimethylbenzoyl)-3-isopropyl-2-oxo-1,4,8-triazaspiro[4,5]dec-1-ylmethyl]-benzonitrile, (377) Ethyl [8-(5-fluoro-2-trifluoromethylbenzoyl)-3-(2-methylsulfanylethyl)-2-oxo-1,4,8-triazaspiro[4,5]dec-1-yl]acetate,
(378) Ethyl [8-cyclopentanecarbonyl-3-(2-methylsulfanylethyl)-2-oxo-1,4,8-triazaspiro[4,5]dec-1-yl]acetate,
(379) Ethyl [3-(2-methylsulfanylethyl)-2-oxo-8-(thiophene-2-carbonyl)-1,4,8-triazaspiro[4,5]dec-1-yl]acetate,
(380) 1-Allyl-8-[1-(4-chlorophenyl)-5-trifluoromethyl-1H-pyrazole-4-carbonyl]-3-(2-methylsulfanylethyl)-1,4,8-triazaspiro[4,5]decan-2-one,
(381) 1-Allyl-3-(2-methylsulfanylethyl)-8-(naphthalin-1-carbonyl)-1,4,8-triazaspiro[4,5]decan-2-one,
(382) 1-(2-fluorobenzyl)-8-(4-trifluoromethoxybenzoyl)-1,4,8-triazaspiro[4,5]decan-2-one,
(383) 3-Benzyl-8-(2-benzyloxyacetyl)-1-(2-fluorobenzyl)-1,4,8-triazaspiro[4,5]decan-2-one,
(384) 3-[8-(2-chloro-6-fluoro-3-methylbenzoyl)-3-isopropyl-2-oxo-1,4,8-triazaspiro[4,5]dec-1-ylmethyl]-benzonitrile,
(385) 1-Allyl-8-(2-chloro-5-trifluoromethylbenzoyl)-3-isopropyl-1,4,8-triazaspiro[4,5]decan-2-one,
(386) 8-(3-Methylbenzoyl)-3-(2-methylsulfanylethyl)-1-naphthalin-2-ylmethyl-1,4,8-triazaspiro[4,5]decan-2-one,
(387) 1-(3,5-Dimethylbenzyl)-8-(2-ethylbutyryl)-3-isobutyl-1,4,8-triazaspiro[4,5]decan-2-one,
(388) 8-(5-tert-Butyl-2-methyl-2H-pyrazole-3-carbonyl)-3-(2-methylsulfanylethyl)-1-(2-nitrobenzyl)-1,4,8-triazaspiro[4,5]decan-2-one,
(389) Benzyl 2-[1-(3-cyanobenzyl)-3-isopropyl-2-oxo-1,4,8-triazaspiro[4,5]decan-8-carbonyl]benzoate,
(390) 8-(4-Methyl-3-nitrobenzoyl)-3-(2-methylsulfanylethyl)-1-(2-nitrobenzyl)-1,4,8-triazaspiro[4,5]decan-2-one,
(391) 1-(2,6-Dichlorobenzyl)-3-isobutyl-8-(3,4,5-trimethoxybenzoyl)-1,4,8-triazaspiro[4,5]decan-2-one,
(392) 3-{8-[2-(2-Bromophenyl)-acetyl]-3-isopropyl-2-oxo-1,4,8-triazaspiro[4,5]dec-1-ylmethyl}-benzonitrile,
(393) 3-[8-(2,3-Dichlorobenzoyl)-3-isopropyl-2-oxo-1,4,8-triazaspiro[4,5]dec-1-ylmethyl]-benzonitrile,
(394) 1-Allyl-8-(6-chloro-2H-chroman-3-carbonyl)-3-isopropyl-1,4,8-triazaspiro[4,5]decan-2-one,
(395) Ethyl {3-benzyl-8-[2-(4-methoxyphenyl)-acetyl]-2-oxo-1,4,8-triazaspiro[4,5]dec-1-yl}acetate,
(396) 3-[3-Isopropyl-2-oxo-8-(1-phenyl-5-propyl-1H-pyrazole-4-carbonyl)-1,4,8-triazaspiro[4,5]dec-1-ylmethyl]-benzonitrile,
(397) 8-(3-Cyclopentylpropionyl)-1-(2-fluorobenzyl)-1,4,8-triazaspiro[4,5]decan-2-one,
(398) 1-Allyl-8-(3-difluoromethylsulfanylbenzoyl)-3-isopropyl-1,4,8-triazaspiro[4,5]decan-2-one,
(399) 3-[8-(2-chloro-4-nitrobenzoyl)-3-isopropyl-2-oxo-1,4,8-triazaspiro[4,5]dec-1-ylmethyl]-benzonitrile,
(400) Ethyl [8-(2-ethoxybenzoyl)-3-(2-methylsulfanylethyl)-2-oxo-1,4,8-triazaspiro[4,5]dec-1-yl]acetate,
(401) 8-(2,5-Bis-trifluoromethylbenzoyl)-1-(2-fluorobenzyl)-1,4,8-triazaspiro[4,5]decan-2-one,
(402) 8-(2-Chloropyridin-4-carbonyl)-3-(2-methylsulfanylethyl)-1-(2-nitrobenzyl)-1,4,8-triazaspiro[4,5]decan-2-one,
(403) Ethyl {3-benzyl-8-[3-(2,6-dichlorophenyl)-5-methylisoxazole-4-carbonyl]-2-oxo-1,4,8-triazaspiro[4,5]dec-1-yl}acetate,
(404) 1-(3,5-Dimethylbenzyl)-3-isobutyl-8-(2-trifluoromethylbenzoyl)-1,4,8-triazaspiro[4,5]decan-2-one,
(405) 8-(3,5-Dimethoxybenzoyl)-3-(2-methylsulfanylethyl)-1-(2-nitrobenzyl)-1,4,8-triazaspiro[4,5]decan-2-one,
(406) Benzyl 2-[3-benzyl-1-(2-fluorobenzyl)-2-oxo-1,4,8-triazaspiro[4,5]decan-8-carbonyl]benzoate,
(407) 3-[8-(Benzo[1,2,5]oxadiazole-5-carbonyl)-3-isopropyl-2-oxo-1,4,8-triazaspiro[4,5]dec-1-ylmethyl]-benzonitrile,
(408) Ethyl [3-(2-methylsulfanylethyl)-2-oxo-8-(4-trifluoromethoxybenzoyl)-1,4,8-triazaspiro[4,5]dec-1-yl]acetate,
(409) 1-Allyl-3-isopropyl-8-[2-(4-methoxyphenyl)-acetyl]-1,4,8-triazaspiro[4,5]decan-2-one,
(410) 3-(2-Methylsulfanylethyl)-1-(2-nitrobenzyl)-8-(4-propylbenzoyl)-1,4,8-triazaspiro[4,5]decan-2-one,
(411) 3-Benzyl-8-(4-tert-butylbenzoyl)-1-(2-fluorobenzyl)-1,4,8-triazaspiro[4,5]decan-2-one,
(412) 1-Allyl-8-(2,6-difluoro-3-methylbenzoyl)-3-(2-methylsulfanylethyl)-1,4,8-triazaspiro[4,5]decan-2-one,
(413) 8-(3,5-Bis-trifluoromethylbenzoyl)-1-(2-fluorobenzyl)-1,4,8-triazaspiro[4,5]decan-2-one,
(414) 3-[8-(4-Iodobenzoyl)-3-isopropyl-2-oxo-1,4,8-triazaspiro[4,5]dec-1-ylmethyl]-benzonitrile,
(415) 3-(2-Methylsulfanylethyl)-1-naphthalin-2-ylmethyl-8-(thiophene-2-carbonyl)-1,4,8-triazaspiro[4,5]decan-2-one,
(416) Ethyl [3-benzyl-8-(2-chloropyridin-4-carbonyl)-2-oxo-1,4,8-triazaspiro[4,5]dec-1-yl]acetate,
(417) Ethyl [3-(2-methylsulfanylethyl)-8-(4-nitrobenzoyl)-2-oxo-1,4,8-triazaspiro[4,5]dec-1-yl]acetate,
(418) 8-(2-Ethylhexanoyl)-3-(2-methylsulfanylethyl)-1-(2-nitrobenzyl)-1,4,8-triazaspiro[4,5]decan-2-one,
(419) 1-(2,6-Dichlorobenzyl)-3-isobutyl-8-(thiophene-2-carbonyl)-1,4,8-triazaspiro[4,5]decan-2-one,
(420) Ethyl [3-benzyl-8-(2-chloro-4-nitrobenzoyl)-2-oxo-1,4,8-triazaspiro[4,5]dec-1-yl]acetate,
(421) 3-Benzyl-8-(3,5-bis-trifluoromethylbenzoyl)-1-(2-fluorobenzyl)-1,4,8-triazaspiro[4,5]decan-2-one,
(422) Ethyl [3-benzyl-8-(4-bromo-3-methylbenzoyl)-2-oxo-1,4,8-triazaspiro[4,5]dec-1-yl]acetate,
(423) 8-Cyclohexanecarbonyl-3-(2-methylsulfanylethyl)-1-(2-nitrobenzyl)-1,4,8-triazaspiro[4,5]decan-2-one,
(424) 8-(2,5-Dimethylfuran-3-carbonyl)-3-(2-methylsulfanylethyl)-1-(2-nitrobenzyl)-1,4,8-triazaspiro[4,5]decan-2-one,
(425) 8-(3-Difluoromethylsulfanylbenzoyl)-3-(2-methylsulfanylethyl)-1-(2-nitrobenzyl)-1,4,8-triazaspiro[4,5]decan-2-one,
(426) 8-(Furan-2-carbonyl)-3-(2-methylsulfanylethyl)-1-(2-nitrobenzyl)-1,4,8-triazaspiro[4,5]decan-2-one,
(427) Ethyl [3-benzyl-8-(2,3-difluorobenzoyl)-2-oxo-1,4,8-triazaspiro[4,5]dec-1-yl]acetate,
(428) 3-[3-Isopropyl-8-(4-methyl[1,2,3]thiadiazole-5-carbonyl)-2-oxo-1,4,8-triazaspiro[4,5]dec-1-ylmethyl]-benzonitrile,
(429) 3-[8-(3-Chloro-2-fluorobenzoyl)-3-isopropyl-2-oxo-1,4,8-triazaspiro[4,5]dec-1-ylmethyl]-benzonitrile,
(430) Ethyl [3-benzyl-8-(naphthalin-1-carbonyl)-2-oxo-1,4,8-triazaspiro[4,5]dec-1-yl]acetate,
(431) 8-(4-tert-Butylbenzoyl)-3-(2-methylsulfanylethyl)-1-(2-nitrobenzyl)-1,4,8-triazaspiro[4,5]decan-2-one,
(432) 3-[3-Benzyl-1-(2-fluorobenzyl)-2-oxo-1,4,8-triazaspiro[4,5]decan-8-carbonyl]-benzonitrile,
(433) 1-(2,6-Dichlorobenzyl)-8-(furan-2-carbonyl)-3-isobutyl-1,4,8-triazaspiro[4,5]decan-2-one, (434) 8-(2,6-Dichlorobenzoyl)-1-(2-fluorobenzyl)-1,4,8-triazaspiro[4,5]decan-2-one,
(435) 1-(3,5-Dimethylbenzyl)-8-(3-fluoro-4-trifluoromethylbenzoyl)-3-isobutyl-1,4,8-triazaspiro[4,5]decan-2-one,
(436) 1-(2-Fluorobenzyl)-8-(3-fluoro-4-methylbenzoyl)-1,4,8-triazaspiro[4,5]decan-2-one,
(437) 1-Allyl-8-(3-cyclopentylpropionyl)-3-(2-methylsulfanylethyl)-1,4,8-triazaspiro[4,5]decan-2-one,
(438) 8-[2-(3-Chlorophenoxy)-acetyl]-3-(2-methylsulfanylethyl)-1-(2-nitrobenzyl)-1,4,8-triazaspiro[4,5]decan-2-one,
(439) 1-(3,5-Dimethylbenzyl)-3-isobutyl-8-(2-methylsulfanylpyridin-3-carbonyl)-1,4,8-triazaspiro[4,5]decan-2-one,
(440) 3-(2-Methylsulfanylethyl)-1-(2-nitrobenzyl)-8-propionyl-1,4,8-triazaspiro[4,5]decan-2-one,
(441) 3-[8-(3,4-Dimethoxybenzoyl)-3-isopropyl-2-oxo-1,4,8-triazaspiro[4,5]dec-1-ylmethyl]-benzonitrile,
(442) 3-(2-Methylsulfanylethyl)-8-(naphthalin-2-carbonyl)-1-naphthalin-2-ylmethyl-1,4,8-triazaspiro[4,5]decan-2-one,
(443) 8-(6-Chloro-2H-chroman-3-carbonyl)-3-(2-methylsulfanylethyl)-1-(2-nitrobenzyl)-1,4,8-triazaspiro[4,5]decan-2-one,
(444) Ethyl {3-benzyl-2-oxo-8-[3-(3-trifluoromethylphenyl)-acryloyl]-1,4,8-triazaspiro[4,5]dec-1-yl}acetate,
(445) 1-(3,5-Dimethylbenzyl)-3-isobutyl-8-(3-phenylacryloyl)-1,4,8-triazaspiro[4,5]decan-2-one,
(446) 3-[3-Isopropyl-2-oxo-8-(2-phenoxypropionyl)-1,4,8-triazaspiro[4,5]dec-1-ylmethyl]-benzonitrile,
(447) 3-[3-Isopropyl-2-oxo-8-(4-trifluoromethoxybenzoyl)-1,4,8-triazaspiro[4,5]dec-1-ylmethyl]-benzonitrile,
(448) 1-Allyl-3-(2-methylsulfanylethyl)-8-(3-nitrobenzoyl)-1,4,8-triazaspiro[4,5]decan-2-one,
(449) Ethyl [3-benzyl-8-(3,4-dichlorobenzoyl)-2-oxo-1,4,8-triazaspiro[4,5]dec-1-yl]acetate,
(450) 1-(2-Fluorobenzyl)-8-[3-(3-trifluoromethylphenyl)-acryloyl]-1,4,8-triazaspiro[4,5]decan-2-one,
(451) 1-Allyl-8-(3,5-bis-trifluoromethylbenzoyl)-3-(2-methylsulfanylethyl)-1,4,8-triazaspiro[4,5]decan-2-one,
(452) 8-(3-Cyclopentylpropionyl)-3-(2-methylsulfanylethyl)-1-(2-nitrobenzyl)-1,4,8-triazaspiro[4,5]decan-2-one,
(453) 1-(3,5-Dimethylbenzyl)-3-isobutyl-8-(4-nitrobenzoyl)-1,4,8-triazaspiro[4,5]decan-2-one,
(454) 8-(3-Cyclopentylpropionyl)-1-(3,5-dimethylbenzyl)-3-isobutyl-1,4,8-triazaspiro[4,5]decan-2-one,
(455) 3-[3-Isopropyl-8-(isoxazole-5-carbonyl)-2-oxo-1,4,8-triazaspiro[4,5]dec-1-ylmethyl]-benzonitrile, and
(456) 3-Benzyl-1-(2-fluorobenzyl)-8-(2-methyl-6-trifluoromethylpyridin-3-carbonyl)-1,4,8-triazaspiro[4,5]decan-2-one,
or a pharmaceutically acceptable salt of any of the foregoing.

15. A process for producing a 1,4,8-triazaspiro[4,5]decan-2-one compound corresponding to formula I,

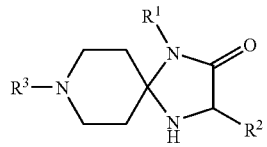

I wherein
$R^1$ represents hydrogen; a linear or branched unsubstituted alkyl group which may comprise at least one heteroatom as a link; a linear or branched, unsubstituted or at least monosubstituted alkenyl group which may comprise at least one heteroatom as a link; a linear or branched, unsubstituted or at least monosubstituted alkynyl group which may comprise at least one heteroatom as a link; an unsubstituted or at least monosubstituted aryl group or heteroaryl group, which is bonded via a linear or branched alkylene group which may comprise at least one heteroatom as a link; a —C(═O)—OR$^5$ group bonded via a linear or branched alkylene group; or an —O—(C═O)—R$^6$ group bonded via a linear or branched alkylene group;

$R^2$ represents hydrogen; a linear or branched, unsubstituted or at least monosubstituted alkyl group which may comprise at least one heteroatom as a link; a linear or branched, unsubstituted or at least monosubstituted alkenyl group which may comprise at least one heteroatom as a link; a linear or branched, unsubstituted or at least monosubstituted alkynyl group which may comprise at least one heteroatom as link; or an unsubstituted or at least monosubstituted aryl group or heteroaryl group, which may be bonded via a linear or branched alkylene group which may comprise at least one heteroatom as a link;

$R^3$ represents hydrogen; a linear or branched unsubstituted or at least monosubstituted alkyl group which may comprise at least one heteroatom as a link; or a linear or branched unsubstituted or at least monosubstituted alkenyl group which may comprise at least one heteroatom as a link; a linear or branched unsubstituted or at least monosubstituted alkynyl group which may comprise at least one heteroatom as a link; an unsubstituted or at least monosubstituted aryl group or heteroaryl group, which is bonded via a linear or branched unsubstituted or at least monosubstituted alkylene group which may comprise at least one heteroatom as a link and may be condensed with an unsubstituted or at least monosubstituted monocyclic ring system; an unsubstituted or at least monosubstituted cycloaliphatic group which may comprise at least one heteroatom as ring member and may be bonded via a linear or branched unsubstituted or at least monosubstituted alkylene group which may comprise at least one heteroatom as link, which may be bridged by a linear or branched unsubstituted or at least monosubstituted alkylene group which may comprise at least one heteroatom as link and may be condensed with an unsubstituted or at least monosubstituted monocyclic ring system; or a —C(═O)—R$^4$ group;

$R^4$ represents
a linear or branched unsubstituted or at least monosubstituted alkyl group which may comprise at least one heteroatom as a link; a linear or branched unsubstituted or at least monosubstituted alkenyl group which may comprise at least one heteroatom as a link; a linear or branched unsubstituted or at least monosubstituted alkynyl group which may comprise at least one heteroatom as a link;
an unsubstituted or at least monosubstituted aryl group or heteroaryl group, which groups may be bonded via a linear or branched unsubstituted or at least monosubstituted alkylene group, alkenylene group, or alkynylene group, which groups may comprise at least one heteroatom as a link and may be condensed with an unsubstituted or at least monosubstituted monocyclic ring system;
an unsubstituted or at least monosubstituted cycloaliphatic group which may comprise at least one heteroatom as ring member and may be bonded via a linear or branched unsubstituted or at least monosubstituted alkylene group which may comprise at least one heteroatom as a link, which may be at least singly bridged by a linear or branched unsubstituted or at least monosubstituted alkylene group and may be condensed with an unsubstituted or at least monosubstituted monocyclic ring system; or a —C(=O)—OR$^7$ group bonded via a linear or branched unsubstituted or at least monosubstituted alkylene group; an —O—(C=O)—R$^8$ group bonded via a linear or branched unsubstituted or at least monosubstituted alkylene group; or a —(C=O)—R$^9$ group bonded via a linear or branched unsubstituted or at least monosubstituted alkylene group;

R$^5$ and R$^6$ each independently represent a linear or branched alkyl group; a linear or branched alkenyl group; or a linear or branched alkynyl group;

R$^7$ and R$^8$ each independently represent hydrogen; a linear or branched alkyl group; a linear or branched alkenyl group; a linear or branched alkynyl group; or an unsubstituted or at least monosubstituted aryl group or heteroaryl group;

R$^9$ is a linear or branched alkyl group; or a linear or branched alkenyl group or a linear or branched alkynyl group, said process comprising:

converting a protected piperidin-4-one compound corresponding to formula II,

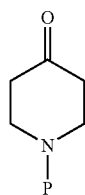

II wherein P stands for a protective group, by reacting said compound corresponding to formula II with at least one compound corresponding to formula III,

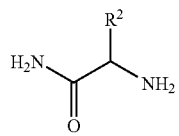

III to at least one compound corresponding to formula IV,

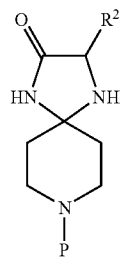

IV and optionally reacting said compound corresponding to formula IV with at least one compound corresponding to formula R$^1$—X$^1$, wherein X$^1$ represents a leaving group, which may be a halogen, to form at least one compound corresponding to formula V,

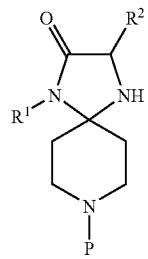

V and, optionally, splitting-off the protective group P, to yield at least one compound corresponding to formula VI,

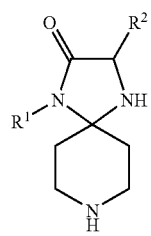

VI and, optionally, converting at least one compound corresponding to formula IV, V or VI, by reacting said at least one compound with a carboxylic derivative corresponding to formula R$^4$—(C=O)—X$^2$, a carboxylic anhydride of corresponding to formula (R$^4$—(C=O)—)$_2$O, or a compound corresponding to formula R$^3$—X$^3$ wherein the group R$^3$ is not hydrogen or —(C=O)—R$^4$, wherein X$^2$ and X$^3$ each represent a suitable leaving group, which may be a halogen group, to form at least one 1,4,8-triazaspiro[4,5]decan-2-one compound corresponding to formula I, or converting a 4-piperidone compound corresponding to formula VII,

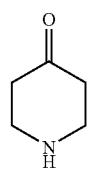

VII by reacting said compound corresponding to formula VII with a carboxylic derivative corresponding to formula R$^4$—(C=O)—X$^2$, a carboxylic anhydride corresponding to formula (R$^4$—(C=O)—)$_2$O or a compound corresponding to formula R$^3$—X$^3$ wherein R$^3$ is not hydrogen or (C=O)—R$^4$, and wherein X$^2$ and X$^3$ each represent a leaving group, to form a compound corresponding to formula VIII,

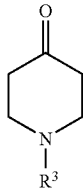

and converting said compound corresponding to formula VII, by reacting said compound with at least one compound corresponding to formula III

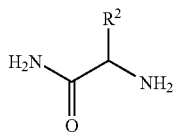

to form at least one compound corresponding to formula IX,

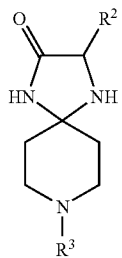

and converting the compound corresponding to formula IX, by reacting said compound corresponding to formula IX with at least one compound of corresponding to formula $R^1-X^1$ to form at least one 1,4,8-triazaspiro[4,5]decan-2-one compound corresponding to formula I.

16. A pharmaceutical formulation comprising at least one 1,4,8-triazaspiro[4,5]decan-2-one compound according to claim 1 and a pharmaceutically acceptable carrier or adjuvant.

17. A method of preparing a pharmaceutical formulation, said method comprising combining at least one 1,4,8-triazaspiro[4,5]decan-2-one compound according to claim 1 with a pharmaceutically acceptable carrier or adjuvant.

18. A method of treating or inhibiting a disease or condition selected from the group consisting of depression, pain, anxiety, obesity, epilepsy and inflammation, said method comprising the step of administering to a patient in need thereof a pharmaceutically effective amount of a compound corresponding to formula I:

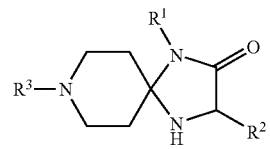

wherein $R^1$ represents hydrogen; a linear or branched unsubstituted alkyl group which may comprise at least one heteroatom as a link; a linear or branched, unsubstituted or at least monosubstituted alkenyl group which may comprise at least one heteroatom as a link; a linear or branched, unsubstituted or at least monosubstituted alkynyl group which may comprise at least one heteroatom as a link; an unsubstituted or at least monosubstituted aryl group or heteroaryl group, which is bonded via a linear or branched alkylene group which may comprise at least one heteroatom as a link; a —C(=O)—OR$^5$ group bonded via a linear or branched alkylene group; or an —O—(C=O)—R$^6$ group bonded via a linear or branched alkylene group;

$R^2$ represents hydrogen; a linear or branched, unsubstituted or at least monosubstituted alkyl group which may comprise at least one heteroatom as a link; a linear or branched, unsubstituted or at least monosubstituted alkenyl group which may comprise at least one heteroatom as a link; a linear or branched, unsubstituted or at least monosubstituted alkynyl group which may comprise at least one heteroatom as link; or an unsubstituted or at least monosubstituted aryl group or heteroaryl group, which may be bonded via a linear or branched alkylene group which may comprise at least one heteroatom as a link;

$R^3$ represents hydrogen; a linear or branched unsubstituted or at least monosubstituted alkyl group which may comprise at least one heteroatom as a link; or a linear or branched unsubstituted or at least monosubstituted alkenyl group which may comprise at least one heteroatom as a link; a linear or branched unsubstituted or at least monosubstituted alkynyl group which may comprise at least one heteroatom as a link; an unsubstituted or at least monosubstituted aryl group or heteroaryl group, which is bonded via a linear or branched unsubstituted or at least monosubstituted alkylene group which may comprise at least one heteroatom as a link and may be condensed with an unsubstituted or at least monosubstituted monocyclic ring system; an unsubstituted or at least monosubstituted cycloaliphatic group which may comprise at least one heteroatom as ring member and may be bonded via a linear or branched unsubstituted or at least monosubstituted alkylene group which may comprise at least one heteroatom as link, which may be bridged by a linear or branched unsubstituted or at least monosubstituted alkylene group which may comprise at least one heteroatom as link and may be condensed with an unsubstituted or at least monosubstituted monocyclic ring system; or a —C(=O)—R$^4$ group;

$R^4$ represents a linear or branched unsubstituted or at least monosubstituted alkyl group which may comprise at least one heteroatom as a link; a linear or branched unsubstituted or at least monosubstituted alkenyl group which may comprise at least one heteroatom as a link; a linear or branched unsubstituted or at least monosubstituted alkynyl group which may comprise at least one heteroatom as a link;

an unsubstituted or at least monosubstituted aryl group or heteroaryl group, which groups may be bonded via a linear or branched unsubstituted or at least monosubstituted alkylene group, alkenylene group, or alkynylene group, which groups may comprise at least one heteroatom as a link and may be condensed with an unsubstituted or at least monosubstituted monocyclic ring system;

an unsubstituted or at least monosubstituted cycloaliphatic group which may comprise at least one heteroatom as ring member and may be bonded via a linear or branched unsubstituted or at least monosubstituted alkylene group which may comprise at least one heteroatom as a link, which may be at least singly bridged by a linear or branched unsubstituted or at least monosubstituted alkylene group and may be condensed with an unsubstituted or at least monosubstituted monocyclic ring system; or a —C(=O)—OR$^7$ group bonded via a linear or branched unsubstituted or at least monosubstituted alkylene group; an —O—(C=O)—R$^8$ group bonded via a linear or branched unsubstituted or at least monosubstituted alkylene group; or a —(C=O)—R$^9$ group bonded via a linear or branched unsubstituted or at least monosubstituted alkylene group;

R$^5$ and R$^6$ each independently represent a linear or branched alkyl group; a linear or branched alkenyl group; or a linear or branched alkynyl group;

R$^7$ and R$^8$ each independently represent hydrogen; a linear or branched alkyl group; a linear or branched alkenyl group; a linear or branched alkynyl group; or an unsubstituted or at least monosubstituted aryl group or heteroaryl group; and R$^9$ is a linear or branched alkyl group; or a linear or branched alkenyl group or a linear or branched alkynyl group, or a physiologically acceptable salt thereof.

19. The method of claim 18 wherein said condition to be treated or inhibited is depression or inflammation, and said compound corresponding to formula I excludes those compounds wherein R$^1$ represents hydrogen, a $C_{1-6}$-alkyl group, a $C_{1-6}$ alkoxy group, a $C_{2-6}$ hydroxyalkyl group, a $C_{2-6}$ alkenyl group, a $C_{2-6}$ alkynyl group, a phenyl group or a $C_{1-6}$-alkyl group that is monosubstituted, disubstituted, or trisubstituted by a phenyl group, R$^2$ represents hydrogen, a $C_{1-6}$-alkyl group, a $C_{1-6}$ alkoxy group, a $C_{2-6}$ hydroxyalkyl group, a $C_{2-6}$ alkenyl group, a $C_{2-6}$ alkynyl group, a phenyl group, a $C_{1-6}$-alkyl group that is monosubstituted, disubstituted, or trisubstituted by a phenyl group, an —O—$C_{1-6}$ alkanoyl group, an OH group, an —O—$C_{1-6}$ alkyl group, an —O—$C_{1-6}$ alkoxy group, an —O—$C_{2-6}$ hydroxyalkyl group, a —O—$C_{2-6}$ alkenyl group, an —O—$C_{2-6}$ alkynyl group, an —O-phenyl group or an —O—$C_{1-6}$ alkyl group that is monosubstituted, disubstituted, or trisubstituted by a phenyl group, and R$^3$ represents hydrogen, a $C_{1-6}$-alkyl group, a $C_{2-6}$ alkenyl group, a $C_{2-6}$ alkynyl group, a $C_{3-7}$ cycloalkyl group, a $C_{1-6}$-alkyl group that is substituted by 1 to 6 halogen atoms, a hydroxy-$C_{1-6}$ alkyl group, a $C_{1-6}$ alkoxy group, a $C_{1-6}$ alkylthio group, a ($C_{1-6}$ alkoxy)-($C_{1-6}$ alkyl) group, a carboxy-$C_{1-6}$ alkyl group, a ($C_{1-6}$ alkoxy)-carbonyl-$C_{1-6}$ alkyl group, an amino-$C_{1-6}$ alkyl group, a mono($C_{1-6}$ alkyl)-amino group, a di($C_{1-6}$ alkyl)-amino group, a 2-oxo-pyrrolidin-1-ylmethyl group, an aryl group, a diarylmethylol group, a $C_{1-6}$-alkyl group that is substituted by one or two aryl groups, a $C_{1-6}$ alkanoyl group, or an arylcarbonyl group, wherein aryl in each case stands for an unsubstituted phenyl group or for a phenyl group which is substituted by 1 to 3 substituents selected from the group consisting of halogen, $C_{1-6}$ alkyl, $C_{1-6}$ alkoxy, and $CF_3$, and the salts thereof.

20. A method of alleviating pain in a mammal, said method comprising administering to said mammal an effective pain alleviating amount of a compound corresponding to formula I:

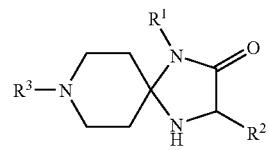

wherein

R$^1$ represents hydrogen; a linear or branched unsubstituted alkyl group which may comprise at least one heteroatom as a link; a linear or branched, unsubstituted or at least monosubstituted alkenyl group which may comprise at least one heteroatom as a link; a linear or branched, unsubstituted or at least monosubstituted alkynyl group which may comprise at least one heteroatom as a link; an unsubstituted or at least monosubstituted aryl group or heteroaryl group, which is bonded via a linear or branched alkylene group which may comprise at least one heteroatom as a link; a —C(=O)—OR$^5$ group bonded via a linear or branched alkylene group; or an —O—(C=O)—R$^6$ group bonded via a linear or branched alkylene group;

R$^2$ represents hydrogen; a linear or branched, unsubstituted or at least mono-substituted alkyl group which may comprise at least one heteroatom as a link; a linear or branched, unsubstituted or at least monosubstituted alkenyl group which may comprise at least one heteroatom as a link; a linear or branched, unsubstituted or at least monosubstituted alkynyl group which may comprise at least one heteroatom as link; or an unsubstituted or at least monosubstituted aryl group or heteroaryl group, which may be bonded via a linear or branched alkylene group which may comprise at least one heteroatom as a link;

R$^3$ represents hydrogen; a linear or branched unsubstituted or at least monosubstituted alkyl group which may comprise at least one heteroatom as a link; or a linear or branched unsubstituted or at least monosubstituted alkenyl group which may comprise at least one heteroatom as a link; a linear or branched unsubstituted or at least monosubstituted alkynyl group which may comprise at least one heteroatom as a link; an unsubstituted or at least monosubstituted aryl group or heteroaryl group, which is bonded via a linear or branched unsubstituted or at least monosubstituted alkylene group which may comprise at least one heteroatom as a link and may be condensed with an unsubstituted or at least monosubstituted monocyclic ring system; an unsubstituted or at least monosubstituted cycloaliphatic group which may comprise at least one heteroatom as ring member and may be bonded via a linear or branched unsubstituted or at least monosubstituted alkylene group which may comprise at least one heteroatom as link, which may be bridged by a linear or branched unsubstituted or at least monosubstituted alkylene group which may comprise at least one heteroatom as link and may be condensed with an unsubstituted or at least monosubstituted monocyclic ring system; or a —C(=O)—$R^4$ group;

$R^4$ represents
- a linear or branched unsubstituted or at least monosubstituted alkyl group which may comprise at least one heteroatom as a link; a linear or branched unsubstituted or at least monosubstituted alkenyl group which may comprise at least one heteroatom as a link; a linear or branched unsubstituted or at least monosubstituted alkynyl group which may comprise at least one heteroatom as a link;
- an unsubstituted or at least monosubstituted aryl group or heteroaryl group, which groups may be bonded via a linear or branched unsubstituted or at least monosubstituted alkylene group, alkenylene group, or alkynylene group, which groups may comprise at least one heteroatom as a link and may be condensed with an unsubstituted or at least monosubstituted monocyclic ring system;
- an unsubstituted or at least monosubstituted cycloaliphatic group which may comprise at least one heteroatom as ring member and may be bonded via a linear or branched unsubstituted or at least monosubstituted alkylene group which may comprise at least one heteroatom as a link, which may be at least singly bridged by a linear or branched unsubstituted or at least monosubstituted alkylene group and may be condensed with an unsubstituted or at least monosubstituted monocyclic ring system; or
- a —C(=O)—$OR^7$ group bonded via a linear or branched unsubstituted or at least monosubstituted alkylene group; an —O—(C=O)—$R^8$ group bonded via a linear or branched unsubstituted or at least monosubstituted alkylene group; or a —(C=O)—$R^9$ group bonded via a linear or branched unsubstituted or at least monosubstituted alkylene group;

$R^5$ and $R^6$ each independently represent a linear or branched alkyl group; a linear or branched alkenyl group; or a linear or branched alkynyl group;

$R^7$ and $R^8$ each independently represent hydrogen; a linear or branched alkyl group; a linear or branched alkenyl group; a linear or branched alkynyl group; or an unsubstituted or at least monosubstituted aryl group or heteroaryl group; and $R^9$ is a linear or branched alkyl group; or a linear or branched alkenyl group or a linear or branched alkynyl group, or a physiologically acceptable salt thereof excluding those compounds corresponding to formula I wherein $R^1$ represents hydrogen, a $C_{1-6}$-alkyl group, a $C_{1-6}$ alkoxy group, a $C_{2-6}$ hydroxyalkyl group, a $C_{2-6}$ alkenyl group, a $C_{2-6}$ alkynyl group, a phenyl group or a $C_{1-6}$-alkyl group that is monosubstituted, disubstituted, or trisubstituted by a phenyl group, $R^2$ represents hydrogen, a $C_{1-6}$-alkyl group, a $C_{1-6}$ alkoxy group, a $C_{2-6}$ hydroxyalkyl group, a $C_{2-6}$ alkenyl group, a $C_{2-6}$ alkynyl group, a phenyl group, a $C_{1-6}$-alkyl group that is monosubstituted, disubstituted, or trisubstituted by a phenyl group, an —O—$C_{1-6}$ alkanoyl group, an OH group, an —O—$C_{1-6}$ alkyl group, an —O—$C_{1-6}$ alkoxy group, an —O—$C_{2-6}$ hydroxyalkyl group, a —O—$C_{2-6}$ alkenyl group, an —O—$C_{2-6}$ alkynyl group, an —O-phenyl group or an —O—$C_{1-6}$ alkyl group that is monosubstituted, disubstituted, or trisubstituted by a phenyl group, and $R^3$ represents hydrogen, a $C_{1-6}$-alkyl group, a $C_{2-6}$ alkenyl group, a $C_{2-6}$ alkynyl group, a $C_{3-7}$ cycloalkyl group, a $C_{1-6}$-alkyl group that is substituted by 1 to 6 halogen atoms, a hydroxy-$C_{1-6}$ alkyl group, a $C_{1-6}$ alkoxy group, a $C_{1-6}$ alkylthio group, a ($C_{1-6}$ alkoxy)-($C_{1-6}$ alkyl) group, a carboxy-$C_{1-6}$ alkyl group, a ($C_{1-6}$ alkoxy)-carbonyl-$C_{1-6}$ alkyl group, an amino-$C_{1-6}$ alkyl group, a mono($C_{1-6}$ alkyl)-amino group, a di($C_{1-6}$ alkyl)-amino group, a 2-oxo-pyrrolidin-1-ylmethyl group, an aryl group, a diarylmethylol group, a $C_{1-6}$-alkyl group that is substituted by one or two aryl groups, a $C_{1-6}$ alkanoyl group, or an arylcarbonyl group, wherein aryl in each case stands for an unsubstituted phenyl group or for a phenyl group which is substituted by 1 to 3 substituents selected from the group consisting of halogen, $C_{1-6}$ alkyl, $C_{1-6}$ alkoxy, and $CF_3$ and the salts thereof.

21. The method of claim 20 wherein said pain is acute pain, chronic pain, neuropathic pain, or cluster headache pain.

\* \* \* \* \*